US011013745B2

(12) United States Patent
Zhou et al.

(10) Patent No.: US 11,013,745 B2
(45) Date of Patent: May 25, 2021

(54) TRIAZOLOPYRIMIDINE, TRIAZOLOPYRIDINE COMPOUNDS, AND THE COMPOSITION THEREOF FOR TREATING PRC2-MEDIATED DISEASES

(71) Applicants: SHANGHAI INSTITUTE OF MATERIA MEDICA, CHINESE ACADEMY OF SCIENCES, Shanghai (CN); SUZHOU SUPLEAD LIFE SCIENCES CO., LTD., Jiangsu (CN)

(72) Inventors: Bing Zhou, Shanghai (CN); Cheng Luo, Shanghai (CN); Yaxi Yang, Shanghai (CN); Yuanyuan Zhang, Shanghai (CN); Daohai Du, Shanghai (CN); Hualiang Jiang, Shanghai (CN); Gang Qiao, Jiangsu (CN); Xinjun Wang, Jiangsu (CN)

(73) Assignees: SHANGHAI INSTITUTE OF MATERIA MEDICA, CHINESE ACADEMY OF SCIENCES, Shanghai (CN); SUZHOU SUPLEAD LIFE SCIENCES CO., LTD., Jiangsu (CN)

( * ) Notice: Subject to any disclaimer, the term of this patent is extended or adjusted under 35 U.S.C. 154(b) by 0 days.

(21) Appl. No.: 16/651,510

(22) PCT Filed: Aug. 29, 2018

(86) PCT No.: PCT/CN2018/102833
§ 371 (c)(1),
(2) Date: Mar. 27, 2020

(87) PCT Pub. No.: WO2019/062435
PCT Pub. Date: Apr. 4, 2019

(65) Prior Publication Data

US 2020/0261459 A1 Aug. 20, 2020

(30) Foreign Application Priority Data

Sep. 28, 2017 (CN) ........................ 201710898099.5
Dec. 22, 2017 (CN) ........................ 201711408714.6

(51) Int. Cl.
*A61K 31/519* (2006.01)
*C07D 487/04* (2006.01)

(52) U.S. Cl.
CPC .......... *A61K 31/519* (2013.01); *C07D 487/04* (2013.01)

(58) Field of Classification Search
CPC .............. A61K 31/519; A61K 31/5377; A61K 31/541; A61K 31/551; A61P 11/00; A61P 35/00; A61P 35/02; C07D 487/04
See application file for complete search history.

(56) References Cited

U.S. PATENT DOCUMENTS 9,580,437 B2 * 2/2017 Chan .................... C07D 487/04

FOREIGN PATENT DOCUMENTS

WO 2016103155 A1 6/2016

OTHER PUBLICATIONS

Huang et al., "Discovery of First-in-Class, Potent, and Orally Bioavailable Embryonic Ectoderm Development (EED) Inhibitor with Robust Anticancer Efficacy," J. Med. Chem., vol. 60, Jan. 16, 2017, pp. 2215-2226.
Yang et al., "Allosteric Inactivation of Polycomb Repressive Complex 2 (PRC2) by Inhibiting Its Adapter Protein: Embryotic Ectodomain Development (EED)," J. Med. Chem., vol. 60, Mar. 3, 2017, pp. 2212-2214.
Qi et al., "An Allosteric PRC2 Inhibitor Targeting the H3K27me3 Binding Pocket of EED," Nature Chemical Biology, vol. 13, Jan. 30, 2017, pp. 381-388.
International Search Report and Written Opinion for International Application No. PCT/CN2018/102833 dated Nov. 30, 2018.
International Preliminary Report on Patentability for International Application No. PCT/CN2018/102833 dated Mar. 31, 2020.

* cited by examiner

*Primary Examiner* — Erich A Leeser
(74) *Attorney, Agent, or Firm* — Meunier Carlin & Curfman LLC

(57) ABSTRACT

The present invention provides a compound represented by formula I, pharmaceutically acceptable salts, enantiomers, diastereomers or racemates thereof, the preparation method thereof, the pharmaceutical composition comprising the same, and the use thereof in the preparation of a medicament for treating a disease or condition mediated by EED and/or PRC2. The compound of the present invention can be used treating PRC2-mediated diseases or conditions.

Formula I

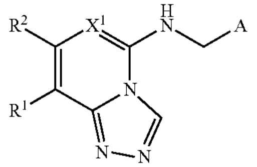

18 Claims, No Drawings

TRIAZOLOPYRIMIDINE, TRIAZOLOPYRIDINE COMPOUNDS, AND THE COMPOSITION THEREOF FOR TREATING PRC2-MEDIATED DISEASES

TECHNICAL FIELD

The present invention relates to pharmaceutical chemistry and pharmaceutical therapeutics, and generally relates to a triazolopyrimidine, triazolopyridine compounds, and pharmaceutical compositions, and their use in the treatment of tumor diseases. In particular, such compounds can be prepared for medicine of the treatment of PRC2-mediated diseases or conditions.

BACKGROUND ART

Polycomb Repressive Complex 2 (PRC2) is a core member of the Polycomb Group. It has histone methyltransferase activity, and can specifically catalyze the trimethylation modification (H3K27me3) of lysine at position 27 of histone H3 to suppress the expression of specific genes. The methyltransferase activity of PRC2 is derived from its catalytic member EZH2. However, EZH2 has no catalytic activity when it is alone. It needs to form a complex with at least two other members of PRC2, i.e., EED and SUZ12, to catalyze the methylation modification. Therefore, EZH2, EED and SUZ12 are considered as the core components of the PRC2 complex. Recent studies have found that the core components of PRC2 are overexpressed in a variety of tumor cells, and their abnormal activity is the direct reason of the onset and deterioration of various malignant tumors. At the same time, recent gene sequencing results of lymphoma patients showed that EZH2 exhibits activating mutation in patients with germinal center B cell lymphoma (GCB-DLBCL). The mutated EZH2 alters the substrate specificity of PRC2, thereby increases the level of H3K27me3 in cells. Downregulating the expression of EZH2 or other core components by the siRNA method will significantly inhibit the proliferation of lymphoma cells, which indicates that the occurrence and development of GCB-DLBCL is closely related to the excessive activation of PRC2. Therefore, PRC2 is a very promising target for the development of anticancer drugs, and the discovery of inhibitors that target PRC2 is currently a hot topic in the pharmaceutical industry. Recently, two major pharmaceutical companies, Novartis and AbbVie, have invented a small molecules that inhibit PRC2 activity by targeting EED (Reference: Novartis EED226, US 2016/0176682, J. Med. Chem. 2017, 60, 2215-2226, J. Med. Chem. 2017, 60, 415-427, Nat. Chem. Biol. 2017, 13, 381-388; AbbVie's A-395, Nat. Chem. Biol. 2017, 13, 389-395), this kind of compound shows very strong inhibitory activity at the molecular level, cell level and animal experiments. In summary, the PRC2 complex is considered to be a key driver for the occurrence and development of a variety of malignant tumors, and the development of inhibitors that target EED to inhibit PRC2 activity is currently very hot in the industry and is conducive to the use in the related new drug development.

SUMMARY OF THE INVENTION

The present invention relates to a triazolopyrimidine, triazolopyndine compounds as shown in Formula I, and pharmaceutical compositions thereof, by combining the evaluation of binding activity and related biological experiments, it can be used for the preparation for the drugs for the treatment of EED and/or PRC2-mediated diseases or conditions.

It is an object of the present invention to provide a triazolopyrimidine, triazolopyridine compounds, pharmaceutically acceptable salts, enantiomers, diastereomers or racemates.

It is another object of the present invention to provide a method for preparing the compound.

It is a further object of the present invention to provide a pharmaceutical composition comprising a therapeutically effective amount of one or more of the above compounds or a pharmaceutically acceptable salt thereof.

It is yet another object of the present invention to provide the use of the above compound in the preparation of a medicament for treating a disease or condition mediated by EED and/or PRC2.

It is yet another object of the present invention to provide a method for treating a disease or condition mediated by EED and/or PRC2, characterized in that a therapeutically effective amount of one or more of the above-mentioned compounds or a pharmacological salt thereof is administered to a subject.

Specifically, according to one aspect of the invention, it provides a compound of formula I:

Formula I

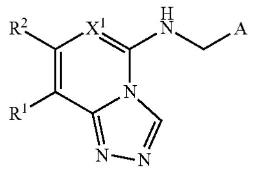

wherein

1) $X^1$ is independently selected from N and C—CN;

2) $R^2$ is independently selected from H, halogen, $C_1$-$C_4$ haloalkyl and $C_1$-$C_4$ alkyl;

3) A is independently selected from the following structures:

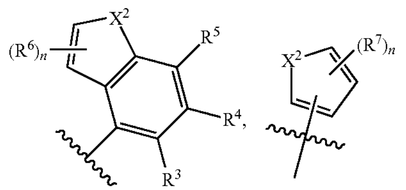

------ is a single bond or double bond;

$R^3$, $R^4$ and $R^5$ are independently selected from H, halogen, $C_1$-$C_4$ alkyl, $C_1$-$C_4$ haloalkyl, —O—($C_1$-$C_4$ alkyl), $C_1$-$C_4$ haloalkoxy, $C_3$-$C_6$ cycloalkyl;

$R^6$ is independently selected from H, OH, =O and $C_1$-$C_4$ alkyl;

$R^7$ is independently selected from H, OH, halogen, $C_N$ and $C_1$-$C_4$ alkyl;

n is each independently selected from 0, 1 and 2;

$X^2$ is independently selected from O, $NR^a$ and $S(O)_p$ heteroatoms;

Each $R^a$ is independently selected from H, O, $C_1$-$C_{10}$ alkyl substituted by 0-2 $R^b$, $C_1$-$C_6$ haloalkyl, —O—($C_1$-$C_6$ alkyl), $C_1$-$C_6$ haloalkoxy, $C_3$-$C_6$ cycloalkyl, —C(=O)($C_1$-$C_4$ alkyl), —$CO_2$ ($C_1$-$C_4$ alkyl), heteroalkyl and heterocycloalkyl comprising carbon atoms and 1-4 heteroatoms selected from O, N, $S(O)_p$, —C(═O)H, aryl, 5- to 6-membered heteroaryl comprising carbon atoms and 1 to 2 heteroatoms selected from N, O and S;

$R^b$ is independently selected from halogen, OH, $NH_2$, NHC(═O)($C_1$-$C_4$ alkyl), NHS(═O)$_2$ ($C_1$-$C_4$ alkyl), ═O, CN, $C_1$-$C_4$ alkyl and $C_1$-$C_4$ alkoxy;

p is each independently selected from 0, 1 and 2;

4) $R^1$ is independently selected from the following structures:

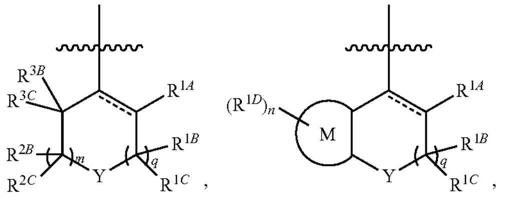

------ is a single bond or double bond;

4a) $R^{1A}$ is independently selected from H, hydroxy, halogen, CN, —$(O)_z$—($C_1$-$C_{10}$ alkyl comprising 0-2 of substituent $R^c$), $C_1$-$C_6$ alkyl group, $C_1$-$C_6$ alkoxy, $C_1$-$C_6$ haloalkyl, $C_1$-$C_6$ haloalkoxy, $SCF_3$, $C_3$-$C_8$ cycloalkyl, —C(═O)($C_1$-$C_4$ alkyl), —C(═O)NH($C_1$-$C_4$ alkyl), amino, $C_1$-$C_6$ linear, branched and cyclic alkylamino, heteroalkyl and heterocycloalkyl comprising carbon atoms and 1-4 heteroatoms selected from O, N, $S(O)_p$, —C(═O)H, aryl, 5- to 6-membered heteroaryl comprising carbon atoms and 1 to 2 heteroatoms selected from N, O and S; wherein the aryl and heteroaryl may be substituted by 0-2 of $R^{1X}$;

p is each independently selected from 0, 1 and 2;

$R^c$ is independently selected from OH, halogen, CN, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, —$(OCH_2CH_2)_m OR^d$, NHC(═O)$NR^dR^e$, NHC(═S)$NR^dR^e$, —NHC(═NH)$NR^dR^e$, $(OCH_2CH_2)$m$NR^dR^e$, —C(═O)$R^d$, —S(═O)$R^d$, —C(═O)$NR^dR^e$, —S(═O)$_2R^d$, —NHC(═O)$R^d$, —NHC(═S)$R^d$, —NHS(═O)$_2R^d$, —S(═O)$_2$NH$R^d$, heteroalkyl and heterocycloalkyl comprising carbon atoms and 1 to 2 heteroatoms selected from N, $NR^a$, O and $S(O)_p$, aryl, and heteroaryl comprising carbon atoms and 1 to 2 heteroatoms selected from N, $NR^a$, O and $S(O)_p$, wherein the aryl and heteroaryl may be substituted by 0-2 of $R^{1X}$;

$R^d$ and $R^e$ are independently selected from H, $C_1$-$C_6$ alkyl comprising 0-2 of $R^b$, $C_1$-$C_6$ haloalkyl, $C_3$-$C_6$ cycloalkyl, —C(═O)($C_1$-$C_4$ alkyl). —$CO_2$($C_1$-$C_4$ alkyl), —C(═O)NH($C_1$-$C_4$ alkyl), $C_1$-$C_6$ branched or cyclic heteroalkyl comprising 0-2 of heteroatoms selected from O, N, and $S(O)_p$, —C(═O)H, aryl and heteroaryl comprising carbon atoms and 1 to 2 heteroatoms selected from N, $NR^a$, O and $S(O)_p$, wherein the aryl and heteroaryl may be substituted by 0-2 of $R^{1X}$;

Each $R^a$ is independently selected from H, O, $C_1$-$C_{10}$ alkyl substituted by 0-2 of $R^b$, $C_1$-$C_6$ haloalkyl, —O—($C_1$-$C_6$ alkyl), $C_1$-$C_6$ haloalkoxy, $C_3$-$C_6$ cycloalkyl, —C(═O)($C_1$-$C_4$ alkyl). —$CO_2$($C_1$-$C_4$ alkyl), heteroalkyl and heterocycloalkyl comprising carbon atoms and 1-4 heteroatoms selected from O, N, $S(O)_p$, —C(═O)H, aryl, 5- to 6-membered heteroaryl comprising carbon atoms and 1 to 2 heteroatoms selected from N, O and S;

$R^b$ is independently selected from halogen, OH, $NH_2$, NHC(═O)($C_1$-$C_4$ alkyl), NHS(═O)$_2$($C_1$-$C_4$ alkyl), ═O, CN, $C_1$-$C_4$ alkyl and $C_1$-$C_4$ alkoxy;

p is each independently selected from 0.1 and 2;

$R^d$ and $R^e$ can be connected in the form of $R^d$—$R^e$ or 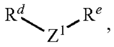, wherein the $Z^1$ may be selected from $C_1$-$C_6$ alkyl comprising 0-2 of substituent $R^b$, $C_1$-$C_6$ heteroalkyl comprising 0-2 of substituent heteroatoms of O, N, $S(O)_p$, O, —N($C_1$-$C_6$ alkyl), —NH, —N(C═O) $C_1$-$C_6$ alkyl, —NS(═O)$_2$($C_1$-$C_6$ alkyl), $S(O)_p$; $R^b$ is independently selected from halogen, OH, $NH_2$, —NHC(═O)($C_1$-$C_4$ alkyl). —NHS(═O)($C_1$-$C_4$ alkyl), ═O, CN, $C_1$-$C_4$ alkyl and $C_1$-$C_4$alkoxy; p is each independently selected from 0, 1 and 2;

$R^{1X}$ is independently selected from halogen, OH, CN, $C_1$-$C_4$ alkyl, $C_1$-$C_4$ haloalkyl, $C_1$-$C_4$ alkoxy, $C_1$-$C_4$ haloalkoxy, $C_3$-$C_8$ cycloalkyl and cyclic heteroalkyl;

$R^{1B}$ and $R^{1C}$ are independently selected from H, OH, halogen, CN, —(O)—($C_1$-$C_{10}$ alkyl comprising 0-2 of substituent $R^c$), $C_1$-$C_6$ alkyl group, $C_1$-$C_6$ alkoxy, $C_1$-$C_6$ haloalkyl, $C_1$—C haloalkoxy, $SCF_3$, $C_3$-$C_8$ cycloalkyl, —C(═O)($C_1$-$C_4$ alkyl), —C(═O)NH($C_1$-$C_4$ alkyl), heteroalkyl and heterocycloalkyl comprising carbon atoms and 1-4 heteroatoms selected from O, N, $S(O)_p$, —C(═O)H, aryl, 5- to 6-membered heteroaryl comprising carbon atoms and 1 to 2 heteroatoms selected from N, O and S; wherein the aryl and heteroaryl may be substituted by 0-2 of $R^{1X}$; p is each independently 0, 1 and 2;

$R^{2B}$ and $R^{2C}$ are independently selected from H, OH, halogen, CN, —$(O)_7$—($C_1$-$C_{10}$ alkyl comprising 0-2 of substituent $R^c$), $C_1$-$C_6$ alkyl group, $C_1$-$C_6$ alkoxy, $C_1$-$C_6$ haloalkyl, $C_1$-$C_6$ haloalkoxy, $SCF_3$, $C_3$-$C_8$ cycloalkyl, —C(═O)($C_1$-$C_4$ alkyl), —C(═O)NH($C_1$-$C_4$ alkyl), heteroalkyl and heterocycloalkyl comprising carbon atoms and 1-4 heteroatoms selected from O, N, $S(O)_p$, —C(═O)H, aryl, 5- to 6-membered heteroaryl comprising carbon atoms and 1 to 2 heteroatoms selected from N, O and S; wherein the aryl and heteroaryl may be substituted by 0-2 of $R^{1X}$; p is each independently 0, 1 and 2;

$R^{3B}$ and $R^{3C}$ are independently selected from H, OH, halogen, CN, —$(O)_z$—($C_1$-$C_{10}$ alkyl comprising 0-2 of substituent $R^c$), $C_1$-$C_6$ alkyl group, $C_1$-$C_6$ alkoxy, $C_1$-$C_6$ haloalkyl, $C_1$-$C_6$ haloalkoxy, $SCF_3$, $C_3$-$C_8$ cycloalkyl, —C(═O)($C_1$-$C_4$ alkyl), —C(═O)NH($C_1$-$C_4$ alkyl), heteroalkyl and heterocycloalkyl comprising carbon atoms and 1-4 heteroatoms selected from O, N, $S(O)_p$, —C(═O)H, aryl, 5- to 6-membered heteroaryl comprising carbon atoms and 1 to 2 heteroatoms selected from N, O and S; wherein the aryl and heteroaryl may be substituted by 0-2 of $R^{1X}$; p is each independently 0, 1 and 2;

Alternatively, $R^{1B}$ and $R^{1C}$, $R^{2B}$ and $R^{2C}$, $R^{3B}$ and $R^{3C}$ may form a carbonyl group (═O) or a thiocarbonyl group (═S) with a carbon atom to which they are attached;

$R^{1D}$ is independently selected from H, —OH, halogen, CN, —C(═O)H, —$(O)_7$—($C_1$-$C_6$ alkyl comprising 0-2 of substituent $R^c$), $C_1$-$C_6$ haloalkyl, $C_1$-$C_6$ haloalkoxy, $SCF_3$, $R^f$, —$OR^f$, —C(═O)R, $NR^dR^e$, —C(═O) $NR^dR^e$, —NHC(═O)$R^c$, —S(═O)$_2R^c$, —S(═O)$_2$, $NR^dR^e$, —NHS(═O)$_2R^d$, —$(OCH_2CH_2)_m OR^d$, —$(OCH_2CH_2)_m NR^dR^e$;

$R^f$ is independently selected from $C_3$-$C_8$ cycloalkyl, heteroalkyl and heterocycloalkyl comprising carbon atoms and 1-4 heteroatoms selected from O, N, $S(O)_p$, aryl, heteroaryl comprising carbon atoms and 1 to 2 heteroatoms selected from N, $NR^a$, O and $S(O)_p$; wherein the aryl and heteroaryl are substituted by 0-2 of $R^{1X}$;

M is independently selected from a 3 to 7 membered saturated or unsaturated cycloalkyl, a heterocycloalkyl comprising carbon atoms and 1-4 heteroatoms selected from O, N, $S(O)_p$, an aryl, 5- to 6-membered heteroaryl comprising carbon atoms and 1 to 2 heteroatoms selected from N, O and S;

In the definition of $R^{1B}$ and $R^{1C}$, $R^{2B}$ and $R^{2C}$, $R^{3B}$ and $R^{3C}$, $R^{1D}$ and $R^f$, the definitions of $R^a$, $R^c$, $R^d$, $R^e$, p, z, m and $R^{1X}$ are the same as those of $R^{1A}$ in the part 4a);

n is each independently selected from 0, 1 and 2;

m is each independently selected from 0-4;

p is each independently selected from 0-2;

q is each independently selected from 0-3;

z is each independently selected from 0 and 1;

4a') Preferably, $R^1$ is independently selected from the following structures:

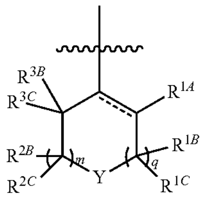
,
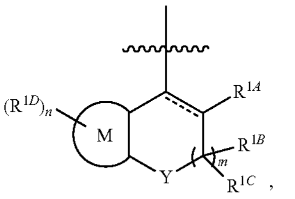
, wherein

====== is a single bond or double bond;

$R^{1A}$ is independently selected from H, hydroxy, halogen, CN, —$(O)_z$($C_1$-$C_{10}$ alkyl comprising 0-2 of substituent $R^e$), $C_1$-$C_6$ alkyl, $C_1$-$C_6$ alkoxy, $C_1$-$C_6$ haloalkyl, $C_1$-$C_6$ haloalkoxy, $SCF_3$, $C_3$-$C_8$ cycloalkyl, —C(═O)($C_1$-$C_4$ alkyl), —C(═O)NH($C_1$-$C_4$ alkyl), —C(═O)H;

$R^c$ is independently selected from OH, halogen, CN, $C_1$-$C_6$ alkyl, carboxyl, $C_1$-$C_6$ haloalkyl, $C_1$-$C_6$ alkoxy, $C_1$-$C_6$ haloalkoxy, $C_3$-$C_8$ cycloalkyl; $R^{1B}$ and $R^{1C}$, $R^{2B}$ and $R^{2C}$, and $R^{3B}$ and $R^{3C}$ are independently selected from H, OH, halogen, CN, —$(O)_z$—($C_1$-$C_{10}$ alkyl comprising 0-2 of substituent $R^c$), $C_1$-$C_6$ alkyl group, $C_1$-$C_6$ alkoxy, $C_1$-$C_6$ haloalkyl, $C_1$-$C_6$ haloalkoxy, $SCF_3$, $C_3$-$C_8$ cycloalkyl, —C(═O)($C_1$-$C_4$ alkyl), —C(═O)NH($C_1$-$C_4$ alkyl);

Alternatively, $R^{1B}$ and $R^{1C}$, $R^{2B}$ and $R^{2C}$, $R^{3B}$ and $R^{1C}$ may form a carbonyl group (═O) or a thiocarbonyl group (═S) with a carbon atom to which they are attached;

$R^{1D}$ is independently selected from H, —OH, halogen, CN. —C(═O)H, —$(O)_z$—($C_1$-$C_6$ alkyl comprising 0-2 of substituent $R^c$), $C_1$-$C_6$ haloalkyl, $C_1$-$C_6$ haloalkoxy, $SCF_3$, $C_3$-$C_8$ cycloalkyl;

$R^c$ is independently selected from OH, halogen, CN, $C_1$-$C_6$ alkyl, carboxyl, $C_1$-$C_6$ haloalkyl, $C_1$-$C_6$ alkoxy, $C_1$-$C_6$ haloalkoxy, $C_3$-$C_8$ cycloalkyl;

M is independently selected from a 3 to 7 membered saturated or unsaturated cycloalkyl, a heterocycloalkyl comprising carbon atoms and 1-4 heteroatoms selected from O, N, $S(O)_p$, an aryl, 5- to 6-membered heteroaryl comprising carbon atoms and 1 to 2 heteroatoms selected from N, O and S;

n is each independently selected from 0, 1 and 2;

m is each independently selected from 0-4;

p is each independently selected from 0-2;

q is each independently selected from 0-3;

z is each independently selected from 0 and 1;

4a") more preferably, in $R^1$, $R^{1A}$ is independently selected from H, hydroxyl, halogen, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl;

$R^{1B}$ and $R^{1C}$, $R^{2B}$ and $R^{2C}$, and $R^{1B}$ and $R^{3C}$ are independently selected from H, OH, halogen, $C_1$-$C_6$ alkyl group, $C_1$-$C_6$ alkoxy, $C_1$-$C_6$ haloalkyl, $C_1$-$C_6$ haloalkoxy, $C_3$-$C_8$ cycloalkyl;

Alternatively, $R^{1B}$ and $R^{1C}$, $R^{1B}$ and $R^{2C}$, $R^{3B}$ and $R^{3C}$ may form a carbonyl group (═O) or a thiocarbonyl group (═S) with a carbon atom to which they are attached;

$R^{1D}$ is independently selected from H, —OH, halogen, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl;

M is independently selected from a 5 to 6 membered saturated or unsaturated cycloalkyl, a heterocycloalkyl comprising carbon atoms and 1-4 heteroatoms selected from O, N, $S(O)_p$, an aryl, 5- to 6-membered heteroaryl comprising carbon atoms and 1 to 2 heteroatoms selected from N, O and S;

n is each independently selected from 0, 1 and 2;

m is each independently selected from 0-4;

p is each independently selected from 0-2;

q is each independently selected from 0-3;

z is each independently selected from 0 and 1;

4b) Y is independently selected from heteroatoms of O, $NR^g$, $S(O)_p$, etc., and $CH_2$, C═O, —$CR^i(CH_2)_mNR^gR^h$ and —$CR^i(CH_2)_mOR^g$;

$R^g$ and $R^h$ are independently selected from H, O, $C_1$-$C_{10}$ alkyl comprising 0-3 of substituent $R^s$, $C_1$-$C_6$ haloalkyl, $C_3$-$C_6$ cycloalkyl,

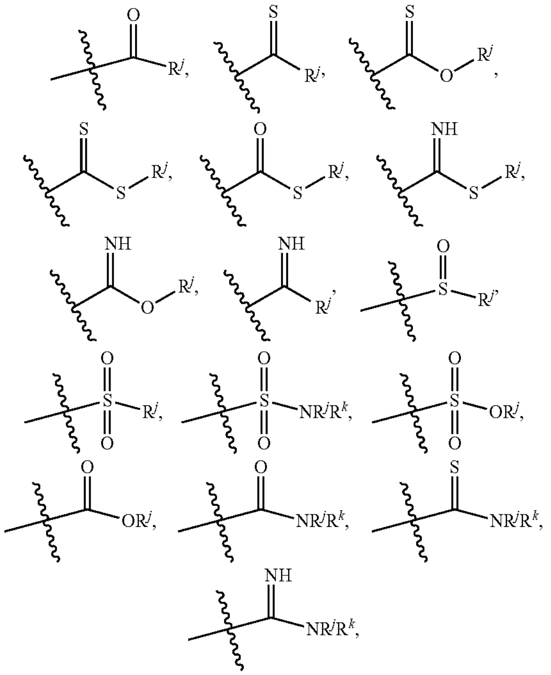

—C(═S)NHC(═O)—$R^j$, heteroalkyl and heterocycloalkyl comprising carbon atoms and 1-4 heteroatoms selected from O, N, $S(O)_p$, aryl, 5- to 6-membered heteroaryl comprising carbon atoms and 1 to 2 heteroatoms selected from N, O and S; wherein the aryl and heteroaryl may be substituted by 0-2 of $R^{1X}$;

$R^s$ is independently selected from OH, CN, halogen, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, —$(OCH_2CH_2)_mOR^d$, NHC(═O)$NR^dR^e$, NHC(═S)$NR^dR^e$, —NHC(═NH)$NR^dR^e$, $(OCH_2CH_2)_mNR^dR^e$, —C(═O)$R^d$, —C(═S)$R^d$, —S(═O)

$R^d$, —C(═O)NR$^d$R$^e$, —S(═O)$_2$R$^d$, —NHC(═O)R$^d$, —NHC(═S)R$^d$. —NHS(═O)$_2$R$^d$, —S(═O)$_2$NR$^d$R$^e$, —NHS(═O)$_2$NR$^d$R$^e$, —C(═S)NR$^d$R$^e$, NHC(═O)OR$^d$, NHC(═S)OR$^d$, —NHS(═O)$_2$OR$^d$, NHC(═O)SR$^d$, NHC(═S)SR$^d$, —NHC(═NH)OR$^d$, —C(═O)OR$^d$, —C(═O)SR$^d$, —S(═O)$_2$OR$^d$, heteroalkyl and heterocycloalkyl comprising carbon atoms and 1 to 2 heteroatoms selected from N, NR$^a$, O and S(O)$_p$, aryl, heteroaryl comprising carbon atoms and 1 to 2 heteroatoms selected from N, NR$^a$, O and S(O)$_p$; wherein the aryl and heteroaryl may be substituted by 0-2 of R$^{1Y}$;

R$^d$ and R$^e$ are independently selected from H, $C_1$-$C_6$ alkyl comprising 0-2 of R$^b$, $C_1$-$C_6$ haloalkyl, $C_3$-$C_6$ cycloalkyl, —C(═O)($C_1$-$C_4$ alkyl), —CO$_2$($C_1$-$C_4$ alkyl), —C(═O)NH ($C_1$-$C_4$ alkyl), $C_1$-$C_6$ branched or cyclic heteroalkyl comprising 0-2 of heteroatoms selected from O, N, and S(O)$_p$, —C(═O)H, aryl, and heteroaryl comprising carbon atoms and 1 to 2 heteroatoms selected from N, NR$^a$, O and S(O)$_p$, wherein the aryl and heteroaryl may be substituted by 0-2 of R$^{1X}$;

R$^d$ and R$^e$ may be connected by the following manner $R^d$—$R^e$ or 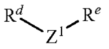

to form a ring, wherein Z$^1$ can be selected from $C_1$-$C_6$ alkyl comprising from 0-2 of substituent R$^b$; $C_1$-$C_6$ alkyl comprising 0-2 heteroatoms of O, N, S(O)$_p$, O; —N($C_1$-$C_6$ alkyl); —NH; —N(C═O) $C_1$-$C_6$ alkyl; —NS(═O)$_2$($C_1$-$C_6$ alkyl); S(O)$_p$;

Each R$^a$ is independently selected from H; O; $C_1$-$C_{10}$ alkyl substituted by 0-2 of R$^b$; $C_1$-$C_6$ haloalkyl; —O—($C_1$-$C_6$ alkyl); $C_1$-$C_6$ haloalkoxy; $C_3$-$C_6$ cycloalkyl; —C(═O)($C_1$-$C_4$ alkyl); —CO$_2$($C_1$-$C_4$ alkyl); heteroalkyl and heterocycloalkyl comprising carbon atoms and 1-4 heteroatoms selected from O, N, S(O)$_p$; —C(═O)H; aryl; 5- to 6-membered heteroaryl comprising carbon atoms and 1 to 2 heteroatoms selected from N, O and S;

R$^b$ is independently selected from halogen, OH, NH$_2$, NHC(═O)($C_1$-$C_4$ alkyl), NHS(═O)$_2$($C_1$-$C_4$ alkyl), ═O, CN, $C_1$-$C_4$ alkyl and $C_1$-$C_4$ alkoxy; p is independently selected from 0.1 and 2;

R$^{1X}$ is independently selected from halogen, OH, CN, $C_1$-$C_4$ alkyl, $C_1$-$C_4$ haloalkyl, $C_1$-$C_4$ alkoxy, $C_1$-$C_4$ haloalkoxy, $C_3$-$C_8$ cycloalkyl and cyclic heteroalkyl;

R$^{1Y}$ is independently selected from $C_1$-$C_{10}$ alkyl; halogen; CN; —(O)$_2$—($C_1$-$C_{10}$ alkyl comprising 0-2 of the substituent R$^e$); $C_1$-$C_6$ haloalkyl; $C_1$-$C_6$ haloalkoxy; SCF$_3$; $C_3$-$C_8$ cycloalkyl; —C(═O)(C)—$C_4$ alkyl); —CO$_2$($C_1$-$C_4$ alkyl); NR$^d$R$^e$; —C(═O)NR$^d$R$^e$; —S(═O)$_2$R$^d$; —NHC(═O)R$^d$; —NHC(═S)R$^d$; —NHS(═O)$_2$R$^d$; —NHC(═O)NR$^d$R$^e$; —NHC(═S)NR$^d$R$^e$; —NHS(═O)$_2$NR$^d$R$^e$; —C(═S)NR$^d$R$^e$; —S(═O)$_2$NHR$^d$; heteroalkyl and heterocycloalkyl comprising carbon atoms and 1-4 heteroatoms selected from O, N, S(O)$_p$; —C(═O)H; p is each independently 0, 1 and 2;

wherein, R$^c$ is the same definition of R as defined in the above part 4a);

wherein, R$^d$ and R$^e$ may be connected by the manner of $R^d$—$R^e$ or 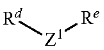 , wherein Z$^1$ can be selected from $C_1$-$C_6$ alkyl comprising from 0-2 of substituent R$^b$; $C_1$-$C_6$ heteroalkyl comprising 0-2 heteroatoms of O, N, S(O)$_P$; O; —N($C_1$-$C_6$ alkyl); —NH; —N(C═O) $C_1$-$C_6$ alkyl; —NS(═O)$_2$($C_1$-$C_6$ alkyl); S(O)$_p$;

R$^b$ is independently selected from halogen, OH, NH$_2$. NHC(═O)($C_1$-$C_4$ alkyl), NHS(═O)$_2$($C_1$-$C_4$ alkyl), ═O, CN, $C_1$-$C_4$ alkyl and $C_1$-$C_4$ alkoxy; p is independently selected from 0, 1 and 2;

R$^j$ and R$^k$ are independently selected from H, CN, $C_1$-$C_{10}$ alkyl comprising 0-3 of substituent R$^5$, $C_1$-$C_6$ haloalkyl, $C_3$-$C_{10}$ cycloalkyl, heteroalkyl and heterocycloalkyl comprising carbon atoms and 1-4 heteroatoms selected from O, N, S(O)$_p$, alkenyl or alkynyl group substituted by R$^y$ ( 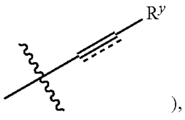 ), 6 to 10 membered aryl, 5 to 10 membered heteroaryl comprising carbon atoms and 1 to 2 heteroatoms selected from N, O, and S; wherein the aryl and heteroaryl groups may be substituted by 0-2 of R$^{1Y}$;

wherein, R$^{1Y}$ is the same definition of R$^{1Y}$ as defined in the above R$^5$ in the part 4b);

R$^y$ is independently selected from H; $C_1$-$C_{10}$ alkyl comprising 0-3 of substituent R$^e$; $C_1$-$C_6$ haloalkyl; $C_3$-$C_{10}$ cycloalkyl; heteroalkyl and heterocycloalkyl comprising carbon atoms and 1-4 heteroatoms selected from O, N, S(O)$_p$; NR$^d$R$^e$; OR$^d$ aryl; 5- to 6-membered heteroaryl comprising carbon atoms and 1 to 2 heteroatoms selected from N, O and S; wherein the aryl and heteroaryl may be substituted by 0-2 of R$^{1X}$; R$^{1X}$ is independently selected from halogen, OH, CN, $C_1$-$C_4$ alkyl, $C_1$-$C_4$ haloalkyl, $C_1$-$C_4$ alkoxy, $C_1$-$C_4$ haloalkoxy, $C_3$-$C_8$ cycloalkyl and cyclic heteroalkyl;

wherein, R$^e$ is the same definition of R as defined in the above part 4a); R$^d$ and R$^e$ are the same definition of R$^d$ and R$^e$ as defined in the above R$^5$ in the part 4b);

In particular, R$^g$ and R$^h$, as well as R$^j$ and R$^k$ may be connected by the following manner $R^g$—$R^h$, 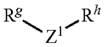 , $R^j$—$R^k$, and 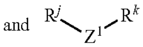 , wherein Z$^1$ may be selected from $C_1$-$C_6$ alkyl comprising 0-2 of substituent R$^c$; $C_1$-$C_6$ alkyl comprising 0-2 heteroatoms of O, N, S(O)$_p$; O; —N($C_1$-$C_6$ alkyl); —NH; —N(C═O) $C_1$-$C_6$ alkyl; —NS(═O)$_2$($C_1$-$C_6$ alkyl); S(O)$_p$; p is each independently selected from 0, 1 and 2;

wherein, R$^c$ is the same definition of R$^c$ as defined in the above part 4a);

R$^i$ is independently selected from H, CN, $C_1$-$C_4$ alkyl;

m is each independently selected from 0-4:

4b') Preferably, Y is independently selected from O, NR$^5$, S(O)$_p$, —CR$^i$(CH$_2$)$_m$NR$^g$R$^h$ and —CR$^i$(CH$_2$)$_m$OR$^g$;

R$^g$ and R$^h$ are independently selected from H; $C_1$-$C_6$ haloalkyl;

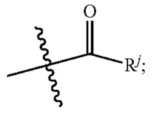 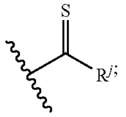 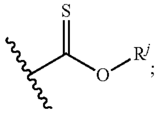

-continued

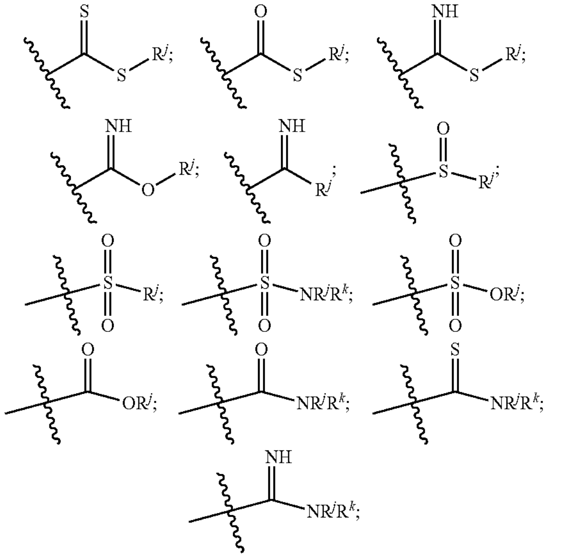

—C(═S)NHC(═O)—$R^j$; heteroalkyl and heterocycloalkyl comprising carbon atoms and 1-4 heteroatoms selected from O, N, $S(O)_p$; aryl; 5- to 6-membered heteroaryl comprising carbon atoms and 1 to 2 heteroatoms selected from N, O and S; wherein the aryl and heteroaryl may be substituted by 0-2 of $R^{1X}$;

$R^j$ and $R^k$ are independently selected from H; CN; $C_1$-$C_{10}$ alkyl comprising 0-3 of substituent $R^5$; $C_1$-$C_6$ haloalkyl; $C_3$-$C_{10}$ cycloalkyl; heteroalkyl and heterocycloalkyl comprising carbon atoms and 1-4 heteroatoms selected from O, N, $S(O)_p$; $C_2$-$C_{10}$ alkenyl or alkynyl; 6 to 10 membered aryl; 5 to 10 membered heteroaryl comprising carbon atoms and 1 to 2 heteroatoms selected from N, O, and S; wherein the aryl and heteroaryl may be substituted by 0-2 of $R^{1Y}$:

wherein, the definition of $R^s$ is the same definition of $R^s$ in the above part 4b);

p is each independently selected from 0, 1 and 2;

$R^{1X}$ is independently selected from halogen, OH, CN, $C_1$-$C_4$ alkyl, $C_1$-$C_4$ haloalkyl, $C_1$-$C_4$ alkoxy, $C_1$-$C_4$ haloalkoxy, $C_3$-$C_8$ cycloalkyl and cyclic heteroalkyl;

$R^{1Y}$ is independently selected from $C_1$-$C_{10}$ alkyl, halogen, CN, $C_1$-$C_6$ haloalkyl, $C_1$-$C_6$ haloalkoxy, $C_3$-$C_8$ cycloalkyl;

p is each independently 0, 1 and 2;

In particular, $R^g$ and $R^h$, as well as $R^j$ and $R^k$ may be connected by the following manner $R^g$—$R^h$, 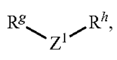 $R^j$—$R^k$, and 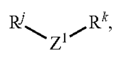

wherein $Z^1$ may be selected from $C_1$-$C_6$ alkyl comprising 0-2 of substituent $R^c$; $C_1$-$C_6$ alkyl comprising 0-2 heteroatoms of O, N, $S(O)_p$; O; —N($C_1$-$C_6$ alkyl); —NH; —N(C═O) $C_1$-$C_6$ alkyl; —NS(═O)$_2$($C_1$-$C_6$ alkyl); $S(O)_p$;

wherein, $R^c$ is the same definition of R as defined in the above part 4a);

p is each independently selected from 0, 1 and 2:

$R^1$ is independently selected from H, CN and $C_1$-$C_4$ alkyl;

m is each independently selected from 0-4;

4b") More preferably, the Y is independently selected from O, $NR^g$, S, —$CR^iNR^gR^h$ and —$CR^iOR^g$;

$R^g$ and $R^h$ are independently selected from H; $C_1$-$C_6$ haloalkyl;

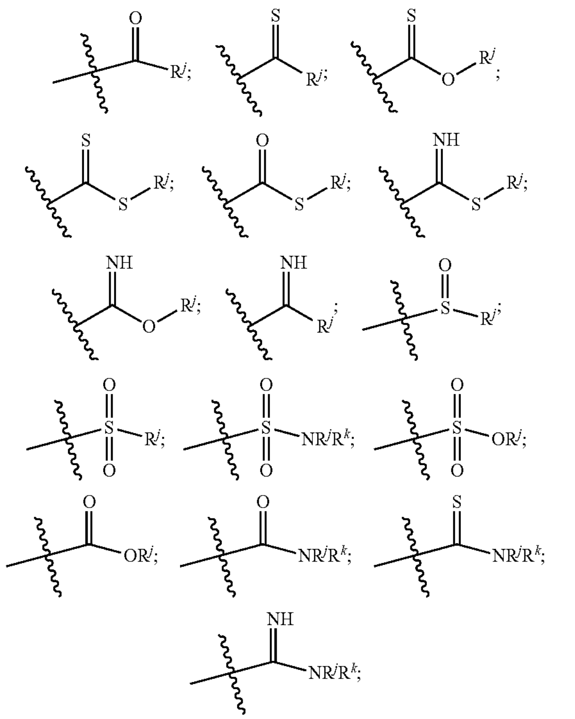

—C(═S)NHC(═O)—$R^j$; heteroalkyl and heterocycloalkyl comprising carbon atoms and 1-4 heteroatoms selected from O, N, S; aryl; 5- to 6-membered heteroaryl comprising carbon atoms and 1 to 2 heteroatoms selected from N, O and S; wherein the aryl and heteroaryl may be substituted by 0-2 of $R^{1X}$;

$R^j$ and $R^k$ are independently selected from H; CN; $C_1$-$C_{10}$ alkyl comprising 0-3 of substituent $R^s$; $C_1$-$C_6$ haloalkyl; $C_3$-$C_{10}$ cycloalkyl; heteroalkyl and heterocycloalkyl comprising carbon atoms and 1-4 heteroatoms selected from O, N, S; $C_2$-$C_{10}$ alkenyl or alkynyl; 6 to 10 membered aryl; 5 to 10 membered heteroaryl comprising carbon atoms and 1 to 2 heteroatoms selected from N, O, and S; wherein the aryl and heteroaryl may be substituted by 0-2 of $R^{1Y}$;

$R^s$ is independently selected from OH; CN; halogen; $C_1$-$C_6$ alkyl; $C_1$-$C_6$ haloalkyl; $C_1$-$C_6$ alkoxy; $C_1$-$C_6$ haloalkoxy; $C_3$-$C_8$ cycloalkyl, —$(OCH_2CH_2)_mOR^d$, $(OCH_2CH_2)_mNR^dR^e$, heteroalkyl and heterocycloalkyl comprising carbon atoms and 1 to 2 heteroatoms selected from N, O, S; aryl; and heteroaryl comprising carbon atoms and 1 to 2 heteroatoms selected from N, O, and S; wherein the aryl and heteroaryl may be substituted by 0-2 of $R^{1Y}$;

wherein, $R^d$, $R^e$ are the same definition of $R^d$, $R^e$ as defined in the above part 4b);

$R^{1Y}$ is independently selected from $C_1$-$C_{10}$ alkyl, halogen, CN, $C_1$-$C_6$ haloalkyl, $C_1$-$C_6$ haloalkoxy, $C_3$-$C_8$ cycloalkyl:

In particular, $R^g$ and $R^h$, as well as $R^j$ and $R^k$ may be connected by the following manner $R^g$—$R^h$, 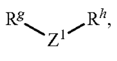 $R^j$—$R^k$, and 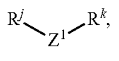

wherein $Z^1$ may be selected from $C_1$-$C_6$ alkyl comprising 0-2 of substituent $R^e$; $C_1$-$C_6$ alkyl comprising 0-2 heteroatoms of O, N, $S(O)_p$; O; —$N(C_1$-$C_6$ alkyl); —NH; —N(C═O) $C_1$-$C_6$ alkyl; —$NS(═O)_2(C_1$-$C_6$ alkyl); $S(O)_p$;

wherein, $R^c$ is the same definition of $R^c$ as defined in the above part 4a):

p is each independently selected from 0, 1 and 2:

$R^1$ is independently selected from H, CN and $C_1$-$C_4$ alkyl;

m is each independently selected from 0-4;

Preferably, the compound of formula I has formula Ia-1 or Ia-2;

Ia-1

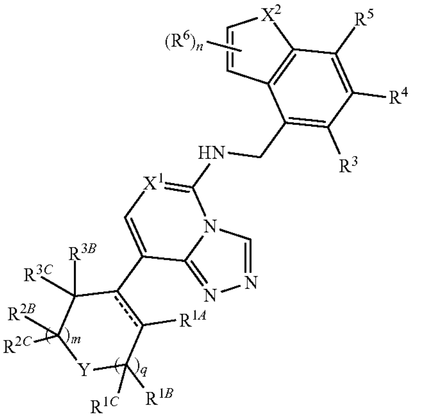

Ia-2

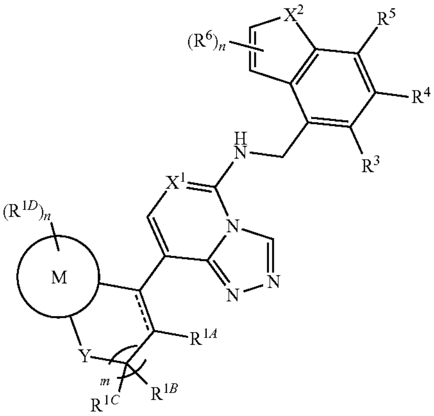

Wherein, $X^1$ is the same definition as defined in the part 1) of Formula I:

------ is a single bond or double bond;

$X^2$, $R^3$-$R^5$, $R^6$ and n are the same definition as defined in the part 3) of Formula I;

$R^{1A}$, $R^{1B}$ and $R^{1C}$, $R^{2B}$ and $R^{2C}$, $R^{3B}$ and $R^{3C}$, $R^{1D}$, n, n, q, Y, M are the same definition as defined in the part 4) of Formula I;

Preferably, the compound of formula I has formula Ia-3 or Ia-4:

Ia-3

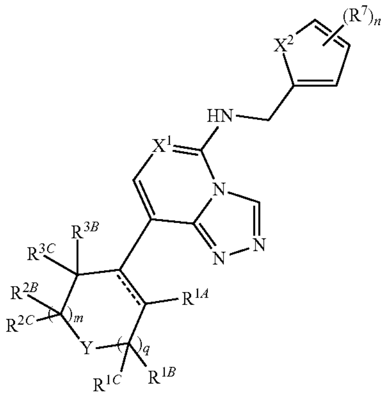

Ia-4

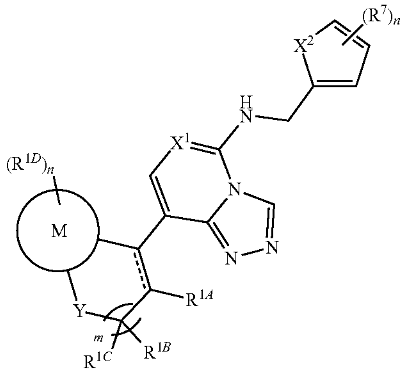

Wherein, $X^1$ is the same definition as defined in the part 1) of Formula I;

------ is a single bond or double bond;

$X^2$, $R^7$ and n are the same definition as defined in the part 3) of Formula I;

$R^{1A}$, $R^{1B}$ and $R^{1C}$, $R^{1B}$ and $R^{2C}$, $R^{3B}$ and $R^{3C}$, $R^{1D}$, n, m, q, Y, M are the same definition as defined in the part 4) of Formula I;

Preferably, the compound of formula I has formula Ia-5 or Ia-6:

Ia-5

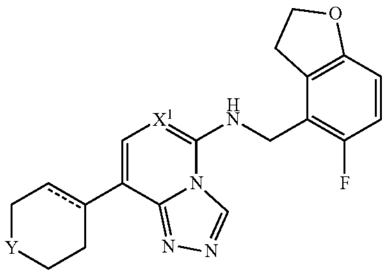

Ia-6

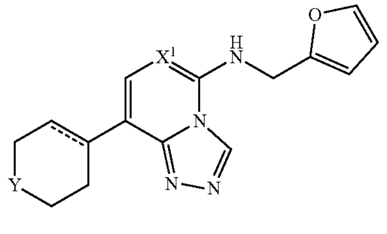

Wherein, $X^1$ is the same definition as defined in the part 1) of Formula I;

------ is a single bond or double bond;

Y is the same definition as defined in the part 4) of Formula I:

Preferably, the compound of formula I has formula Ia-7 or Ia-8:

Ia-7

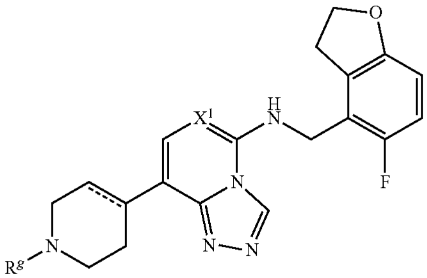

Ia-8

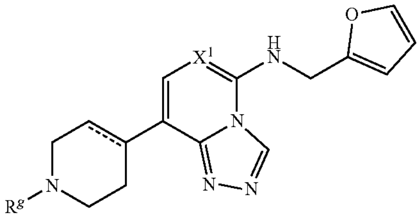

Wherein, $X^1$ is the same definition as defined in the part 1) of Formula I;

------ is a single bond or double bond;

The definition of $R^g$ is the same definition as defined in the part 4b) of part 4) of Formula I;

Preferably, the compound of formula I has formula Ia-9:

Ia-9

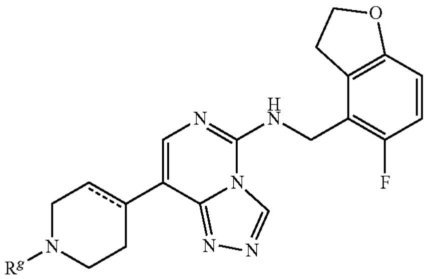

wherein

------ is a single bond or double bond;

The definition of $R^g$ is the same definition as defined in the part 4b) of part 4) of Formula I:

Preferably, the compound of formula I has one of the following formulae:

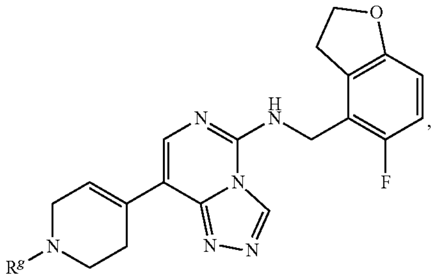

,

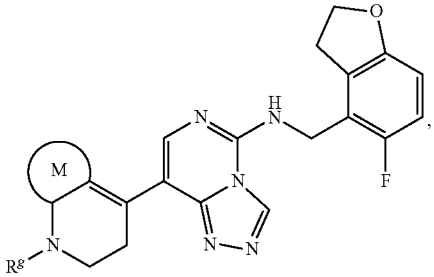

,

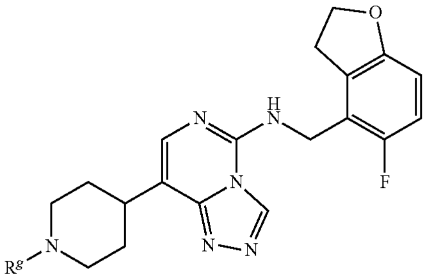

or

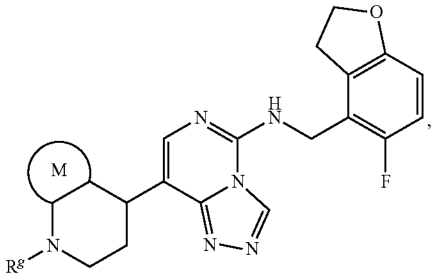

, wherein

M is the same definition as defined in the part 4) of Formula I;

The definition of $R^g$ is the same definition as defined in the part 4b) of part 4) of Formula I;

Preferably, the compound of formula I is selected from the following compounds:

E-Y1

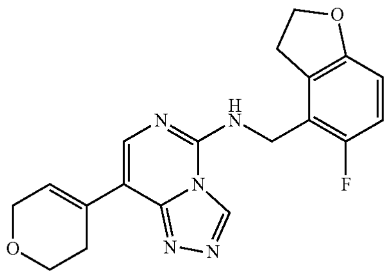

-continued
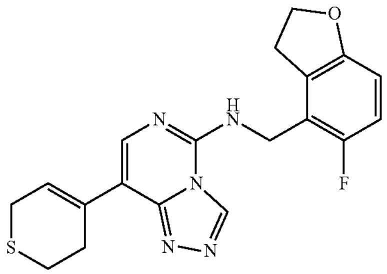
E-Y2
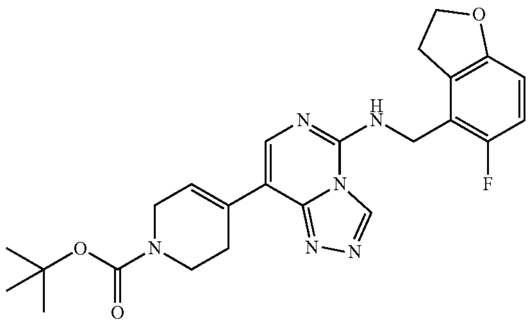
E-Y3
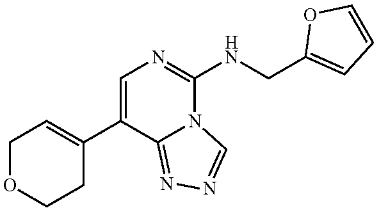
E-Y4
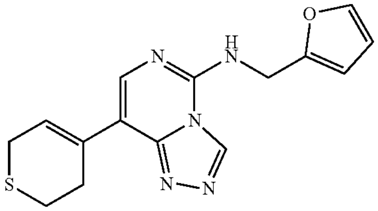
E-Y5
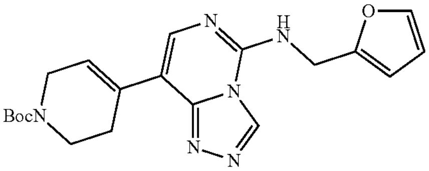
E-Y6
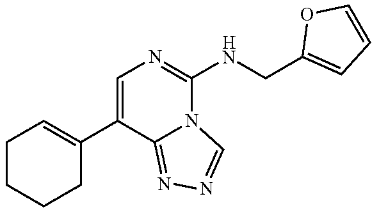
E-Y7
-continued
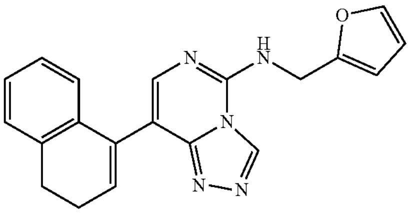
E-Y8
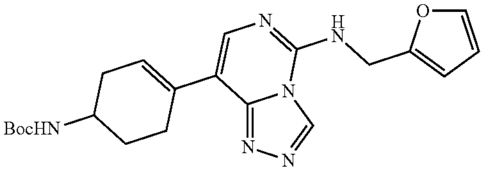
E-Y9
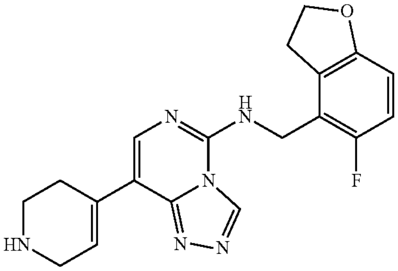
E-Y10
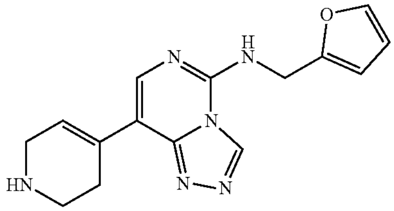
E-Y11
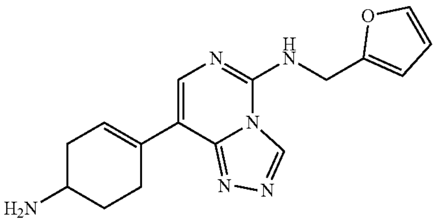
E-Y12
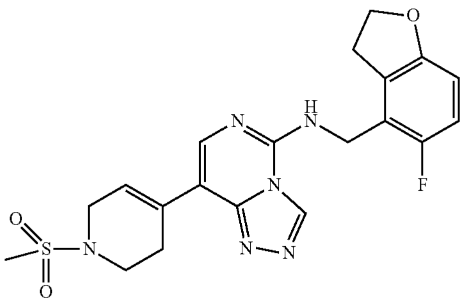
E-Y13

-continued
E-Y14
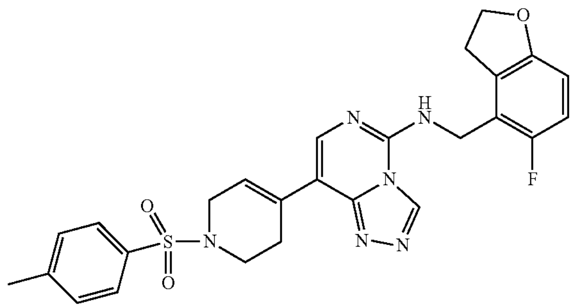
E-Y15
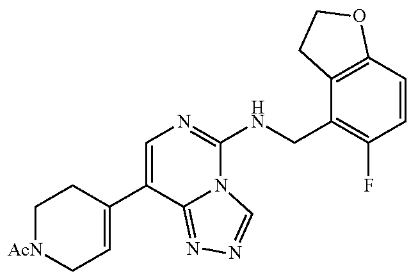
E-Y16
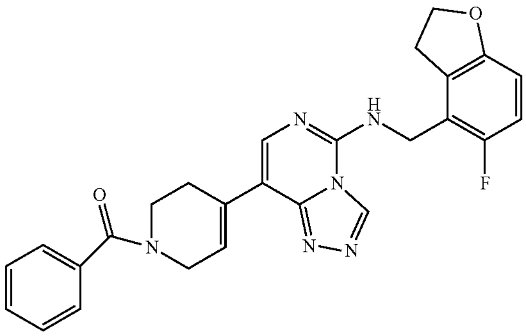
E-Y17
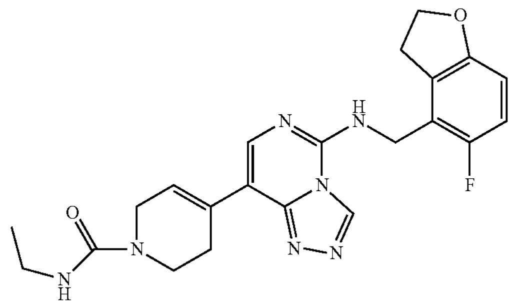
E-Y18
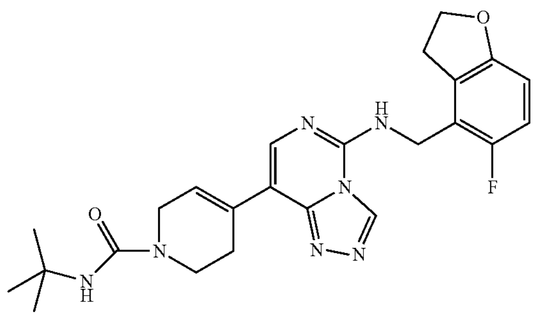
-continued
E-Y19
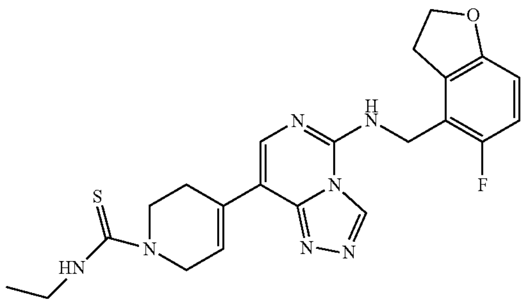
E-Y20
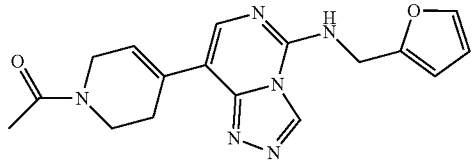
E-Y21
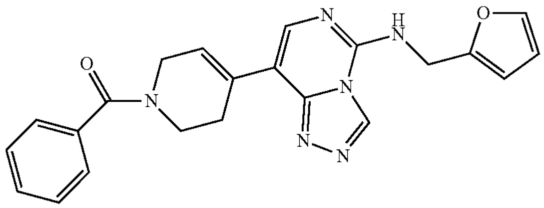
E-Y22
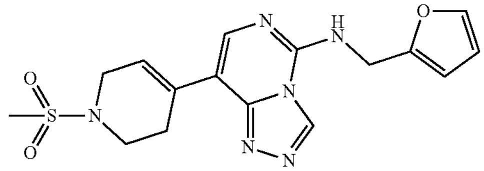
E-Y23
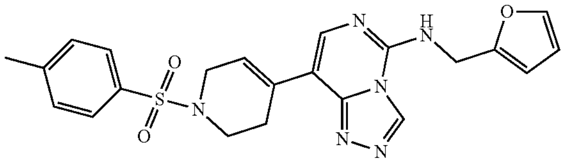
E-Y24
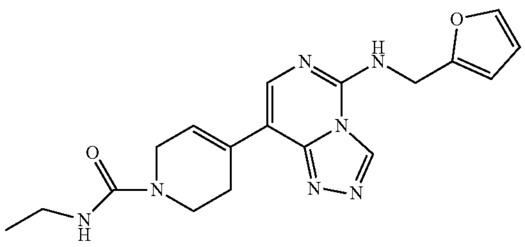

-continued
E-Y25
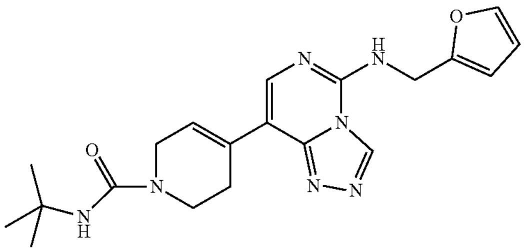
E-Y26
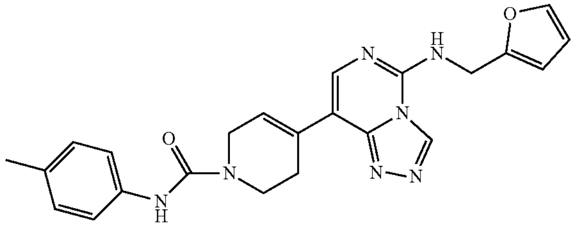
E-Y27
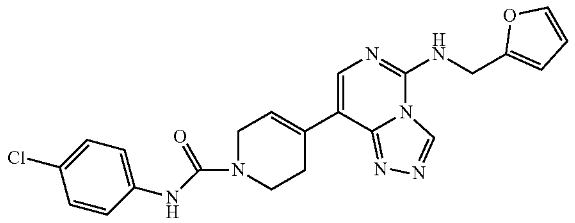
E-Y28
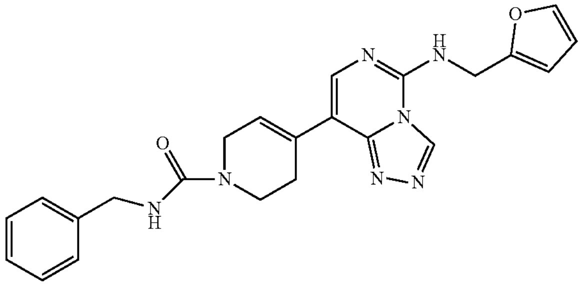
E-Y29
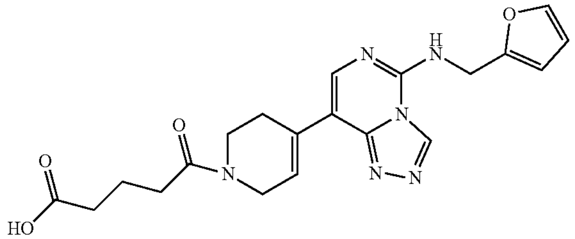
E-Y30
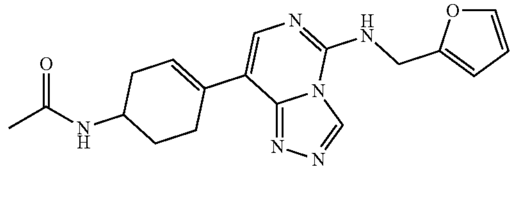
-continued
E-Y31
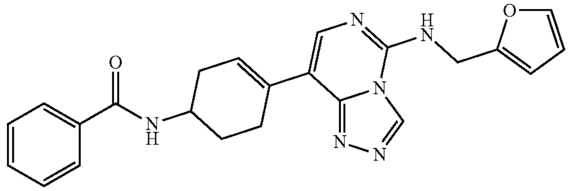
E-Y32
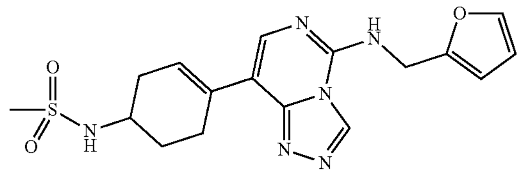
E-Y33
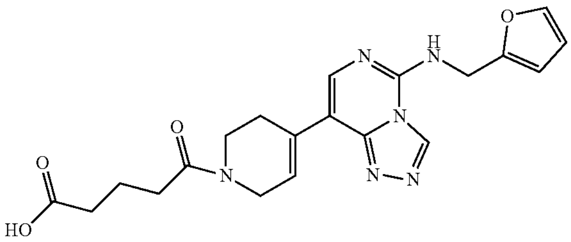
E-Y34
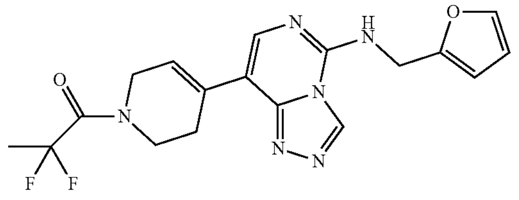
E-Y35
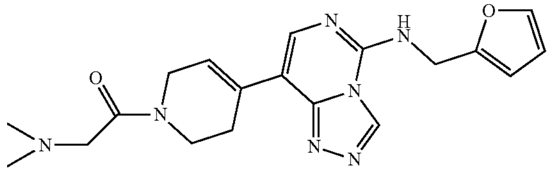
E-Y36
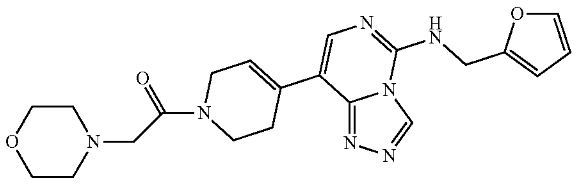

-continued
E-Y37
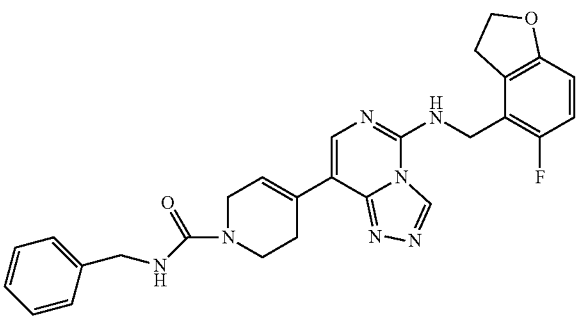
E-Y38
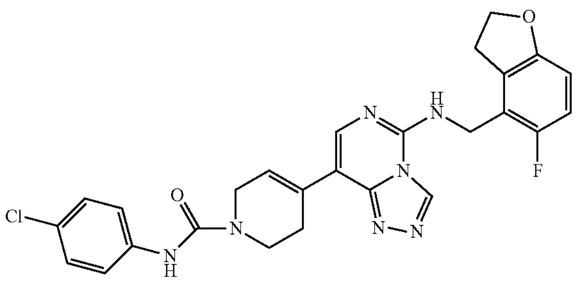
E-Y39
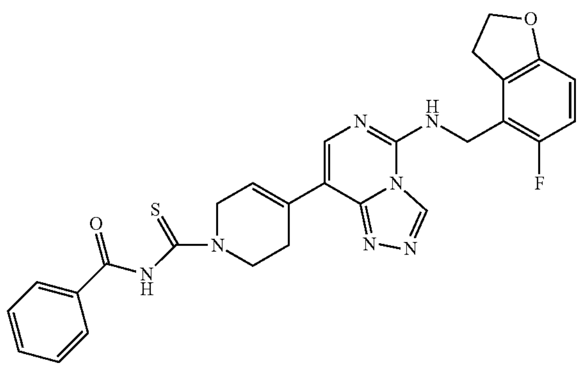
E-Y40
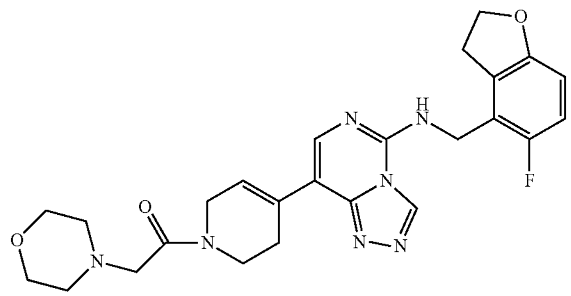
-continued
E-Y41
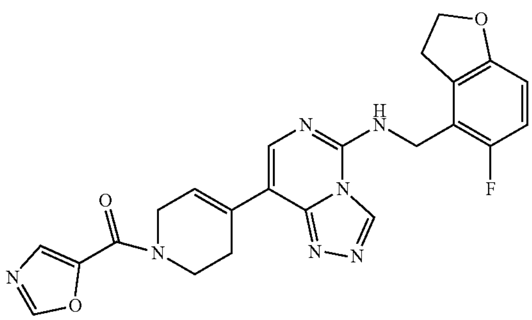
E-Y42
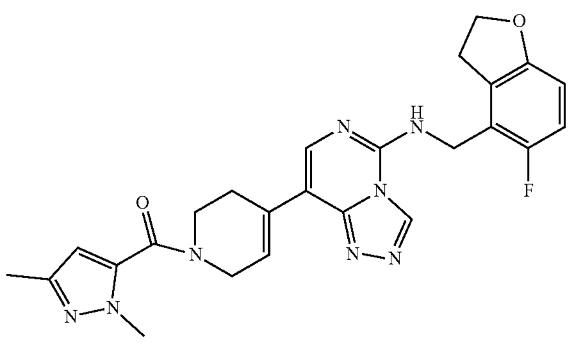
E-Y43
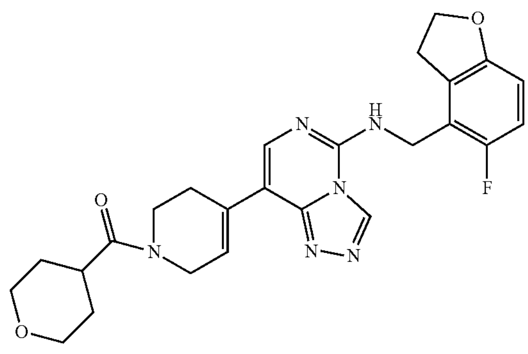
E-Y44
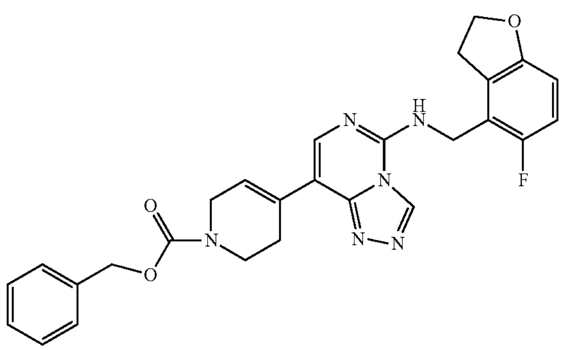

-continued
E-Y45
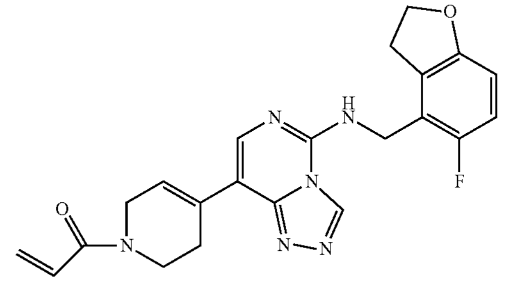
E-Y46
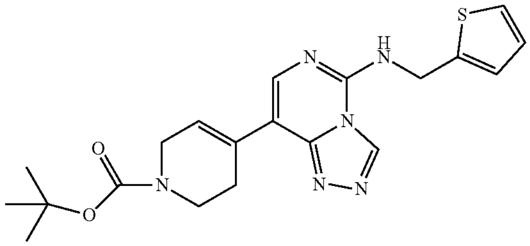
E-Y47
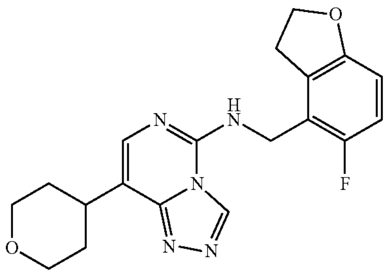
E-Y48
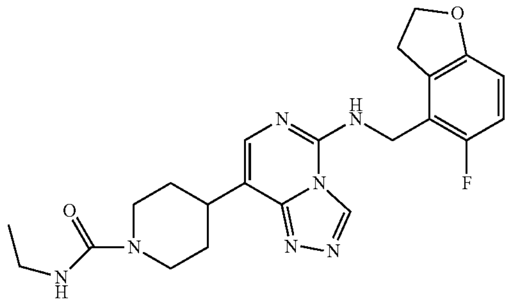
E-Y49
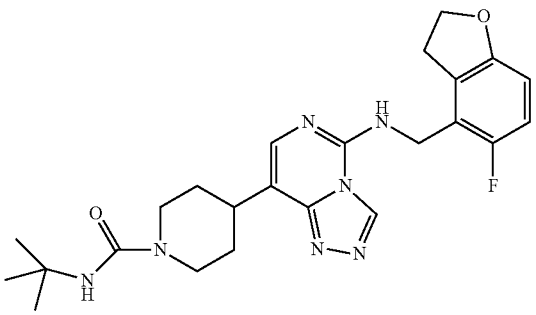
-continued
E-Y50
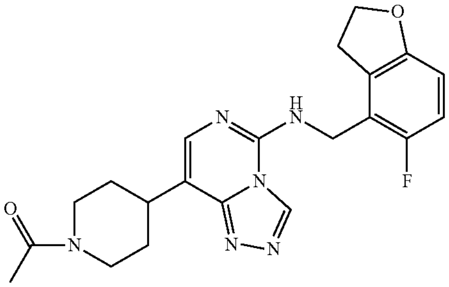
E-Y51
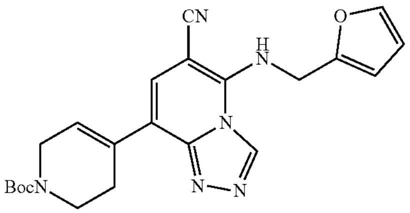
E-Y52
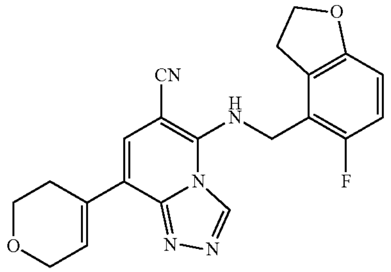
E-Y53
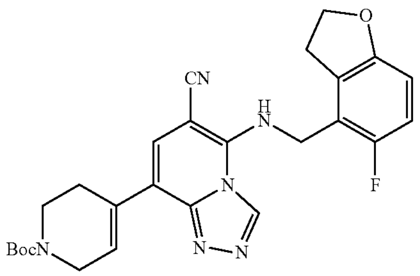
E-Y54
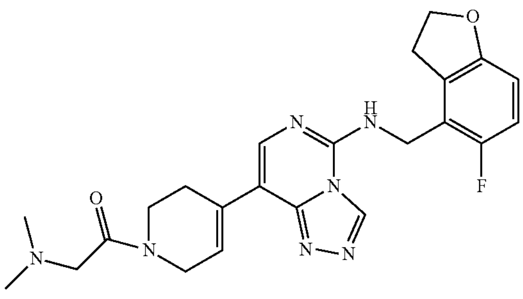

-continued
SL-ZYE-07
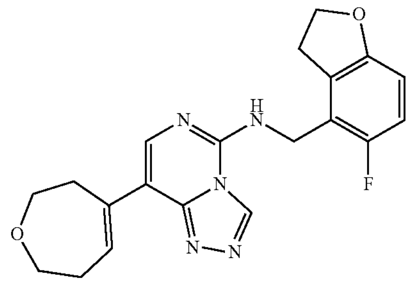
SL-ZYE-08
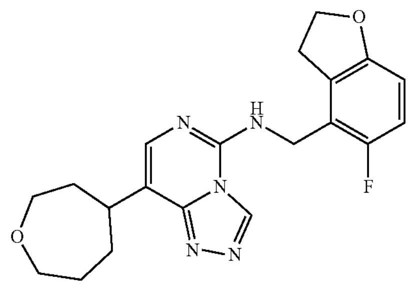
SL-ZYE-09
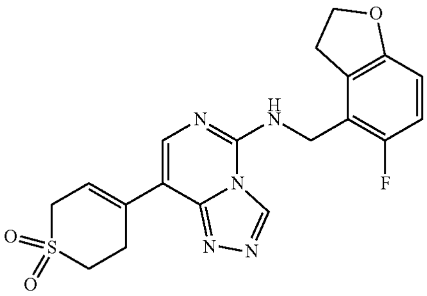
SL-ZYE-11
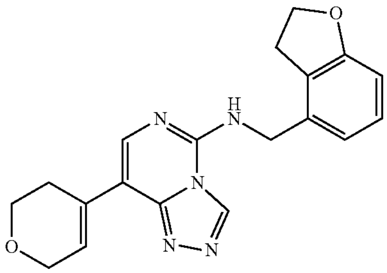
SL-ZYE-14
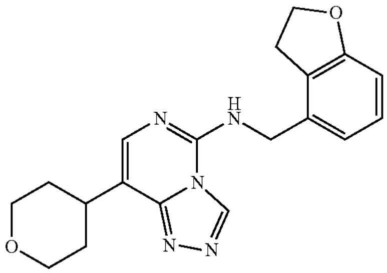
-continued
SL-ZYE-17
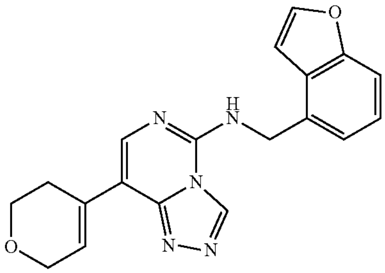
SL-ZYE-18
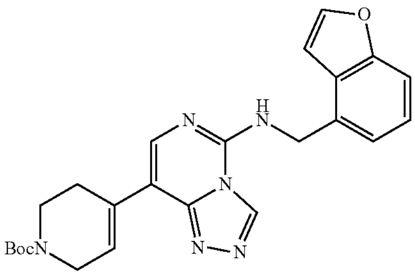
E-Y20-H
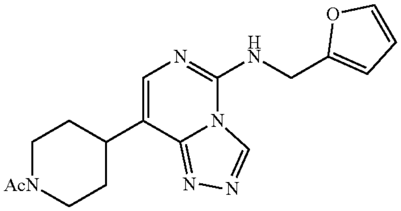
E-Y13-H
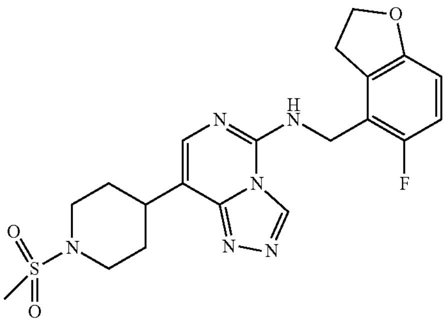
SL-ZYE-34
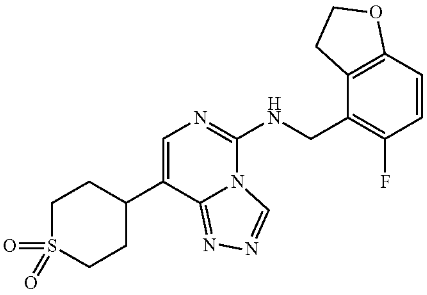

-continued
SL-ZYE-23
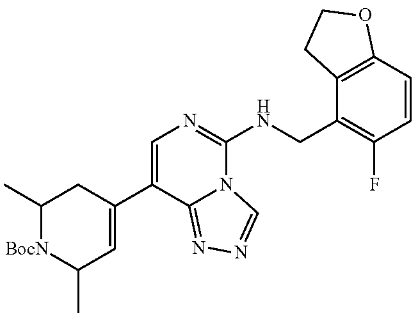
SL-ZYE-24
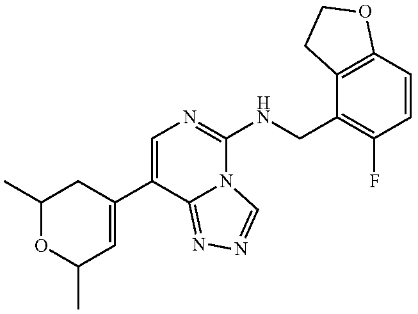
SL-ZYE-28
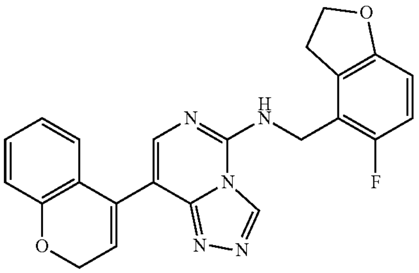
E-Y54-H
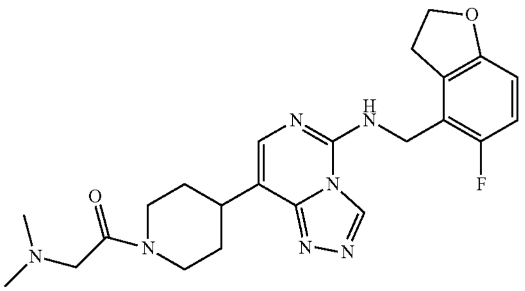
SL-E1
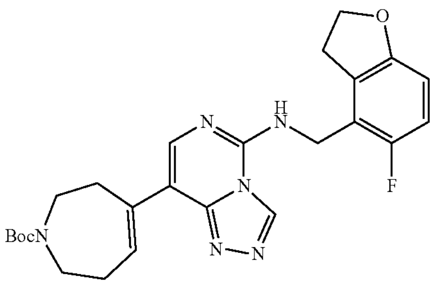
-continued
SL-E2
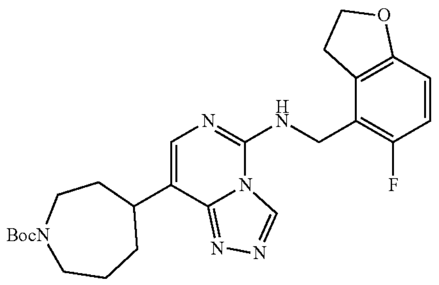
SL-E3
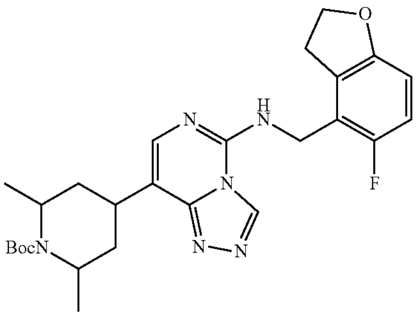
SL-E4
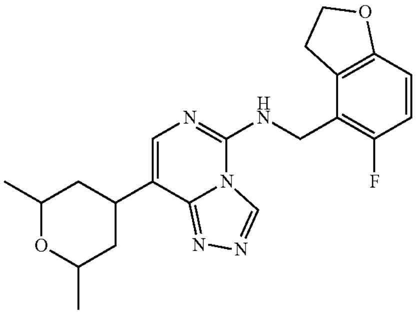
SL-E5
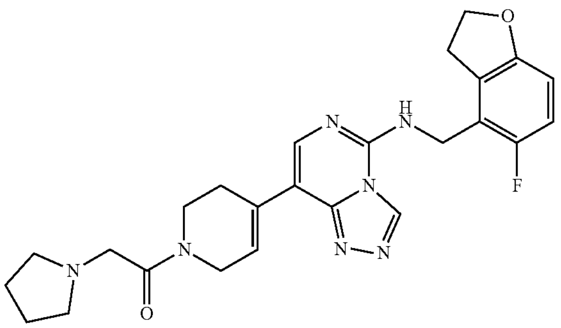
SL-E6
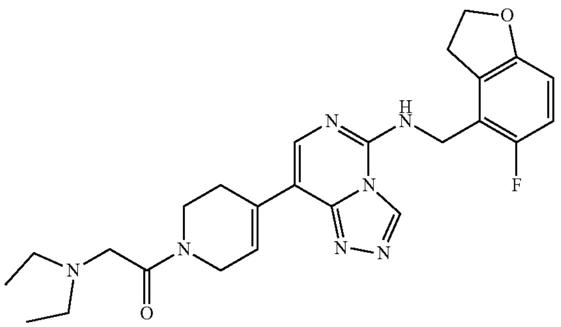

-continued
SL-E7
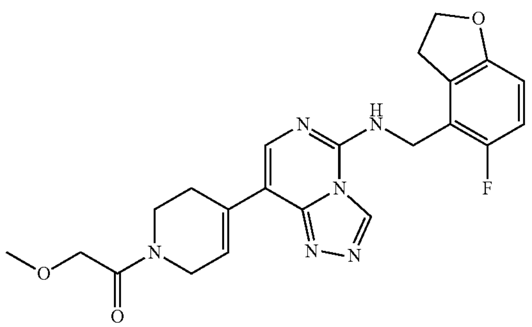
SL-E8
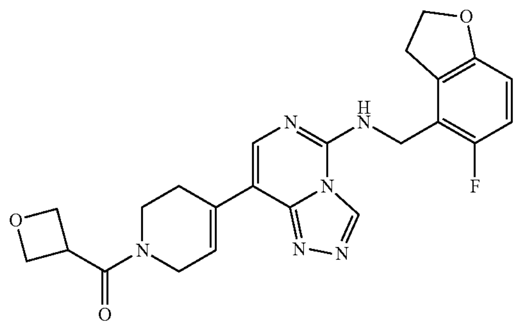
SL-E9
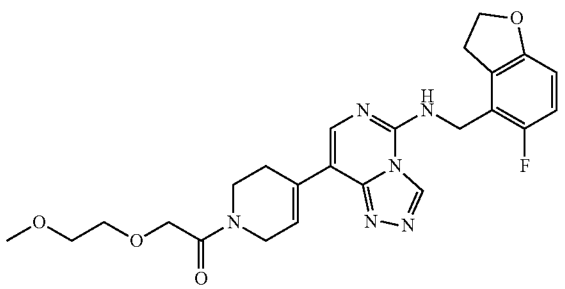
SL-E10
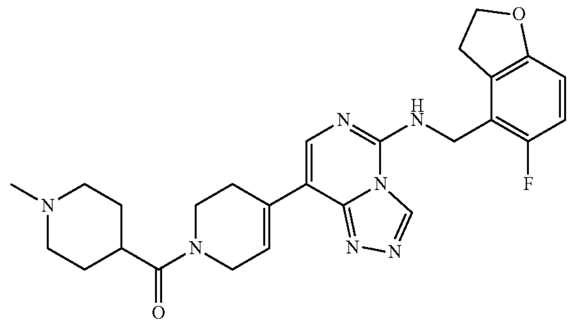
SL-E11
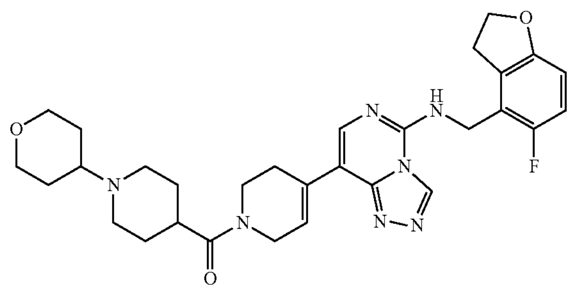
-continued
SL-E12
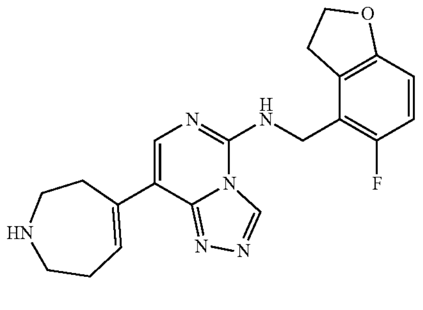
SL-E13
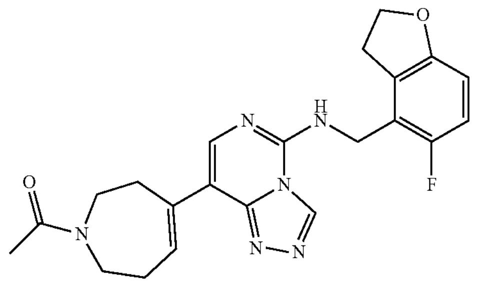
SL-E14
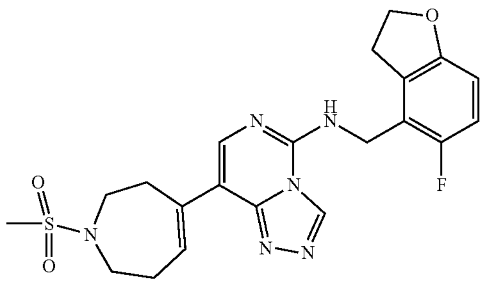
SL-E15
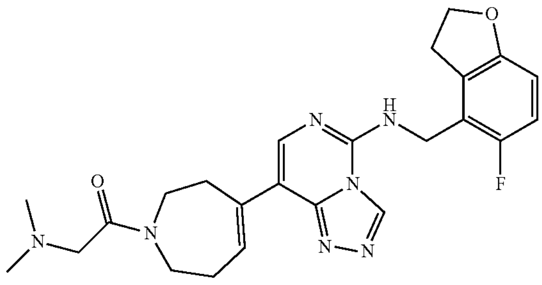
SL-E16
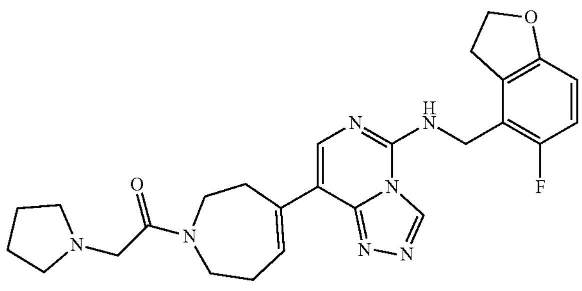

-continued
SL-E17
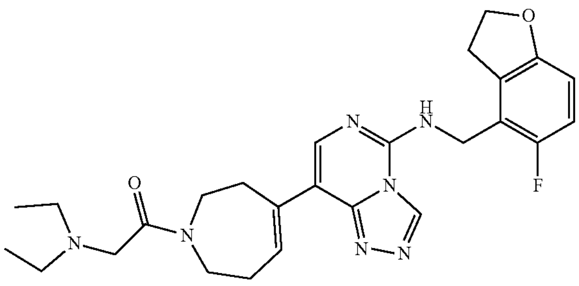
SL-E18
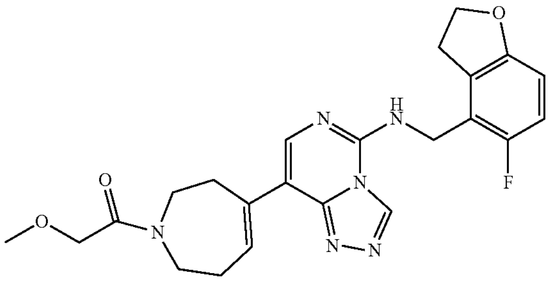
SL-E19
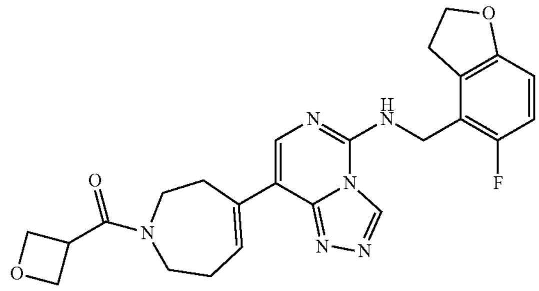
SL-E20
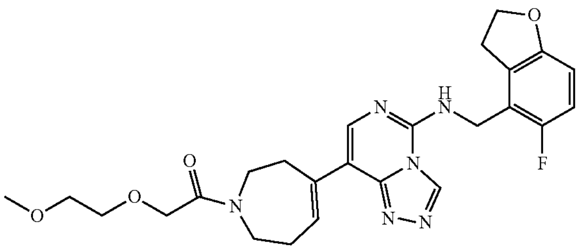
SL-E21
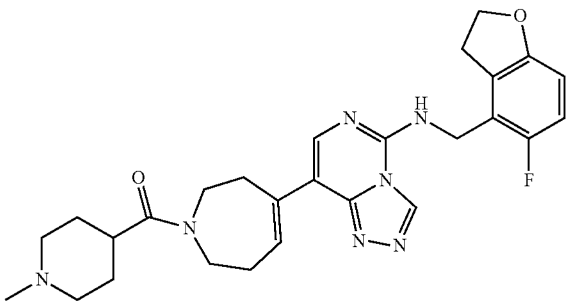
-continued
SL-E22
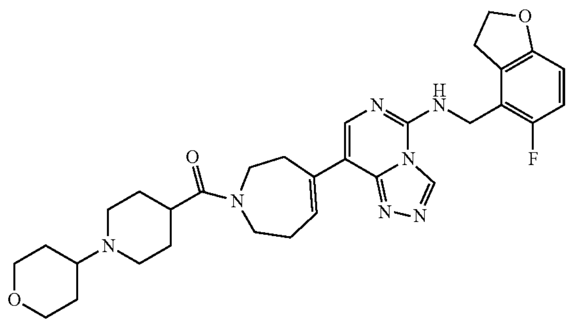
SL-E23
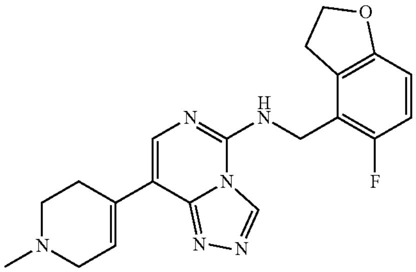
SL-E24
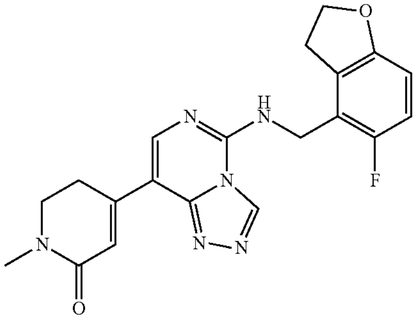
SL-E25
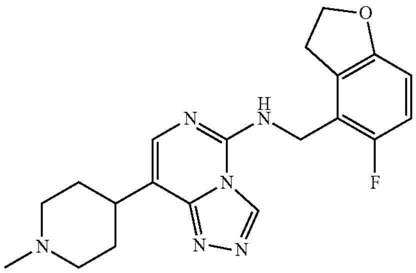
SL-E26
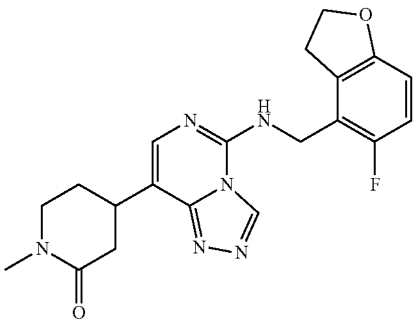

-continued
SL-E29
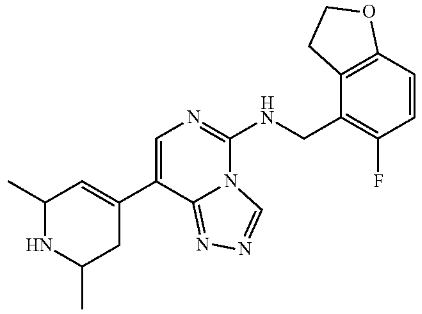
SL-E30
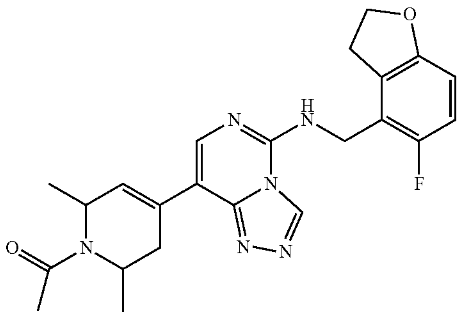
SL-E31
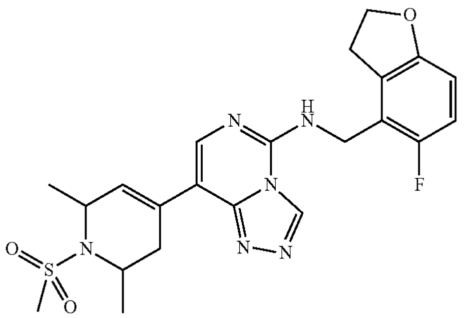
SL-E32
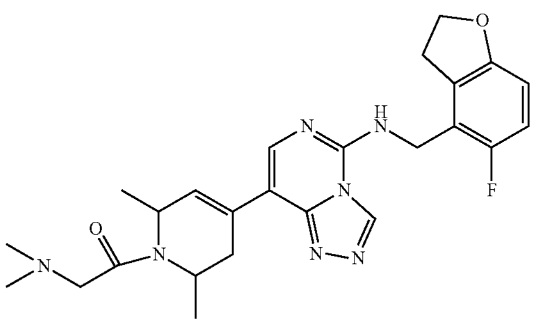
-continued
SL-E33
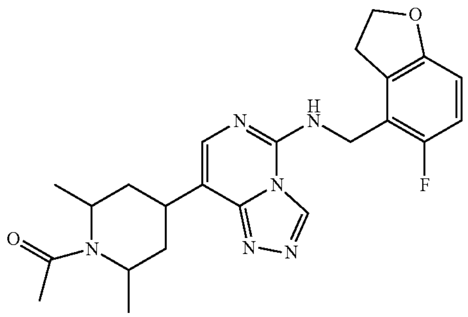
SL-E34
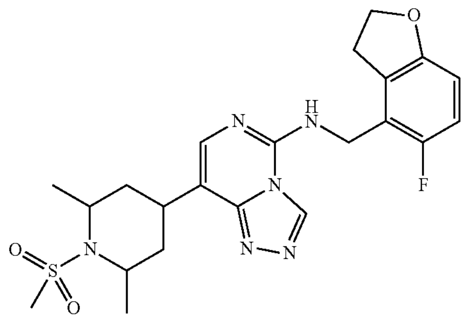
SL-E35
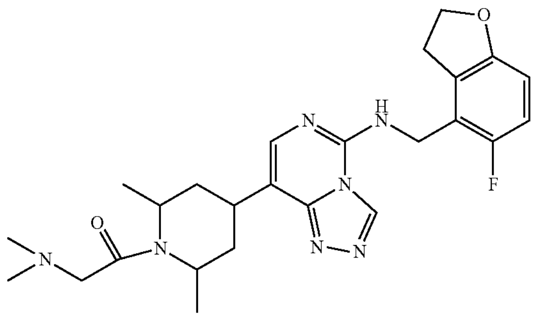
SL-E36
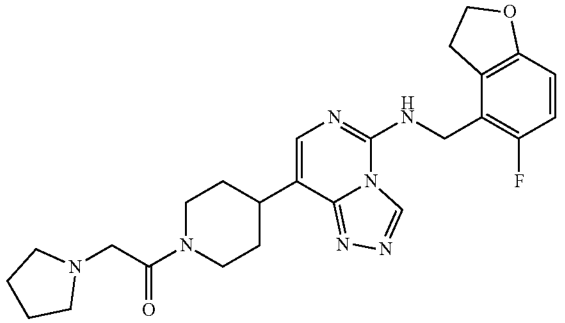

-continued
SL-E37
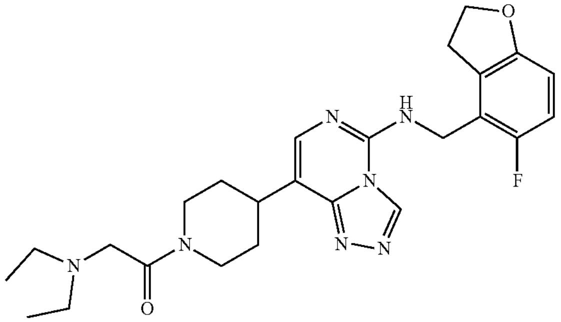
SL-E38
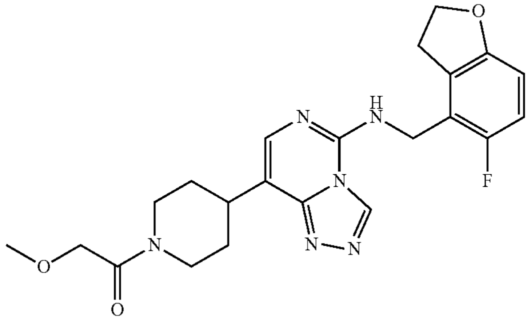
SL-E39
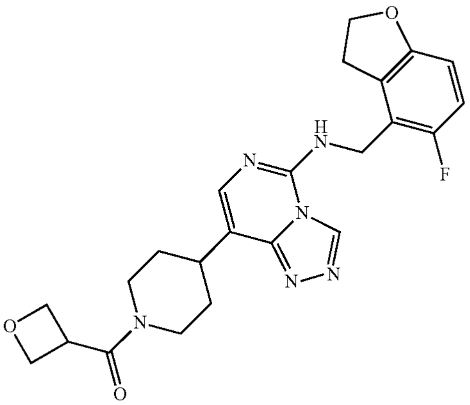
SL-E40
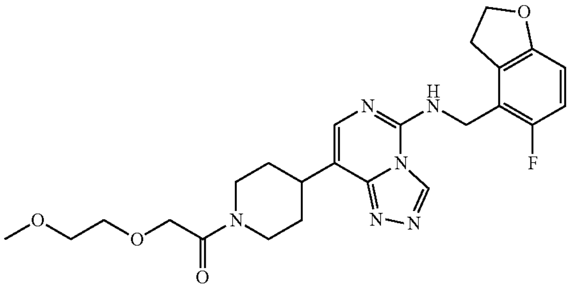
-continued
SL-E41
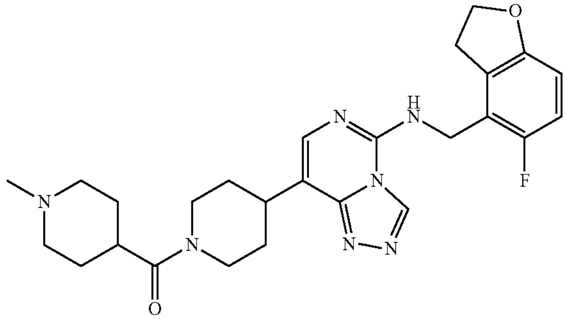
SL-E42
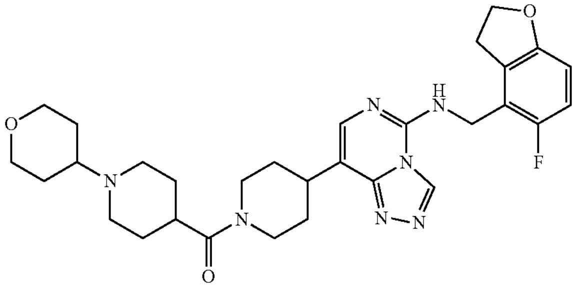
SL-E43
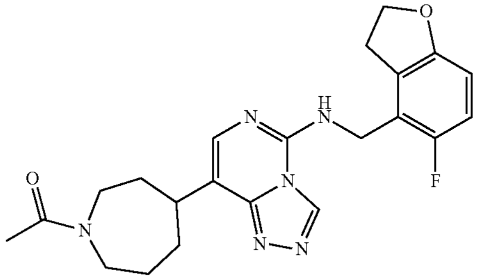
SL-E44
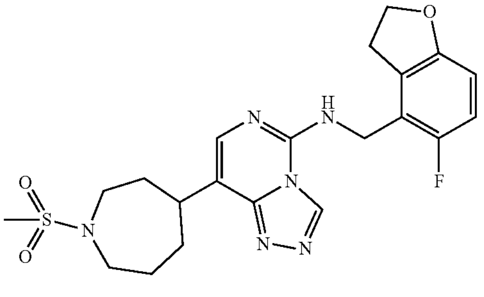
SL-E45
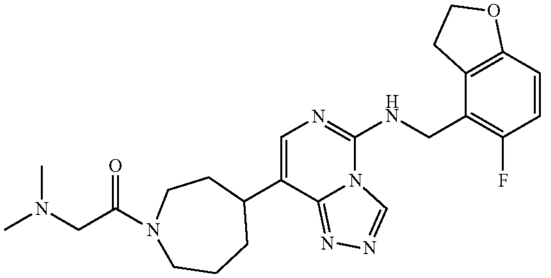

-continued
SL-E46
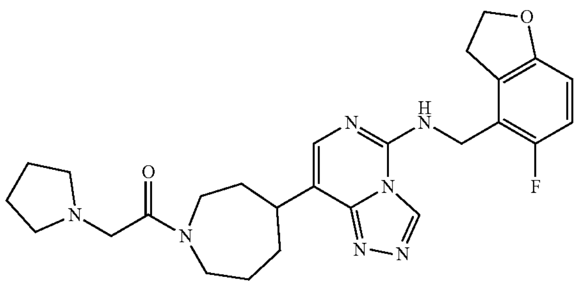
SL-E47
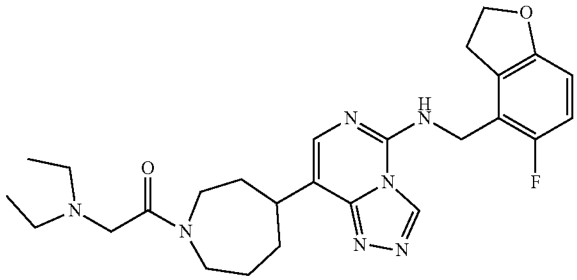
SL-E48
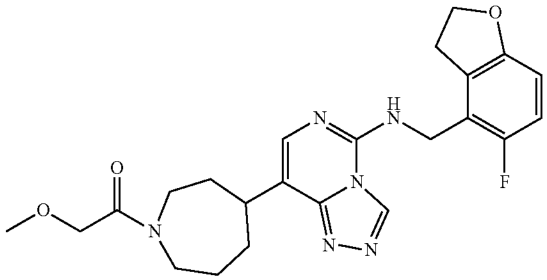
SL-E49
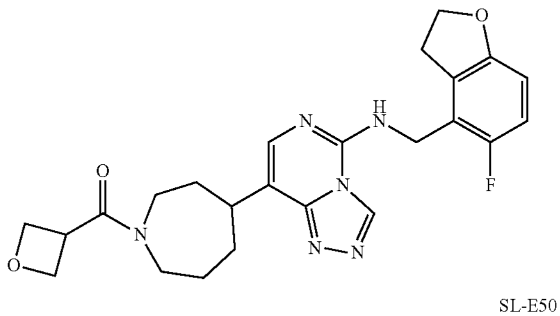
SL-E50
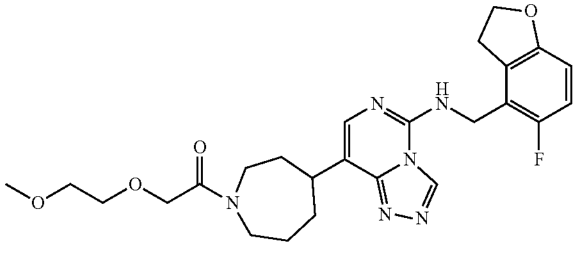
-continued
SL-E51
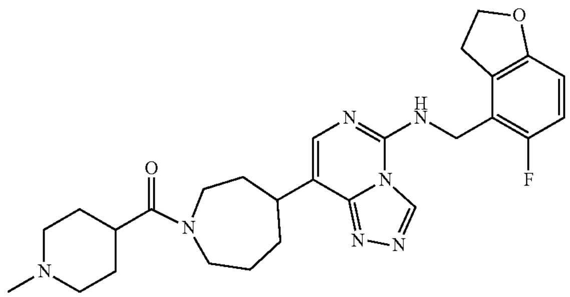
SL-E52
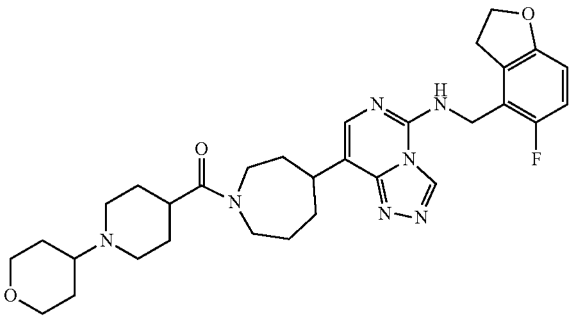
SL-E53
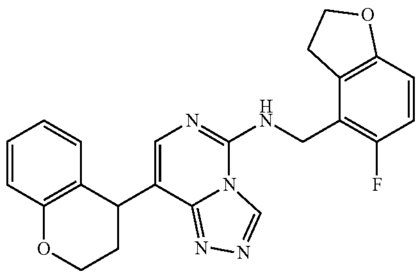
E-Y2-H
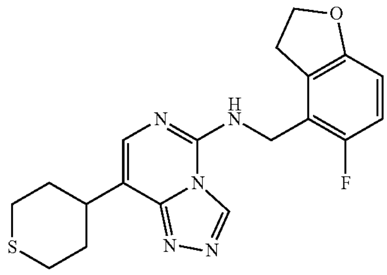
SL-ZYE-08-S
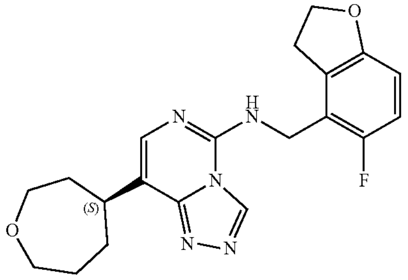

-continued
SL-ZYE-08-R
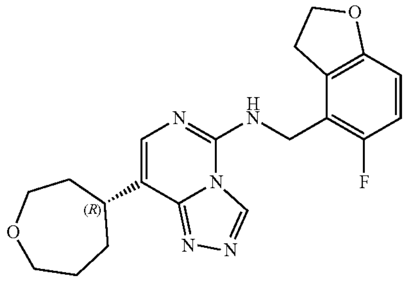
SL-E43-S
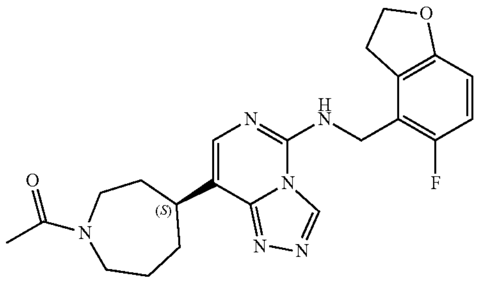
SL-E43-R
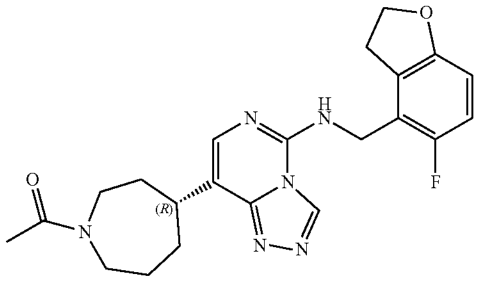
SL-E44-S
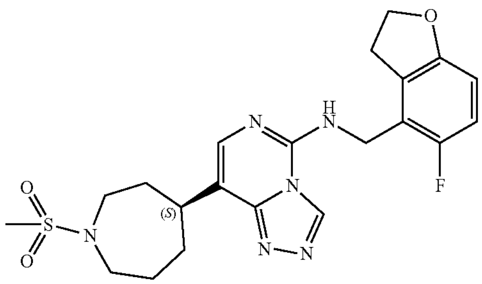
SL-E44-R
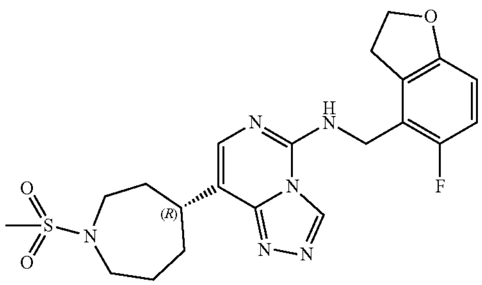
-continued
SL-E45-S
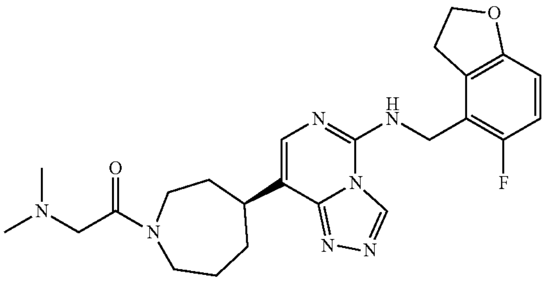
SL-E45-R
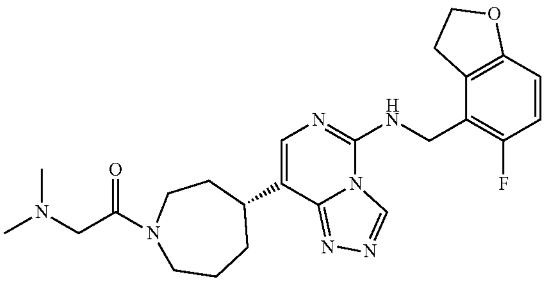
SL-E46-S
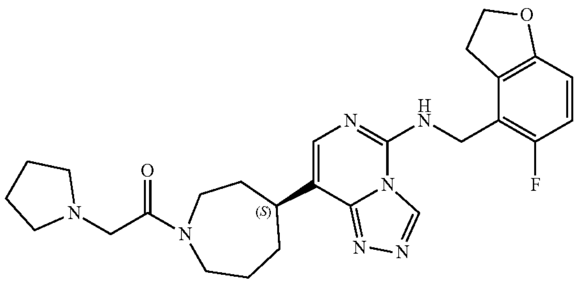
SL-E46-R
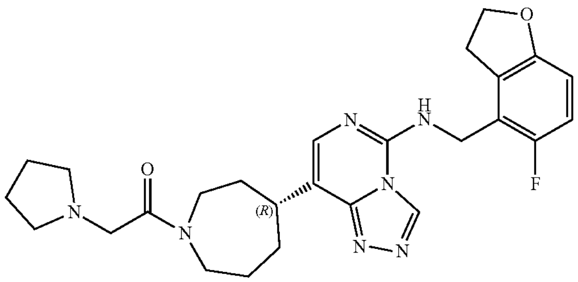
SL-E47-S
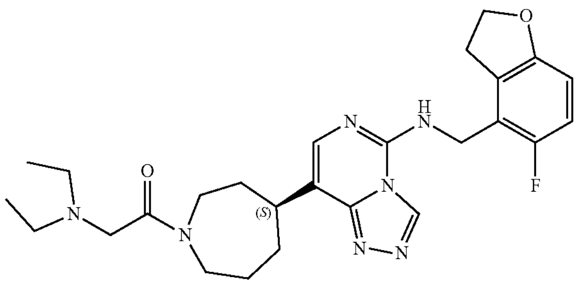

-continued
SL-E47-R
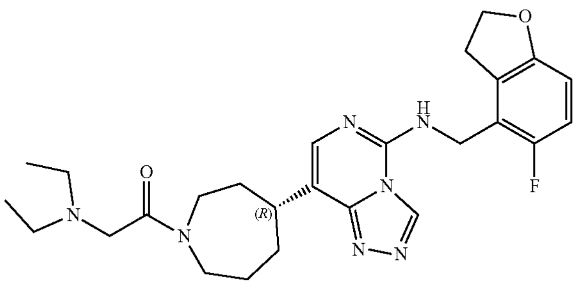
SL-E48-S
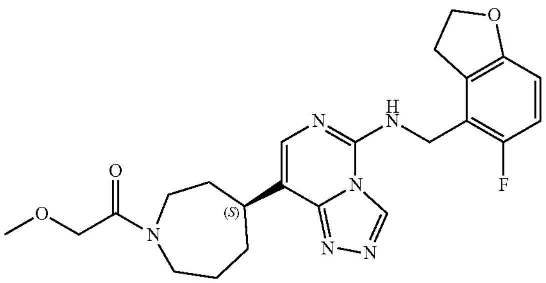
SL-E48-R
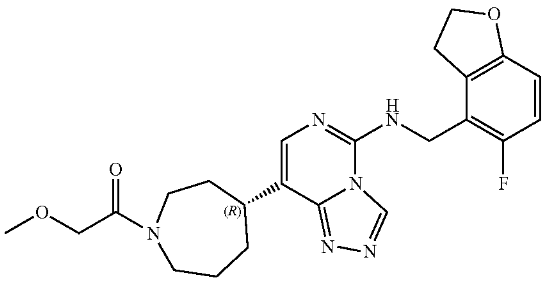
SL-E49-S
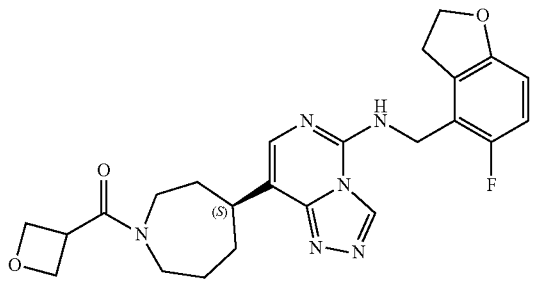
SL-E49-R
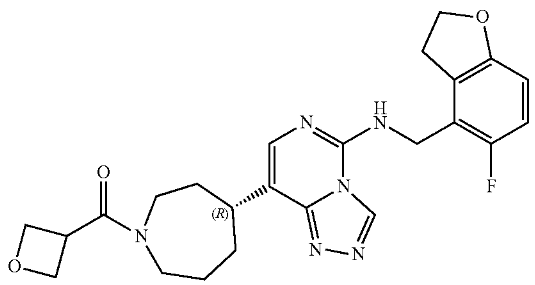
-continued
SL-E50-S
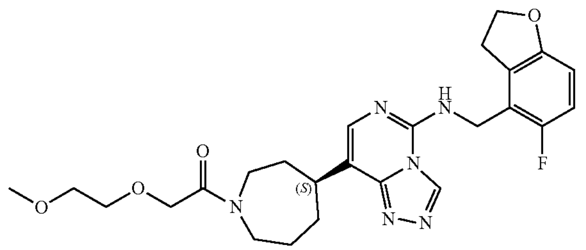
SL-E50-R
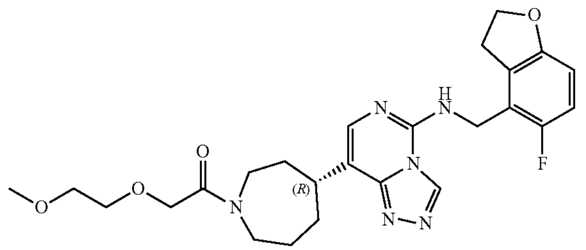
SL-E51-S
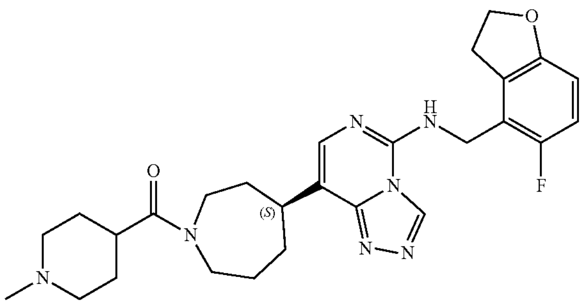
SL-E51-R
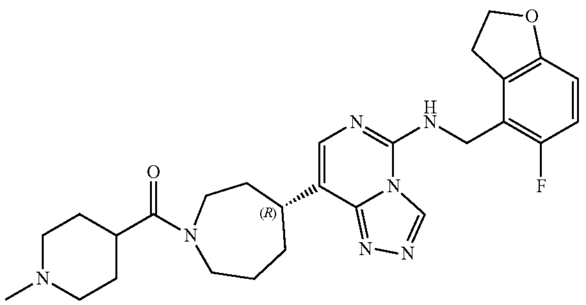
SL-E52-S
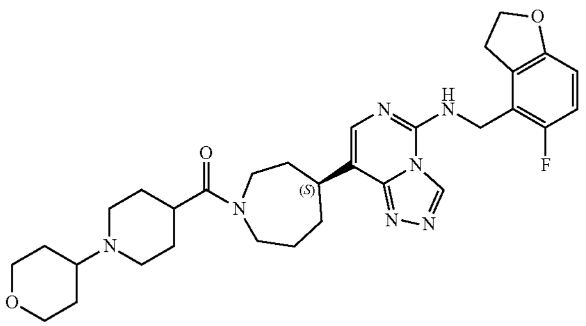

-continued
SL-E52-R
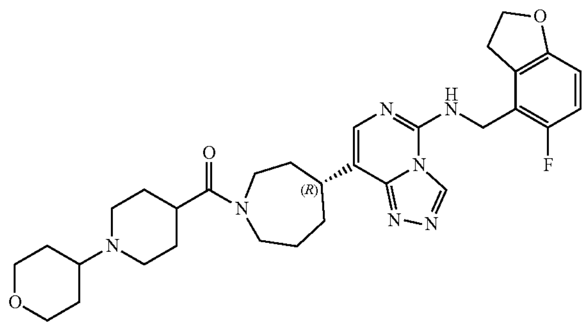
SL-E2-S
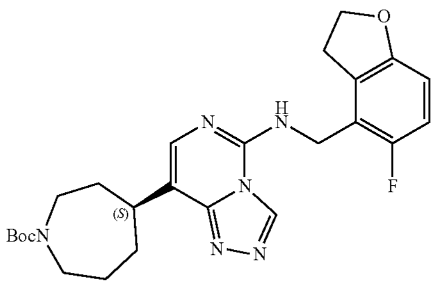
SL-E2-R
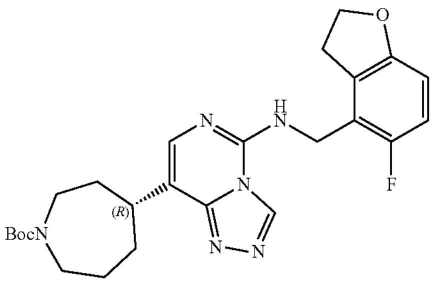
SL-ZYE-120
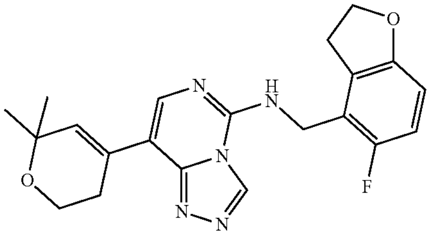
SL-ZYE-119
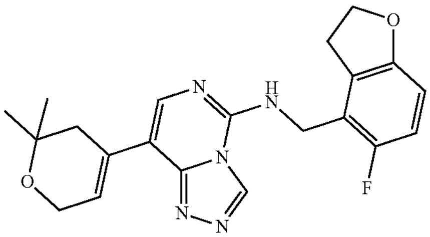
-continued
SL-ZYE-144
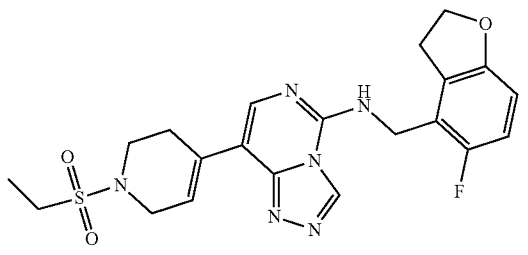
SL-ZYE-146
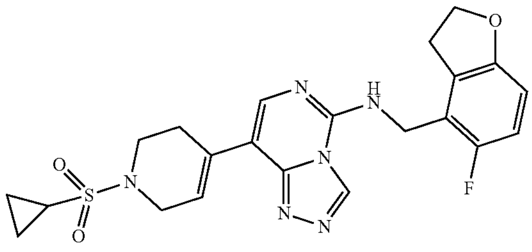
SL-ZYE-147
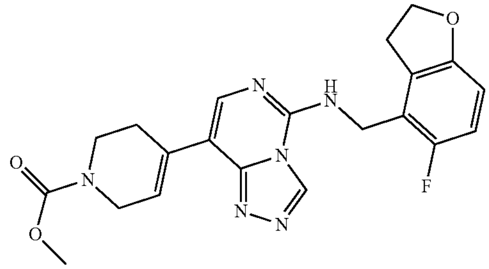
SL-ZYE-148
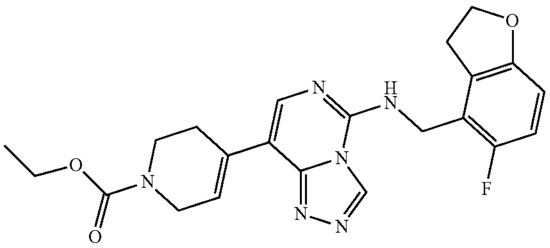
SL-ZYE-161
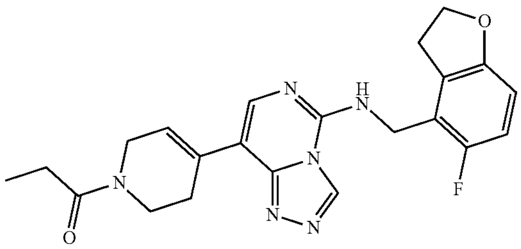

-continued

SL-ZYE-162

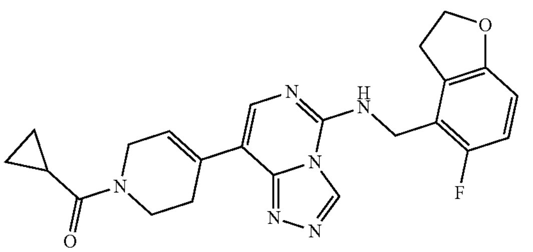

SL-ZYE-145

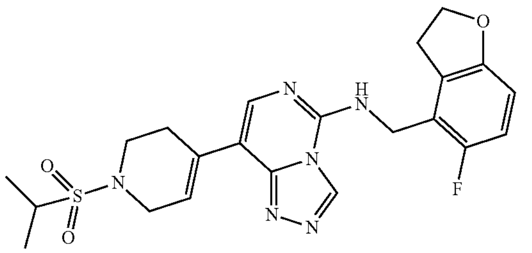

SL-ZYE-121

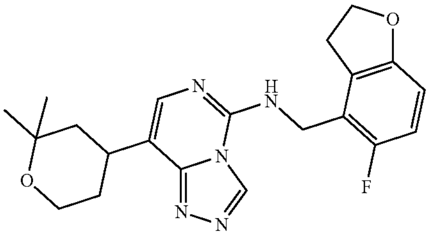

SL-ZYE-183

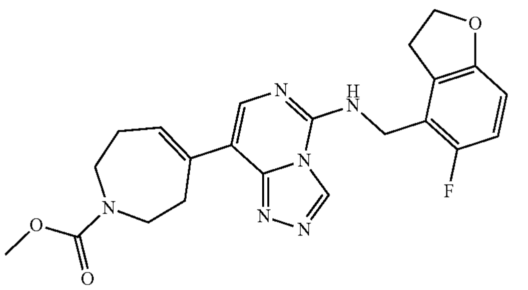

SL-ZYE-195

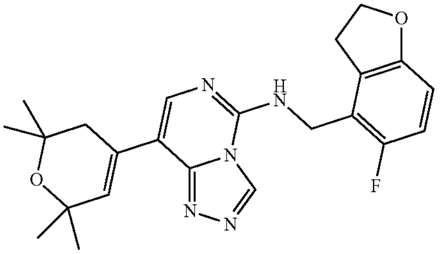

SL-ZYE-196

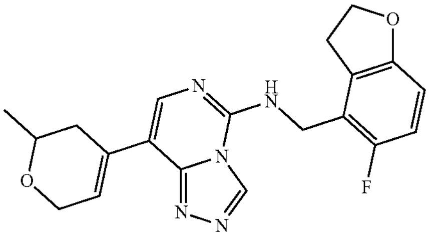

-continued

SL-ZYE-197

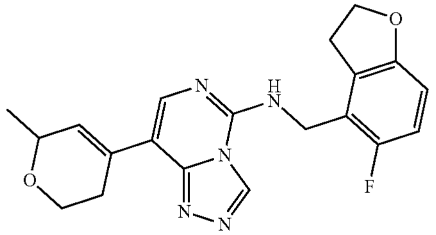

Preferably, the compound also includes the stereoisomers, tautomers, atropisomers, isotopically labeled compounds (including deuterium substitution), medically acceptable salts, polymorphs, solvates thereof, which can be used to treat diseases or conditions mediated by EED and/or PRC2.

According to another aspect of the invention, methods and intermediates for preparing the compounds of the invention are provided.

Wherein, the method comprises the following steps:

Scheme 1

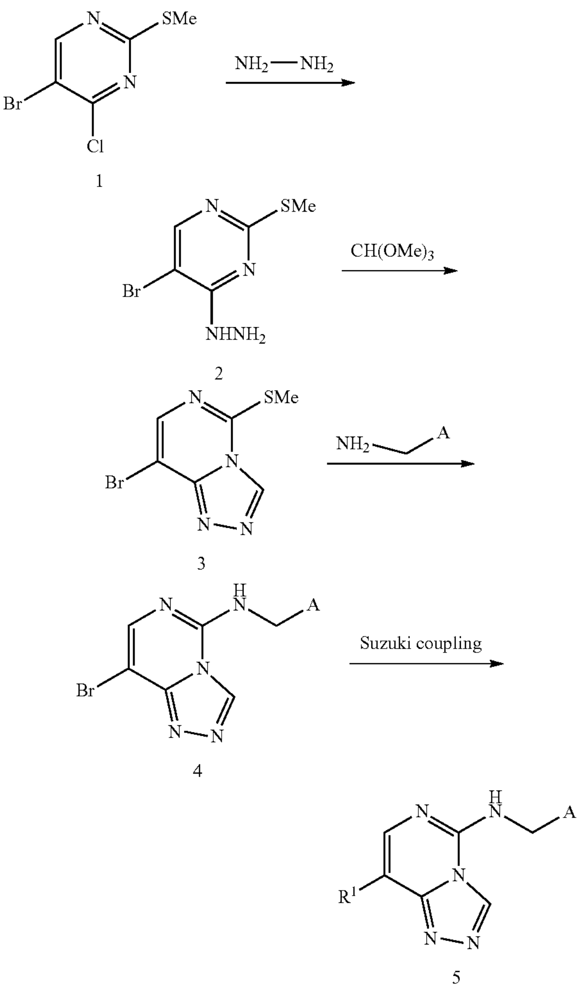

(1a) treating 5-bromo-4-chloro-2-(methylthio) pyrimidine 1 with hydrated hydrazine to produce 5-bromo-4-hydrazinyl-2-(methylthio) pyrimidine 2, (1b) converting 5-bromo-4-hydrazinyl-2-(methylthio) pyrimidine 2 with trimethyl orthoformate to triazole product 3, (1c) conducting a substitution reaction of triazole product 3 with an amine $NH_2CH_2A$ to produce compound 4, (1d) conducting a suzuki coupling reaction of compound 4 with various of boric acid having $R^1$ group or its equivalent under the action of palladium catalyst to obtain product 5.

wherein, the definitions of A, $R^1$ are the same as defined above.

Scheme 2

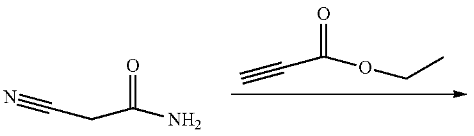

6

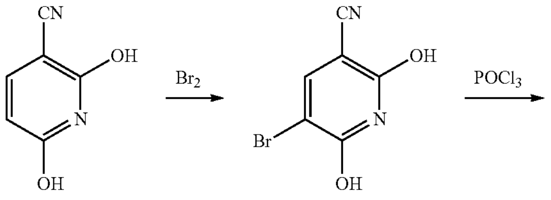

7 8

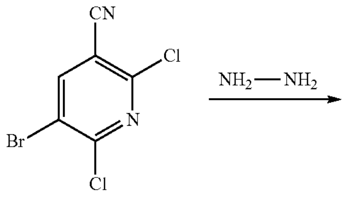

9

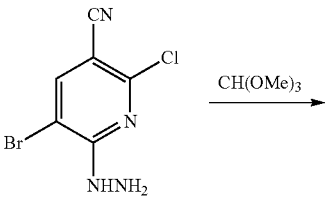

10

-continued

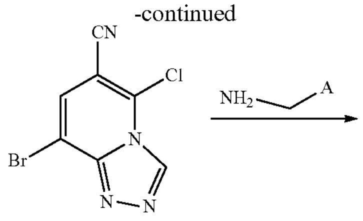

11

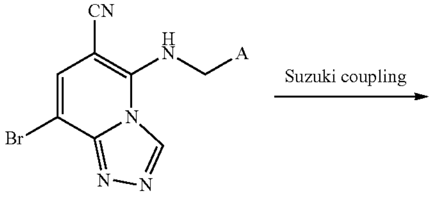

12

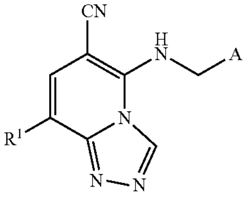

13

(2a) reacting the cyanoethyl amide 6 with ethyl propiolate to produce intermediate 7, (2b) treating intermediate 7 with bromine to conduct a bromation reaction to obtain bromide 8, (2c) reacting bromide 8 with phosphorus oxychloride to obtain intermediate 9, (2d) treating intermediate 9 with hydrated hydrazine to produce intermediate 10, (2e) converting intermediate 10 with trimethyl orthoformate to triazole intermediate 11, (2f) conducting a substitution reaction of triazole intermediate 11 with various amines to produce compound 12, (2g) conducting a suzuki coupling reaction of compound 12 with various of boric acid having $R^1$ group or its equivalent under the action of palladium catalyst to obtain product 13.

wherein, the definitions of A, $R^1$ are the same as defined above.

The amines described in Scheme 1 and Scheme 2 can be prepared according to the patent US2016/0176682A1 (such as the preparation of A1 in the following reaction formula), or can be purchased from a reagent company (the following reaction formula, furfurylamine A2, purchased from Bellingway Technology Co., Ltd.), the boric acid or its equivalent B may be purchased from a reagent company or may be prepared according to conventional literature.

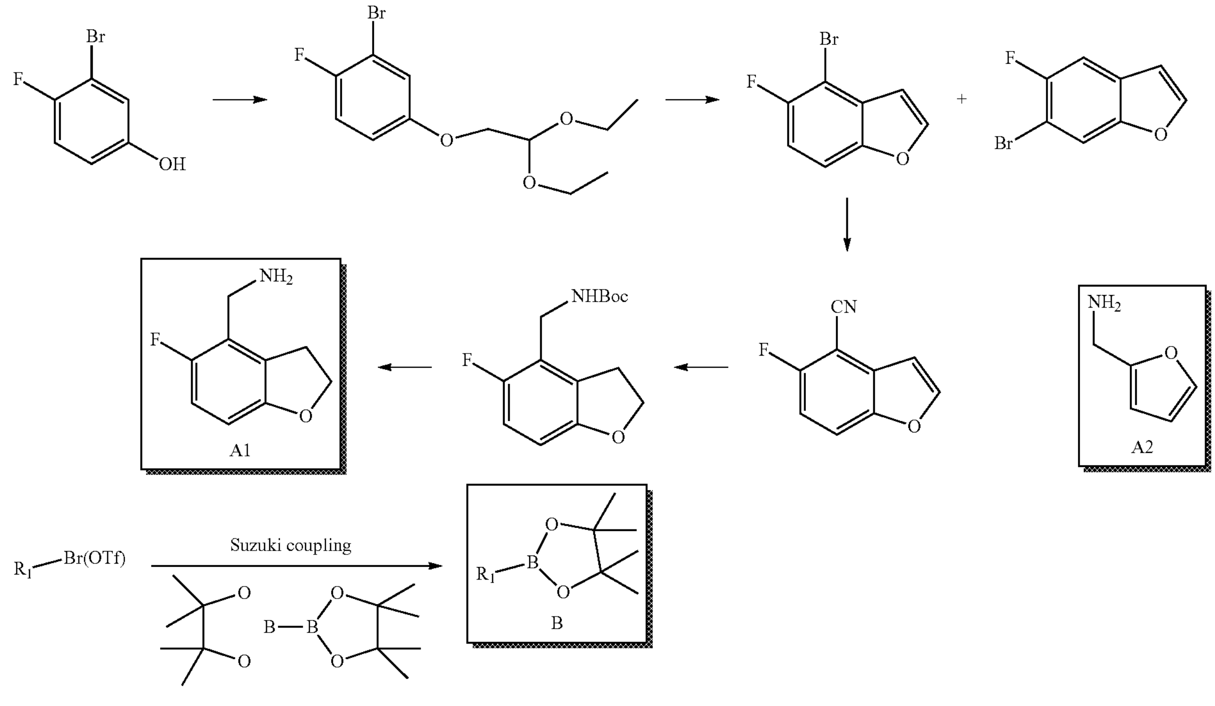

A1

A2

B

Scheme 3

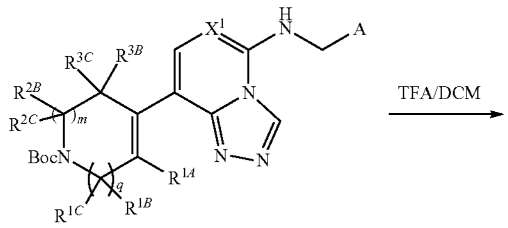

14

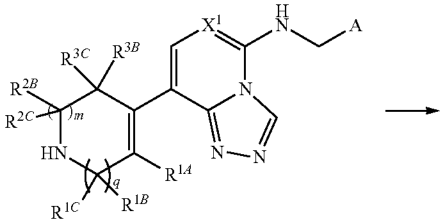

15

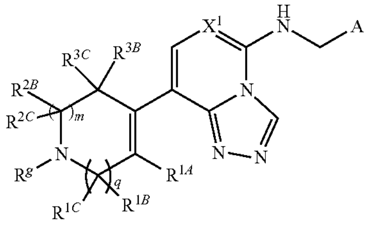

16

(3a) removing the Boc protecting group in 14 using dichloromethane as a solvent and under the action of trifluoroacetic acid to obtain an amine compound 15, (3b) reacting the amine compound 15 with a reagent or compound having $R^g$ under basic conditions to give a compound 16, the agent or compound is, for example, but not limited to acid anhydrides, sulfonic anhydride, isocyanate, thioisocyanate, acyl chloride, sulfonyl chloride, carbonate, chloroformate, urethane, etc., the base is, for example, but not limited to, triethylamine, diisopropylethylamine, DMAP, potassium carbonate, sodium hydroxide, potassium hydroxide, potassium tert-butoxide, NaH, the organic solvents is, for example, but not limited to, methylene chloride, tetrahydrofuran, acetonitrile, 1,4-dioxanene, wherein, the definitions of A, $X^1$, $R^8$, $R^{1A}$, $R^{1B}$, $R^{1C}$, $R^{2B}$, $R^{2C}$, $R^{3B}$, $R^{3C}$, q, m are the same as defined above.

Scheme 4

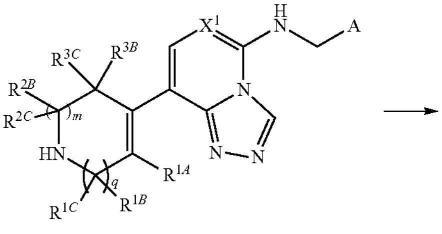

15

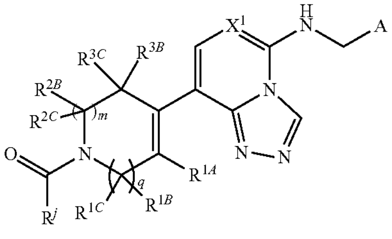

17

(4a) conducting a condensation reaction of product 15 obtained by removing the protective group in step (3a) of Scheme 3 with a carboxylic acid having an $R^j$ group under the action of a condensing agent to obtain an amide compound 17, the condensing agent is, for example, but not limited to carbonyldiimidazole, dicyclohexylcarbodiimide, diisopropylcarbodiimide, 1-(-3-dimethylaminopropyl)-3-ethylcarbodiimide, 1-hydroxybenzotriazole, 2-(7-azabenzotriazole)-N,N,N',N'-tetramethylurea hexafluorophosphate, benzotriazole-N,N,N',N'-tetramethylurea hexafluorophosphate, 6-chlorobenzotriazole-1,1,3,3-tetramethylurea hexafluorophosphate, o-benzotriazole-N,N,N',N'-tetramethylurea tetrafluoroborate, 6-chlorobenzotriazole-1,1,3,3-tetramethylurea tetrafluoroborate, 2-succinimidyl-1,1,3,3-tetramethylurea tetrafluoroborate and 2-(5-norbornene-2,3-dicarboximido)-1,1,3,3-tetramethylurea quaternary ammonium tetrafluoroborate, the condensation reaction can be performed in an organic solvent in the presence of a base, the base is, for example, but not limited to, triethylamine, diisopropylethylamine, 1,5-diazabicyclo[5.4.0]undec-5-ene, the organic solvent is, for example, but not limited to dichloromethane, chloroform, N,N-dimethylformamide, tetrahydrofuran, wherein, the definitions of A, $X^1$, $R^j$, $R^{1A}$, $R^{1B}$, $R^{1C}$, $R^{2B}$, $R^{2C}$, $R^{3B}$, $R^{3C}$, q, m are the same as defined above.

Scheme 5

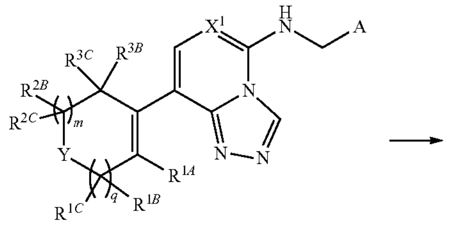

18

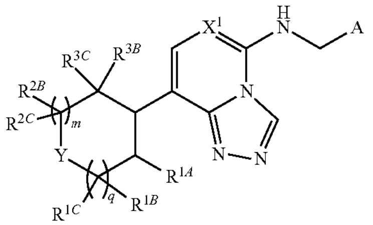

19

(5a) dissolving 18 in a solvent, the solvent is, for example, but not limited to, methanol, ethanol, ethyl acetate, and tetrahydrofuran, adding a metal catalyst, the metal catalyst is, for example, but not limited to 10% palladium carbon. $Pd(OH)_2$, Raney nickel, $RhCl(PPh_3)_3$, introducing hydrogen gas, and reacting at room temperature to obtain compound 19 with double bond reduction.

wherein, the definitions of A, $X^1$, Y, $R^{1A}$, $R^{1B}$, $R^{1C}$, $R^{2B}$, $R^{2C}$, $R^{3B}$, $R^{3C}$, q, m are the same as defined above.

Scheme 6

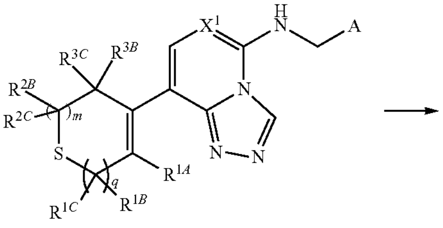

20

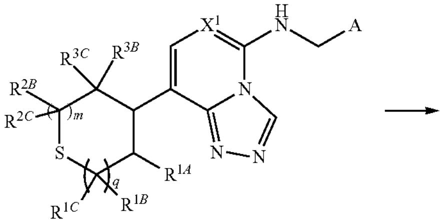

21

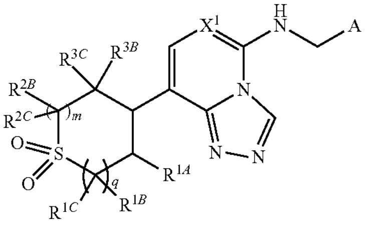

22

(6a) obtaining the compound 21 by reduction reaction of 20, and then conducting an oxidation reaction with mCPBA (m-chloroperoxybenzoic acid) or hydrogen peroxide to obtain compound 22.

wherein, the definitions of A, $X^1$, $R^{1A}$, $R^{1B}$, $R^{1C}$, $R^{2B}$, $R^{2C}$, $R^{3B}$, $R^{3C}$, q, m are the same as defined above.

Scheme 7

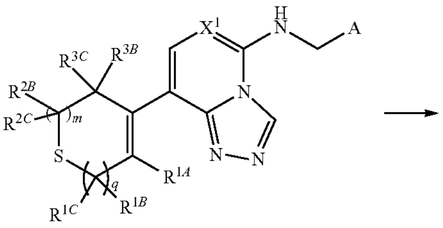

20

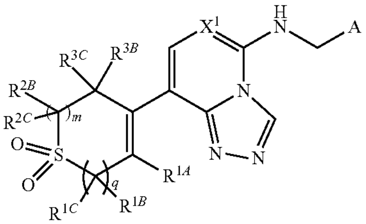

23

(7a) conducting an oxidation reaction of 20 with mCPBA or hydrogen peroxide to obtain compound 23.

wherein, the definitions of A, $X^1$, $R^{1A}$, $R^{1B}$, $R^{1C}$, $R^{2B}$, $R^{2C}$, $R^{3B}$, $R^{3C}$, q, m are the same as defined above.

Scheme 8

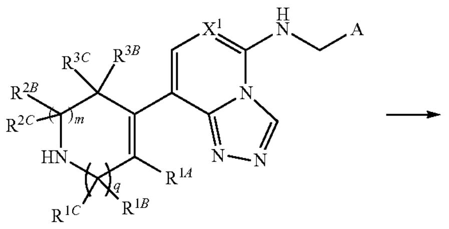

15

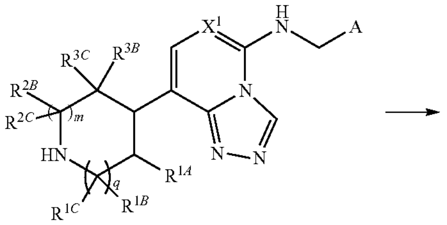

24

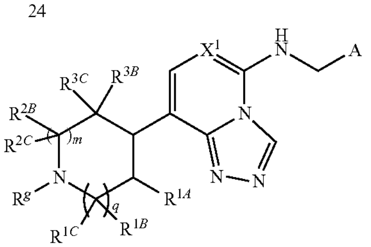

25

Reducing (for example, but not limited to, under the conditions of hydrogenation reduction) the double bond of 15 to obtain 24, and then reacting with a reagent or compound having an $R^9$ group in the presence of a base to obtain 25, said reagent or compound is, for example, but not limited to acid anhydrides, sulfonic anhydride, isocyanate, thioisocyanate, acyl chloride, sulfonyl chloride, carbonate, chloroformate, urethane, the base is, for example, but not limited to, triethylamine, diisopropylethylamine. DMAP, potassium carbonate, sodium hydroxide, potassium hydroxide, potassium tert-butoxide, NaH, the reaction can be performed in an organic solvent is, for example, but not limited to, methylene chloride, tetrahydrofuran, acetonitrile, 1,4-dioxane; or conducting a condensation reaction of 24 with various carboxylic acids in the presence of a condensing agent to obtain an amide compound 25, the condensing agent is, for example, but not limited to carbonyldiimidazole, dicyclohexylcarbodiimide, diisopropylcarbodiimide, 1-(-3-dimethylaminopropyl)-3-ethylcarbodiimide, 1-hydroxybenzotriazole, 2-(7-azabenzotriazole)-N,N,N',N'-tetramethylurea hexafluorophosphate, benzotriazole-N,N,N',N'-tetramethylurea hexafluorophosphate, 6-chlorobenzotriazole-1,1,3,3-tetramethylurea hexafluorophosphate, o-benzotriazole-N,N,N',N'-tetramethylurea tetrafluoroborate, 6-chlorobenzotriazole-1,1,3,3-tetramethylurea tetrafluoroborate, 2-succinimidyl-1,1,3,3-tetramethylurea tetrafluoroborate and 2-(5-norbornene-2,3-dicarboximido)-1,1,3,3-tetramethylurea quaternary ammonium tetrafluoroborate, the condensation reaction can be performed in an organic solvent in the presence of a base, the base is triethylamine, diisopropylethylamine, 1,5-diazabicyclo[5.4.0]undec-5-ene, the organic solvent is dichloromethane, chloroform, N,N-dimethylformamide, tetrahydrofuran, wherein, the definitions of A, $X^1$, $R^{1A}$, $R^{1B}$, $R^{1C}$, $R^{2B}$, $R^{2C}$, $R^{3B}$, $R^{3C}$, q, m are the same as defined above.

Preferably, the method comprises the following steps:

Scheme 1

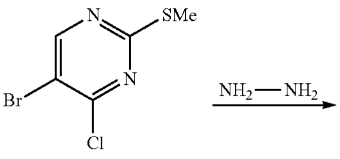

1

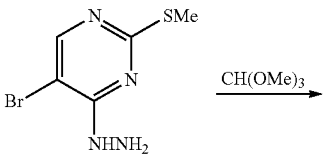

2

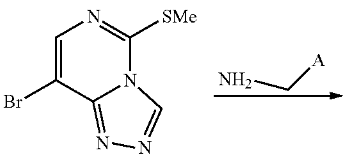

3

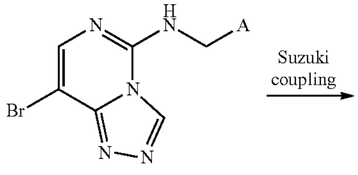

4

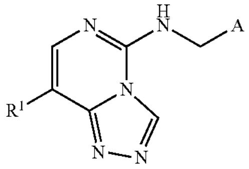

5

(1a) treating 5-bromo-4-chloro-2-(methylthio) pyrimidine 1 with hydrated hydrazine to produce 5-bromo-4-hydrazinyl-2-(methylthio) pyrimidine 2, (1b) converting 5-bromo-4-hydrazinyl-2-(methylthio) pyrimidine 2 with trimethyl orthoformate to triazole product 3, (1c) conducting a substitution reaction of triazole product 3 with an amine $NH_2CH_2A$ to produce compound 4, (1d) conducting a suzuki coupling reaction of compound 4 with various of boric acid having $R^1$ group or its equivalent under the action of palladium catalyst to obtain product 5.

wherein, the definitions of A, $R^1$ are the same as defined above;

Scheme 2

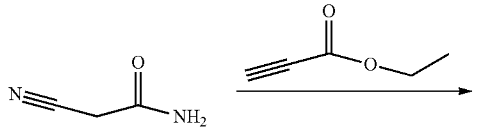

6

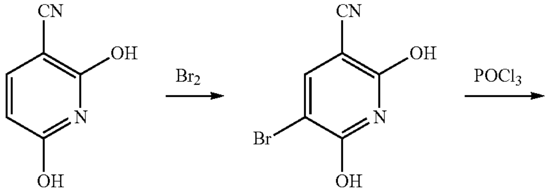

7 8

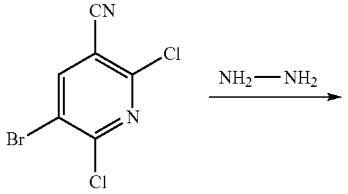

9

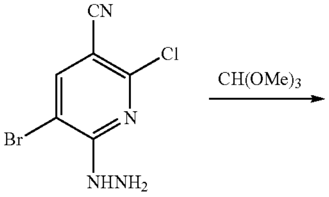

10

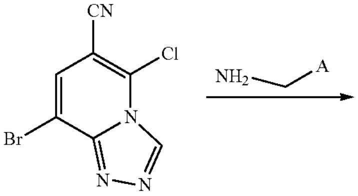

11

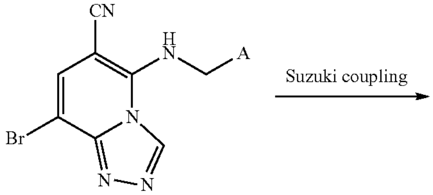

12

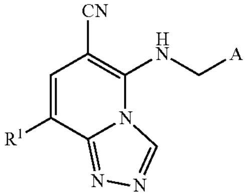

13

(2a) reacting the cyanoethyl amide 6 with ethyl propiolate to produce intermediate 7, (2b) treating intermediate 7 with bromine to conduct a bromation reaction to obtain bromide 8, (2c) reacting bromide 8 with phosphorus oxychloride to obtain intermediate 9, (2d) treating intermediate 9 with hydrated hydrazine to produce intermediate 10, (2e) converting intermediate 10 with trimethyl orthoformate to triazole product 11, (2f) conducting a substitution reaction of triazole product 11 with various amines to produce compound 12, (2g) conducting a suzuki coupling reaction of compound 12 with various of boric acid having $R^1$ group or its equivalent under the action of palladium catalyst to obtain product 13, wherein, the definitions of A, $R^1$ are the same as defined above;

Scheme 3

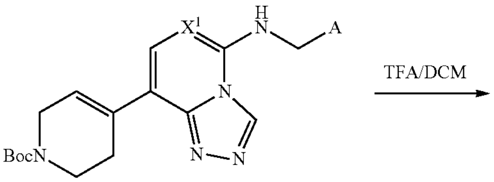

14'

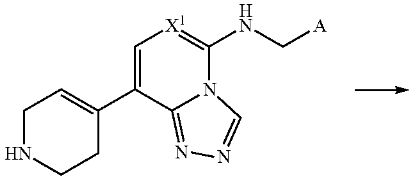

15'

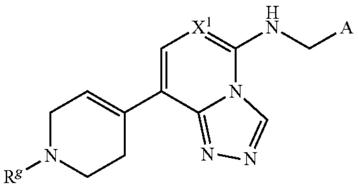

16'

(3a) removing the Boc protecting group in 14' using dichloromethane as a solvent and under the action of trifluoroacetic acid to obtain an amine compound 15'.

(3b) further reacting the amine compound 15' with an acid anhydride, a sulfonic anhydride, an isocyanate, and a thioisocyanate with an $R^9$ group under basic conditions to obtain a compound 16', the base is triethylamine, diisopropylethylamine, the reaction may be performed in an organic solvent, the organic solvent is dichloromethane, tetrahydrofuran, acetonitrile, 1,4-dioxane, wherein, the definitions of A, $X^1$, $R^g$ are the same as defined above:

Scheme 4

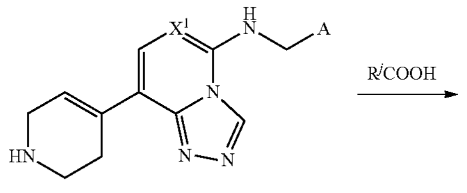

15'

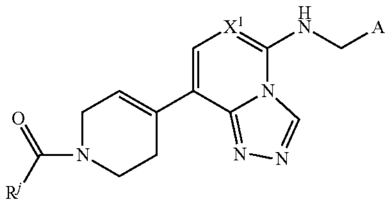

17'

(4a) conducting a condensation reaction of product 15' obtained by removing the protective group in step (3b) of Scheme 3 with a carboxylic acid having an $R^j$ group under the action of a condensing agent to obtain an amide compound 17', the condensing agent is selected from carbonyldiimidazole, dicyclohexylcarbodiimide, diisopropylcarbodiimide, 1-(-3-dimethylaminopropyl)-3-ethylcarbodiimide, 1-hydroxybenzotriazole, 2-(7-azabenzotriazole)-N,N,N',N'-tetramethylurea hexafluorophosphate, benzotriazole-N,N,N',N'-tetramethylurea hexafluorophosphate, 6-chlorobenzotriazole-1,1,3,3-tetramethylurea hexafluorophosphate, o-benzotriazole-N,N,N',N'-tetramethylurea tetrafluoroborate, 6-chlorobenzotriazole-1,1,3,3-tetramethylurea tetrafluoroborate, 2-succinimidyl-1,1,3,3-tetramethylurea tetrafluoroborate and 2-(5-norbornene-2,3-dicarboximido)-1,1,3,3-tetramethylurea quaternary ammonium tetrafluoroborate, the condensation reaction can be performed in an organic solvent in the presence of a base, the base is triethylamine, diisopropylethylamine, 1,5-diazabicyclo[5.4.0]undec-5-ene, the organic solvent is dichloromethane, chloroform, N,N-dimethylformamide, tetrahydrofuran, wherein, the definitions of A, $X^1$, $R^j$ are the same as defined above;

Scheme 5

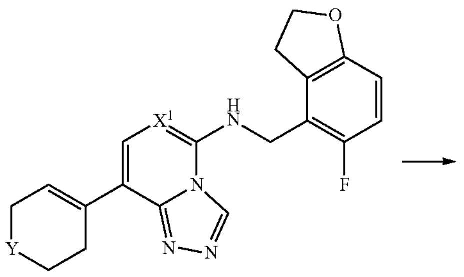

18'

-continued

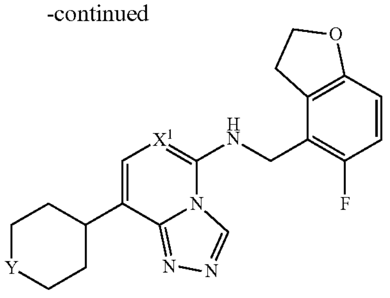

19'

(5a) using methanol as a solvent, and catalyzed by 10% palladium on carbon, introducing hydrogen gas, reacting 18' at room temperature for 6 hours to obtain a compound 19' with the double bond reduced.

wherein, the definitions of $X^1$, Y are the same as defined above. The above-mentioned compounds 14, 14', 18, 18' and 20 can be obtained by a Suzuki coupling reaction according to step (1d) or step (2g) in Scheme 1 or Scheme 2.

When an optically active form of a compound of the invention is required, it can be obtained by using optically active starting materials, or can be obtained by resolving the mixture of stereoisomers of the compound or intermediate by using standard procedures known to those skilled in the art, such as separation by a chiral chromatography column.

Similarly, when pure geometric isomers of the compounds of the present invention are required, they can be obtained by using pure geometric isomers as starting materials, or can be obtained by resolving the mixture of geometric isomers of compounds or intermediates by using standard procedures, such as chromatographic separation.

According to another aspect of the present invention, a pharmaceutical composition is provided, which comprises one or more of triazolopyrimidine, triazolopyridine compounds, pharmaceutically acceptable salts, enantiomers, diastereomers or racemates.

Preferably, the pharmaceutical composition further comprises at least one other therapeutic agent.

Preferably, at least one other therapeutic agent included in the pharmaceutical composition is selected from other anticancer agents, immunomodulators, antiallergic agents, antiemetics, pain relief agents, cytoprotective agents, and combinations thereof.

Preferably, the pharmaceutical composition comprises at least one compound of the present invention and at least one pharmaceutically acceptable carrier, diluent or excipient, According to another aspect of the present invention, the use of the above compound or the pharmaceutical composition in the preparation of a medicament for treating a disease or condition mediated by EED and/or PRC2 is provided.

Preferably, the disease or condition includes diffuse large B-cell lymphoma, follicular lymphoma, other lymphoma, leukemia, multiple myeloma, mesothelioma, gastric cancer, malignant rhabdoid tumor, hepatocellular carcinoma, prostate Cancer, breast cancer, bile duct and gallbladder cancer, bladder cancer; brain tumors, including neuroblastoma, schwannoma, glioma, glioblastoma and astrocytoma; cervical cancer, colon cancer, melanin tumor, endometrial cancer, esophageal cancer, head and neck cancer, lung cancer, nasopharyngeal cancer, ovarian cancer, pancreatic cancer, renal cell cancer, rectal cancer, thyroid cancer, parathyroid tumor, uterine tumor and soft tissue sarcoma.

According to another aspect of the invention, a method of treating a disease or condition mediated by EED and/or PRC2 is provided, the method comprising Providing a subject in need with a therapeutically effective amount of a compound of formula I or a pharmaceutical composition thereof.

Preferably, the disease or condition is selected from diffuse large B-cell lymphoma, follicular lymphoma, other lymphoma, leukemia, multiple myeloma, mesothelioma, gastric cancer, malignant rhabdoid tumor, hepatocellular carcinoma, prostate Cancer, breast cancer, bile duct and gallbladder cancer, bladder cancer; brain tumors, including neuroblastoma, schwannoma, glioma, glioblastoma and astrocytoma; cervical cancer, colon cancer, melanin tumor, endometrial cancer, esophageal cancer, head and neck cancer, lung cancer, nasopharyngeal cancer, ovarian cancer, pancreatic cancer, renal cell cancer, rectal cancer, thyroid cancer, parathyroid tumor, uterine tumor and soft tissue sarcoma.

DETAILED EMBODIMENTS

All features disclosed in this specification, or the disclosed methods or steps can be combined in any way unless that the features and/or steps are mutually exclusive. The following examples are only used to explain partial scope of the present invention and are not intended to limit the protection scope of the present invention.

Example 1: Synthesis of Compound E-Y1

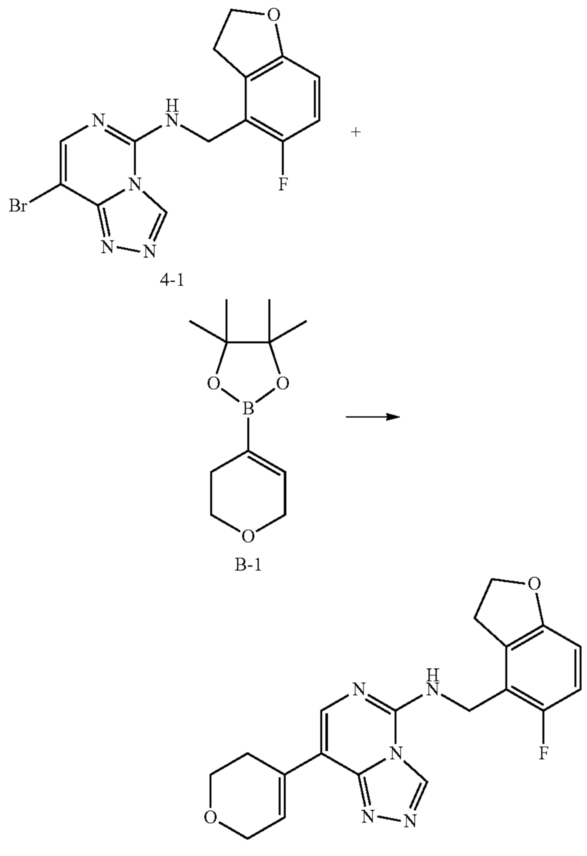

4-1

B-1

E-Y1

Bromide 4-1 (72 mg, 0.2 mmol) was dissolved in 6 mL of 1,4-dioxane and 2 mL of a 2 M $Na_2CO_3$ aqueous solution, and borate B-1 (84 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y1 as a white solid (41 mg, 57%).

$^1$H NMR (400 MHz, MeOD-$d_4$) δ 9.33 (s, 1H), 7.83 (s, 1H), 6.96 (s, 1H), 6.90-6.84 (m, 1H), 6.69-6.63 (m, 1H), 4.81 (s, 2H), 4.59 (t, J=8.7 Hz, 2H), 4.39 (m, 2H), 3.99 (t, J=5.5 Hz, 2H), 3.38 (m, 2H), 2.62 (m, 2H). LC-MS: $[M+H]^+$=368.1.

Example 2: Synthesis of Compound E-Y2

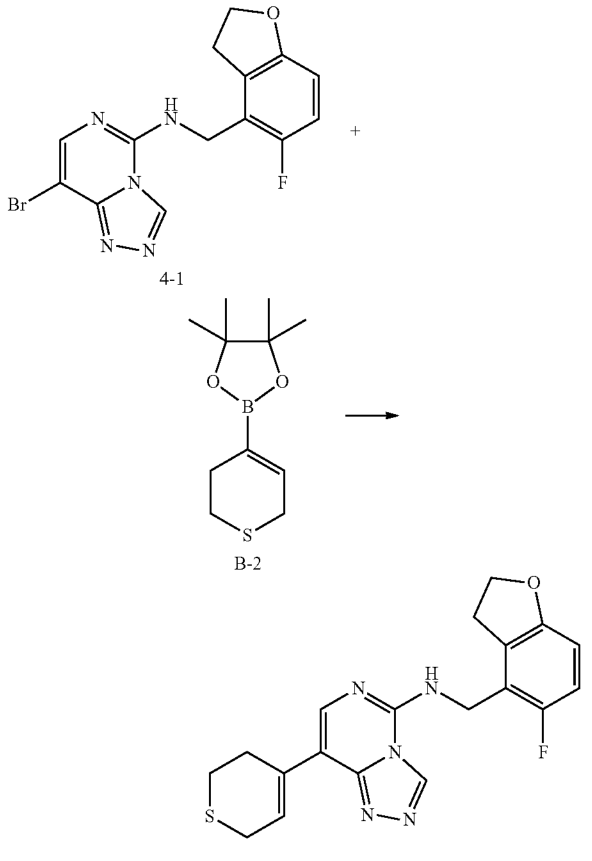

4-1

B-2

E-Y2

Bromide 4-1 (72 mg, 0.2 mmol) was dissolved in 6 mL of 1,4-dioxane and 2 mL of a 2 M $Na_2CO_3$ aqueous solution, and borate B-2 (90 mg, 0.4 mmol) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y2 as a white solid (34 mg, 45%).

$^1$H NMR (400 MHz, DMSO-$d_6$) δ 9.49 (s, 1H), 8.70 (t, J=4.7 Hz, 1H), 7.67 (s, 1H), 7.26 (s, 1H), 6.94 (t, J=9.5 Hz, 1H), 6.70 (dd, J=8.6, 3.9 Hz, 1H), 4.68 (d, J=4.6 Hz, 2H), 4.53 (t, J=8.7 Hz, 2H), 3.36 (m, 2H), 3.29 (t, J=8.6 Hz, 2H), 2.86 (t, J=5.6 Hz, 2H), 2.74 (m, 2H). LC-MS: $[M+H]^+$=384.1.

Example 3: Synthesis of Compound E-Y3

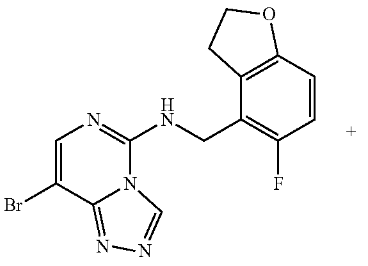

4-1

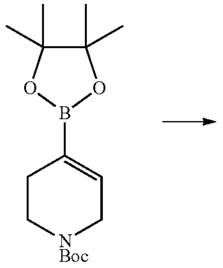

B-3

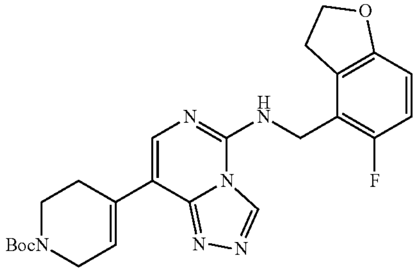

E-Y3

Bromide 4-1 (72 mg, 0.2 mmol) was dissolved in 6 mL of 1,4-dioxane and 2 mL of a 2 M $Na_2CO_3$ aqueous solution, and borate B-3 (123 mg, 0.4 mmol) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y3 as a white solid (67 mg, 72%).

$^1$H NMR (400 MHz, MeOD-$d_4$) δ 9.36 (s, 1H), 7.88 (s, 1H), 6.91-6.82 (m, 1H), 6.73 (s, 1H), 6.66 (dd, J=8.7, 3.9 Hz, 1H), 4.81 (s, 2H), 4.59 (t, J=8.7 Hz, 2H), 4.16 (s, 2H), 3.76-3.66 (m, 2H), 3.38 (t, J=8.7 Hz, 2H), 2.62 (s, 2H), 1.52 (s, 9H). LC-MS: $[M+H]^+$=467.2.

Example 4: Synthesis of Compound E-Y4

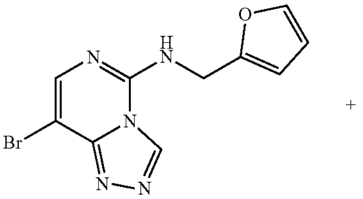

4-2

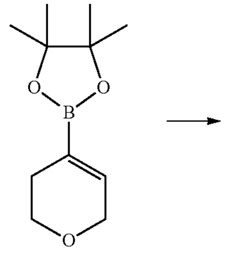

B-1

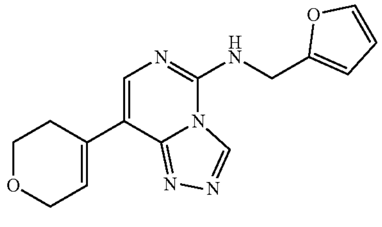

E-Y4

Bromide 4-2 (58 mg, 0.2 mmol) was dissolved in 6 mL of 1,4-dioxane and 2 mL of a 2 M $Na_2CO_3$ aqueous solution, and borate B-1 (84 mg, 0.4 mmol) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y4 as a white solid (37 mg, 64%).

$^1$H NMR (400 MHz, MeOD-$d_4$) δ 9.24 (s, 1H), 7.70 (s, 1H), 7.46 (d, J=0.9 Hz, 1H), 7.06 (s, 1H), 6.44-6.31 (m, 2H), 4.77 (s, 2H), 4.37 (m, 2H), 3.96 (t, J=5.5 Hz, 2H), 2.60 (m, 2H). LC-MS: $[M+H]^+$=298.1.

Example 5: Synthesis of Compound E-Y5

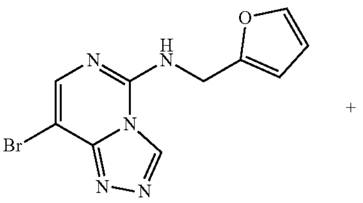

4-2

-continued

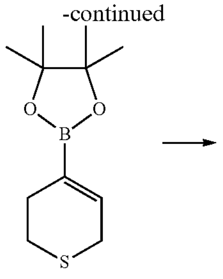

B-2

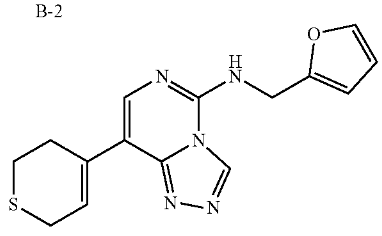

E-Y5

Bromide 4-2 (58 mg, 0.2 mmol) was dissolved in 6 mL of 1,4-dioxane and 2 mL of a 2 M $Na_2CO_3$ aqueous solution, and borate B-2 (90 mg, 0.4 mmol) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y5 as a white solid (37 mg, 60%).

$^1$H NMR (400 MHz, MeOD-$d_4$) δ 9.25 (s, 1H), 7.68 (s, 1H), 7.48 (d, J=0.9 Hz, 1H), 6.85-6.81 (m, 1H), 6.42-6.36 (m, 2H), 4.79 (s, 2H), 3.43-3.37 (m, 2H), 2.93 (t, J=5.7 Hz, 2H), 2.81 (dd, J=5.7, 2.0 Hz, 2H). LC-MS: $[M+H]^+$=314.1.

Example 6: Synthesis of Compound E-Y6

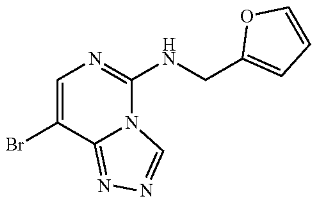

4-2

+

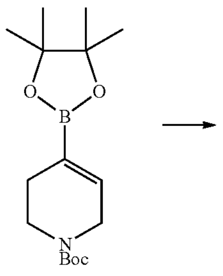

B-3

-continued

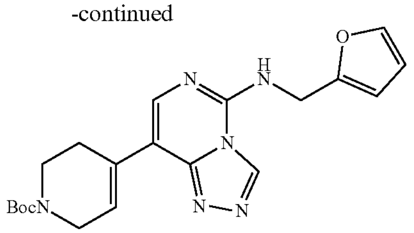

E-Y6

Bromide 4-2 (58 mg, 0.2 mmol) was dissolved in 6 mL of 1,4-dioxane and 2 mL of a 2 M $Na_2CO_3$ aqueous solution, and borate B-3 (123 mg, 0.4 mmol) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y6 as a white solid (55 mg, 70%).

$^1$H NMR (400 MHz, MeOD-$d_4$) δ 9.24 (s, 1H), 7.68 (s, 1H), 7.47 (dd, J=1.8, 0.8 Hz, 1H), 6.94 (s, 1H), 6.40 (ddd, J=5.1, 3.2, 2.2 Hz, 2H), 4.78 (s, 2H), 4.15 (m, 2H), 3.69 (m, 2H), 2.62 (m, 2H), 1.51 (s, 9H). LC-MS: $[M+H]^+$=397.1.

Example 7: Synthesis of Compound E-Y7

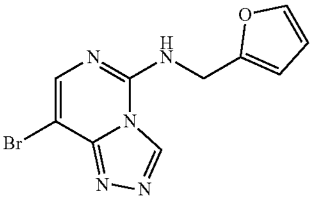

4-2

+

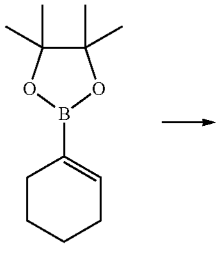

B-4

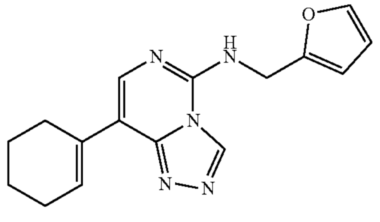

E-Y7

Bromide 4-2 (58 mg, 0.2 mmol) was dissolved in 6 mL of 1,4-dioxane and 2 mL of a 2 M $Na_2CO_3$ aqueous solution, and borate B-4 (83 mg, 0.4 mmol) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y7 as a white solid (38 mg, 64%).

$^{1}$H NMR (400 MHz, MeOD-$d_4$) δ 9.24 (s, 1H), 7.66 (s, 1H), 7.49 (s, 1H), 6.83 (s, 1H), 6.44-6.36 (m, 2H), 4.79 (s, 2H), 2.52 (s, 2H), 2.31 (s, 2H), 1.87 (dd, J=11.7, 6.1 Hz, 2H), 1.79-1.70 (m, 2H). LC-MS: $[M+H]^+$=296.1.

Example 8: Synthesis of Compound E-Y8

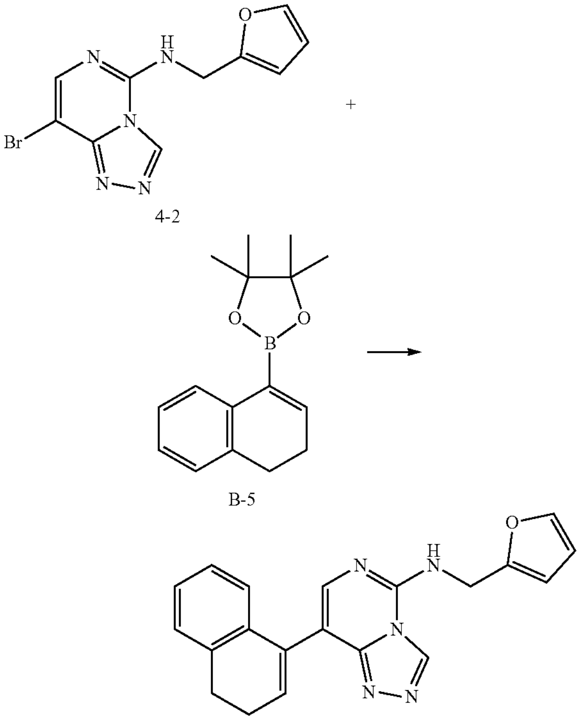

4-2

B-5

E-Y8

Bromide 4-2 (58 mg, 0.2 mmol) was dissolved in 6 mL of 1,4-dioxane and 2 mL of a 2 M $Na_2CO_3$ aqueous solution, and borate B-5 (102 mg, 0.4 mmol) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y8 as a white solid (39 mg, 57%).

$^{1}$H NMR (400 MHz, MeOD-$d_4$) δ 9.24 (s, 1H), 7.65 (s, 1H), 7.48 (d, J=1.0 Hz, 1H), 7.20 (d, J=6.9 Hz, 1H), 7.12 (t, J=6.9 Hz, 1H), 7.03 (t, J=7.0 Hz, 1H), 6.80 (d, J=7.3 Hz, 1H), 6.46-6.38 (m, 2H), 6.34 (t, J=4.6 Hz, 1H), 4.81 (s, 2H), 2.91 (t, J=8.0 Hz, 2H), 2.46 (td, J=8.0, 4.7 Hz, 2H). LC-MS: $[M+H]^+$=344.1.

Example 9: Synthesis of Compound E-Y9

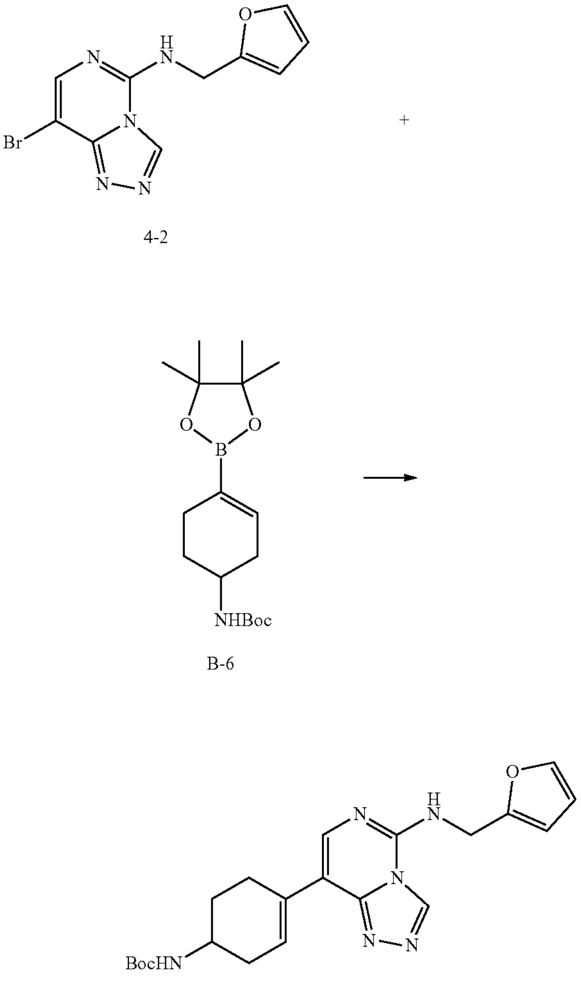

4-2

B-6

E-Y9

Bromide 4-2 (58 mg, 0.2 mmol) was dissolved in 6 mL of 1,4-dioxane and 2 mL of a 2 M $Na_2CO_3$ aqueous solution, and borate B-6 (129 mg, 0.4 mmol) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y9 as a white solid (42 mg, 51%).

$^{1}$H NMR (400 MHz, MeOD-$d_4$) δ 9.23 (s, 1H), 7.62 (s, 1H), 7.47 (dd, J=1.8, 0.9 Hz, 1H), 6.76 (s, 1H), 6.39 (ddd, J=5.1, 3.2, 1.3 Hz, 2H), 4.77 (s, 2H), 3.75 (m, 1H), 2.68-2.51 (m, 3H), 2.25-2.14 (m, 1H), 2.04 (m, 1H), 1.80-1.68 (m, 1H), 1.46 (s, 9H). LC-MS: $[M+H]^+$=411.2.

Example 10: Synthesis of Compound E-Y10

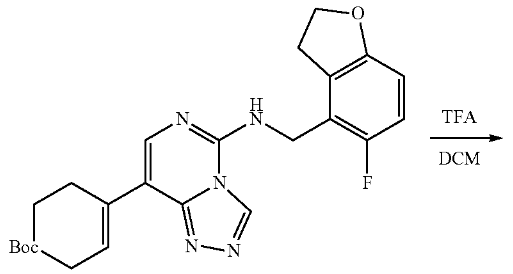

E-Y3

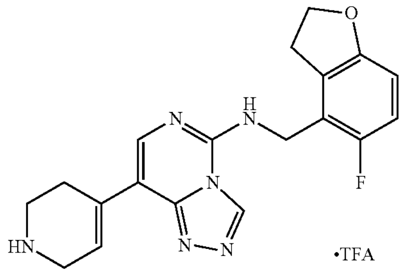

E-Y10

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After being concentrated, the resultant was directly separated by HPLC. Mobile phase: 40% acetonitrile/60% water (containing 0.1% TFA), retention time 4.7 min, yield 70%.

LC-MS: $[M+H]^+$=367.1.

Example 11: Synthesis of Compound E-Y11

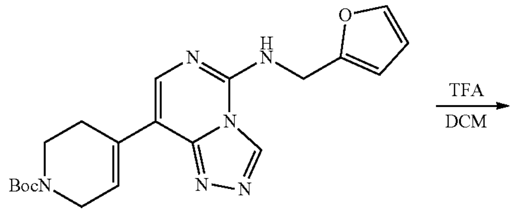

E-Y6

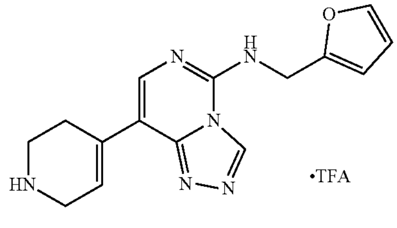

E-Y11

Compound E-Y6 (46 mg, 0.1 mmol) was dissolved in 3 mL of dichloromethane (DCM) and 1 mL of trifluoroacetic acid (TFA), and the mixture was stirred at room temperature for 30 min. After being concentrated, the resultant was directly separated by HPLC. Mobile phase: 40% acetonitrile/60% water (containing 0.1% TFA), retention time 5.4 min, yield 82%.

$^1$H NMR (400 MHz, MeOD-$d_4$) δ 9.27 (s, 1H), 7.77 (s, 1H), 7.45 (dd, J=1.8, 0.8 Hz, 1H), 7.02 (s, 1H), 6.38 (dt, J=3.2, 2.2 Hz, 2H), 4.79 (s, 2H), 3.92 (m, 2H), 3.50 (t, J=6.1 Hz, 2H), 2.95-2.85 (m, 2H). LC-MS: $[M+H]^+$=297.1.

Example 12: Synthesis of Compound E-Y12

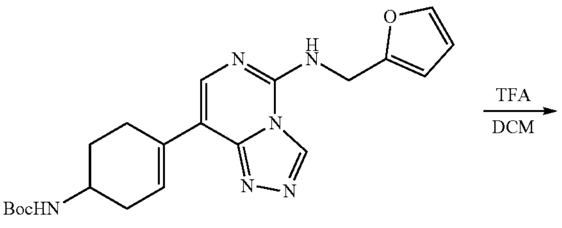

E-Y9

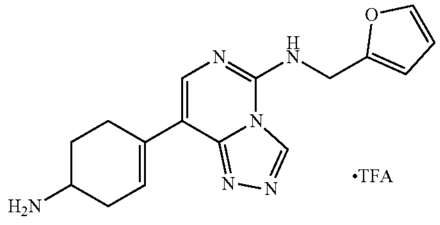

E-Y12

Compound E-Y9 (41 mg, 0.1 mmol) was dissolved in 3 mL of dichloromethane (DCM) and 1 mL of trifluoroacetic acid (TFA), and the mixture was stirred at room temperature for 30 min. After being concentrated, the resultant was directly separated by HPLC. Mobile phase: 40% acetonitrile/60% water (containing 0.1% TFA), retention time 5.4 min, yield 69%.

$^1$H NMR (400 MHz, MeOD-$d_4$) δ 9.29 (s, 1H), 7.79 (s, 1H), 7.46 (s, 1H), 6.61 (s, 1H), 6.45-6.34 (m, 2H), 4.79 (s, 2H), 3.51 (m, 1H), 2.70 (m, 2H), 2.41-2.32 (m, 1H), 2.20 (m, 1H), 1.91 (m, 2H). LC-MS: $[M+H]^+$=311.1.

Example 13: Synthesis of Compound E-Y13

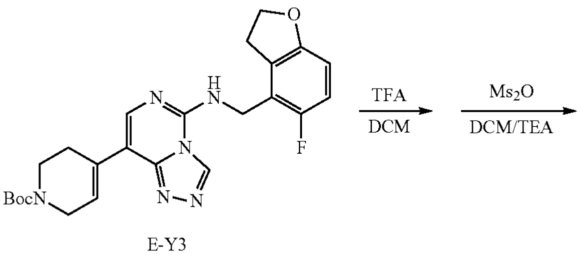

E-Y3

-continued

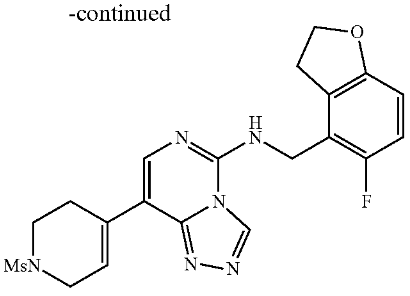

E-Y13

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. methanesulfonic anhydride ($Ms_2O$, 26 mg, 0.15 mmol) was added at room temperature, and the reaction was further performed for 1 hour. When the reaction was completed as indicated by TLC (DCM: MeOH=10:1, Rf=0.5), the resultant was directly separated by column chromatography (DCM:MeOH=30:1) to obtain the target compound E-Y13 as a white solid (24 mg, yield in two steps 51%).

$^{1}$H NMR (400 MHz, DMSO-$d_6$) δ 9.46 (s, 1H), 8.67 (t, J=4.9 Hz, 1H), 7.71 (s, 1H), 7.32 (s, 1H), 7.01-6.88 (m, 1H), 6.70 (dd, J=8.6, 4.0 Hz, 1H), 4.69 (d, J=4.8 Hz, 2H), 4.54 (t, J=8.8 Hz, 2H), 3.94 (m, 2H), 3.40 (m, 2H), 3.29 (m, 2H), 2.95 (s, 3H), 2.70 (m, 2H). LC-MS: $[M+H]^+$=445.1

Example 14: Synthesis of Compound E-Y14

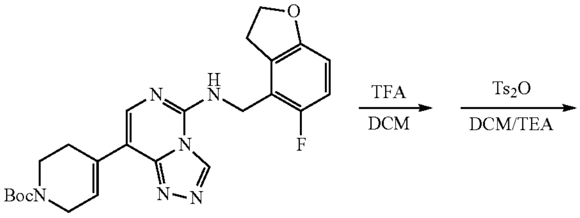

E-Y3

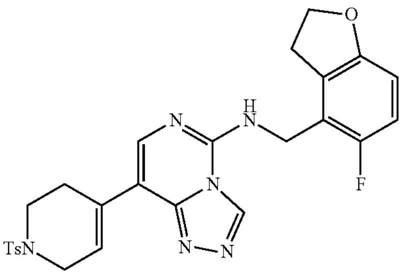

E-Y14

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. p-toluenesulfonic acid anhydride ($Ts_2O$, 48 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y14 as a white solid (16 mg, yield in two steps 32%).

$^{1}$H NMR (400 MHz, MeOD-$d_4$) δ 9.45 (s, 1H), 7.89-7.64 (m, 3H), 7.44 (d, J=7.9 Hz, 2H), 6.85 (t, J=9.4 Hz, 1H), 6.76 (s, 1H), 6.64 (dd, J=8.5, 3.6 Hz, 1H), 4.77 (s, 2H), 4.57 (t, J=8.6 Hz, 2H), 3.79 (s, 2H), 3.44-3.33 (m, 4H), 2.67 (s, 2H), 2.45 (s, 3H). LC-MS: $[M+H]^+$=521.2.

Example 15: Synthesis of Compound E-Y15

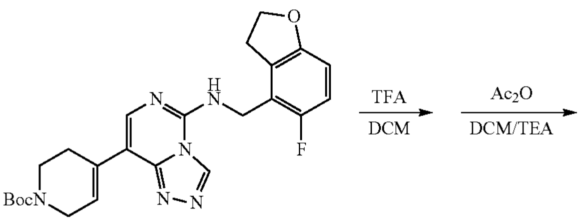

E-Y3

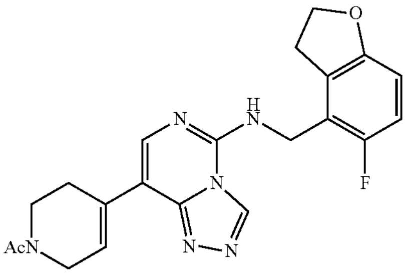

E-Y15

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Acetic anhydride ($Ac_2O$, 15 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y15 as a white solid (14 mg, yield in two steps 35%).

$^{1}$H NMR (400 MHz, DMSO-$d_6$) δ 9.46 (d, J=1.1 Hz, 1H), 8.65 (s, 1H), 7.70 (d, J=8.3 Hz, 1H), 7.27 (d, J=21.1 Hz, 1H), 6.97-6.89 (m, 1H), 6.71 (dd, J=8.7, 3.8 Hz, 1H), 4.69 (d, J=4.2 Hz, 2H), 4.54 (t, J=8.7 Hz, 2H), 4.19 (d, J=25.2 Hz, 2H), 3.67 (dt, J=11.2, 5.7 Hz, 2H), 3.28 (t, J=8.7 Hz, 2H), 2.64 (s, 1H), 2.52 (s, 1H), 2.06 (d, J=15.7 Hz, 3H). LC-MS: $[M+H]^+$=409.1.

Example 16: Synthesis of Compound E-Y16

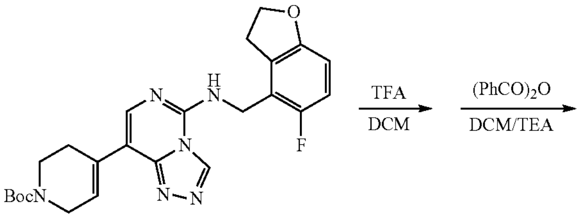

E-Y3

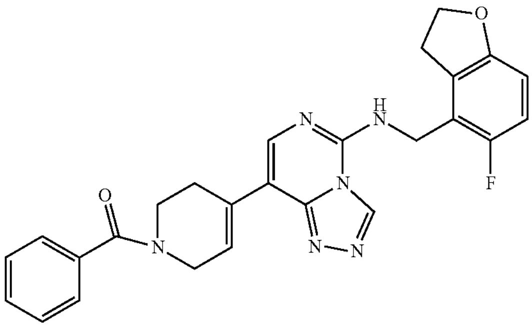

E-Y16

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Benzoic anhydride ($(PhCO)_2O$, 34 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y16 as a white solid (14 mg, yield in two steps 30%).

$^1$H NMR (400 MHz, DMSO-$d_6$) δ 9.46 (s, 1H), 8.66 (s, 1H), 7.70 (s, 1H), 7.47 (d, J=3.9 Hz, 5H), 7.01-6.90 (m, 1H), 6.71 (dd, J=8.7, 3.9 Hz, 1H), 4.69 (d, J=4.9 Hz, 2H), 4.54 (t, J=8.8 Hz, 2H), 4.35 (s, 1H), 4.15 (s, 1H), 3.87 (s, 1H), 3.56 (s, 1H), 3.28 (t, J=8.6 Hz, 2H), 2.64 (s, 2H). LC-MS: $[M+H]^+$=471.1.

Example 17: Synthesis of Compound E-Y17

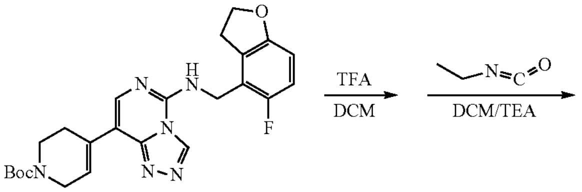

E-Y3

-continued

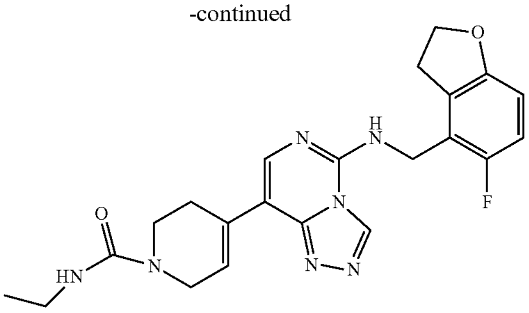

E-Y17

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Ethyl isocyanate (11 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y17 as a white solid (17 mg, yield in two steps 40%).

$^1$H NMR (400 MHz, DMSO-$d_6$) δ 9.45 (s, 1H), 8.64 (s, 1H), 7.69 (s, 1H), 7.27 (s, 1H), 6.95 (t, J=9.2 Hz, 1H), 6.78-6.64 (m, 1H), 6.51 (s, 1H), 4.69 (s, 2H), 4.54 (t, J=8.8 Hz, 2H), 4.03 (s, 2H), 3.54 (s, 2H), 3.27 (m, 2H), 3.15-2.98 (m, 2H), 1.03 (t, J=7.1 Hz, 3H). LC-MS: $[M+H]^{+}$=438.2.

Example 18: Synthesis of Compound E-Y18

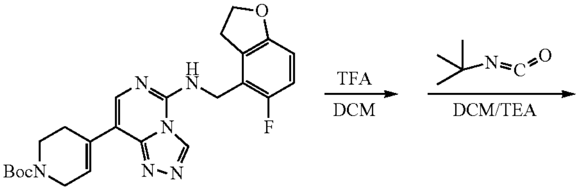

E-Y3

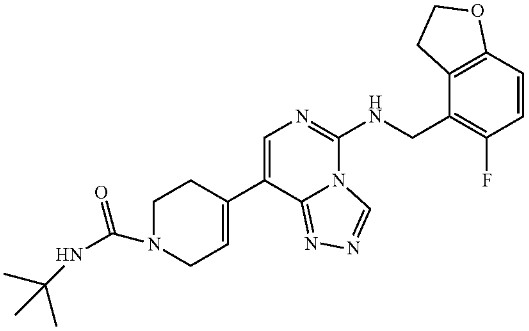

E-Y18

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring, t-butyl isocyanate (11 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y18 as a white solid (15 mg, yield in two steps 33%).

$^1$H NMR (400 MHz, MeOD-$d_4$) δ 9.38 (s, 1H), 7.93 (s, 1H), 6.93-6.83 (m, 1H), 6.69 (s, 1H), 6.66 (dd, J=8.7, 3.9 Hz, 1H), 4.82 (s, 2H), 4.59 (t, J=8.7 Hz, 2H), 4.10 (d, J=2.9 Hz, 2H), 3.66 (t, J=5.6 Hz, 2H), 3.39 (t, J=7.7 Hz, 2H), 2.62 (s, 2H), 1.38 (s, 9H). LC-MS: $[M+H]^+$=466.2.

Example 19: Synthesis of Compound E-Y19

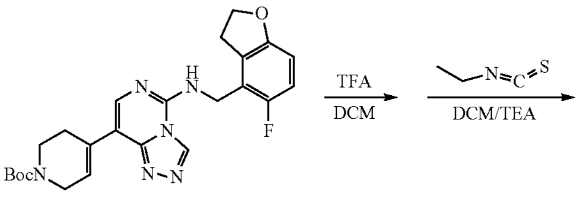

E-Y3

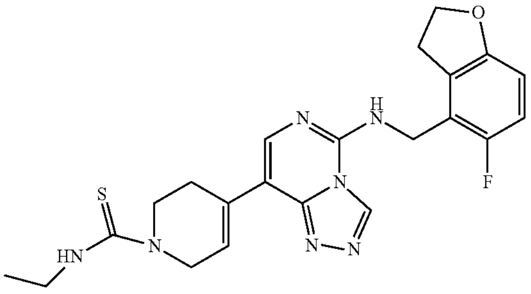

E-Y19

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Ethyl isothiocyanate (13 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y19 as a white solid (14 mg, yield in two steps 31%).

$^1$H NMR (400 MHz, DMSO-$d_6$) δ 9.46 (s, 1H), 8.66 (d, J=5.0 Hz, 1H), 7.71 (d, J=9.9 Hz, 2H), 7.27 (s, 1H), 7.02-6.90 (m, 1H), 6.71 (dd, J=8.5, 3.8 Hz, 1H), 4.70 (d, J=4.7 Hz, 2H), 4.54 (t, J=8.7 Hz, 2H), 4.41 (s, 2H), 4.07 (t, J=5.4 Hz, 2H), 3.55 (dd, J=12.3, 6.8 Hz, 2H), 3.27 (d, J=8.7 Hz, 2H), 2.61 (s, 2H), 1.12 (t, J=7.1 Hz, 3H). LC-MS: $[M+H]^+$=454.1.

Example 20: Synthesis of Compound E-Y20

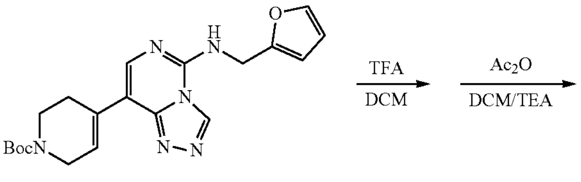

E-Y6

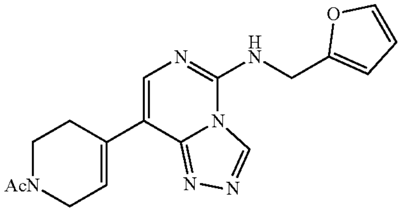

E-Y20

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Acetic anhydride ($Ac_2O$, 15 mg, 0.15 mmol) was added at room temperature, and the reaction was performed for 1 hour. When the reaction was completed as indicated by TLC (DCM:MeOH=10:1, Rf=0.5), the resultant was directly separated by column chromatography (DCM:MeOH=30:1) to obtain the target compound E-Y20 as a white solid (14 mg, yield in two steps 42%).

$^1$H NMR (400 MHz, MeOD-$d_4$) δ 9.33 (s, 1H), 7.91 (s, 1H), 7.49 (s, 1H), 6.73 (brs, 1H), 6.48-6.36 (m, 2H), 4.83 (s, 2H), 4.30 (m, 2H), 3.84 (m, 2H), 2.67 (m, 2H), 2.20 (s, 3H). LC-MS: $[M+H]^+$=339.1.

Example 21: Synthesis of Compound E-Y21

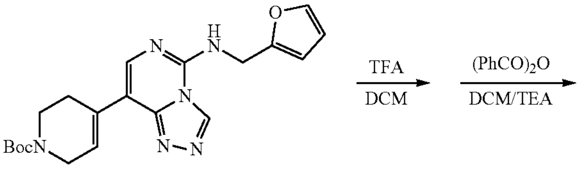

E-Y6

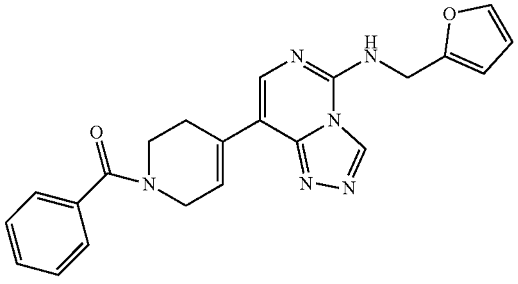

E-Y21

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Benzoic anhydride ($(PhCO)_2O$, 15 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y21 as a white solid (13 mg, yield in two steps 32%).

$^1$H NMR (400 MHz, MeOD-$d_4$) δ 9.30 (s, 1H), 7.82 (s, 1H), 7.51 (m, 5H), 7.48 (s, 1H), 6.92 (s, 1H), 6.47-6.36 (m, 2H), 4.82 (s, 2H), 4.46 (m, 1H), 4.24 (m, 1H), 4.06 (m, 1H), 3.71 (m, 1H), 2.74 (m, 2H). LC-MS: $[M+H]^+$=401.1

Example 22: Synthesis of Compound E-Y22

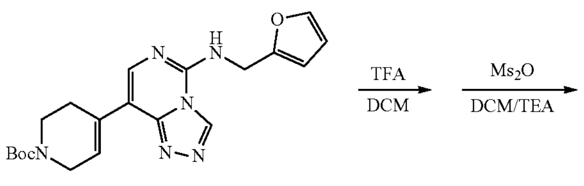

E-Y6

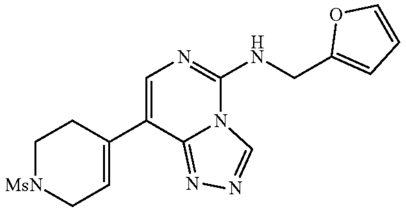

E-Y22

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Methanesulfonic anhydride ($Ms_2O$, 26 mg, 0.15 mmol) was added at room temperature, and the reaction was further performed for 1 hour. When the reaction was completed as indicated by TLC (DCM: MeOH=10:1. Rf=0.5), the resultant was directly separated by column chromatography (DCM:MeOH=30:1) to obtain the target compound E-Y22 as a white solid (18 mg, yield in two steps 47%).

$^1$H NMR (400 MHz, DMSO-$d_6$) δ 9.43 (s, 1H), 8.86 (s, 1H), 7.71 (s, 1H), 7.63 (s, 1H), 7.30 (s, 1H), 6.43 (m, 2H), 4.73 (s, 2H), 3.94 (m, 2H), 3.40 (m, 2H), 2.95 (s, 3H), 2.69 (m, 2H). LC-MS: $[M+H]^+$=375.1.

Example 23: Synthesis of Compound E-Y23

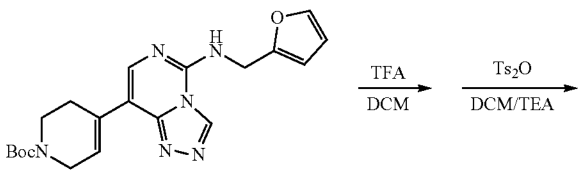

E-Y6

-continued

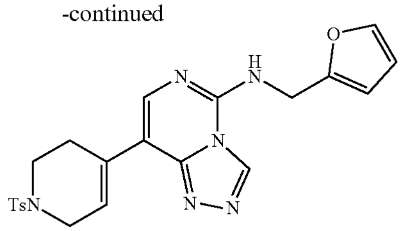

E-Y23

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. p-toluenesulfonic acid anhydride ($Ts_2O$, 48 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y23 as a white solid (16 mg, yield in two steps 35%).

$^1$H NMR (400 MHz, MeOD-$d_4$) δ 9.24 (s, 1H), 7.76 (d, J=7.9 Hz, 2H), 7.67 (s, 1H), 7.47 (s, 1H), 7.46 (d, J=8.4 Hz, 2H), 6.93 (s, 1H), 6.40 (m, 2H), 4.78 (s, 2H), 3.82 (m, 2H), 3.36 (m, 2H), 2.71 (m, 2H), 2.46 (s, 3H). LC-MS: $[M+H]^+$=451.1.

Example 24: Synthesis of Compound E-Y24

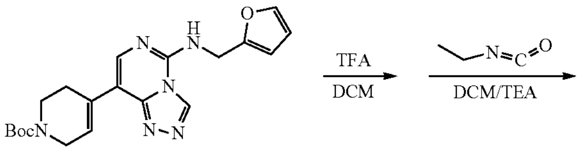

E-Y6

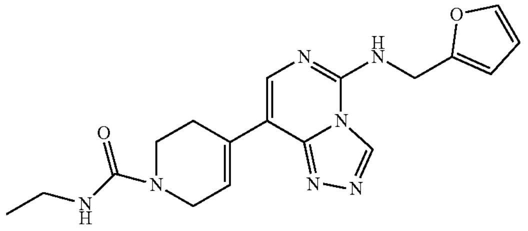

E-Y24

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Ethyl isocyanate (11 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y24 as a white solid (20 mg, yield in two steps 55%).

$^{1}H$ NMR (400 MHz, MeOD-$d_4$) δ 9.25 (s, 1H), 7.70 (s, 1H), 7.47 (d, J=1.0 Hz, 1H), 6.98 (m, 1H), 6.44-6.36 (m, 2H), 4.79 (s, 2H), 4.11 (d, J=2.8 Hz, 2H), 3.69 (t, J=5.6 Hz, 2H), 3.25 (q, J=7.2 Hz, 2H), 2.66 (d, J=16.7 Hz, 2H), 1.16 (t, J=7.2 Hz, 3H). LC-MS: $[M+H]^+$=368.1.

Example 25: Synthesis of Compound E-Y25

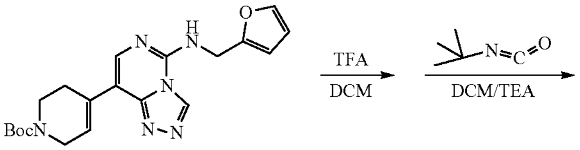

E-Y6

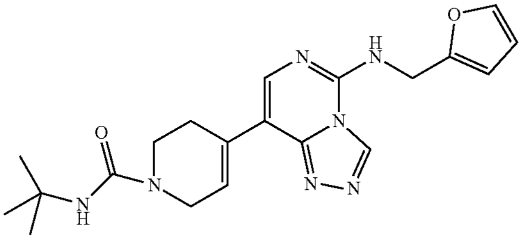

E-Y25

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring, t-butyl isocyanate (11 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y25 as a white solid (14 mg, yield in two steps 37%).

$^{1}H$ NMR (400 MHz, MeOD-$d_4$) δ 9.28 (s, 1H), 7.76 (s, 1H), 7.48 (m, 1H), 6.90 (s, 1H), 6.45-6.34 (m, 2H), 4.80 (s, 2H), 4.10 (d, J=2.5 Hz, 2H), 3.65 (t, J=5.6 Hz, 2H), 2.63 (m, 2H), 1.38 (s, 9H). LC-MS: $[M+H]^+$=396.1.

Example 26: Synthesis of Compound E-Y26

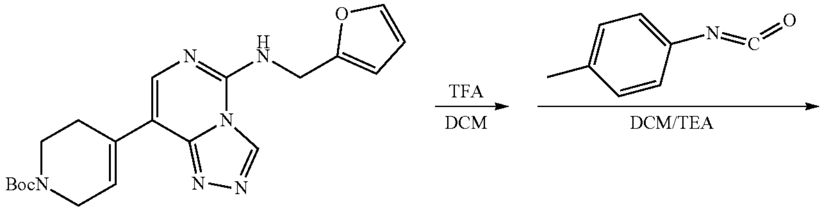

E-Y6

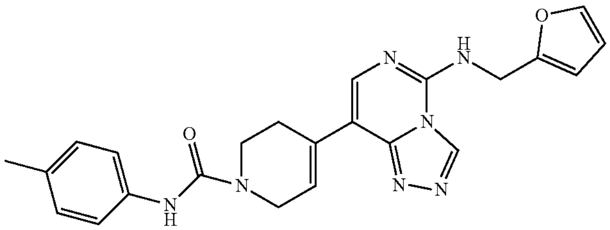

E-Y26

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring, p-toluene isocyanate (20 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y26 as a white solid (20 mg, yield in two steps 46%).

$^1$H NMR (400 MHz, DMSO-$d_6$) δ 9.44 (s, 1H), 8.81 (m, 1H), 8.46 (s, 1H), 7.72 (s, 1H), 7.63 (s, 1H), 7.37 (d, J=8.4 Hz, 2H), 7.32 (s, 1H), 7.05 (d, J=8.2 Hz, 2H), 6.43 (s, 2H), 4.74 (d, J=4.8 Hz, 2H), 4.22 (s, 2H), 3.69 (t, J=5.4 Hz, 2H), 2.62 (s, 2H), 2.24 (s, 3H). LC-MS: $[M+H]^+$=430.1.

Example 27: Synthesis of Compound E-Y27

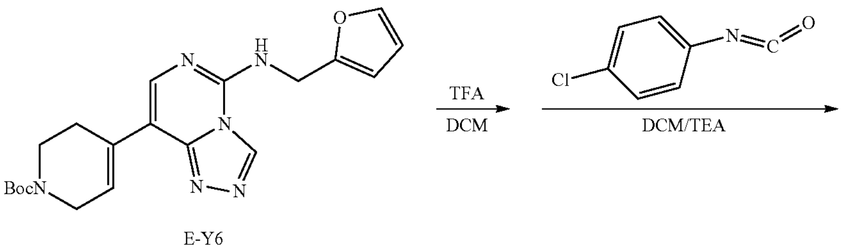

E-Y6

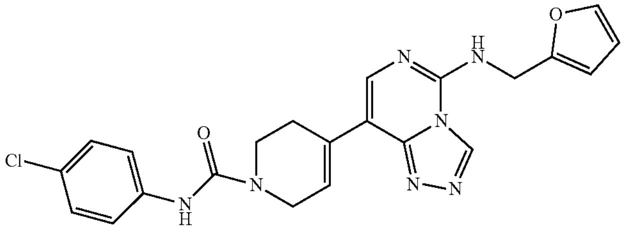

E-Y27

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. p-chlorobenzene isocyanate (23 mg, 0.15 mmol) was added at room temperature, and the reaction was further performed for 1 hour. When the reaction was completed as indicated by TLC (DCM:MeOH=10:1. Rf=0.5), the resultant was directly separated by column chromatography (DCM:MeOH=30:1) to obtain the target compound E-Y27 as a white solid (23 mg, yield in two steps 51%).

$^1$H NMR (400 MHz, DMSO-$d_6$) δ 9.44 (s, 1H), 8.81 (s, 1H), 8.70 (s, 1H), 7.72 (s, 1H), 7.63 (s, 1H), 7.54 (d, J=8.9 Hz, 2H), 7.32 (s, 1H), 7.29 (d, J=8.9 Hz, 2H), 6.43 (s, 2H), 4.74 (s, 2H), 4.23 (s, 2H), 3.71 (t, J=5.6 Hz, 2H), 2.63 (s, 2H). LC-MS: $[M+H]^+$=450.1.

Example 28: Synthesis of Compound E-Y28

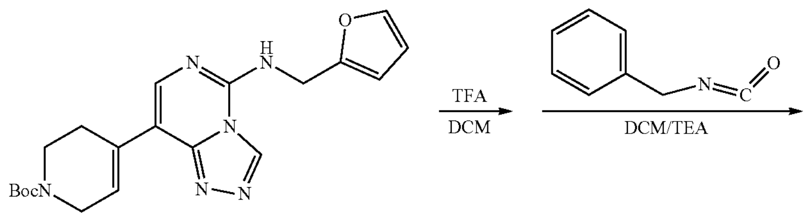

E-Y6

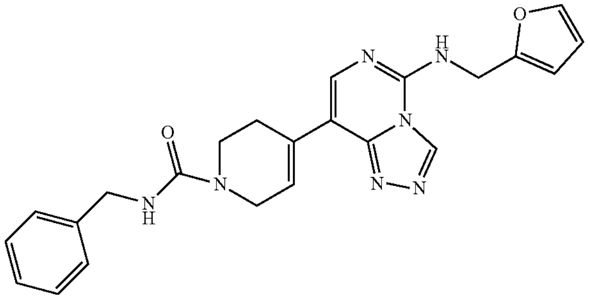

E-Y28

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Benzyl isocyanate (20 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y28 as a white solid (20 mg, yield in two steps 47%).

$^1$H NMR (400 MHz, DMSO-$d_6$) δ 9.43 (s, 1H), 8.79 (s, 1H), 7.69 (s, 1H), 7.63 (s, 1H), 7.37-7.25 (m, 5H), 7.21 (t, J=6.6 Hz, 1H), 7.16 (dd, J=14.8, 9.1 Hz, 1H), 6.43 (d, J=1.7 Hz, 2H), 4.74 (s, 2H), 4.29 (d, J=5.8 Hz, 2H), 4.11 (s, 2H), 3.60 (t, J=5.6 Hz, 2H), 2.55 (s, 2H). LC-MS: $[M+H]^+$=430.1.

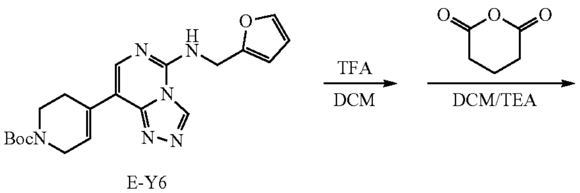

E-Y6

-continued

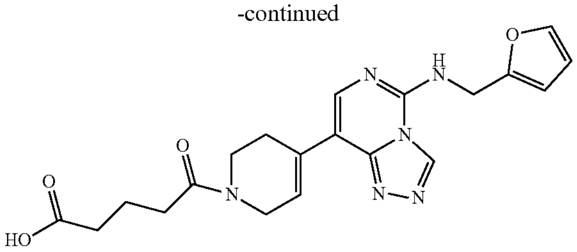

E-Y29

Example 29: Synthesis of Compound E-Y29

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Glutaric anhydride (17 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y29 as a white solid (20 mg, yield in two steps 47%).

$^1$H NMR (400 MHz, MeOD-$d_4$) δ 9.32 (s, 1H), 7.89 (d, J=4.5 Hz, 1H), 7.49 (s, 1H), 6.76 (d, J=26.4 Hz, 1H), 6.46-6.34 (m, 2H), 4.83 (s, 2H), 4.31 (m, 2H), 3.92-3.79 (m, 2H), 2.67 (m, 2H), 2.60-2.49 (m, 2H), 2.46-2.36 (m, 2H), 1.95 (m, 2H). LC-MS: $[M+H]^+$=411.1.

Example 30: Synthesis of Compound E-Y30

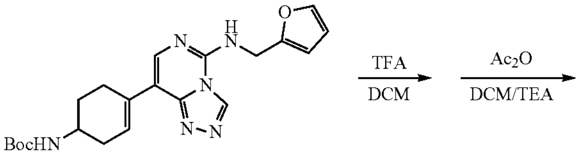

E-Y9

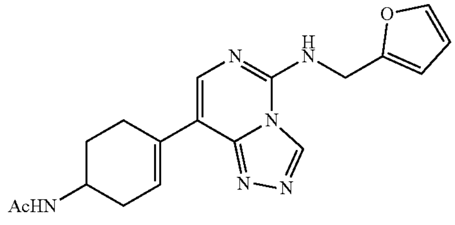

E-Y30

Compound E-Y9 (41 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Acetic anhydride ($Ac_2O$, 15 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y30 as a white solid (12 mg, yield in two steps 33%).

$^1$H NMR (400 MHz, MeOD-$d_4$) δ 9.33 (s, 1H), 7.94 (s, 1H), 7.49 (dd, J=1.8, 0.8 Hz, 1H), 6.49 (s, 1H), 6.47-6.37 (m, 2H), 4.84 (s, 2H), 4.06 (m, 1H), 2.62 (m, 3H), 2.32-2.15 (m, 1H), 2.07 (m, 1H), 1.99 (s, 3H), 1.80 (m, 1H). LC-MS: $[M+H]^+$=353.1.

Example 31: Synthesis of Compound E-Y31

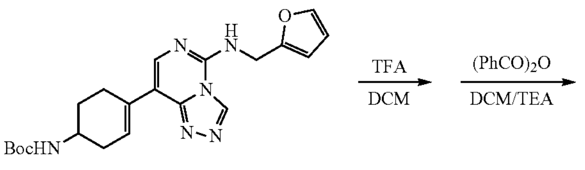

E-Y9

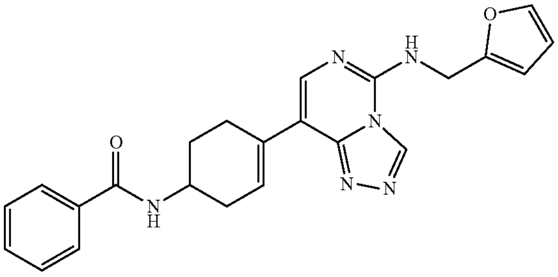

E-Y31

Compound E-Y9 (41 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Benzoic anhydride ($(PhCO)_2O$, 15 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y31 as a white solid (12 mg, yield in two steps 27%).

$^1$H NMR (400 MHz, MeOD-$d_4$) δ 9.29 (s, 1H), 7.90-7.83 (m, 2H), 7.81 (s, 1H), 7.56 (m, 1H), 7.51-7.44 (m, 3H), 6.73 (m, 1H), 6.47-6.37 (m, 2H), 4.81 (s, 2H), 4.30 (m, 1H), 2.73 (m, 3H), 2.21 (m, 1H), 2.05 (m, 1H), 1.97 (m, 1H). LC-MS: $[M+H]^+$=415.1.

Example 32: Synthesis of Compound E-Y32

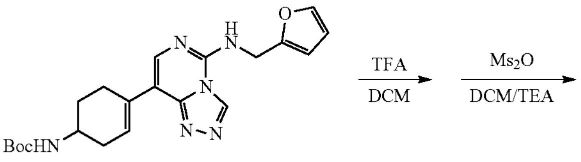

E-Y9

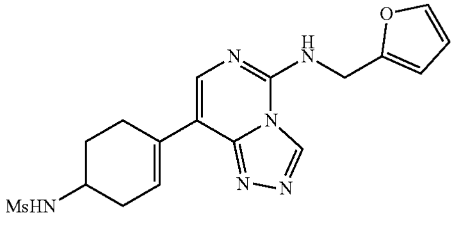

E-Y32

Compound E-Y9 (41 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Methanesulfonic anhydride ($Ms_2O$, 26 mg, 0.15 mmol) was added at room temperature, and the reaction was further performed for 1 hour. When the reaction was completed as indicated by TLC (DCM: MeOH=10:1, Rf=0.5), the resultant was directly separated by column chromatography (DCM:MeOH=30:1) to obtain the target compound E-Y32 as a white solid (11 mg, yield in two steps 29%).

$^1$H NMR (400 MHz, MeOD-$d_4$) δ 9.32 (s, 1H), 7.89 (s, 1H), 7.49 (dd, J=1.8, 0.8 Hz, 1H), 6.51 (m, 1H), 6.45-6.38 (m, 2H), 4.83 (s, 2H), 3.66 (m, 1H), 3.03 (s, 3H), 2.67 (m, 3H), 2.38-2.25 (m, 1H), 2.23-2.14 (m, 1H), 1.94-1.79 (m, 1H). LC-MS: $[M+H]^+$=389.1.

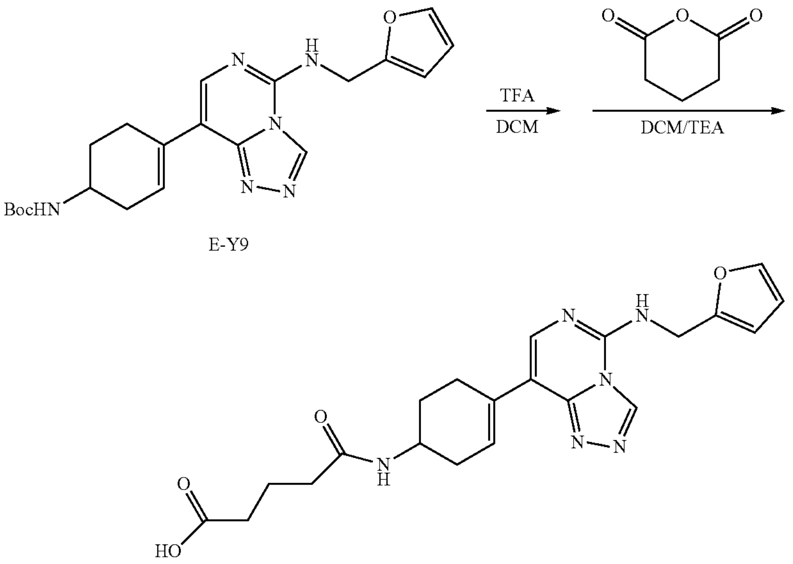

E-Y9

E-Y33

Example 33: Synthesis of Compound E-Y33

Compound E-Y9 (41 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Glutaric anhydride (17 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y33 as a white solid (16 mg, yield in two steps 38%).

$^1$H NMR (400 MHz, DMSO-$d_6$) δ 12.21 (brs, 1H), 9.41 (s, 1H), 8.75 (s, 1H), 7.85 (d, J=6.9 Hz, 1H), 7.64 (d, J=4.0 Hz, 2H), 7.19 (s, 1H), 6.42 (s, 2H), 4.72 (s, 2H), 3.85 (m, 1H), 2.60 (m, 2H), 2.48-2.33 (m, 2H), 2.21 (m, 2H), 2.11 (m, 2H), 1.91 (m, 1H), 1.73 (m, 2H), 1.61 (m 1H). LC-MS: $[M+H]^+$=425.1.

Example 34: Synthesis of Compound E-Y34

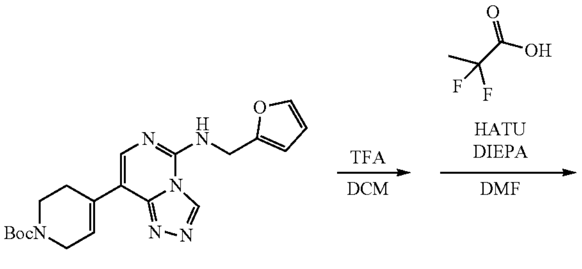

E-Y6

-continued

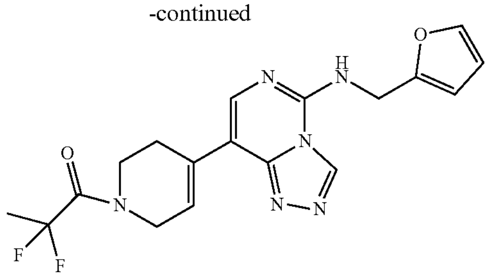

E-Y34

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 1 mL of DMF and 0.1 mL of diisopropylethylamine (DIEPA) were added and dissolved by stirring. HATU (76 mg, 0.2 mmol), 2,2-difluoropropionic acid (18 mg, 0.16 mmol) were added at room temperature, and the reaction was performed for 6 hours. When the reaction was completed as indicated by TLC (DCM:MeOH=10:1, Rf=0.5), the reaction solution was poured into water, and extracted with a large amount of ethyl acetate. After being dried and concentrated, the resultant was separated by column chromatography (DCM:MeOH=30:1) to obtain the target compound E-Y34 as a white solid (10 mg, yield in two steps 25%).

$^1$H NMR (400 MHz, MeOD-$d_4$) δ 9.29 (s, 1H), 7.82 (m, 1H), 7.49 (dd, J=1.8, 0.8 Hz, 1H), 6.91 (m, 1H), 6.50-6.35 (m, 2H), 4.81 (s, 2H), 4.51 (m, 1H), 4.34 (m, 1H), 4.03 (t, J=5.6 Hz, 1H), 3.93 (t, J=5.6 Hz, 1H), 2.76 (m, 2H), 1.87 (td, J=19.9, 6.4 Hz, 3H). LC-MS: $[M+H]^+$=389.1.

Example 35: Synthesis of Compound E-Y35

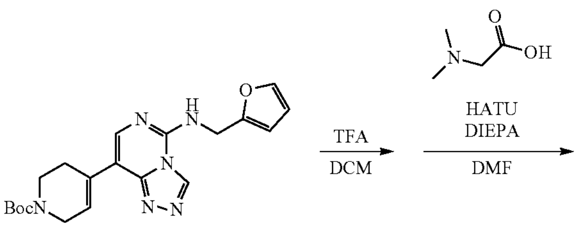

E-Y6

-continued

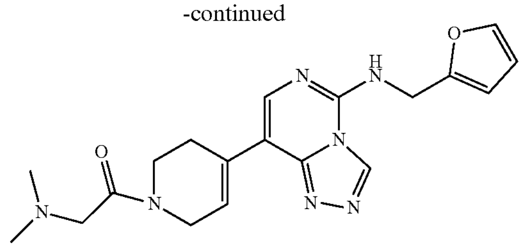

E-Y35

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 1 mL of DMF and 0.1 mL of diisopropylethylamine (DIEPA) were added and dissolved by stirring. HATU (76 mg, 0.2 mmol) and N,N-dimethylglycine (17 mg, 0.16 mmol) were added at room temperature, and the reaction was performed for 6 hours. When the reaction was completed as indicated by TLC (DCM:MeOH=10:1. Rf=0.5), the reaction solution was poured into water, and extracted with a large amount of ethyl acetate. After being dried and concentrated, the resultant was separated by column chromatography (DCM:MeOH=30:1) to obtain the target compound E-Y35 as a white solid (11 mg, yield in two steps 28%).

$^1$H NMR (400 MHz, MeOD-$d_4$) δ 9.29 (s, 1H), 7.77 (d, J=8.5 Hz, 1H), 7.48 (m, 1H), 6.92 (d, J=30.7 Hz, 1H), 6.47-6.32 (m, 2H), 4.81 (s, 2H), 4.38 (s, 1H), 4.35 (m, 1H), 4.32 (s, 1H), 4.20 (m, 1H), 3.93 (t, J=5.8 Hz, 1H), 3.70 (t, J=5.7 Hz, 1H), 3.00 (d, J=3.4 Hz, 6H). LC-MS: $[M+H]^+$=382.1.

Example 36: Synthesis of Compound E-Y36

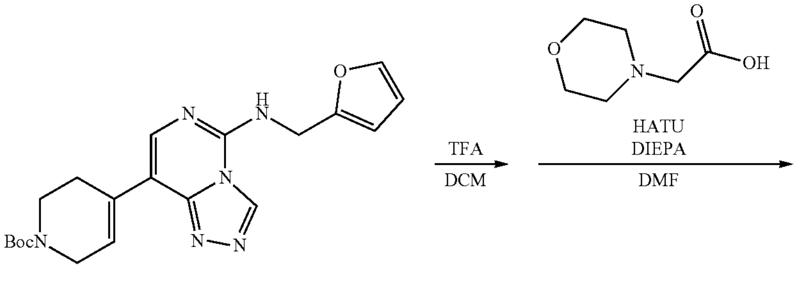

E-Y6

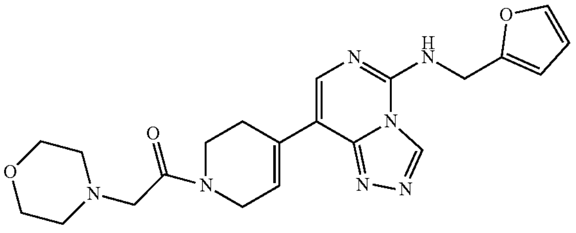

E-Y36

Compound E-Y6 (39 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 1 mL of DMF and 0.1 mL of diisopropylethylamine (DIEPA) were added and dissolved by stirring. HATU (76 mg, 0.2 mmol) and morpholin-4-ylacetic acid (23 mg, 0.16 mmol) were added at room temperature, and the reaction was performed for 6 hours. When the reaction was completed as indicated by TLC (DCM:MeOH=10:1, Rf=0.5), the reaction solution was poured into water, and extracted with a large amount of ethyl acetate. After being dried and concentrated, the resultant was separated by column chromatography (DCM: MeOH=30:1) to obtain the target compound E-Y36 as a white solid (9 mg, yield in two steps 21%).

LC-MS: $[M+H]^+$=424.2.

Example 37: Synthesis of Compound E-Y37

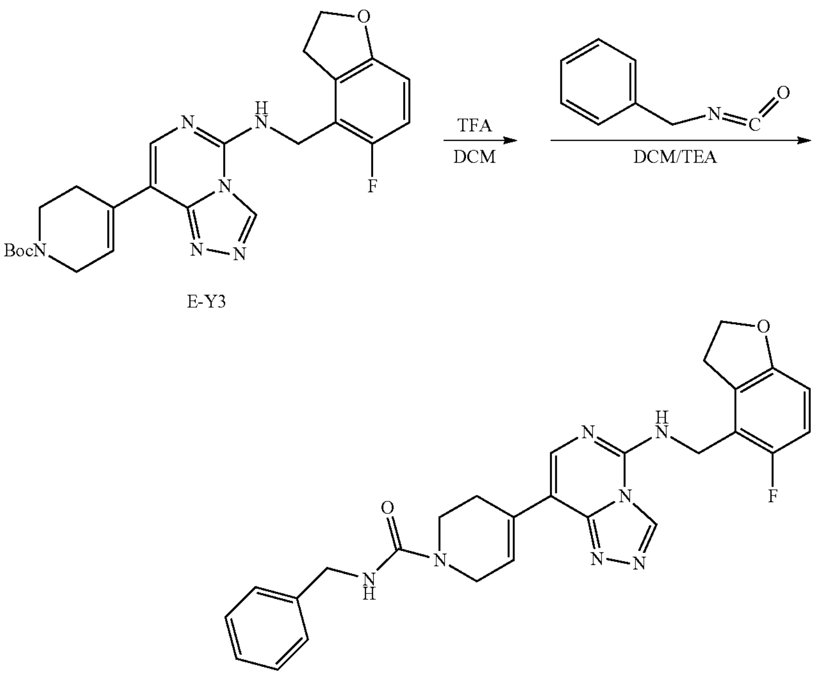

E-Y3

E-Y37

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Benzyl isocyanate (20 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y37 as a white solid (12 mg, yield in two steps 23%).

$^1$H NMR (400 MHz, DMSO-$d_6$) δ 9.45 (s, 1H), 8.64 (t, J=4.9 Hz, 1H), 7.69 (s, 1H), 7.30 (dd, J=12.0, 5.0 Hz, 6H), 7.25-7.12 (m, 2H), 7.00-6.91 (m, 1H), 6.70 (dd, J=8.6, 3.8 Hz, 1H), 4.69 (d, J=4.9 Hz, 2H), 4.54 (t, J=8.7 Hz, 2H), 4.28 (d, J=5.6 Hz, 2H), 4.10 (s, 2H), 3.28 (t, J=8.8 Hz, 3H), 2.55 (s, 2H). LC-MS: $[M+H]^+$=500.1.

Example 38: Synthesis of Compound E-Y38

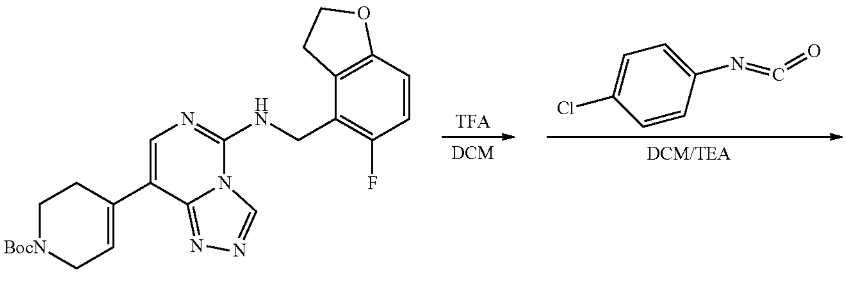

E-Y3

-continued

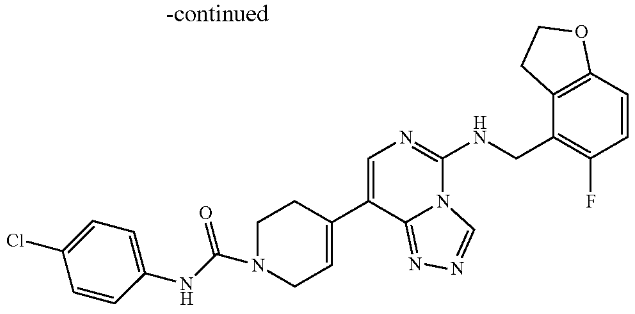

E-Y38

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. p-chlorobenzene isocyanate (23 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y38 as a white solid (18 mg, yield in two steps 34%).

$^1$H NMR (400 MHz, DMSO-$d_6$) δ 9.46 (s, 1H), 8.67 (d, J=21.7 Hz, 2H), 7.72 (s, 1H), 7.54 (d, J=8.1 Hz, 2H), 7.29 (d, J=8.4 Hz, 3H), 6.95 (s, 1H), 6.72 (s, 1H), 4.70 (s, 2H), 4.53 (d, J=8.2 Hz, 2H), 4.23 (s, 2H), 3.70 (s, 2H), 3.29 (s, 2H), 2.63 (s, 2H).

LC-MS: $[M+H]^+$=520.1.

Example 39: Synthesis of Compound E-Y39

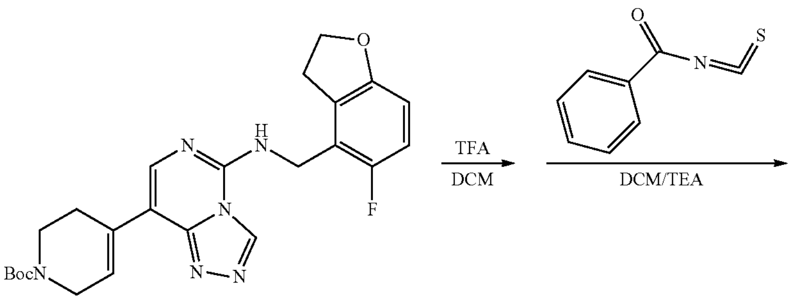

E-Y3

-continued

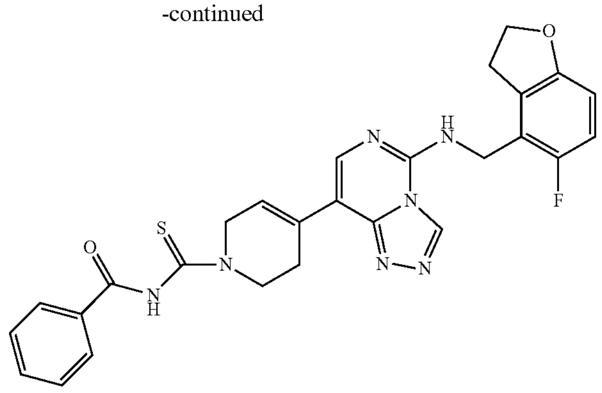

E-Y39

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Benzoyl isothiocyanate (24 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y39 as a white solid (10 mg, yield in two steps 19%).

$^1$H NMR (400 MHz, DMSO-$d_6$) δ 10.89 (d, J=17.5 Hz, 1H), 9.47 (d, J=5.7 Hz, 1H), 8.69 (s, 1H), 7.98 (t, J=8.1 Hz, 2H), 7.75 (d, J=25.1 Hz, 1H), 7.63 (s, 1H), 7.53 (d, J=8.1 Hz, 2H), 7.21 (s, 1H), 7.01-6.91 (m, 1H), 6.79-6.63 (m, 1H), 4.76 (s, 1H), 4.70 (d, J=5.0 Hz, 2H), 4.54 (t, J=8.6 Hz, 2H), 4.36 (s, 2H), 3.82 (s, 1H), 3.29 (t, J=8.7 Hz, 3H), 2.79 (s, 2H). LC-MS: $[M+H]^+$=530.1.

Example 40: Synthesis of Compound E-Y40

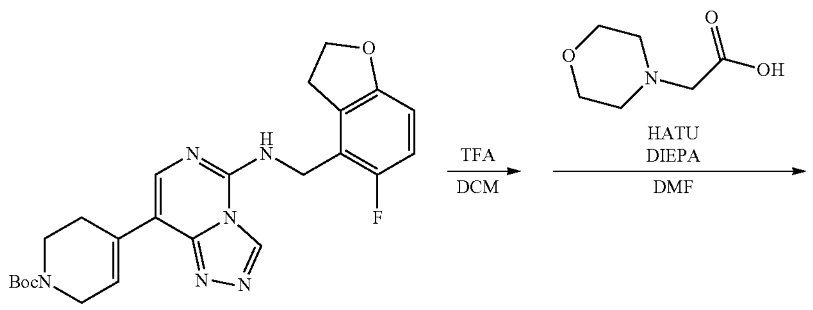

E-Y3

-continued

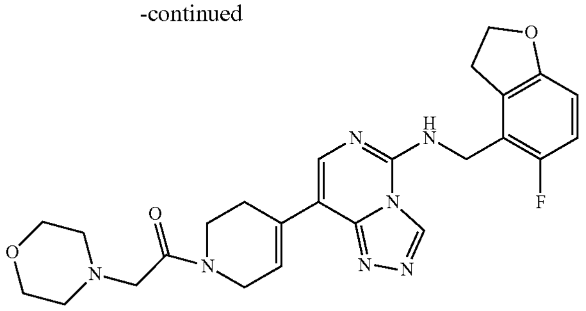

E-Y40

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 1 mL of DMF and 0.1 mL of diisopropylethylamine (DIEPA) were added and dissolved by stirring. HATU (CAS No.: 148893-10-1) (76 mg, 0.2 mmol) and morpholin-4-ylacetic acid (23 mg, 0.16 mmol) were added at room temperature, and the reaction was performed for 6 hours. When the reaction was completed as indicated by TLC (DCM:MeOH=10:1, Rf=0.5), the reaction solution was poured into water, and extracted with a large amount of ethyl acetate. After being dried and concentrated, the resultant was separated by column chromatography (DCM:MeOH=30:1) to obtain the target compound E-Y40 as a white solid (5 mg, yield in two steps 10%).

$^{1}$H NMR (400 MHz, DMSO-$d_6$) δ 9.48 (d, J=2.5 Hz, 1H), 8.72 (s, 1H), 7.73 (d, J=9.0 Hz, 1H), 7.31 (d, J=17.2 Hz, 1H), 6.95 (t, J=9.4 Hz, 1H), 6.71 (dd, J=8.6, 3.7 Hz, 1H), 4.70 (m, 2H), 4.54 (t, J=8.4 Hz, 2H), 4.44 (d, J=25.8 Hz, 2H), 4.23 (d, J=30.0 Hz, 2H), 3.96 (m, 2H), 3.78 (m, 2H), 3.61 (m, 2H), 3.44 (m, 2H), 3.29 (m, 2H), 3.17 (m, 2H), 2.67 (m, 2H). LC-MS: $[M+H]^+$=494.2.

Example 41: Synthesis of Compound E-Y41

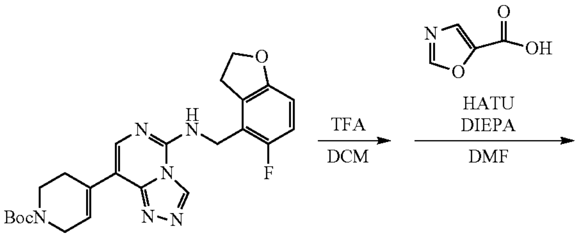

E-Y3

-continued

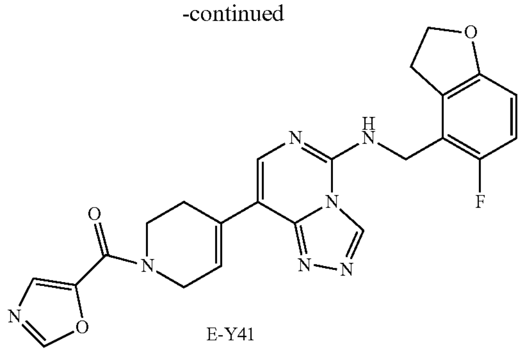

E-Y41

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 1 mL of DMF and 0.1 mL of diisopropylethylamine (DIEPA) were added and dissolved by stirring. HATU (76 mg, 0.2 mmol) and oxazole-5-carboxylic acid (18 mg, 0.16 mmol) were added at room temperature, and the reaction was performed for 6 hours. When the reaction was completed as indicated by TLC (DCM:MeOH=10:1, Rf=0.5), the reaction solution was poured into water, and extracted with a large amount of ethyl acetate. After being dried and concentrated, the resultant was separated by column chromatography (DCM: MeOH=30:1) to obtain the target compound E-Y41 as a white solid (10 mg, yield in two steps 22%).

$^{1}$H NMR (400 MHz, MeOD-$d_4$) δ 9.32 (s, 1H), 8.41 (s, 1H), 7.81 (s, 1H), 7.77 (s, 1H), 6.95 (s, 1H), 6.91-6.81 (m, 1H), 6.66 (dd, J=8.6, 3.9 Hz, 1H), 4.80 (s, 2H), 4.59 (t, J=8.7 Hz, 3H), 4.43 (m, 1H), 4.05 (m, 2H), 3.38 (t, J=8.7 Hz, 2H), 2.93-2.65 (m, 2H). LC-MS: $[M+H]^+$=462.2.

Example 42: Synthesis of Compound E-Y42

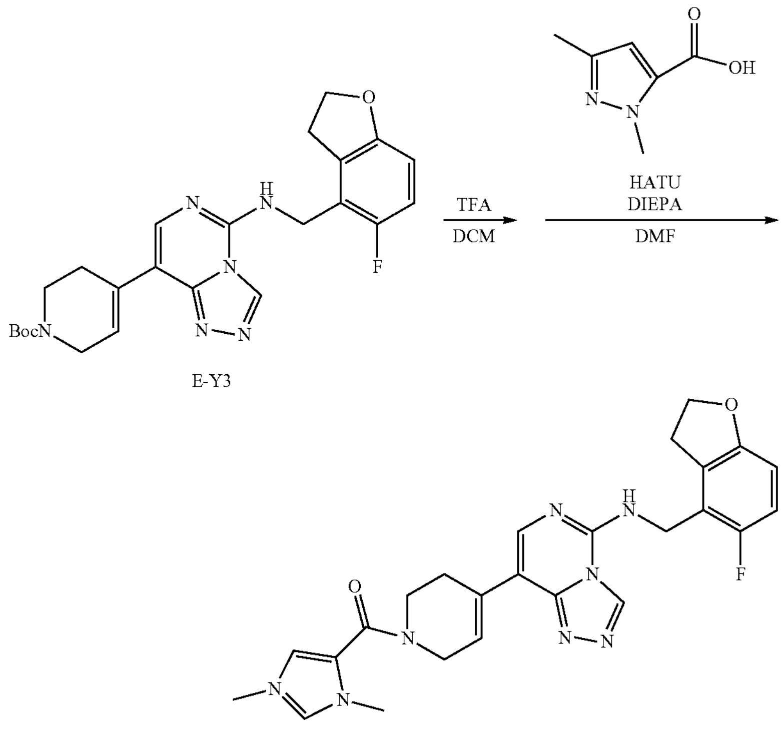

E-Y3

E-Y42

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 1 mL of DMF and 0.1 mL of diisopropylethylamine (DIEPA) were added and dissolved by stirring. HATU (76 mg, 0.2 mmol) and 1,3-dimethyl-1H-pyrazole-5-carboxylic acid (22 mg, 0.16 mmol) were added at room temperature, and the reaction was performed for 6 hours. When the reaction was completed as indicated by TLC (DCM:MeOH=10:1, Rf=0.5), the reaction solution was poured into water, and extracted with a large amount of ethyl acetate. After being dried and concentrated, the resultant was separated by column chromatography (DCM:MeOH=30:1) to obtain the target compound E-Y42 as a white solid (10 mg, yield in two steps 19%).

$^1$H NMR (400 MHz, MeOD-$d_4$) δ 9.40 (s, 1H), 7.98 (s, 1H), 6.95-6.80 (m, 1H), 6.76-6.52 (m, 2H), 6.37 (s, 1H), 4.82 (s, 2H), 4.59 (t, J=8.7 Hz, 2H), 4.40 (d, J=24.2 Hz, 2H), 4.01 (d, J=10.7 Hz, 1H), 3.87 (s, 4H), 3.39 (t, J=8.5 Hz, 2H), 2.72 (s, 2H), 2.28 (s, 3H). LC-MS: $[M+H]^+$=489.2.

Example 43: Synthesis of Compound E-Y43

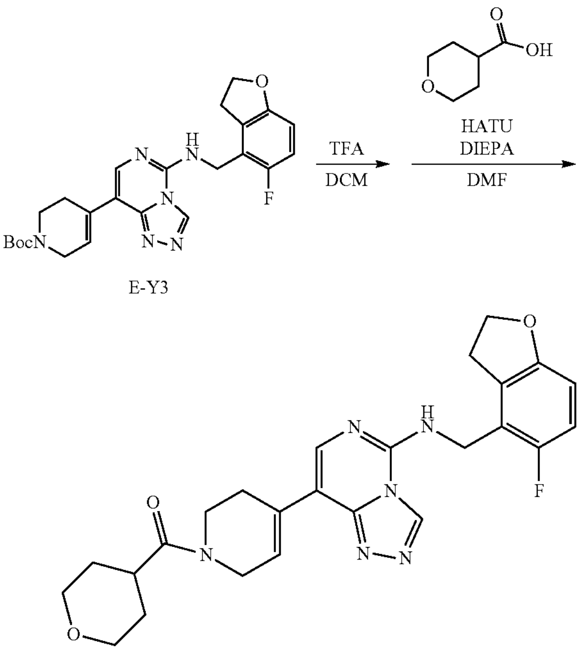

E-Y3

E-Y43

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 1 mL of DMF and 0.1 mL of diisopropylethylamine (DIEPA) were added and dissolved by stirring. HATU (76 mg, 0.2 mmol) and tetrahydropyran-4-carboxylic acid (21 mg, 0.16 mmol) were added at room temperature, and the reaction was performed for 6 hours. When the reaction was completed as indicated by TLC (DCM:MeOH=10:1, Rf=0.5), the reaction solution was poured into water, and extracted with a large amount of ethyl acetate. After being dried and concentrated, the resultant was separated by column chromatography (DCM:MeOH=30:1) to obtain the target compound E-Y43 as a white solid (10 mg, yield in two steps 21%).

$^1$H NMR (400 MHz, MeOD-$d_4$) δ 9.36 (s, 1H), 7.86 (d, J=5.7 Hz, 1H), 6.91-6.58 (m, 3H), 4.79 m, 2H), 4.58 (m, 2H), 4.38 (s, 1H), 4.27 (s, 1H), 3.99 (m, 2H), 3.87 (m, 2H), 3.55 (m, 2H), 3.37 (m, 2H), 3.04 (m, 1H), 2.65 (m, 2H), 1.83 (m, 2H), 1.68 (m, 2H). LC-MS: $[M+H]^+$=479.2.

Example 44: Synthesis of Compound E-Y44

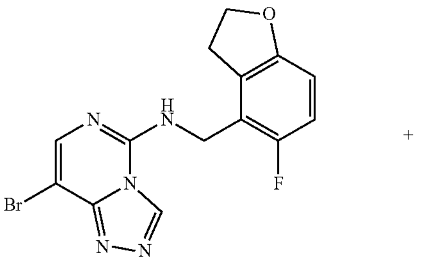

4-1

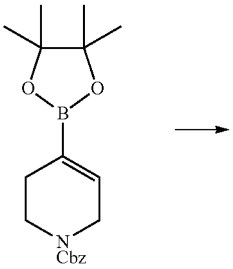

B-7

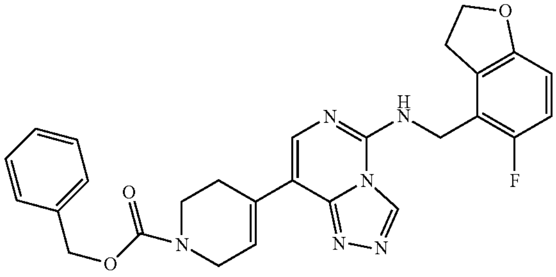

E-Y44

Bromide 4-1 (72 mg, 0.2 mmol) was dissolved in 6 mL of 1,4-dioxane and 2 mL of a 2 M $Na_2CO_3$ aqueous solution, and borate B-7 (137 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y44 as a white solid (18 mg, 36%).

$^1$H NMR (400 MHz, DMSO-$d_6$) δ 9.46 (s, 1H), 8.67 (s, 1H), 7.69 (s, 1H), 7.38 (dd, J=7.5, 4.3 Hz, 6H), 7.24 (s, 1H), 7.03-6.88 (m, 1H), 6.70 (dd, J=8.7, 3.9 Hz, 1H), 5.12 (d, J=12.1 Hz, 2H), 4.68 (s, 2H), 4.61-4.46 (m, 2H), 4.17 (m, 2H), 3.65 (m, 2H), 3.28 (t, J=8.7 Hz, 2H), 2.58 (m, 2H). LC-MS: $[M+H]^+$=501.1.

Example 45: Synthesis of Compound E-Y45

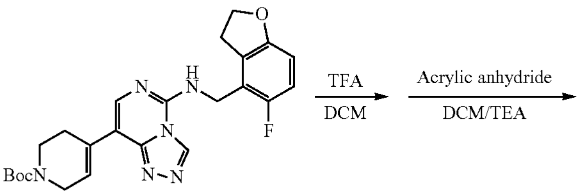

E-Y3

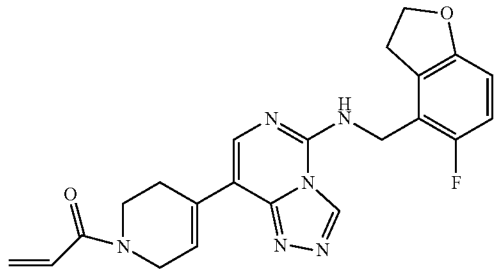

E-Y45

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 3 mL of dichloromethane and 0.1 mL of triethylamine (TEA) were added and dissolved by stirring. Acrylic anhydride (20 mg, 0.15 mmol) was added at room temperature, and the reaction was further performed for 1 hour. When the reaction was completed as indicated by TLC (DCM:MeOH=10:1, Rf=0.5), the resultant was directly separated by column chromatography (DCM:MeOH=30:1) to obtain the target compound E-Y45 as a white solid (14 mg, yield in two steps 35%).

$^1$H NMR (400 MHz, MeOH-$d_4$) δ 9.38 (s, 1H), 7.92 (s, 1H), 6.94-6.80 (m, 2H), 6.79-6.68 (m, 1H), 6.65 (dd, J=8.6, 3.9 Hz, 1H), 6.27 (d, J=16.7 Hz, 1H), 5.81 (d, J=10.6 Hz, 1H), 4.81 (s, 2H), 4.59 (t, J=8.7 Hz, 2H), 4.37 (m, 2H), 3.92 (m, 2H), 3.38 (m, 2H), 2.68 (m, 2H). LC-MS: $[M+H]^+$=421.1.

Example 46: Synthesis of Compound E-Y46

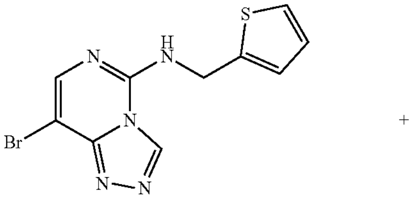

4-3

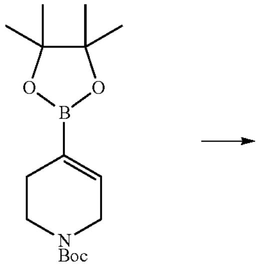

B-3

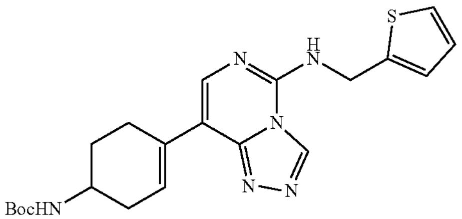

E-Y46

Bromide 4-3 (62 mg, 0.2 mmol) was dissolved in 6 mL of 1,4-dioxane and 2 mL of a 2 M $Na_2CO_3$ aqueous solution, and borate B-3 (123 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y46 as a white solid (32 mg, 40%).

$^1$H NMR (400 MHz, MeOD-$d_4$) δ 9.43 (s, 1H), 7.71 (s, 1H), 7.47 (m, 1H), 7.16 (m, 1H), 6.99 (m, 2H), 4.91 (s, 2H), 4.08 (m, 2H), 3.57 (m, 2H), 2.78 (m, 2H), 1.44 (s, 9H). LC-MS: $[M+H]^+$=412.1.

Example 47: Synthesis of Compound E-Y47

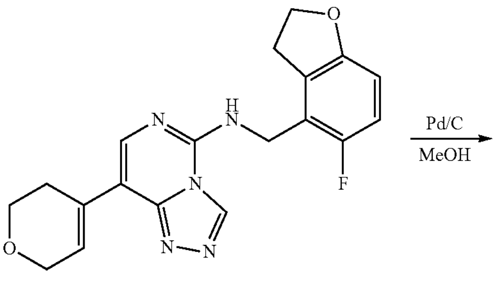

E-Y1

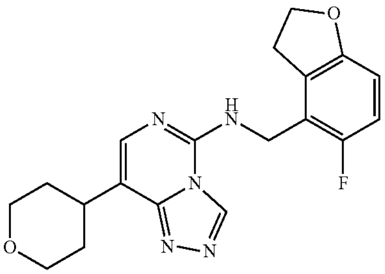

E-Y47

Compound E-Y1 (10 mg) was dissolved in 2 mL of methanol, and 10% Pd/C (5 mg) was added, and the reaction was performed at room temperature for 6 hours. The resultant was filtered and separated by column chromatography (DCM:MeOH=20:1) to obtain the target compound E-Y47 as a white solid (8 mg, 80%).

$^1$H NMR (400 MHz, MeOD-$d_4$) δ 9.33 (s, 1H), 7.74 (s, 1H) 殘, 6.93-6.80 (m, 1H), 6.66 (dd, J=8.7, 3.8 Hz, 1H), 4.78 (s, 2H), 4.59 (t, J=8.7 Hz, 2H), 4.09 (d, J=11.2 Hz, 2H), 3.71-3.57 (m, 2H), 3.38 (t, J=8.7 Hz, 2H), 3.21 (m, 1H), 1.96 (m, 4H). LC-MS: $[M+H]^+$=370.1.

Example 48: Synthesis of Compound E-Y48

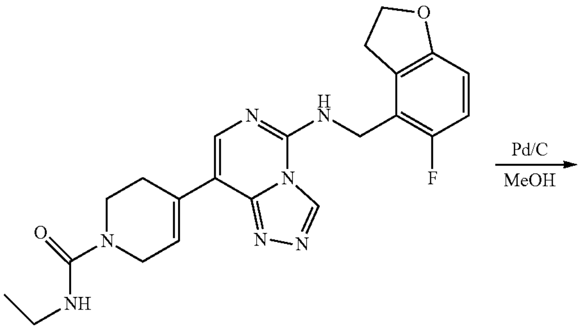

E-Y17

-continued

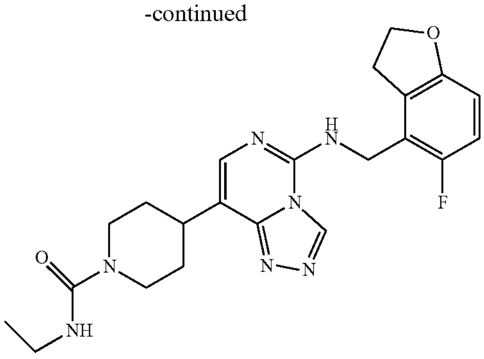

E-Y48

Compound E-Y17 (10 mg) was dissolved in 2 mL of methanol, and 10% Pd/C (5 mg) was added, and the reaction was performed at room temperature for 6 hours. The resultant was filtered and separated by column chromatography (DCM:MeOH=20:1) to obtain the target compound E-Y48 as a white solid (5 mg, 50%).

$^1$H NMR (400 MHz, MeOD-$d_4$) δ 9.27 (s, 1H), 7.58 (s, 1H), 6.99-6.77 (m, 1H), 6.66 (dd, J=8.5, 3.7 Hz, 1H), 4.76 (s, 2H), 4.59 (t, J=8.7 Hz, 2H), 4.20 (m, 2H), 3.37 (m, 2H), 3.23 (dd, J=14.2, 7.1 Hz, 2H), 2.96 (t, J=11.7 Hz, 2H), 2.04 (m, 4H), 1.15 (t, J=7.2 Hz, 3H). LC-MS: $[M+H]^+$=440.2.

Example 49: Synthesis of Compound E-Y49

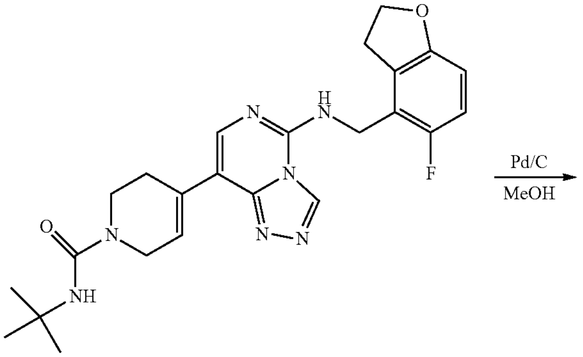

E-Y18

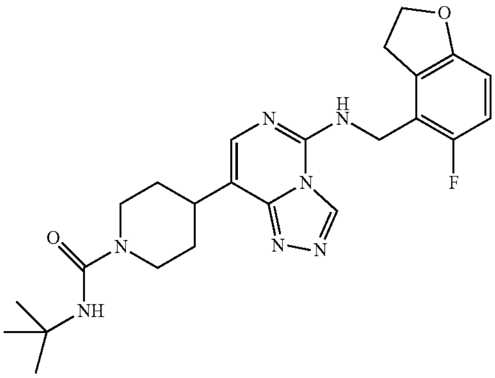

E-Y49

Compound E-Y18 (10 mg) was dissolved in 2 mL of methanol, and 10% Pd/C (5 mg) was added, and the reaction was performed at room temperature for 6 hours. The resultant was filtered and separated by column chromatography (DCM:MeOH=20:1) to obtain the target compound E-Y49 as a white solid (6 mg, 60%).

$^1$H NMR (400 MHz, DMSO-$d_6$) δ 9.40 (s, 1H), 8.44 (s, 1H), 7.49 (s, 1H), 7.02-6.87 (m, 1H), 6.70 (dd, J=8.6, 3.9 Hz, 1H), 4.64 (d, J=4.8 Hz, 2H), 4.54 (t, J=8.8 Hz, 2H), 4.10 (d, J=12.9 Hz, 2H), 3.29 (t, J=8.7 Hz, 2H), 2.96 (s, 1H), 2.77-2.64 (m, 2H), 1.90-1.68 (m, 4H), 1.27 (s, 9H). LC-MS: $[M+H]^+$=468.2.

Example 50: Synthesis of Compound E-Y50

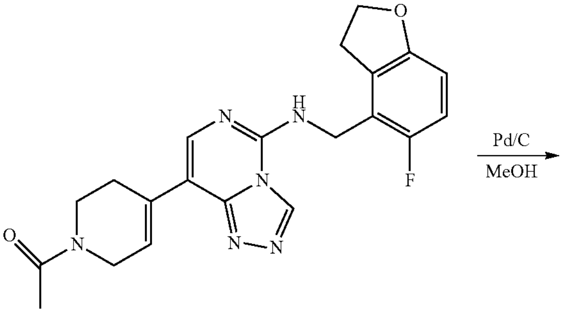

E-Y15

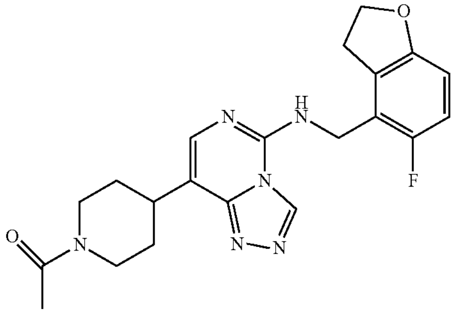

E-Y50

Compound E-Y15 (10 mg) was dissolved in 2 mL of methanol, and 10% Pd/C (5 mg) was added, and the reaction was performed at room temperature for 6 hours. The resultant was filtered and separated by column chromatography (DCM:MeOH=20:1) to obtain the target compound E-Y50 as a white solid (7 mg, 72%).

$^1$H NMR (400 MHz, MeOD) δ 9.28 (s, 1H), 7.63 (s, 1H), 6.92-6.78 (m, 1H), 6.66 (dd, J=8.7, 3.9 Hz, 1H), 4.77 (s, 2H), 4.71 (m, 1H), 4.59 (t, J=8.7 Hz, 2H), 4.09 (m, 1H), 3.37 (t, J=8.6 Hz, 2H), 3.30-3.14 (m, 1H), 2.80 (m, 1H), 2.25-2.18 (m, 1H), 2.17 (s, 3H), 2.06 (m, 2H), 1.91 (m, 1H), 1.81 (m, 1H). LC-MS: $[M+H]^+$=411.2.

Example 51: Synthesis of Compound E-Y51

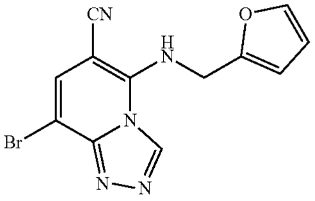

13-2

+

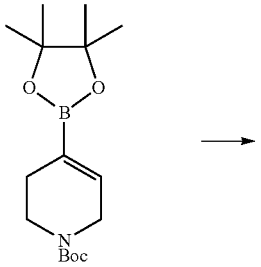

B-3

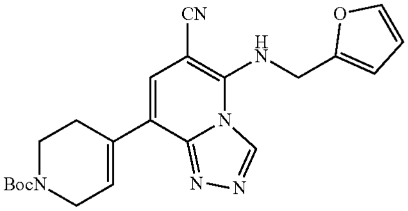

E-Y51

Bromide 13-2 (63 mg, 0.2 mmol) was dissolved in 6 mL of 1,4-dioxane and 2 mL of a 2 M $Na_2CO_3$ aqueous solution, and borate B-3 (123 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y51 as a white solid (17 mg, 20% o).

$^1$H NMR (400 MHz, MeOD-$d_4$) δ 9.48 (s, 1H), 7.50 (s, 1H), 7.34 (s, 1H), 6.95 (s, 1H), 6.47 (m, 2H), 5.08 (s, 2H), 4.18 (m, 2H), 3.72 (m, 2H), 2.62 (m, 2H), 1.48 (s, 9H). LC-MS: $[M+H]^+$=421.2.

Example 52: Synthesis of Compound E-Y52

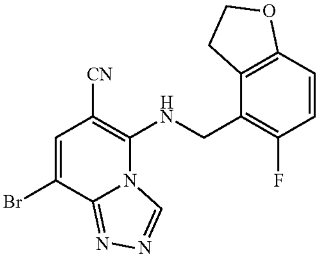

13-1

+

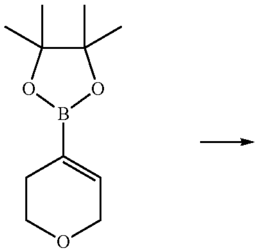

B-1

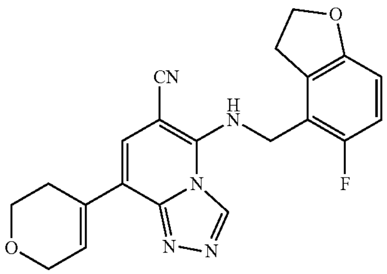

E-Y52

Bromide 13-1 (77 mg, 0.2 mmol) was dissolved in 6 mL of 1,4-dioxane and 2 mL of a 2 M $Na_2CO_3$ aqueous solution, and borate B-1 (84 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y52 as a white solid (20 mg, 21%). LC-MS: $[M+H]^+$=392.2.

Example 53: Synthesis of Compound E-Y53

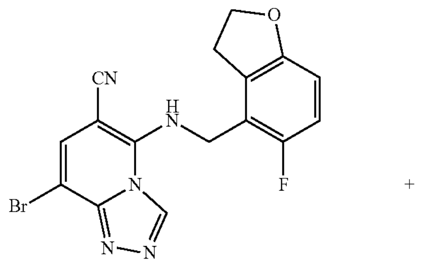

13-1

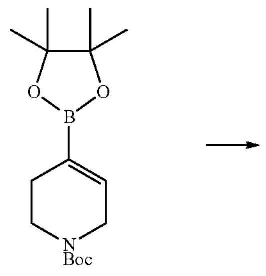

B-3

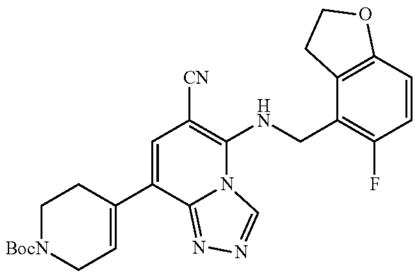

E-Y53

Bromide 13-1 (77 mg, 0.2 mmol) was dissolved in 6 mL of 1,4-dioxane and 2 mL of a 2 M $Na_2CO_3$ aqueous solution, and borate B-3 (123 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound E-Y53 as a white solid (13 mg, 14%). LC-MS: $[M+H]^+$=491.2.

Example 54: Synthesis of Compound E-Y54

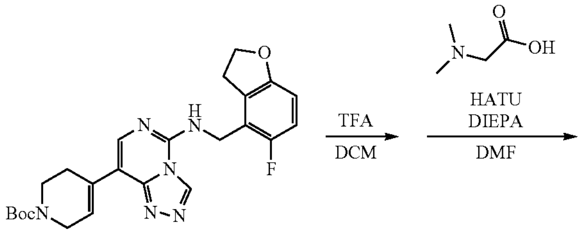

E-Y3

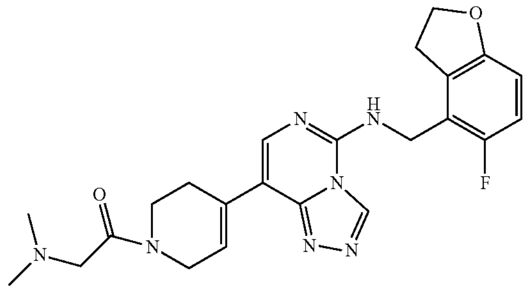

E-Y54

Compound E-Y3 (46 mg, 0.1 mmol) was dissolved in 3 mL of dichloromethane (DCM) and 1 mL of trifluoroacetic acid (TFA), and the mixture was stirred at room temperature for 30 min. After the solvent was concentrated, 1 mL of DMF and 0.1 mL of diisopropylethylamine (DIEPA) were added and dissolved by stirring. HATU (76 mg, 0.2 mmol) and N,N-dimethylglycine (17 mg, 0.16 mmol) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound E-Y54 (6 mg).

$^1H$ NMR (400 MHz, DMSO-$d_6$) δ 9.54 (d, J=3.3 Hz, 1H), 8.79 (s, 1H), 7.70 (d, J=6.1 Hz, 1H), 7.30 (s, 1H), 6.95 (t, J=9.4 Hz, 1H), 6.70 (dd, J=8.5, 3.7 Hz, 1H), 4.69 (d, J=4.6 Hz, 2H), 4.53 (t, J=8.7 Hz, 2H), 4.24 (d, J=41.1 Hz, 2H), 3.71 (s, 2H), 3.48 (s, 2H), 3.29 (t, J=8.7 Hz, 2H), 2.60 (d, J=38.4 Hz, 2H), 2.37 (s, 6H). LC-MS: $[M+H]^+$=452.2.

Example 55: Synthesis of Compound SL-ZYE-07

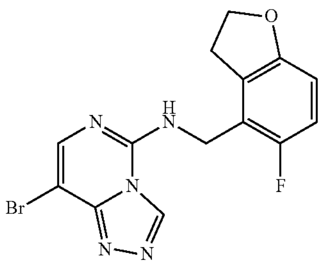

4-1

-continued

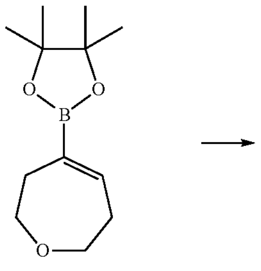

B-8

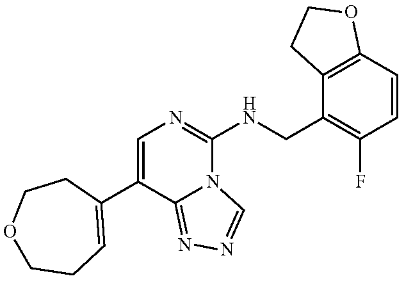

SL-ZYE-07

Bromide 4-1 (72 mg, 0.2 mmol) was dissolved in 6 mL of 1,4-dioxane and 2 mL of a 2 M $Na_2CO_3$ aqueous solution, and borate B-8 (89 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound SL-ZYE-07 (47 mg, 62%). $^1$H NMR (400 MHz, DMSO-$d_6$) δ 9.39 (s, 1H), 8.51 (s, 1H), 7.56 (s, 1H), 6.91 (t, J=9.3 Hz, 1H), 6.69 (m, 2H), 4.65 (d, J=3.8 Hz, 2H), 4.51 (t, J=8.5 Hz, 2H), 3.71 (m, 2H), 3.62 (m, 2H), 3.26 (m, 2H), 2.79 (m, 2H), 2.45 (m, 2H). LC-MS: $[M+H]^+$=382.2.

Example 56: Synthesis of Compounds SL-ZYE-08, SL-ZYE-08-S and SL-ZYE-08-R

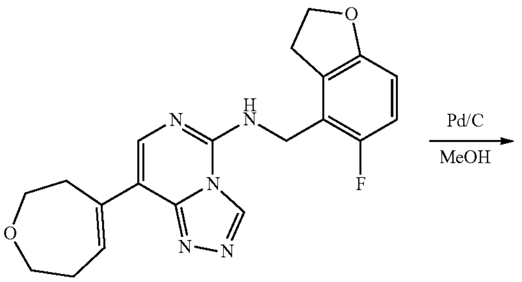

SL-ZYE-07

-continued

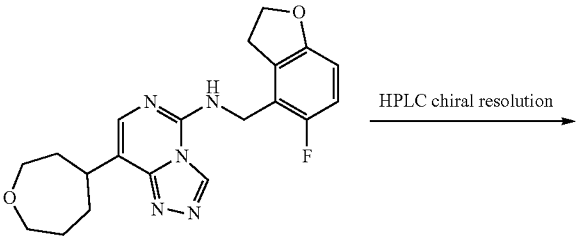

SL-ZYE-08

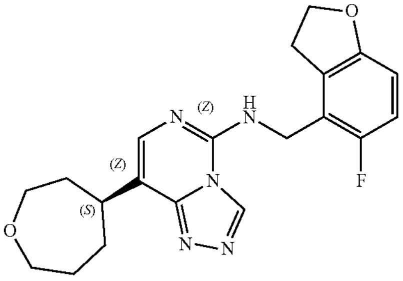

SL-ZYE-08-S

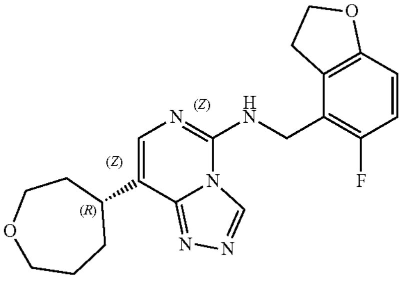

SL-ZYE-08-R

Compound SL-ZYE-07 (10 mg) was dissolved in 2 mL of methanol, and 10% Pd/C (5 mg) was added, and the reaction was performed at room temperature for 6 hours. The resultant was filtered and separated by column chromatography (DCM:MeOH=20:1) to obtain the target compound SL-ZYE-08 (8 mg, 82%).

$^1$H NMR (400 MHz, $CDCl_3$+MeOD-$d_4$) δ 9.05 (s, 1H), 7.41 (s, 1H), 6.82-6.64 (m, 1H), 6.56 (dd, J=8.6, 3.9 Hz, 1H), 4.60 (s, 2H), 4.52 (t, J=8.7 Hz, 2H), 3.91-3.77 (m, 2H), 3.69 (ddd, J=19.0, 10.7, 6.3 Hz, 2H), 3.27 (t, J=8.7 Hz, 2H), 3.16 (d, J=7.8 Hz, 1H), 2.05-1.91 (m, 4H), 1.84 (dd, J=9.0, 5.1 Hz, 2H). LC-MS: $[M+H]^+$=384.2.

SL-ZYE-08 was further separated by chiral chromatography to obtain a pair of optically pure compounds SL-ZYE-08-S and SL-ZYE-08-R. The separation conditions were: (chiral column: Chiralcel OD-3, 4.6 mm×250 mm, particle size: 3 μm, mobile phase: n-hexane:isopropanol=50:50, flow rate=1 ml/min, two fractions were obtained, fraction 1 (Rt=17.085 min); fraction 2 (Rt=18.627 min). The chiral chromatography separation method was a conventional method known to those skilled in the art.

Example 57: Synthesis of Compound SL-ZYE-09

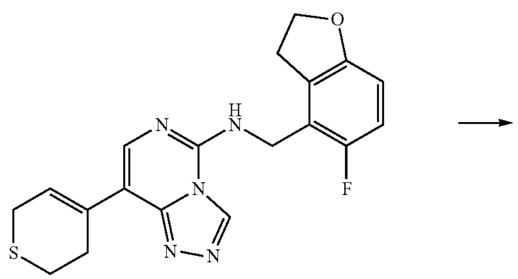

E-Y2

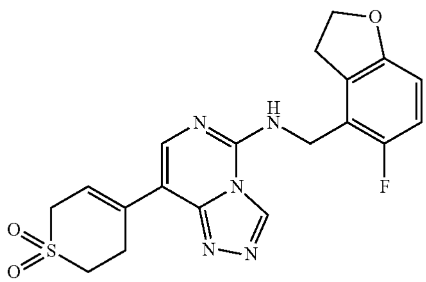

SL-ZYE-09

E-Y2 (5 mg) was dissolved in 1 mL of dichloromethane, mCPBA (m-chloroperoxybenzoic acid) (2 mg) was added thereto and the reaction system was stirred at room temperature for 120 min under Ar atmosphere protection. After being concentrated under reduced pressure, the resultant was separated by column chromatography to obtain the target compound SL-ZYE-09 (2 mg).

$^1$H NMR (400 MHz, DMSO-$d_6$) δ 9.46 (s, 1H), 8.70 (t, J=5.1 Hz, 1H), 7.76 (s, 1H), 7.12 (t, J=4.6 Hz, 1H), 7.01-6.85 (m, 1H), 6.70 (dd, J=8.7, 3.9 Hz, 1H), 4.69 (d, J=4.9 Hz, 2H), 4.54 (t, J=8.7 Hz, 2H), 3.99 (s, 2H), 3.37 (t, J=6.2 Hz, 2H), 3.28 (t, J=8.7 Hz, 2H), 3.17 (d, J=5.3 Hz, 2H). LC-MS: $[M+H]^+$=416.1.

Example 58: Synthesis of Compound SL-ZYE-11

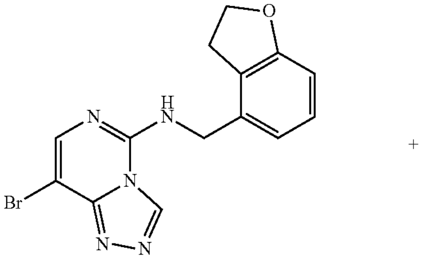

4-4

-continued

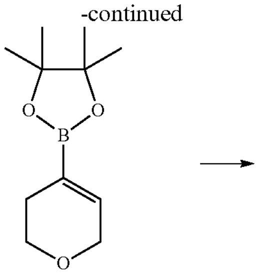

B-1

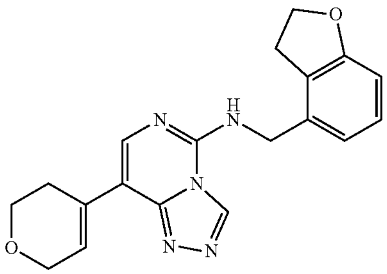

SL-ZYE-11

Bromide 4-4 (69 mg, 0.2 mmol) was dissolved in 6 mL of 1,4-dioxane and 2 mL of a 2 M $Na_2CO_3$ aqueous solution, and borate B-1 (84 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound SL-ZYE-11 (17 mg).

$^1$H NMR (400 MHz, $CDCl_3$+MeOD-$d_4$) δ 9.08 (s, 1H), 7.56 (s, 1H), 7.14 (s, 1H), 7.02 (d, J=7.4 Hz, 1H), 6.79 (d, J=8.0 Hz, 1H), 6.66 (d, J=7.9 Hz, 1H), 4.53 (t, J=8.7 Hz, 2H), 4.35 (s, 2H), 3.92 (t, J=5.3 Hz, 2H), 3.30 (s, 2H), 3.19 (t, J=8.4 Hz, 2H), 2.53 (s, 2H). LC-MS: [M+H]J=350.2.

Example 59: Synthesis of Compound SL-ZYE-14

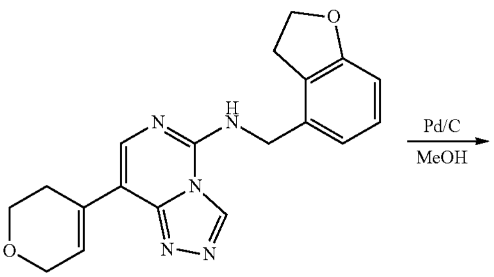

SL-ZYE-11

-continued

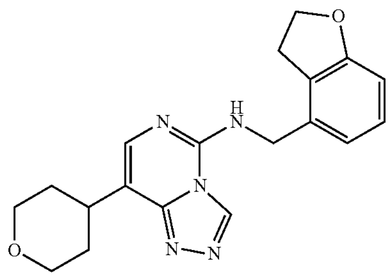

SL-ZYE-14

Compound SL-ZYE-11 (10 mg) was dissolved in 2 mL of methanol, and 10% Pd/C (5 mg) was added, and the reaction was performed at room temperature for 6 hours. The resultant was filtered and separated by column chromatography (DCM:MeOH=20:1) to obtain the target compound SL-ZYE-14 (5 mg).

$^1$H NMR (400 MHz, DMSO-$d_6$) δ 9.41 (s, 1H), 8.55 (t, J=5.4 Hz, 1H), 7.45 (s, 1H), 7.06 (t, J=7.8 Hz, 1H), 6.85 (d, J=7.5 Hz, 1H), 6.69 (d, J=7.9 Hz, 1H), 4.63 (d, J=5.3 Hz, 2H), 4.54 (t, J=8.7 Hz, 2H), 3.96 (dd, J=10.8, 3.6 Hz, 2H), 3.51-3.44 (m, 2H), 3.22 (t, J=8.7 Hz, 2H), 3.09 (ddd, J=15.4, 7.9, 3.7 Hz, 1H), 2.01-1.87 (m, 2H), 1.82 (d, J=12.5 Hz, 2H). LC-MS: $[M+H]^+$=352.2.

Example 60: Synthesis of Compound SL-ZYE-17

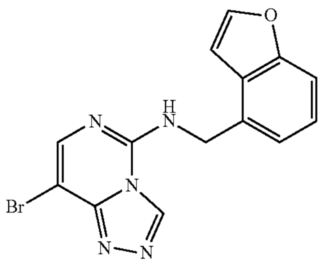

4-5

+

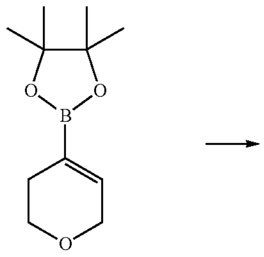

B-1

-continued

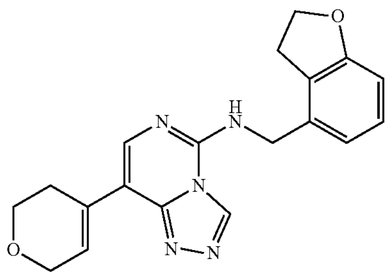

SL-ZYE-17

Bromide 4-5 (68 mg, 0.2 mmol) was dissolved in 6 mL of 1,4-dioxane and 2 mL of a 2 M $Na_2CO_3$ aqueous solution, and borate B-1 (84 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound SL-ZYE-17 (17 mg).

$^1$H NMR (400 MHz, MeOD-$d_4$) δ 9.26 (s, 1H), 7.78 (d, J=2.3 Hz, 1H), 7.74 (s, 1H), 7.47 (d, J=7.9 Hz, 1H), 7.30 (d, J=7.6 Hz, 2H), 7.08 (s, 1H), 7.03 (s, 1H), 5.07 (s, 2H), 4.39 (d, J=2.6 Hz, 2H), 3.98 (t, J=5.5 Hz, 2H), 2.63 (s, 2H). LC-MS: $[M+H]^+$=348.1.

Example 61: Synthesis of Compound SL-ZYE-18

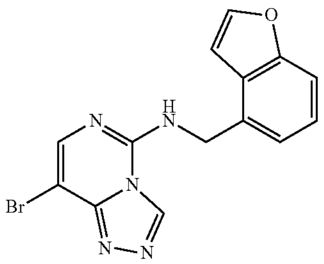

4-5

+

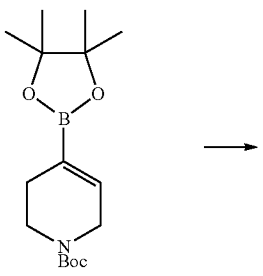

B-3

-continued

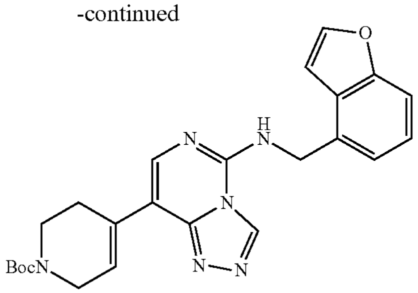

SL-ZYE-18

Bromide 4-5 (68 mg, 0.2 mmol) was dissolved in 6 mL of 1,4-dioxane and 2 mL of a 2 M $Na_2CO_3$ aqueous solution, and borate B-3 (123 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound SL-ZYE-18 (15 mg).

$^1$H NMR (400 MHz, $CDCl_3$) δ 8.77 (s, 1H), 7.71 (s, 1H), 7.67 (d, J=2.3 Hz, 1H), 7.51 (s, 1H), 7.31-7.29 (m, 4H), 6.90 (s, 1H), 5.08 (d, J=5.3 Hz, 2H), 4.18 (s, 2H), 3.70 (s, 2H), 2.64 (s, 2H), 1.51 (s, 9H). LC-MS: $[M+H]^+$=447.1.

Example 62: Synthesis of Compound E-Y20-H

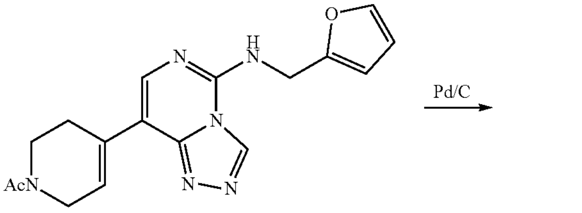

E-Y20

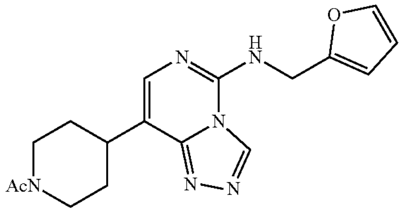

E-Y20-H

Compound E-Y20 (10 mg) was dissolved in 2 mL of methanol, and 10% Pd/C (3 mg) was added, and the reaction was performed at room temperature for 6 hours. The resultant was filtered and separated by column chromatography (DCM:MeOH=20:1) to obtain the target compound E-Y20-H (4 mg, 40%).

$^1$H NMR (400 MHz, MeOD-$d_4$) δ 9.23 (s, 1H), 7.57 (d, J=0.7 Hz, 1H), 7.47 (dd, J=1.8, 0.9 Hz, 1H), 6.42-6.36 (m, 2H), 4.77 (s, 2H), 4.73 (m, 1H), 4.09 (m, 1H), 3.35-3.17 (m, 2H), 2.80 (dd, J=12.9, 10.2 Hz, 1H), 2.24-2.18 (m, 1H), 2.17 (s, 3H), 2.07 (m, 1H), 1.87 (m, 2H). LC-MS: $[M+H]^+$=341.1.

Example 63: Synthesis of Compound E-Y13-H

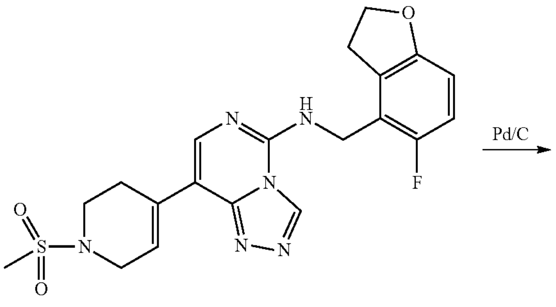

E-Y13

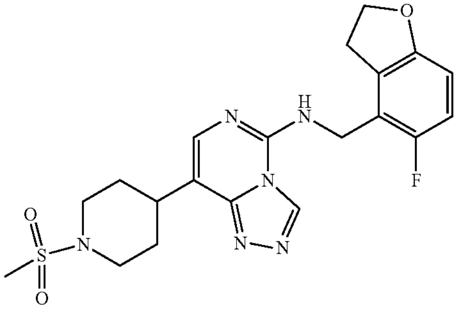

E-Y13-H

Compound E-Y13 (10 mg) was dissolved in 2 mL of methanol, and 10% Pd/C (3 mg) was added, and the reaction was performed at room temperature for 6 hours. The resultant was filtered and separated by column chromatography (DCM:MeOH=20:1) to obtain the target compound E-Y13-H (7 mg, 71%).

$^1$H NMR (400 MHz, DMSO-$d_6$) δ 9.41 (s, 1H), 8.48 (t, J=5.2 Hz, 1H), 7.50 (s, 1H), 6.98-6.90 (m, 1H), 6.70 (dd, J=8.6, 3.9 Hz, 1H), 4.64 (d, J=5.0 Hz, 2H), 4.54 (t, J=8.7 Hz, 2H), 3.69 (d, J=11.6 Hz, 2H), 3.29 (t, J=8.7 Hz, 2H), 3.01 (m, 1H), 2.91 (s, 3H), 2.85 (dd, J=8.7, 6.0 Hz, 2H), 2.07-1.85 (m, 4H). LC-MS: $[M+H]^+$=447.2.

Example 64: Synthesis of Compounds E-Y2-H and SL-ZYE-34

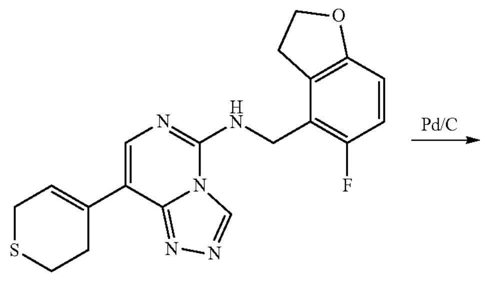

E-Y2

-continued

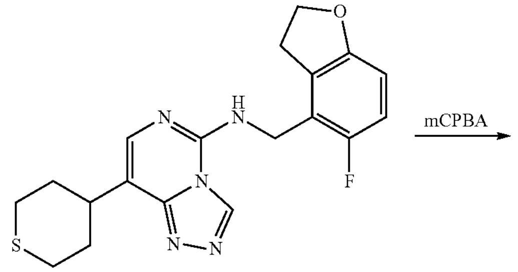

E-Y2-H

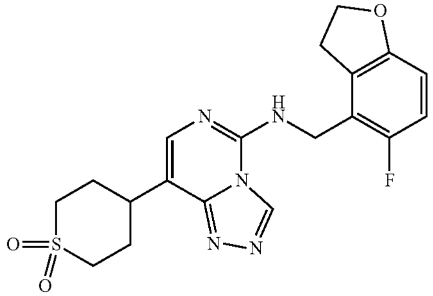

SL-ZYE-34

Compound E-Y (10 mg) was dissolved in 2 mL of methanol, and 10% Pd/C (3 mg) was added, and the reaction was performed at room temperature for 6 hours. The resultant was filtered and the solvent was dried by rotatory evaporator to obtain the target compound E-Y2-H LC-MS: $[M+H]^+$=386.1.

5 mg of E-Y2-H was dissolved in 1 mL of dichloromethane solution, mCPBA (5 mg) was added to the solution, and the reaction was performed at room temperature for 3 h, and the resultant was separated by column chromatography to obtain the target compound SL-ZYE-34 (1.5 mg)

$^1$H NMR (400 MHz, MeOD-$d_4$) δ 9.27 (s, 1H), 7.63 (s, 1H), 6.92-6.78 (m, 1H), 6.65 (dd, J=8.6, 3.7 Hz, 1H), 4.76 (s, 2H), 4.59 (t, J=8.7 Hz, 2H), 3.45-3.33 (m, 5H), 3.17 (d, J=11.8 Hz, 2H), 2.55-2.33 (m, 4H). LC-MS: $[M+H]^+$=418.2.

Example 65: Synthesis of Compound SL-ZYE-23

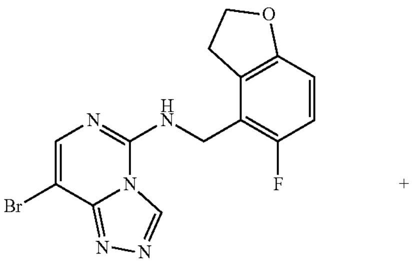

4-1

-continued

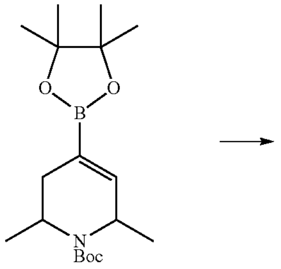

B-10

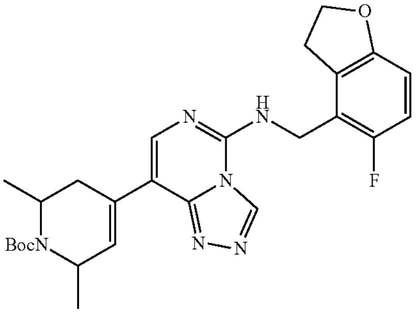

SL-ZYE-23

Bromide 4-1 (72 mg, 0.2 mmol) was dissolved in 6 mL of 1,4-dioxane and 2 mL of a 2 M $Na_2CO_3$ aqueous solution, and borate B-10 (101 mg, 0.4 mmol)) was added thereto and the reaction system was stirred at room temperature for 10 min under Ar atmosphere protection. 10% of allyl palladium (11) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound SL-ZYE-23 (14 mg).

$^1$H NMR (400 MHz, DMSO-$d_6$) δ 9.46 (s, 1H), 8.67 (s, 1H), 7.72 (s, 1H), 7.27 (s, 1H), 7.00-6.87 (m, 1H), 6.70 (dd, J=8.7, 3.8 Hz, 2H), 4.70 (d, J=4.8 Hz, 2H), 4.54 (t, J=8.6 Hz, 2H), 4.30 (d, J=5.7 Hz, 2H), 3.27 (t, J=8.7 Hz, 2H), 2.68 (s, 2H), 1.45 (s, 9H), 1.29 (d, J=6.4 Hz, 3H), 1.09 (d, J=6.4 Hz, 3H). LC-MS: $[M+H]^+$=495.3.

Example 66: Synthesis of Compound SL-ZYE-24

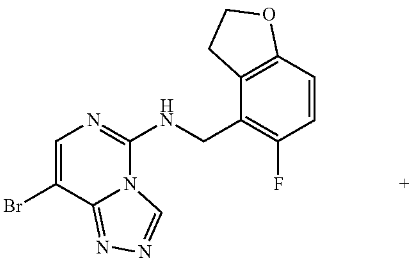

4-1

-continued

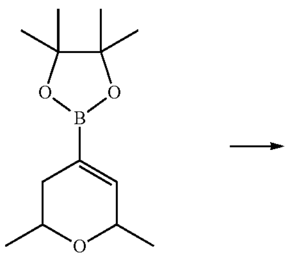

B-11

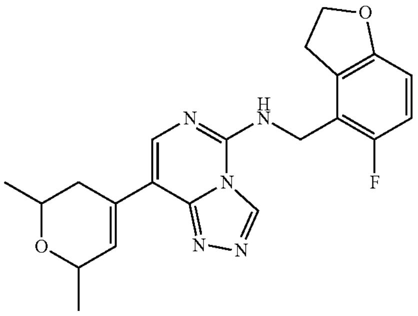

SL-ZYE-24

Bromide 4-1 (72 mg, 0.2 mmol) was dissolved in 6 mL of 1,4-dioxane and 2 mL of a 2 M $Na_2CO_3$ aqueous solution, and borate B-1 (95 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound SL-ZYE-24 (21 mg).

$^1$H NMR (400 MHz, $CDCl_3$) δ 8.93 (s, 1H), 7.66 (s, 1H), 7.24 (s, 1H), 6.88-6.70 (m, 1H), 6.61 (dd, J=8.7, 4.0 Hz, 1H), 6.35 (s, 1H), 4.79 (d, J=5.5 Hz, 2H), 4.61 (t, J=8.7 Hz, 2H), 4.51 (s, 1H), 3.94-3.82 (m, 1H), 3.50 (m, 1H), 3.38 (t, J=8.8 Hz, 2H), 2.45 (t, J=16.4 Hz, 2H), 1.38 (d, J=6.2 Hz, 3H), 1.35 (d, J=6.8 Hz, 3H). LC-MS: $[M+H]^+$=396.2.

Example 67: Synthesis of Compound SL-ZYE-28

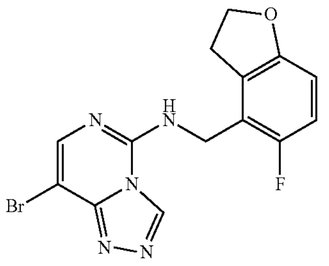

+

4-1

-continued

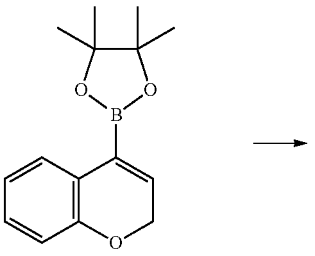

B-12

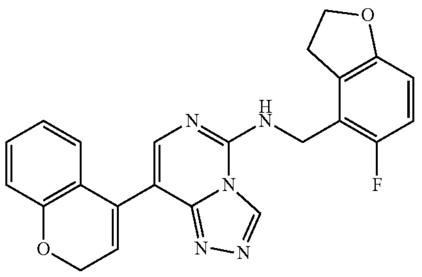

SL-ZYE-28

Bromide 4-1 (72 mg, 0.2 mmol) was dissolved in 6 mL of 1,4-dioxane and 2 mL of a 2 M $Na_2CO_3$ aqueous solution, and borate B-12 (103 mg, 0.4 mmol)) was added thereto and the reaction system was stirred at room temperature for 10 min under Ar atmosphere protection. 10% of allyl palladium (II) chloride dimer (7.3 mg, 0.02 mmol), 20% of sodium 2'-dicyclohexylphosphino-2,6-dimethoxy-1,1'-biphenyl-3-sulfonate hydrate (21.2 mg, 0.04 mmol) were added, and the reaction was performed at 90° C. for 40 min under Ar atmosphere protection. After being cooled and concentrated under reduced pressure, the resultant was separated by column chromatography (DCM:MeOH=20:1), to obtain the target compound SL-ZYE-28 (27 mg, 32%).

$^1$H NMR (400 MHz, MeOD-$d_4$) δ 9.44 (s, 1H), 8.07 (s, 1H), 7.23-7.14 (m, 1H), 6.94-6.79 (m, 4H), 6.68 (dd, J=8.6, 3.9 Hz, 1H), 6.17 (t, J=3.9 Hz, 1H), 4.92 (d, J=3.9 Hz, 2H), 4.88 (s, 2H), 4.61 (t, J=8.7 Hz, 2H), 3.43 (t, J=8.7 Hz, 2H). LC-MS: $[M+H]^+$=416.2.

Example 68: Synthesis of Compound E-Y54-H

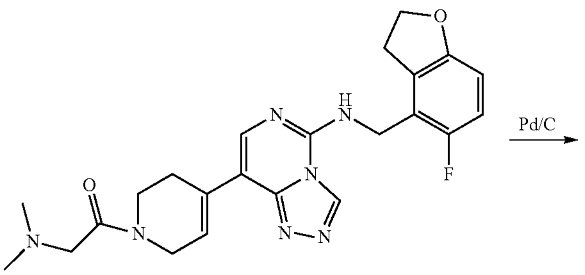

E-Y54

-continued

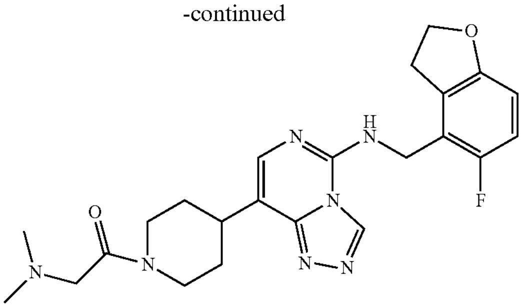

E-Y54-H

Compound E-Y54 (10 mg) was dissolved in 2 mL of methanol, and 10% Pd/C (5 mg) was added, and the reaction was performed at room temperature for 6 hours. The resultant was filtered and separated by column chromatography (DCM:MeOH=20:1) to obtain the target compound E-Y54-H (5 mg).

$^1$H NMR (400 MHz, MeOD-$d_4$) δ 9.27 (s, 1H), 7.57 (s, 1H), 6.91-6.81 (m, 1H), 6.65 (dd, J=8.6, 3.9 Hz, 1H), 4.76 (s, 2H), 4.70 (d, J=13.5 Hz, 1H), 4.58 (t, J=8.7 Hz, 2H), 4.10 (d, J=13.9 Hz, 1H), 3.60 (dd, J=16.9, 6.6 Hz, 2H), 3.36 (dd, J=10.0, 7.6 Hz, 2H), 3.25 (d, J=16.0 Hz, 2H), 2.84 (m, 1H), 2.52 (s, 6H), 2.07 (m, 2H), 1.91 (m, 2H). LC-MS: $[M+H]^+$ =454.2.

Example 69: Synthesis of Compound SL-E1

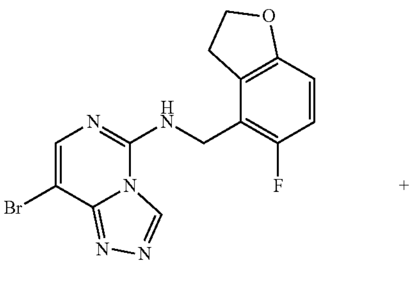

4-1

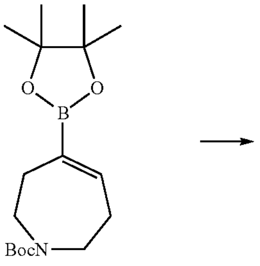

B-13

-continued

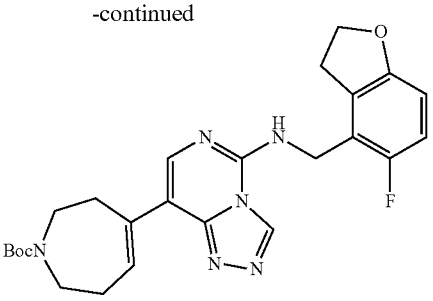

SL-E1

Bromide 4-1 (36 mg, 0.1 mmol) was dissolved in 6 mL of 1,4-dioxane and 2 mL of a 2 M $Na_2CO_3$ aqueous solution, and borate B-13 (64 mg, 0.2 mmol)) was added thereto and the reaction system was stirred at room temperature for 10 min under Ar atmosphere protection. 10% of allyl palladium (II) chloride dimer (3.5 mg, 0.01 mmol), 20% of sodium 2'-dicyclohexylphosphino-2,6-dimethoxy-1,1'-biphenyl-3-sulfonate hydrate (11 mg, 0.02 mmol) were added, and the reaction was performed at 90° C. for 40 min under Ar atmosphere protection. After being cooled and concentrated under reduced pressure, the resultant was separated by column chromatography to obtain the target compound SL-E1 (11 mg). LC-MS: $[M+H]^+$=481.2.

Example 70: Synthesis of Compound SL-E2

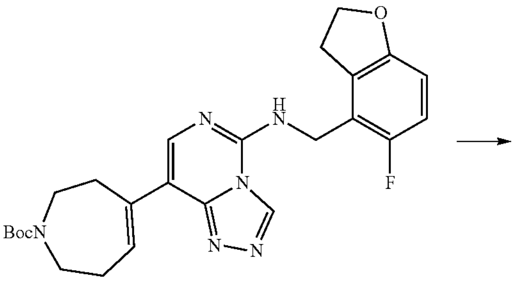

SL-E1

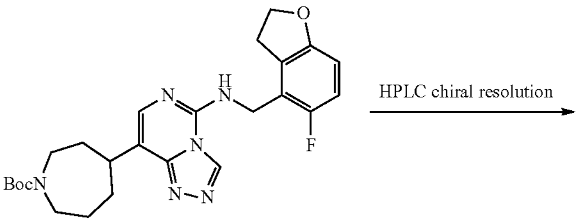

SL-E2

-continued

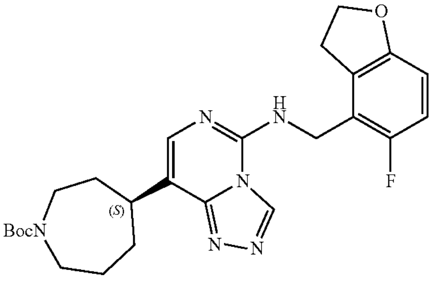

SL-E2-S

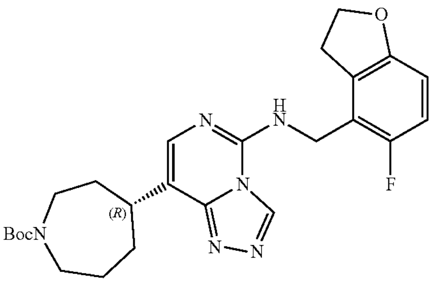

SL-E2-R

Compound SL-E1 (10 mg) was dissolved in 2 mL of methanol, and 10% Pd/C (5 mg) was added, and the reaction was performed at room temperature for 6 hours. The resultant was filtered and separated by column chromatography to obtain the target compound SL-E2 (7 mg). LC-MS: $[M+H]^+$=483.2.

Referring to Example 56, SL-E2 was separated by a chiral chromatography column to obtain optically pure compounds SL-E2-S and SL-E2-R.

Example 71: Synthesis of Compound SL-E3

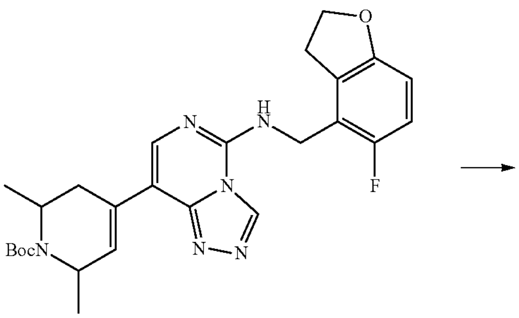

SL-ZYE-23

-continued

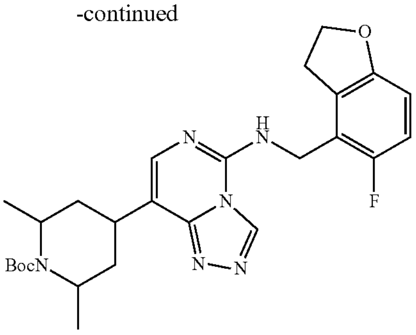

SL-E3

Compound SL-E3 (9 mg) was dissolved in 2 mL of methanol, and 10% Pd/C (4 mg) was added, and the reaction was performed at room temperature for 6 hours. The resultant was filtered and separated by column chromatography to obtain the target compound SL-E3 (5 mg). LC-MS: $[M+H]^+$=497.2.

Example 72: Synthesis of Compound SL-E4

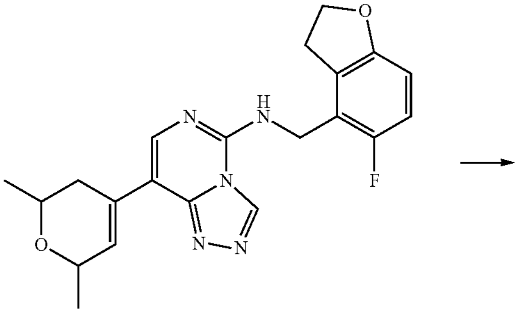

SL-ZYE-24

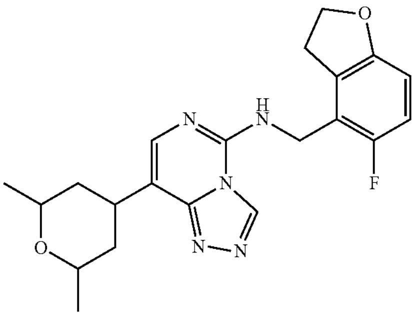

SL-E4

Compound SL-E3 (9 mg) was dissolved in 2 mL of methanol, and 10% Pd/C (4 mg) was added, and the reaction was performed at room temperature for 6 hours. The resultant was filtered and separated by column chromatography to obtain the target compound SL-E4 (5 mg). LC-MS: $[M+H]^+$=398.1.

Example 73: Synthesis of Compound SL-E5

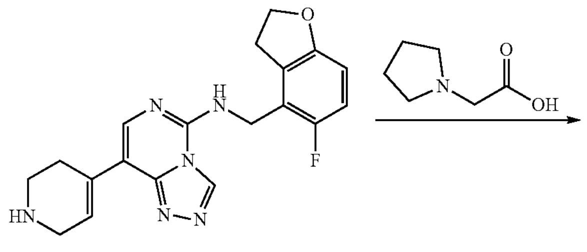

E-Y10

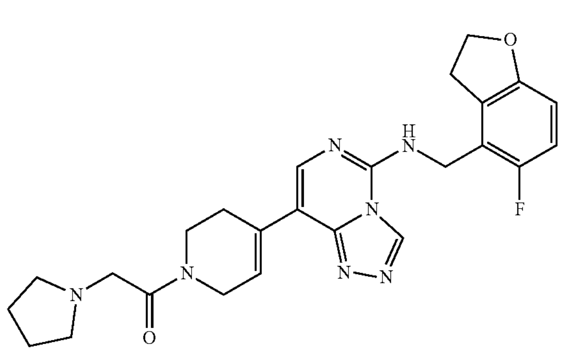

SL-E5

Compound E-Y10 (20 mg) was dissolved in 1 mL of DMF and 0.1 mL of diisopropylethylamine (DIEPA) by stirring. HATU (38 mg) and 2-(1-pyrrolidinyl) acetic acid (CAS: 37386-15-5) (13 mg) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E5 (3 mg). LC-MS: $[M+H]^+$=478.2.

Example 74: Synthesis of Compound SL-E6

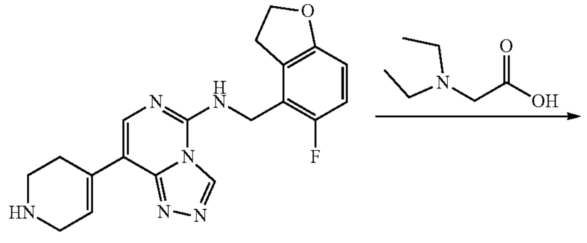

E-Y10

-continued

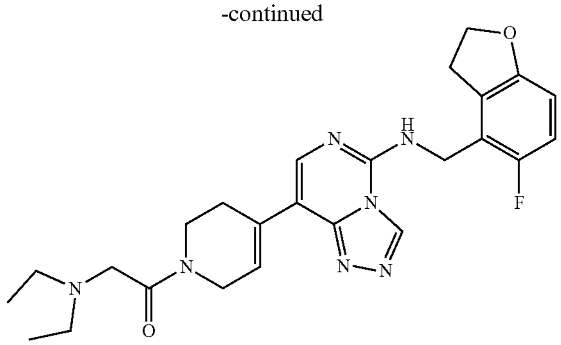

SL-E6

Compound E-Y10 (20 mg) was dissolved in 1 mL of DMF and 0.1 mL of diisopropylethylamine (DIEPA) by stirring. HATU (38 mg, 0.1 mmol) and N. N-diethylglycine (13 mg, 0.1 mmol) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E6 (6 mg). LC-MS: $[M+H]^+$=480.2.

Example 75: Synthesis of Compound SL-E7

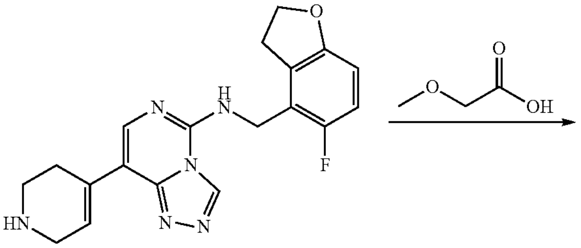

E-Y10

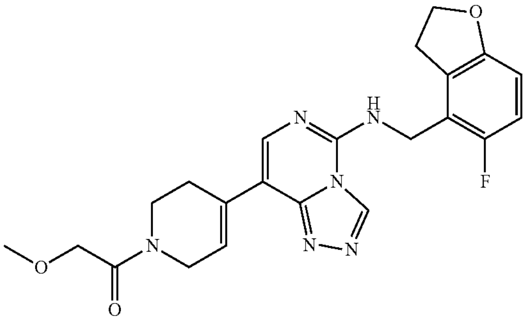

SL-E7

Compound E-Y10 (20 mg) was dissolved in 1 mL of DMF and 0.1 mL of diisopropylethylamine (DIEPA) by stirring. HATU (38 mg) and methoxyacetic acid (CAS: 625-45-6) (9 mg) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E7 (2 mg). LC-MS: $[M+H]^+$=439.2.

Example 76: Synthesis of Compound SL-E8

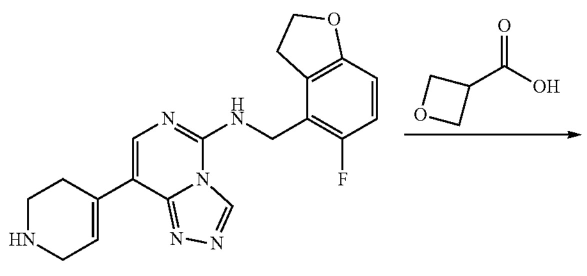

E-Y10

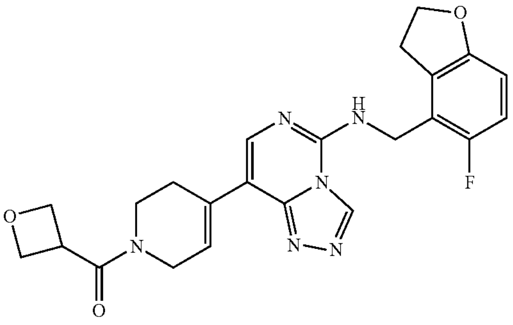

SL-E8

Compound E-Y10 (20 mg) was dissolved in 1 mL of DMF and 0.1 mL of diisopropylethylamine (DIEPA) by stirring. HATU (38 mg, 0.1 mmol) and acid (oxetane-3-carboxylic acid) (10 mg, 0.1 mmol) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E8 (2.5 mg). LC-MS: $[M+H]^+$=451.2.

Example 77: Synthesis of Compound SL-E9

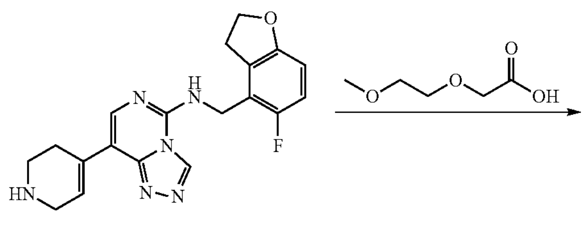

E-Y10

-continued

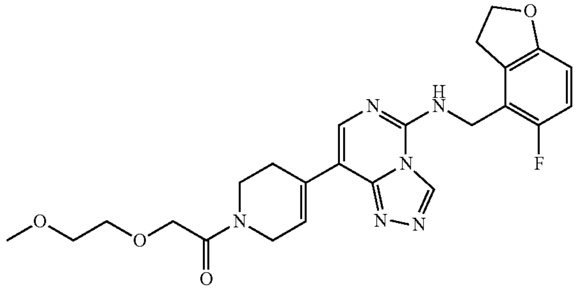

SL-E9

Compound E-Y10 (20 mg) was dissolved in 1 mL of DMF and 0.1 mL of diisopropylethylamine (DIEPA) by stirring. HATU (38 mg) and 2-(2-methoxyethoxy) acetic acid (CAS No.: 16024-56-9) (14 mg) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E9 (5 mg). LC-MS: $[M+H]^+$=483.2.

Example 78: Synthesis of Compound SL-E10

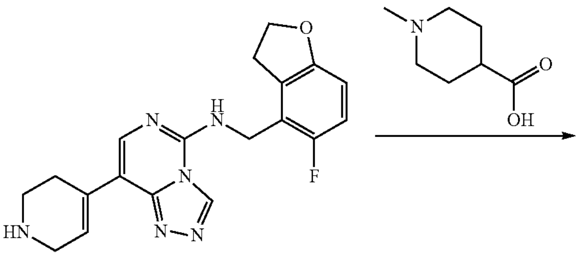

E-Y10

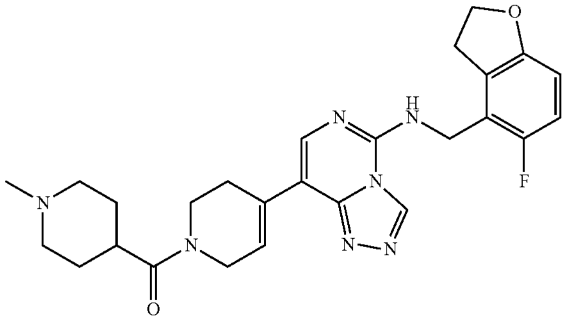

SL-E10

Compound E-Y10 (20 mg) was dissolved in 1 mL of DMF and 0.1 mL of diisopropylethylamine (DIEPA) by stirring. HATU (38 mg, 0.1 mmol) and 1-methylpiperidine-4-carboxylic acid (15 mg, 0.1 mmol) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E10 (6 mg). MS: $[M+H]^{+}$=492.2.

Example 79: Synthesis of Compound SL-E11

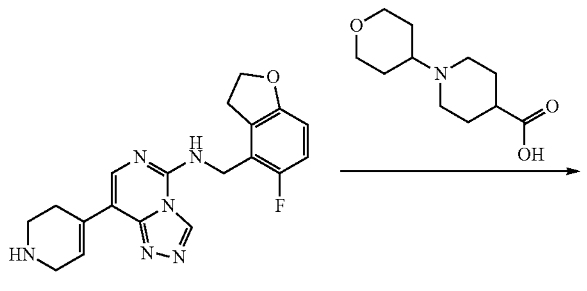

E-Y10

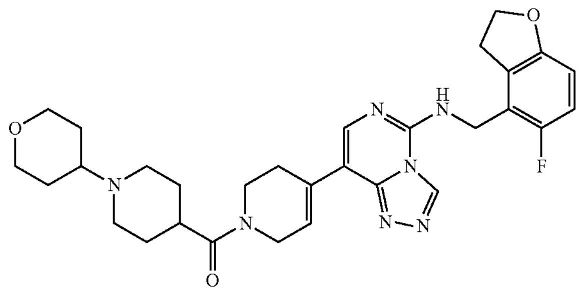

SL-E11

Compound E-Y10 (20 mg) was dissolved in 1 mL of DMF and 0.1 mL of diisopropylethylamine (DIEPA) by stirring. HATU (38 mg, 0.1 mmol) and acid (CAS No.: 1158712-36-7) (22 mg, 0.1 mmol) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E11 (7 mg). LC-MS: $[M+H]^{+}$=562.2.

Example 80: Synthesis of Compound SL-E12

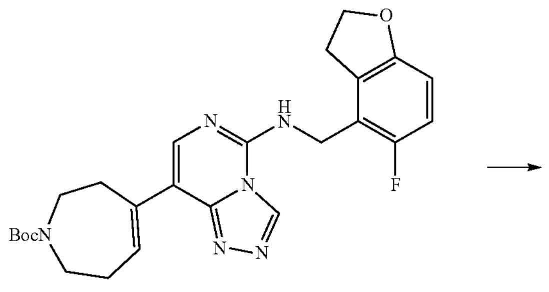

SL-E1

-continued

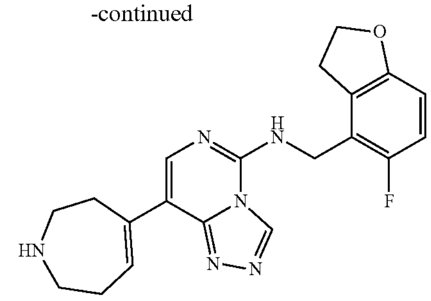

SL-E12

The compound SL-E1 (96 mg, 0.2 mmol) was dissolved in 3 mL of dichloromethane (DCM) and 1 mL of trifluoroacetic acid (TFA), and the mixture was stirred at room temperature for 30 min. After being concentrated, the resultant was directly separated by HPLC to obtain the product SL-E12 (50 mg), LC-MS: $[M+H]^{+}$=381.2.

Example 81: Synthesis of Compound SL-E13

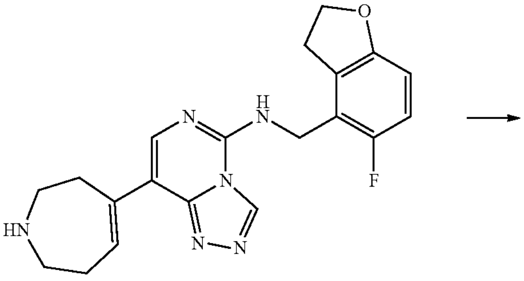

SL-E12

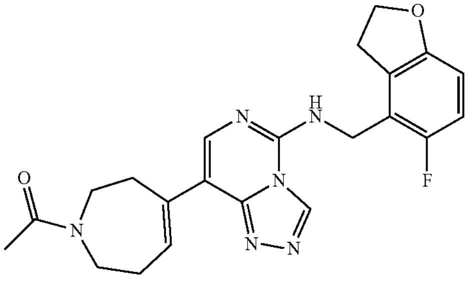

SL-E13

SL-E12 (25 mg) was dissolved in 1 mL of dichloromethane and 0.1 mL of triethylamine (TEA) by stirring. Acetic anhydride ($Ac_2O$, 15 mg) was added at room temperature, and the reaction was performed for 1 hour. After the reaction was completed as indicated by TLC, the resultant was separated by column chromatography to obtain the target compound SL-E13 (6 mg). LC-MS: $[M+H]^{+}$=423.2.

Example 82: Synthesis of Compound SL-E14

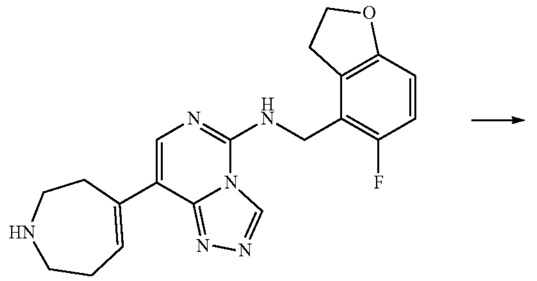

SL-E12

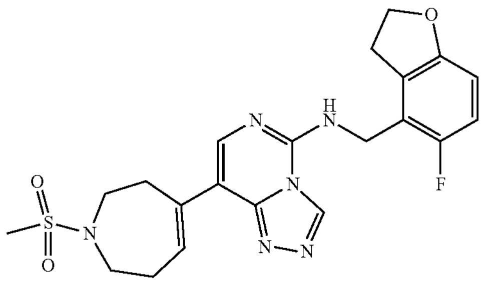

SL-E14

SL-E12 (10 mg) was dissolved in 1 mL of dichloromethane and 0.1 mL of triethylamine (TEA) by stirring. Methanesulfonic anhydride ($Ms_2O$, 8 mg) was added at room temperature, and the reaction was performed for 1 hour. After the reaction was completed as indicated by TLC, the resultant was separated by column chromatography to obtain the target compound SL-E14 (3 mg). $^1H$ NMR (400 MHz, DMSO-$d_6$) δ 9.44 (s, 1H), 8.63 (m, 1H), 7.67 (s, 1H), 6.99-6.90 (m, 1H), 6.82 (t, J=5.9 Hz, 1H), 6.70 (dd, J=8.7, 3.8 Hz, 1H), 4.68 (d, J=4.9 Hz, 2H), 4.54 (t, J=8.7 Hz, 2H), 4.03 (d, J=6.0 Hz, 2H), 3.57-3.48 (m, 2H), 3.31-3.24 (m, 2H), 2.91 (s, 3H), 2.83 (m, 2H), 1.91 (m, 2H). LC-MS: $[M+H]^+$=459.2.

Example 83: Synthesis of Compound SL-E15

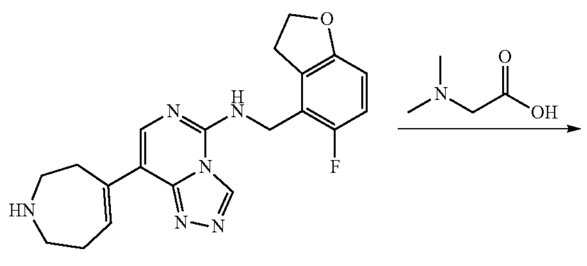

SL-E12

-continued

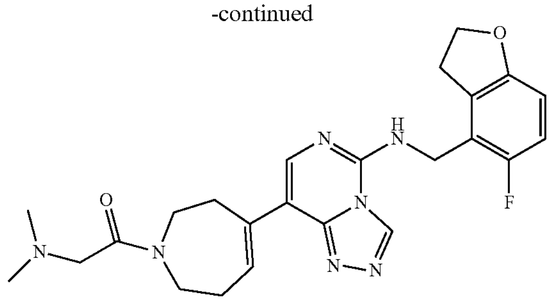

SL-E15

Compound SL-E12 (19 mg, 0.05 mmol) was dissolved in 1 mL of DCM and 0.1 mL of diisopropylethylamine (DIEPA) by stirring. HATU (38 mg, 0.1 mmol) and N, N-dimethylglycine (11 mg, 0.1 mmol) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E15 (2 mg). LC-MS: $[M+H]^+$=466.3.

Example 84: Synthesis of Compound SL-E16

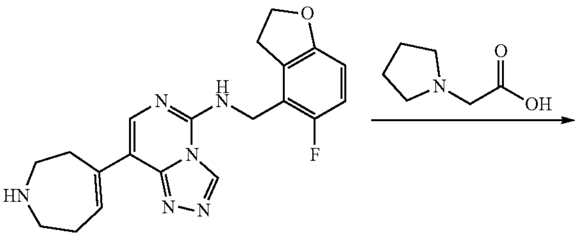

SL-E12

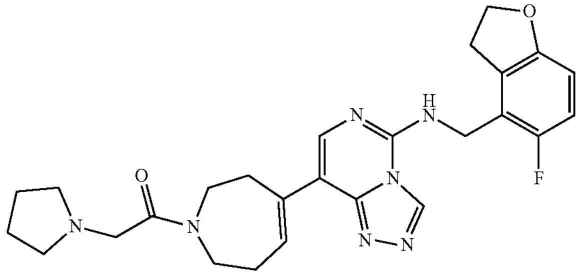

SL-E16

Compound SL-E12 (19 mg, 0.05 mmol) was dissolved in 1 mL of DCM and 0.1 mL of diisopropylethylamine (DIEPA) by stirring. HATU (38 mg, 0.1 mmol) and 2-(1-pyrrolidinyl) acetic acid (CAS: 37386-15-5) (14 mg) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E16 (2 mg). LC-MS: $[M+H]^+$=492.2.

Example 85: Synthesis of Compound SL-E17

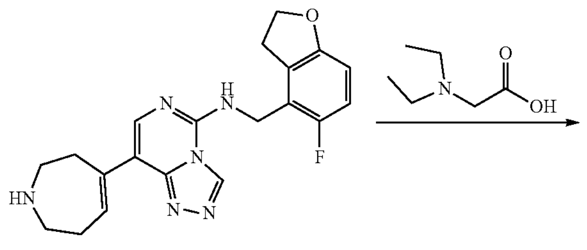

SL-E12

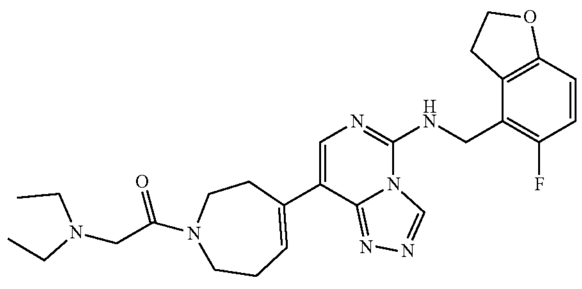

SL-E17

Compound SL-E12 (19 mg, 0.05 mmol) was dissolved in 1 mL of DCM and 0.1 mL of diisopropylethylamine (DIEPA) by stirring. HATU (38 mg, 0.1 mmol) and N, N-diethylglycine (13 mg) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E17 (2 mg). LC-MS: $[M+H]^+$=494.4.

Example 86: Synthesis of Compound SL-E18

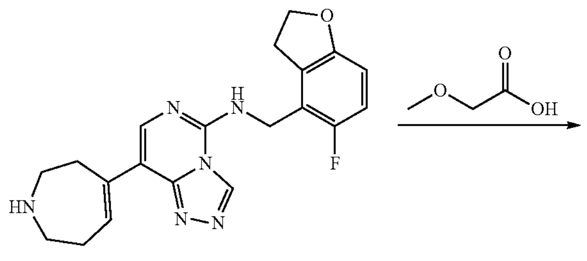

SL-E12

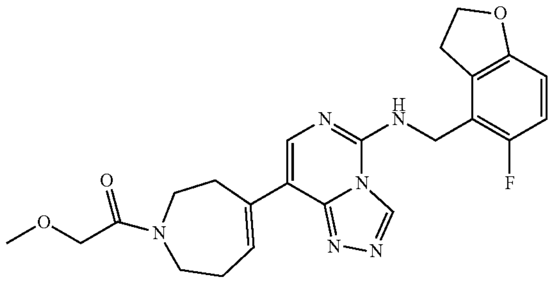

SL-E18

Compound SL-E12 (19 mg, 0.05 mmol) was dissolved in 1 mL of DCM and 0.1 mL of diisopropylethylamine (DIEPA) by stirring. HATU (38 mg) and methoxyacetic acid (CAS: 625-45-6) (11 mg) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E18 (3 mg). LC-MS: $[M+H]^+$=453.2.

Example 87: Synthesis of Compound SL-E19

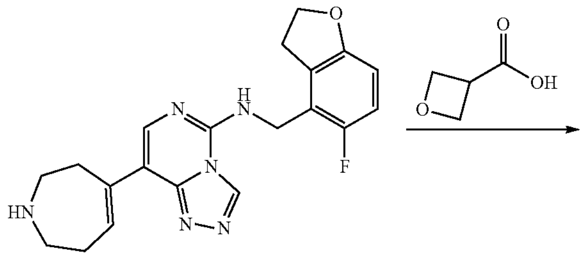

SL-E12

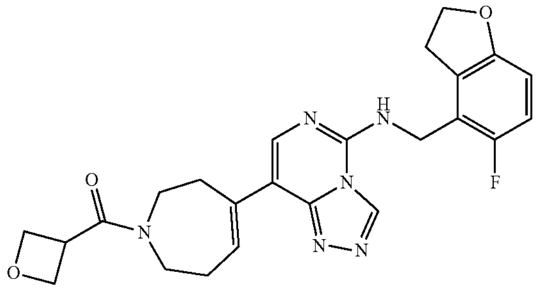

SL-E19

Compound SL-E12 (19 mg, 0.05 mmol) was dissolved in 1 mL of DCM and 0.1 mL of diisopropylethylamine (DIEPA) by stirring. HATU (38 mg, 0.1 mmol) and acid (oxetane-3-carboxylic acid) (10 mg, 0.1 mmol) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E19 (1.5 mg). LC-MS: $[M+H]^+$=465.2.

Example 88: Synthesis of Compound SL-E20

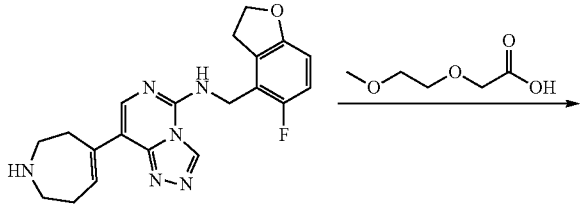

SL-E12

-continued

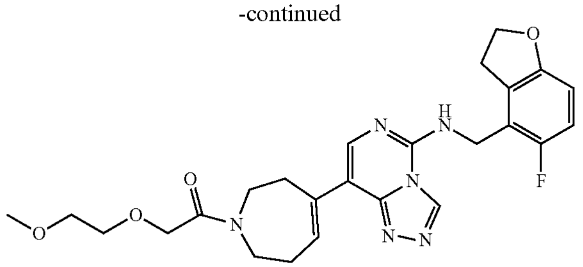

SL-E20

Compound SL-E12 (19 mg, 0.05 mmol) was dissolved in 1 mL of DCM and 0.1 mL of diisopropylethylamine (DIEPA) by stirring. HATU (38 mg) and 2-(2-methoxy-ethoxy) acetic acid (CAS No.: 16024-56-9) (15 mg) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E20 (2 mg). LC-MS: $[M+H]^+=497.2$.

Example 89: Synthesis of Compound SL-E21

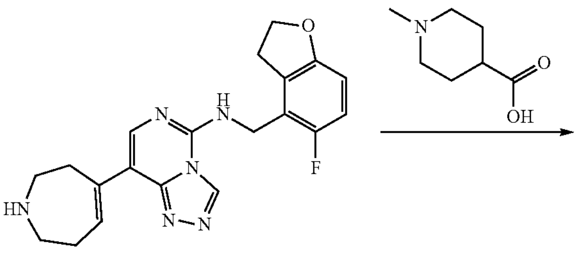

SL-E12

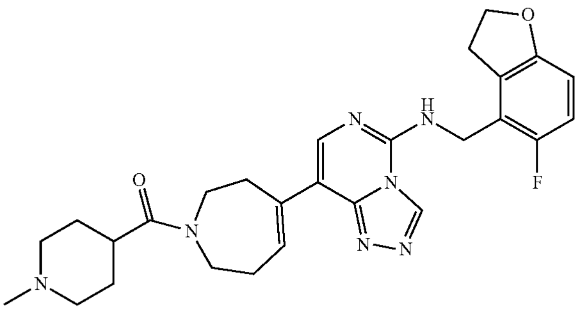

SL-E21

Compound SL-E12 (19 mg, 0.05 mmol) was dissolved in 1 mL of DCM and 0.1 mL of diisopropylethylamine (DIEPA) by stirring. HATU (38 mg, 0.1 mmol) and 1-methylpiperidine-4-carboxylic acid (15 mg, 0.1 mmol) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E21 (3 mg). LC-MS: [M+H1]=506.2.

Example 90: Synthesis of Compound SL-E22

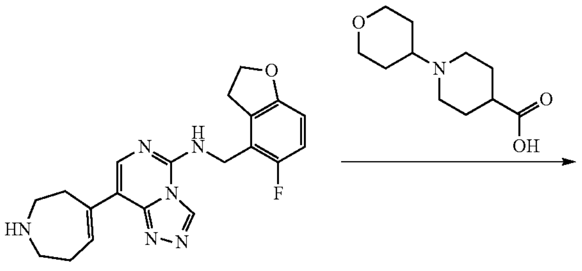

SL-E12

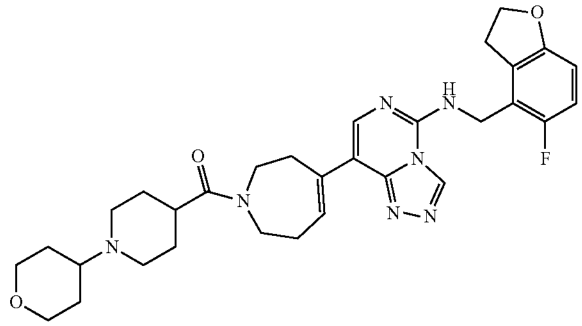

SL-E22

Compound SL-E12 (19 mg, 0.05 mmol) was dissolved in 1 mL of DCM and 0.1 mL of diisopropylethylamine (DIEPA) by stirring. HATU (38 mg, 0.1 mmol) and acid (CAS No.: 1158712-36-7) (22 mg, 0.1 mmol) were added at room temperature, and the reaction was performed for 1 hour. When the reaction was completed as indicated by TLC, the reaction solution was poured into water, and extracted with a large amount of ethyl acetate. After being dried and concentrated, the resultant was separated by column chromatography to obtain the target compound SL-E22 (0.8 mg). LC-MS: $[M+H]^+=576.2$.

Example 91: Synthesis of Compound SL-E23

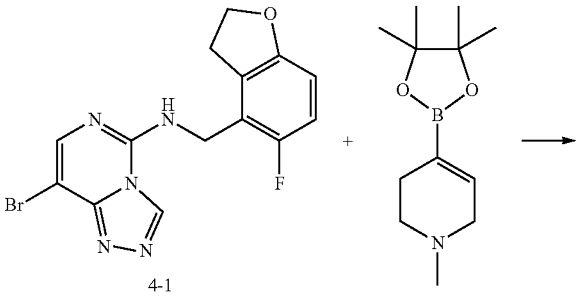

4-1

B-14

-continued

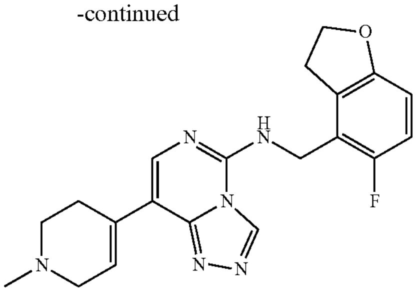

SL-E23

Bromide 4-1 (36 mg, 0.1 mmol) was dissolved in 6 mL of 1,4-dioxane and 2 mL of a 2 M $Na_2CO_3$ aqueous solution, and borate B-14 (44 mg, 0.2 mmol)) was added thereto and the reaction system was stirred at room temperature for 10 min under Ar atmosphere protection. 10% of allyl palladium (II) chloride dimer (3.5 mg, 0.01 mmol), 20% of sodium 2'-dicyclohexylphosphino-2,6-dimethoxy-1,1'-biphenyl-3-sulfonate hydrate (11 mg, 0.02 mmol) were added, and the reaction was performed at 90° C. for 40 min under Ar atmosphere protection. After being cooled and concentrated under reduced pressure, the resultant was separated by column chromatography, to obtain the target compound SL-E23 as a white solid (6 mg). $^1H$ NMR (400 MHz, DMSO-$d_6$) δ 9.47 (d, J=6.2 Hz, 11H), 8.67 (d, J=4.9 Hz, 1H), 7.71 (d, J=8.4 Hz, 1H), 7.30 (m, 1H), 6.94 (t, J=9.4 Hz, 1H), 6.70 (dd, J=8.5, 3.8 Hz, 1H), 4.69 (d, J=4.8 Hz, 2H), 4.57 (m, 2H), 3.47 (m, 2H), 3.28 (t, J=8.8 Hz, 2H), 2.97 (m, 2H), 2.69 (m, 2H), 2.56 (m, 3H). LC-MS: $[M+H]^+$=381.2.

Example 92: Synthesis of Compound SL-E24

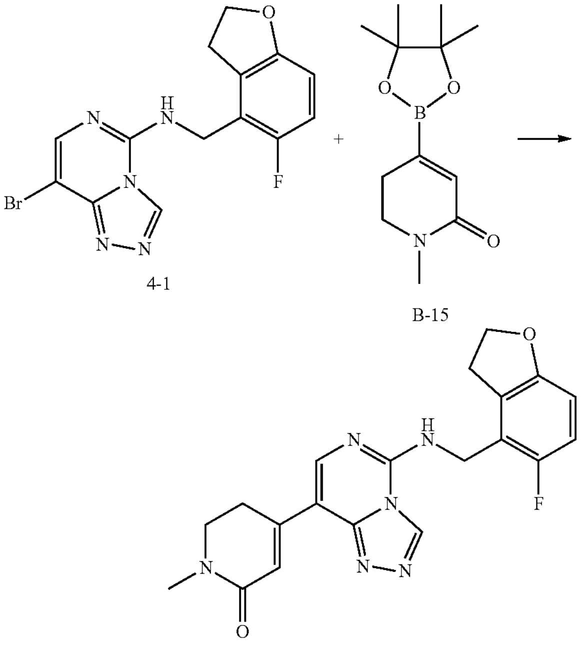

4-1

B-15

SL-E24

Bromide 4-1 (36 mg, 0.1 mmol) was dissolved in 6 mL of 1,4-dioxane and 2 mL of a 2 M $Na_2CO_3$ aqueous solution, and borate B-15 (47 mg, 0.2 mmol)) was added thereto and the reaction system was stirred at room temperature for 10 min under Ar atmosphere protection. 10% of allyl palladium (II) chloride dimer (3.5 mg, 0.01 mmol), 20% of sodium 2'-dicyclohexylphosphino-2,6-dimethoxy-1,1'-biphenyl-3-sulfonate hydrate (11 mg, 0.02 mmol) were added, and the reaction was performed at 90° C. for 40 min under Ar atmosphere protection. After being cooled and concentrated under reduced pressure, the resultant was separated by column chromatography, to obtain the target compound SL-E24 (3.5 mg). $^1H$ NMR (400 MHz, $CD_3OD+CDCl_3$) δ 9.31 (s, 1H), 7.94 (s, 1H), 7.18 (s, 1H), 6.83 (m, 1H), 6.65 (m, 1H), 4.79 (s, 2H), 4.60 (t, J=8.8 Hz, 2H), 3.64 (t, J=7.3 Hz, 2H), 3.37 (m, 2H), 3.06 (s, 3H), 2.99 (m, 2H). LC-MS: $[M+H]^+$=395.1.

Example 93: Synthesis of Compound SL-E25

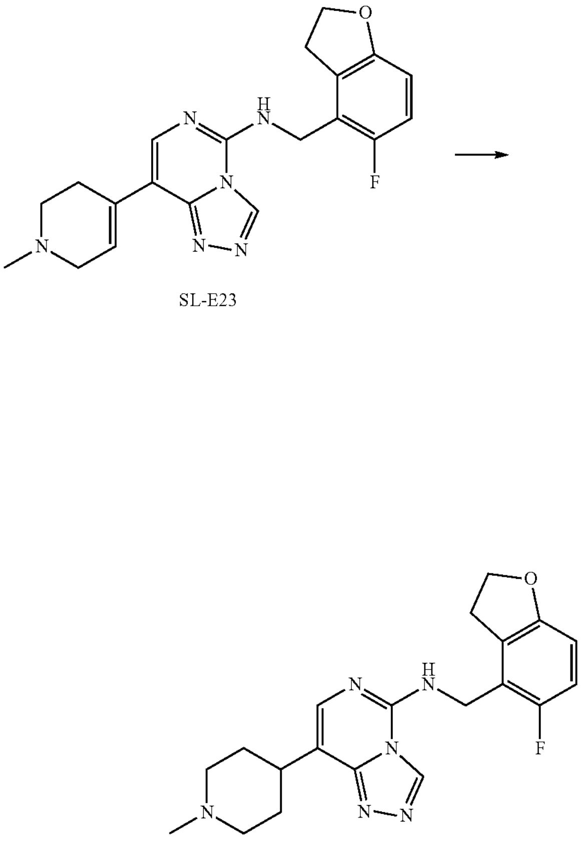

SL-E23

SL-E25

Compound SL-E23 (10 mg) was dissolved in 2 mL of methanol, and 10% Pd/C (4 mg) was added, and the reaction was performed at room temperature for 6 hours. The resultant was filtered and separated by column chromatography to obtain the target compound SL-E25 (5 mg). $^1H$ NMR (400 MHz, $CD_3OD$) δ 9.29 (s, 1H), 7.61 (s, 1H), 6.90-6.80 (m, 1H), 6.63 (m, 1H), 4.76 (s, 2H), 4.66-4.51 (m, 2H), 3.58-3.44 (m, 2H), 3.40-3.34 (m, 2H), 3.23-3.11 (m, 1H), 3.09-2.95 (m, 2H), 2.83 (s, 3H), 2.27-2.17 (m, 4H). LC-MS: $[M+H]^+$=383.2.

Example 94: Synthesis of Compound SL-E26

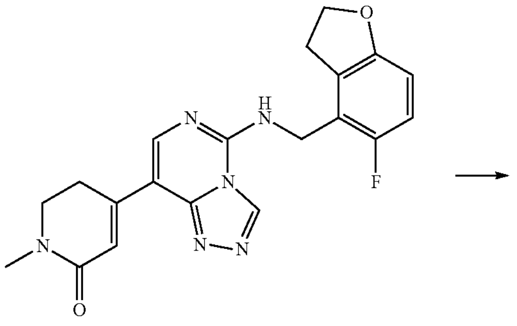

SL-E24

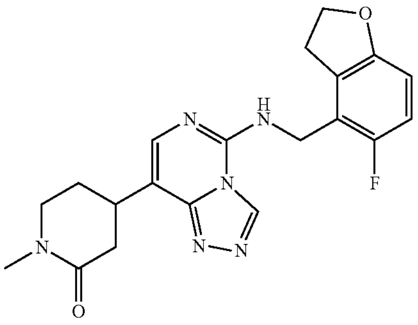

SL-E26

Compound SL-E24 (10 mg) was dissolved in 2 mL of methanol, and 10% Pd/C (4 mg) was added, and the reaction was performed at room temperature for 6 hours. The resultant was filtered and separated by column chromatography to obtain the target compound SL-E26 (2 mg). $^1$H NMR (400 MHz, $CDCl_3$) δ 8.94 (s, 1H), 7.45 (s, 1H), 6.84 (t, J=9.4 Hz, 1H), 6.66 (dd, J=8.6, 3.9 Hz, 1H), 6.37 (m, 1H), 4.77 (d, J=5.3 Hz, 2H), 4.63 (t, J=8.7 Hz, 2H), 3.49 (m, 2H), 3.39 (m, 3H), 2.99 (s, 3H), 2.75 (m, 2H), 2.33 (m, 2H). LC-MS: $[M+H]^+$=397.2.

Example 95: Synthesis of Compound SL-E29

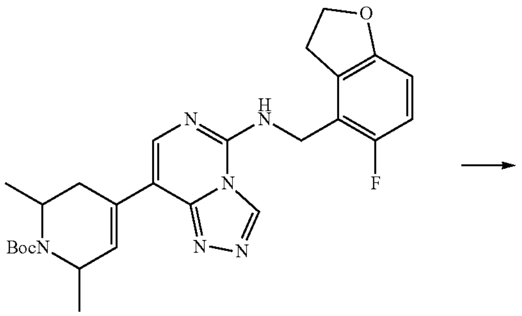

SL-ZYE-23

-continued

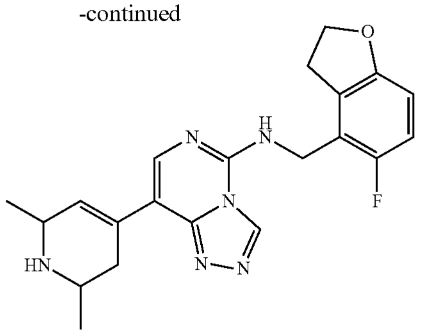

SL-E29

Compound SL-ZYE-23 (50 mg, 0.1 mmol) was dissolved in 3 mL of dichloromethane (DCM) and 1 mL of trifluoroacetic acid (TFA), and the mixture was stirred at room temperature for 30 min. After being concentrated, the resultant was directly separated by HPLC to obtain the product SL-E29 (38 mg), LC-MS: [M+H]+=395.2.

Example 96: Synthesis of Compound SL-E30

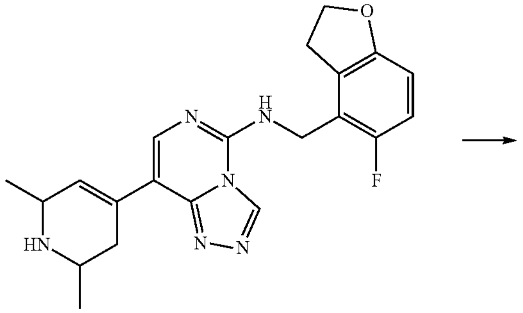

SL-E29

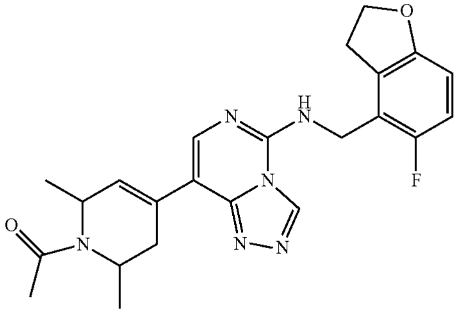

SL-E30

SL-E29 (10 mg) was dissolved in 1 mL of dichloromethane and 0.1 mL of triethylamine (TEA) by stirring. Acetic anhydride ($Ac_2O$, 8 mg) was added at room temperature, and the reaction was performed for 1 hour. After the reaction was completed as indicated by TLC, the resultant was separated by column chromatography to obtain the target compound SL-E30 (4 mg). LC-MS: $[M+H]^+$=437.2.

Example 97: Synthesis of Compound SL-E31

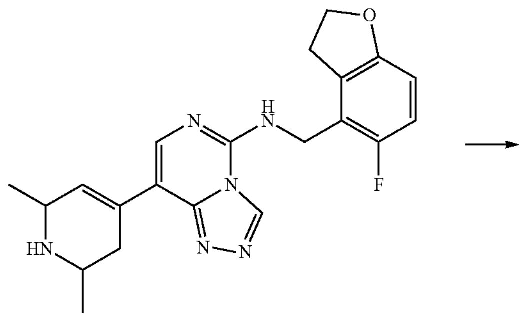

SL-E29

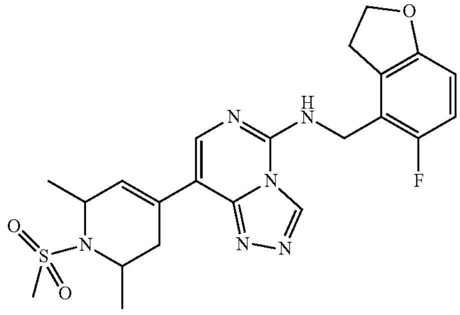

SL-E31

SL-E29 (10 mg) was dissolved in 1 mL of dichloromethane and 0.1 mL of triethylamine (TEA) by stirring. Methanesulfonic anhydride ($Ms_2O$, 7 mg) was added at room temperature, and the reaction was performed for 1 hour. After the reaction was completed as indicated by TLC, the resultant was separated by column chromatography to obtain the target compound SL-E31 (3 mg). LC-MS: $[M+H]^+$=473.2.

Example 98: Synthesis of Compound SL-E32

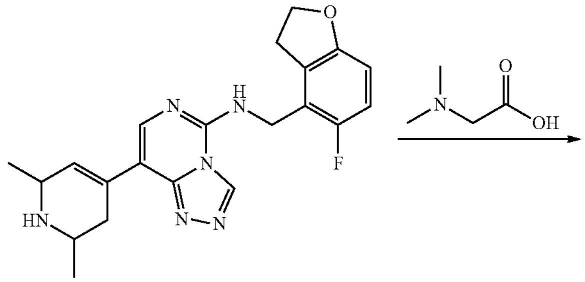

SL-E29

-continued

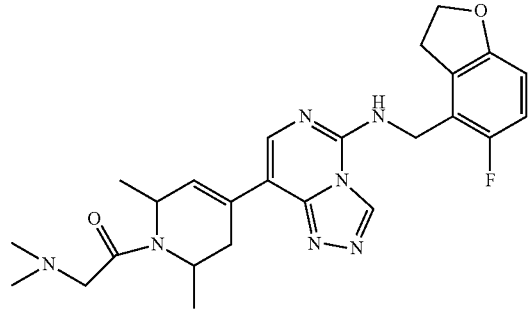

SL-E32

SL-E29 (12 mg) was dissolved in 1 mL of dichloromethane and 0.1 mL of triethylamine (TEA) by stirring. HATU (30 mg) and N,N-dimethylglycine (9 mg) were added at room temperature, and the reaction was performed for 1 hour. After the reaction was completed as indicated by TLC, the reaction solution was poured into water, and extracted with a large amount of ethyl acetate. After being dried and concentrated, the resultant was separated by column chromatography to obtain the target compound SL-E32 (4 mg). LC-MS: $[M+H]^+$=480.2.

Example 99: Synthesis of Compound SL-E33

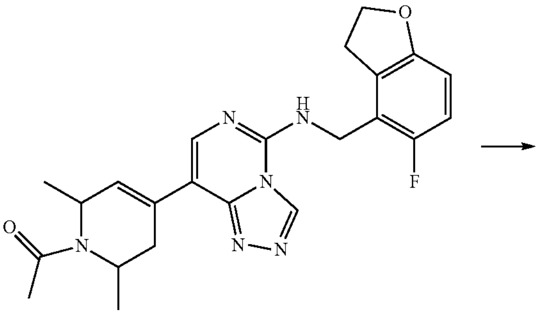

SL-E30

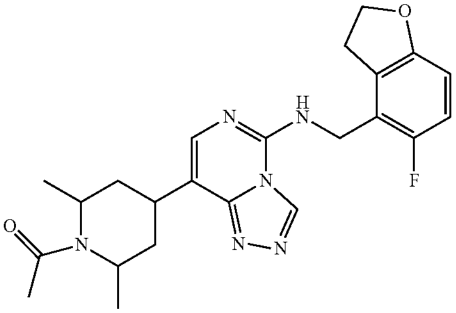

SL-E33

Compound SL-E30 (10 mg) was dissolved in 2 mL of methanol, and 10% Pd/C (4 mg) was added, and the reaction was performed at room temperature for 6 hours. The resultant was filtered and separated by column chromatography to obtain the target compound SL-E33 (4 mg). LC-MS: $[M+H]^+$=439.2.

Example 100: Synthesis of Compound SL-E34

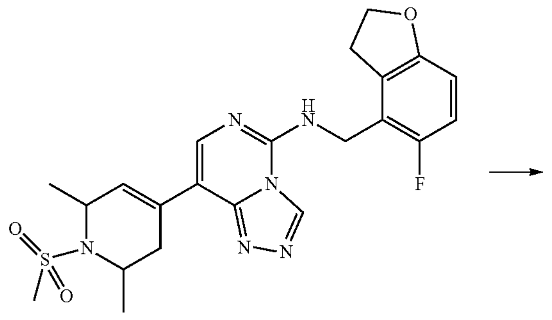

SL-E31

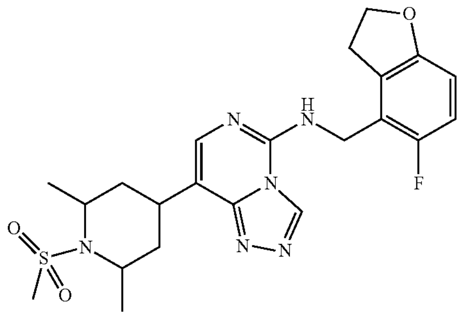

SL-E34

Compound SL-E31 (10 mg) was dissolved in 2 mL of methanol, and 10% Pd/C (4 mg) was added, and the reaction was performed at room temperature for 6 hours. The resultant was filtered and separated by column chromatography to obtain the target compound SL-E34 (4 mg). LC-MS: $[M+H]^+=475.2$.

Example 101: Synthesis of Compound SL-E35

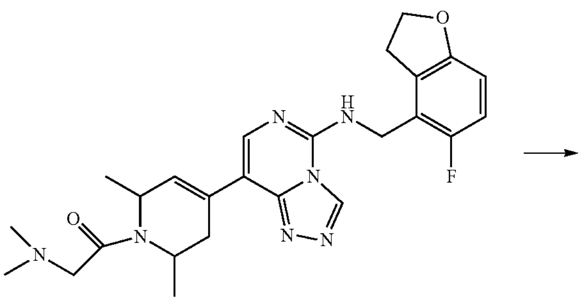

SL-E32

-continued

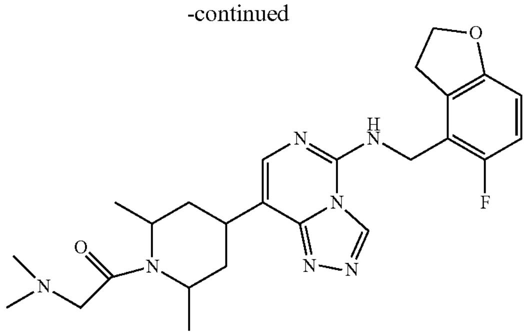

SL-E35

Compound SL-E32 (10 mg) was dissolved in 2 mL of methanol, and 10% Pd/C (4 mg) was added and the reaction was performed at room temperature for 6 hours. The resultant was filtered and separated by column chromatography to obtain the target compound SL-E35 (4 mg). LC-MS: $[M+H]^+=482.2$.

Example 102: Synthesis of Compound SL-E36

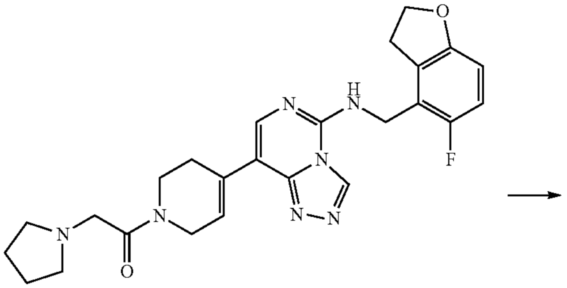

SL-E5

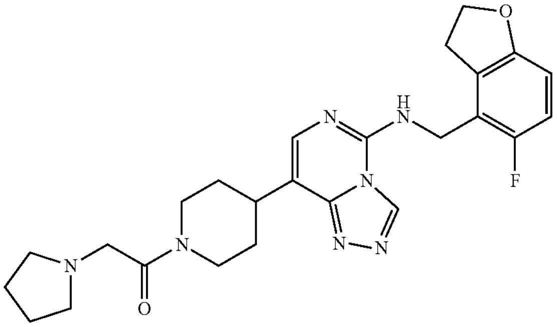

SL-E36

Compound SL-E5 (10 mg) was dissolved in 2 mL of methanol, and 10% Pd/C (4 mg) was added and the reaction was performed at room temperature for 6 hours. The resultant was filtered and separated by column chromatography to obtain the target compound SL-E36 (5 mg). LC-MS: $[M+H]^3=480.2$.

Example 103: Synthesis of Compound SL-E37

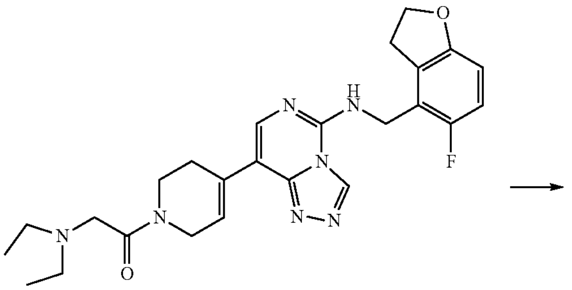

SL-E6

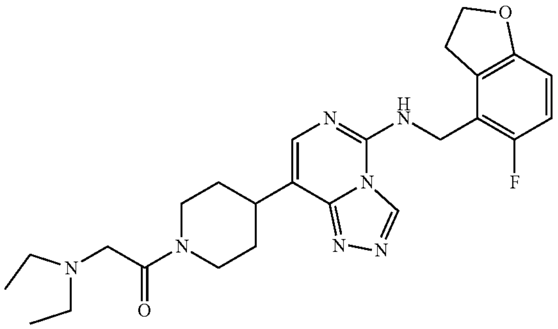

SL-E37

Compound SL-E6 (10 mg) was dissolved in 2 mL of methanol, and 10% Pd/C (4 mg) was added and the reaction was performed at room temperature for 6 hours. The resultant was filtered and separated by column chromatography to obtain the target compound SL-E37 (5 mg). LC-MS: $[M+H]^+$=482.2.

Example 104: Synthesis of Compound SL-E38

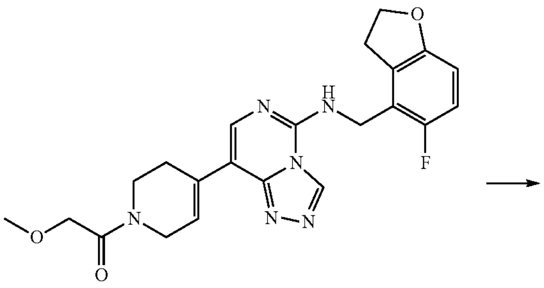

SL-E7

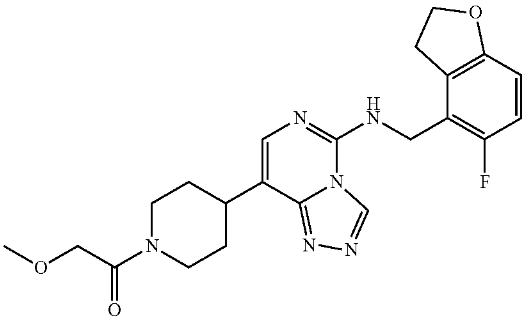

SL-E38

Compound SL-E7 (10 mg) was dissolved in 2 mL of methanol, and 10% Pd/C (4 mg) was added and the reaction was performed at room temperature for 6 hours. The resultant was filtered and separated by column chromatography to obtain the target compound SL-E38 (5 mg). LC-MS: $[M+H]^+$=441.2.

Example 105: Synthesis of Compound SL-E39

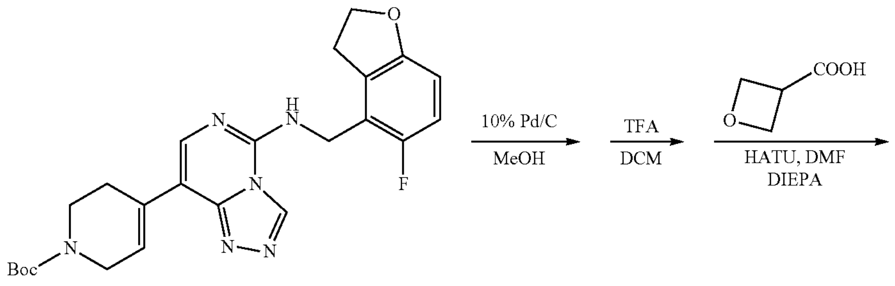

E-Y3

-continued

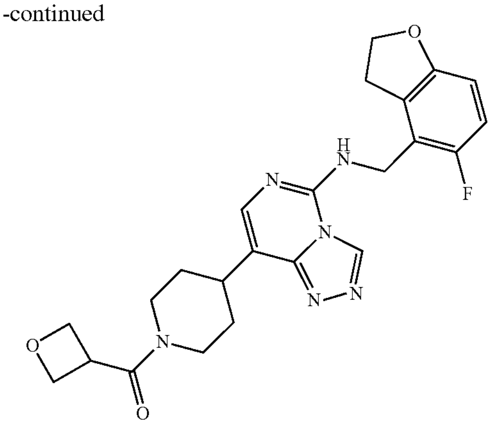

SL-E39

Compound E-Y3 (10 mg) was dissolved in 2 mL of methanol, and 10% Pd/C (4 mg) was added and the reaction was performed at room temperature for 3 hour. The solution was filtered through celite. After the filtrate was dried by rotatory evaporation, the resultant was dissolved in 3 mL of dichloromethane (DCM) and 1 mL of trifluoroacetic acid (TFA), and the reaction system was stirred at room temperature for 30 min. After the solvent was concentrated, the residue was further dissolved in 1 mL of DMF and 0.1 mL of diisopropylethylamine (DIEPA), and HATU (15 mg) and acid (oxetane-3-carboxylic acid) (9 mg) were added at room temperature and the reaction was performed for 1 hour. The reaction solution was poured into water, and extracted with a large amount of ethyl acetate. After being dried and concentrated, the resultant was separated by column chromatography to obtain the target compound SL-E39 (0.7 mg). LC-MS: $[M+H]^+$=453.4.

Example 106: Synthesis of Compound SL-E40

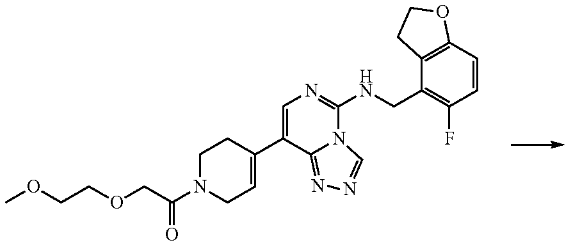

SL-E9

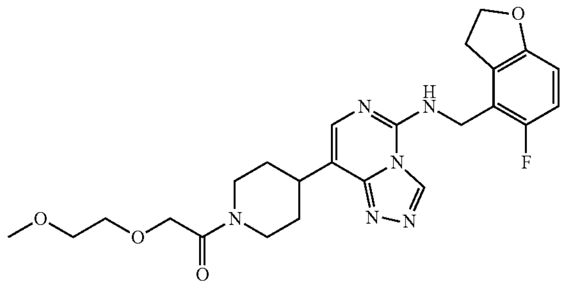

SL-E40

Compound SL-E9 (10 mg) was dissolved in 2 mL of methanol, and 10% Pd/C (4 mg) was added and the reaction was performed at room temperature for 6 hours. The resultant was filtered and separated by column chromatography to obtain the target compound SL-E40 (5 mg). LC-MS: $[M+H]^+$=485.2.

Example 107: Synthesis of Compound SL-E41

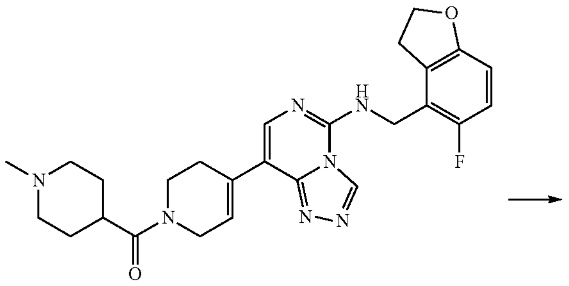

SL-E10

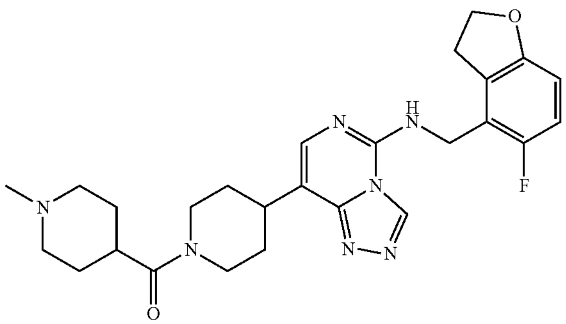

SL-E41

SL-E10 (10 mg) was dissolved in 2 mL of methanol, and 10% Pd/C (4 mg) was added and the reaction was performed at room temperature for 6 hours. The resultant was filtered and separated by column chromatography to obtain the target compound SL-E41 (5 mg). LC-MS: $[M+H]^+$=494.3

Example 108: Synthesis of Compound SL-E42

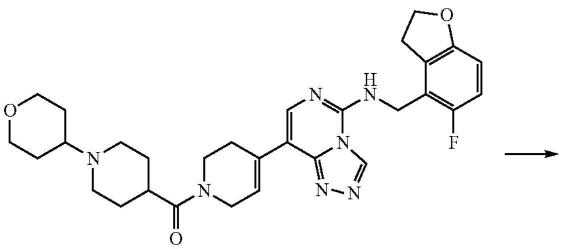

SL-E11

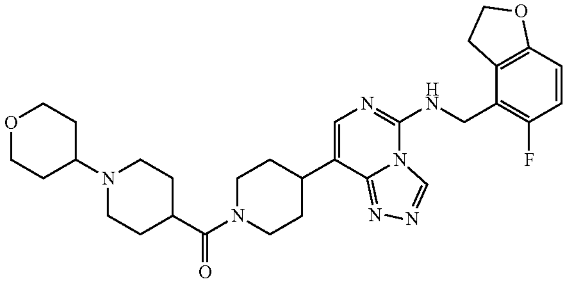

SL-E42

SL-E11 (10 mg) was dissolved in 2 mL of methanol, and 10% Pd/C (4 mg) was added and the reaction was performed at room temperature for 6 hours. The resultant was filtered and separated by column chromatography to obtain the target compound SL-E42 (5 mg). LC-MS: $[M+H]^+=564.2$.

Example 109: Synthesis of Compounds SL-E43, SL-E43-S, SL-E43-R

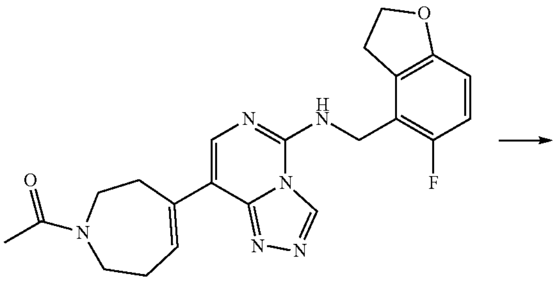

SL-E13

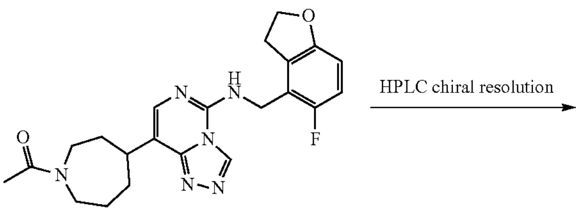

SL-E43

-continued

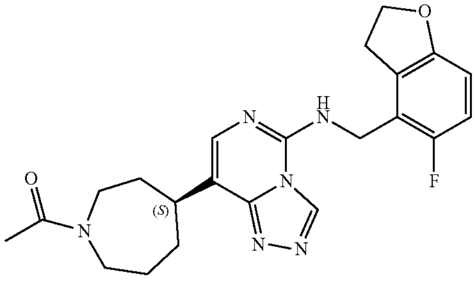

SL-E43-S

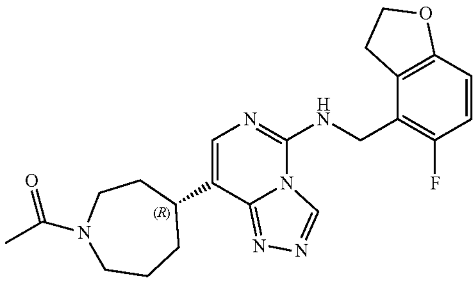

SL-E43-R

SL-E13 (10 mg) was dissolved in 2 mL of methanol, and 10% Pd/C (4 mg) was added and the reaction was performed at room temperature for 6 hours. The resultant was filtered and separated by column chromatography to obtain the target compound SL-E43 (5 mg) LC-MS: $[M+H]^+=425.2$.

Referring to example 56, SL-E43 was separated by chiral chromatography to obtain optically pure compounds SL-E43-S and SL-E43-R.

Example 110; Synthesis of Compounds SL-E44, SL-E44-S, SL-E44-R

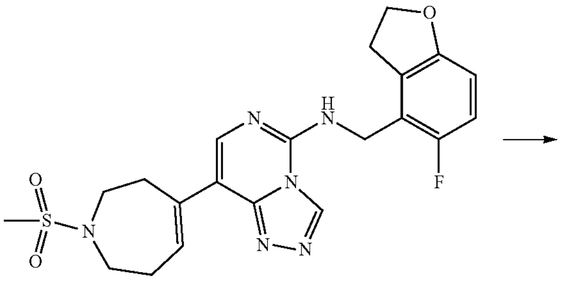

SL-E14

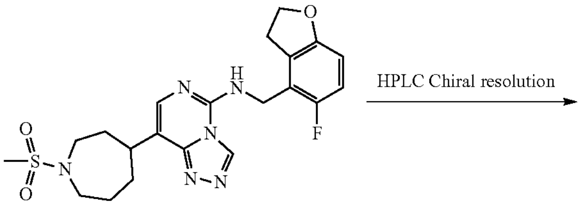

SL-E44

-continued

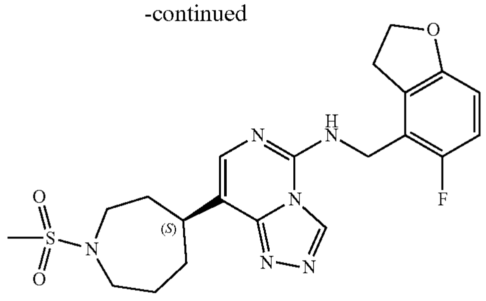

SL-E44-S

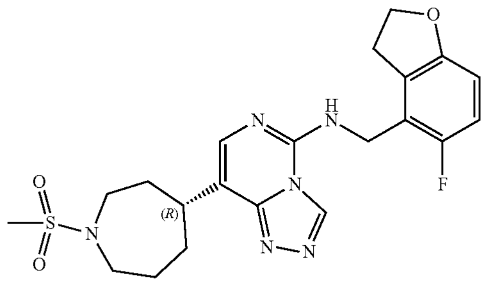

SL-E44-R

SL-E14 (10 mg) was dissolved in 2 mL of methanol, and 10% Pd/C (4 mg) was added and the reaction was performed at room temperature for 6 hours. The resultant was filtered and separated by column chromatography to obtain the target compound SL-E44 (5 mg). LC-MS: $[M+H]^+$=461.2.

Referring to example 56, SL-E44 was separated by chiral chromatography to obtain optically pure compounds SL-E44-S and SL-E44-R.

Example 111 Synthesis of Compound SL-E45, SL-E45-S, SL-E45-R

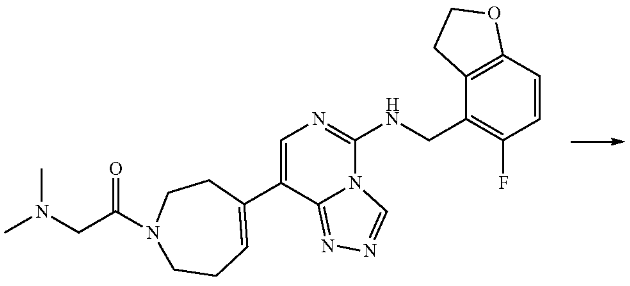

SL-E15

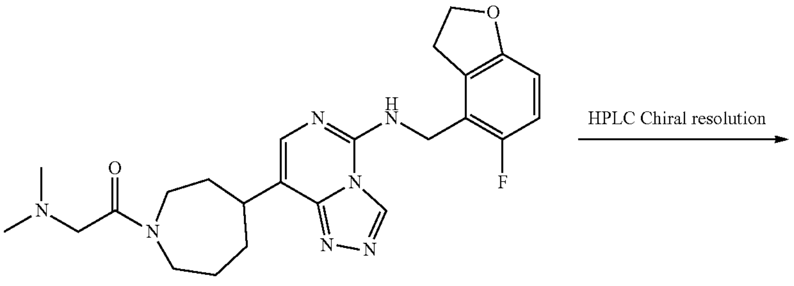

SL-E45

-continued

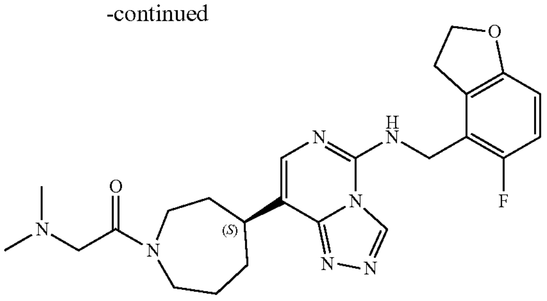

SL-E45-S

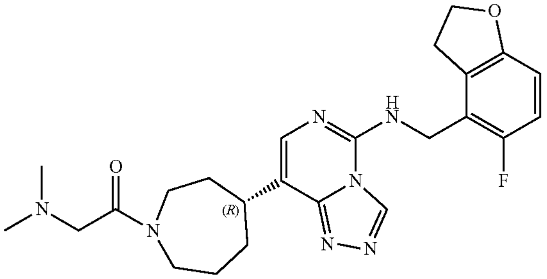

SL-E45-R

SL-E15 (10 mg) was dissolved in 2 mL of methanol, and 10% Pd/C (4 mg) was added and the reaction was performed at room temperature for 6 hours. The resultant was filtered and separated by column chromatography to obtain the target compound SL-E45 (5 mg). LC-MS: $[M+H]^+=468.2$.

Referring to example 56, SL-E45 was separated by chiral chromatography to obtain optically pure compounds SL-E45-S and SL-E45-R.

Example 112: Synthesis of Compounds SL-E46, SL-E46-S, SL-E46-R

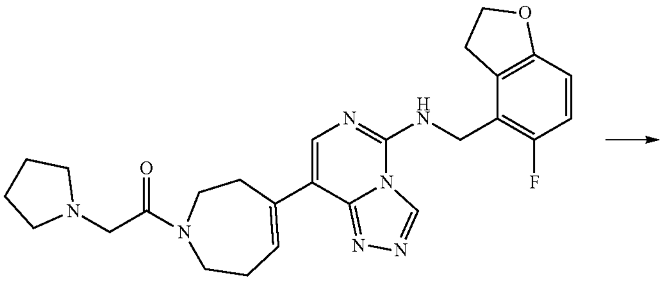

SL-E16

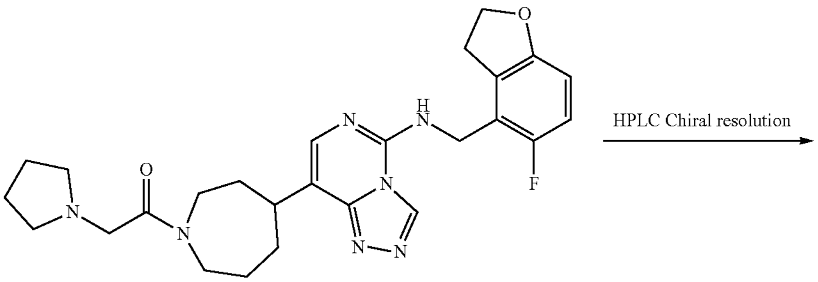

SL-E46

-continued

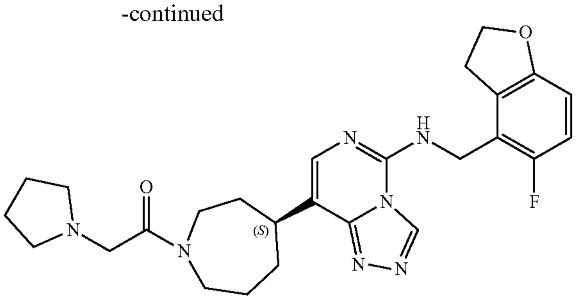

SL-E46-S

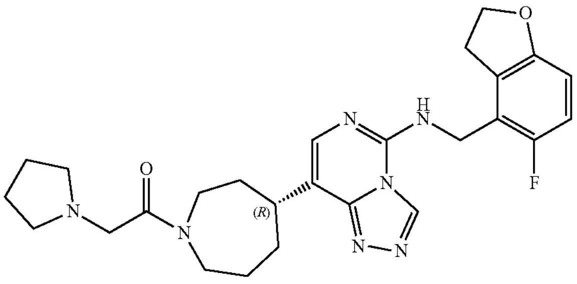

SL-E46-R

SL-E16 (10 mg) was dissolved in 2 mL of methanol, and 10% Pd/C (4 mg) was added and the reaction was performed at room temperature for 6 hours. The resultant was filtered and separated by column chromatography to obtain the target compound SL-E46 (5 mg). LC-MS: $[M+H]^+$=494.2.

Referring to example 56, SL-E46 was separated by chiral chromatography to obtain optically pure compounds SL-E46-S and SL-E46-R.

Example 113: Synthesis of Compound SL-E47

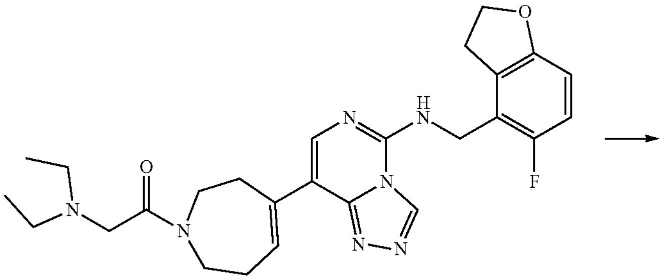

SL-E17

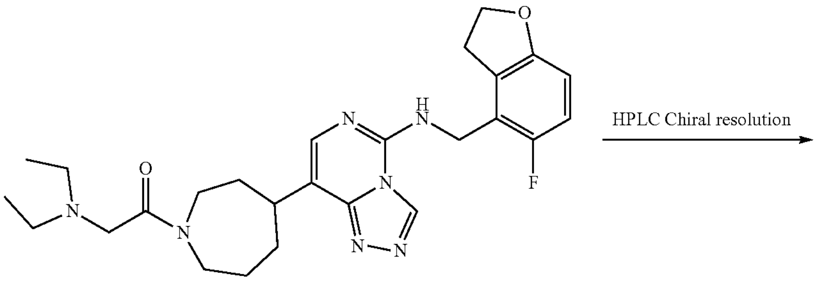

SL-E47

-continued

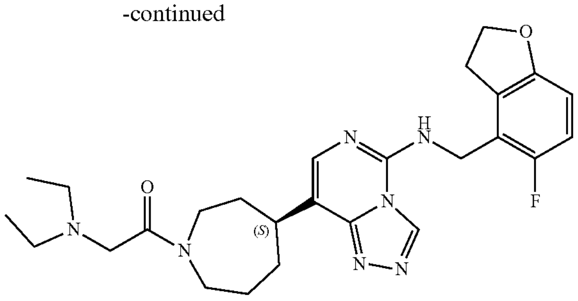

SL-E47-S

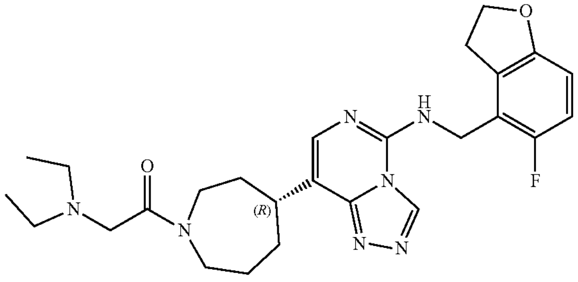

SL-E47-R

SL-E17 (10 mg) was dissolved in 2 mL of methanol, and 10% Pd/C (4 mg) was added and the reaction was performed at room temperature for 6 hours. The resultant was filtered and separated by column chromatography to obtain the target compound SL-E47 (4 mg). LC-MS: $[M+H]^+$=496.2.

Referring to example 56, SL-E47 was separated by chiral chromatography to obtain optically pure compounds SL-E47-S and SL-E47-R.

Example 114: Synthesis of Compound SL-E48

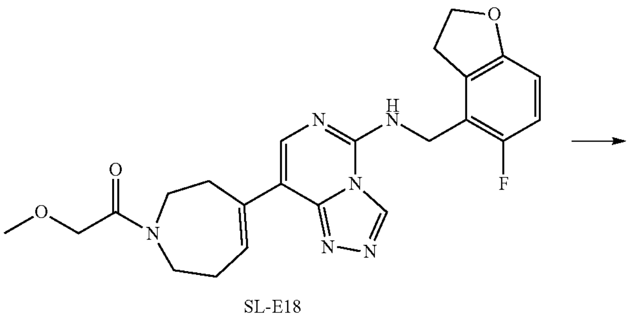

SL-E18

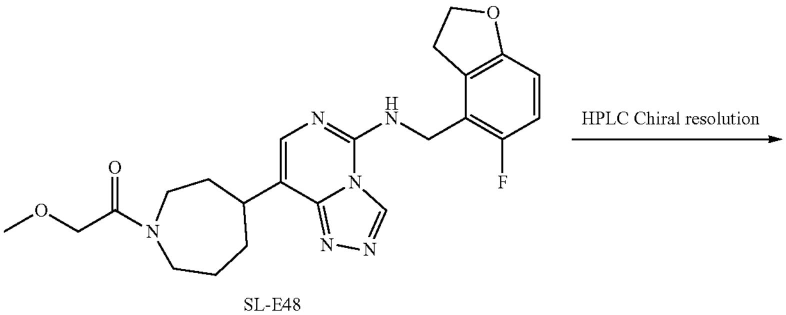

SL-E48

-continued

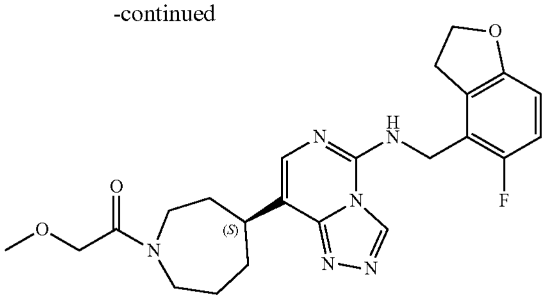

SL-E48-S

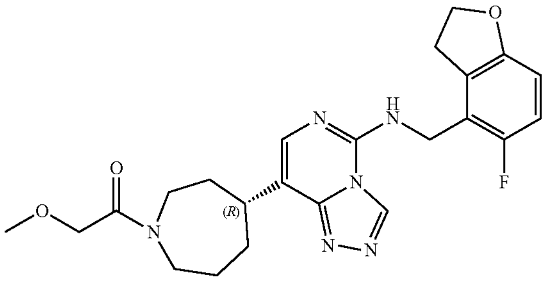

SL-E48-R

SL-E18 (10 mg) was dissolved in 2 mL of methanol, and 10% Pd/C (4 mg) was added and the reaction was performed at room temperature for 6 hours. The resultant was filtered and separated by column chromatography to obtain the target compound SL-E48 (4 mg) LC-MS: $[M+H]^+$=455.2.

Referring to example 56, SL-E48 was separated by chiral chromatography to obtain optically pure compounds SL-E48-S and SL-E48-R.

Example 115: Synthesis of Compound SL-E49

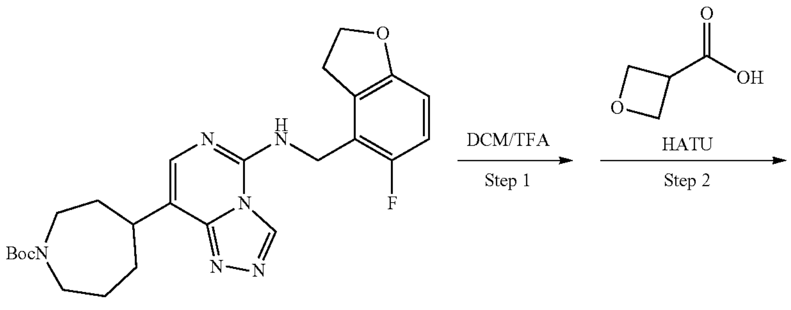

SL-E2

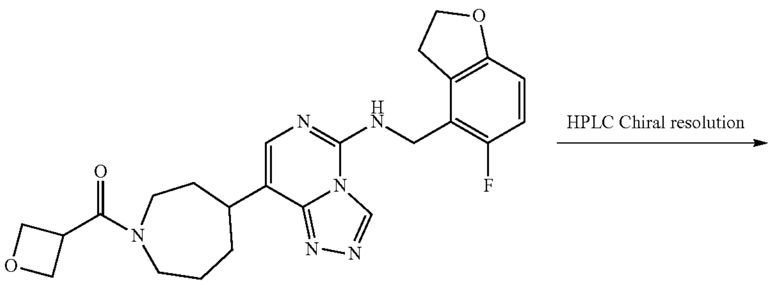

SL-E49

-continued

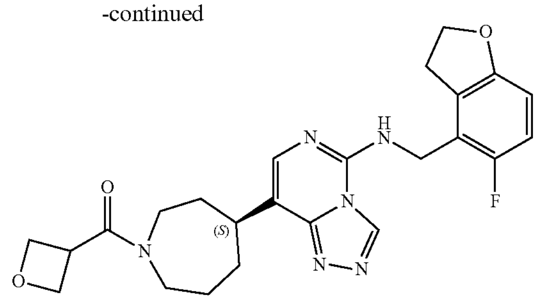

SL-E49-S

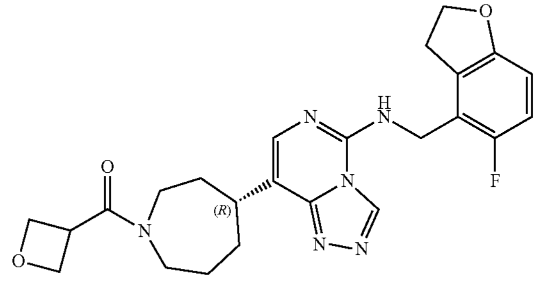

SL-E49-R

Compound SL-E2 (10 mg) was dissolved in 3 mL of dichloromethane (DCM) and 1 mL of trifluoroacetic acid (TFA), and the mixture was stirred at room temperature for 30 min. After the solvent was concentrated, the residue was dissolved in 1 mL of DMF and 0.1 mL of isopropylethylamine (DIEPA), and HATU (30 mg) and acid (oxetane-3-carboxylic acid) (9 mg) were added at room temperature and the reaction was performed for 1 hour. When the reaction was completed as indicated by TLC, the reaction solution was poured into water and extracted with a large amount of ethyl acetate. After being dried and concentrated, the resultant was separated by column chromatography to obtain the target compound SL-E49 (1.2 mg). LC-MS: $[M+H]^+=467.2$.

Referring to example 56, SL-E49 was separated by chiral chromatography to obtain optically pure compounds SL-E49-S and SL-E49-R.

Example 116: Synthesis of Compound SL-E50

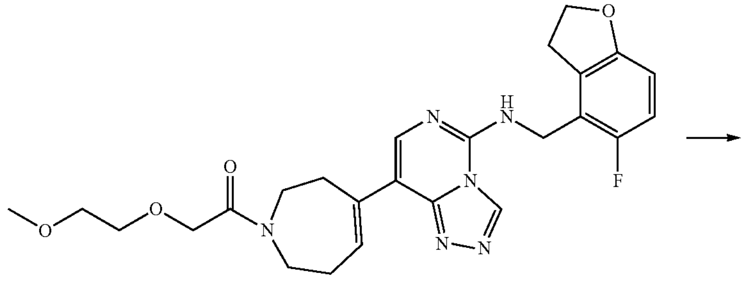

SL-E20

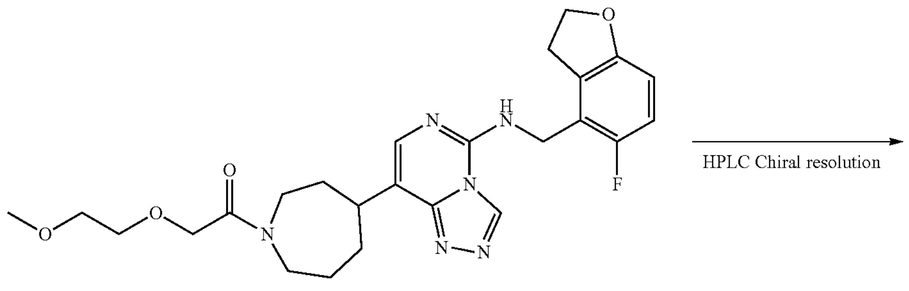

SL-E50

-continued

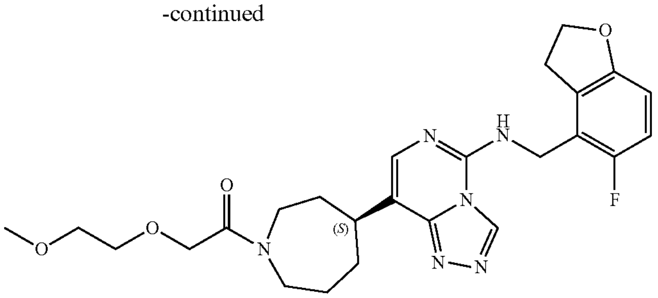

SL-E50-S

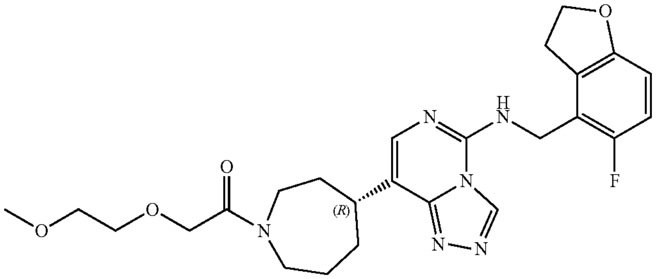

SL-E50-R

SL-E20 (10 mg) was dissolved in 2 mL of methanol, and 10% Pd/C (4 mg) was added and the reaction was performed at room temperature for 6 hours. The resultant was filtered and separated by column chromatography to obtain the target compound SL-E50 (4 mg). LC-MS: $[M+H]^+=499.2$.

Referring to example 56, SL-E50 was separated by chiral chromatography to obtain optically pure compounds SL-E50-S and SL-E50-R.

Example 117: Synthesis of Compound SL-E51

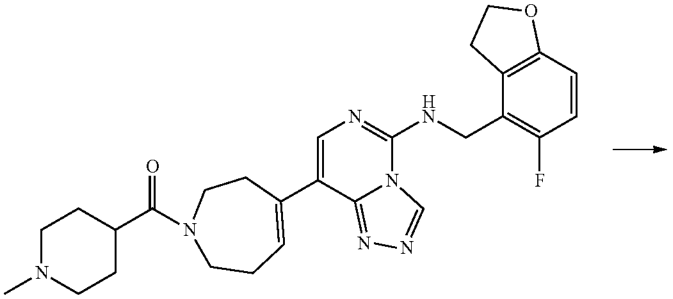

SL-E21

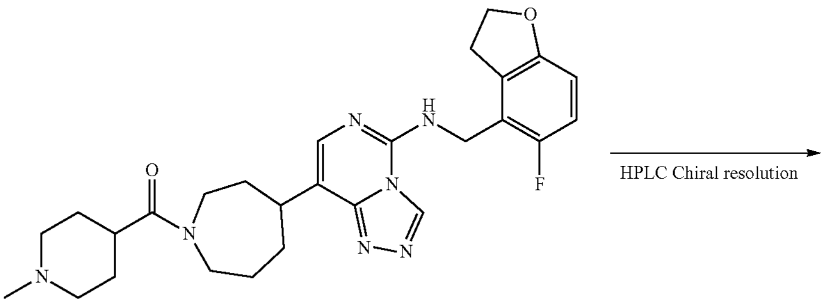

SL-E51

-continued

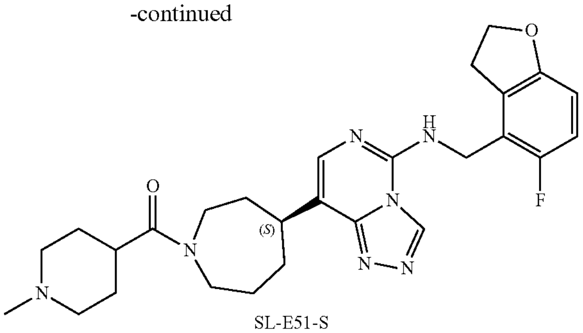

SL-E51-S

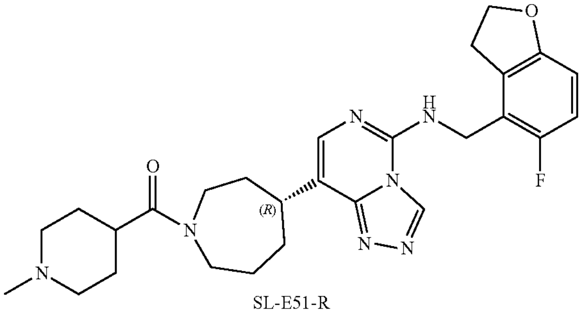

SL-E51-R

SL-E21 (10 mg) was dissolved in 2 mL of methanol, and 10% Pd/C (4 mg) was added and the reaction was performed at room temperature for 6 hours. The resultant was filtered and separated by column chromatography to obtain the target compound SL-E51 (4 mg). LC-MS: $[M+H]^+=508.3$.

Referring to example 56, SL-E51 was separated by chiral chromatography to obtain optically pure compounds SL-E51-S and SL-E51-R.

Example 118: Synthesis of Compound SL-E52

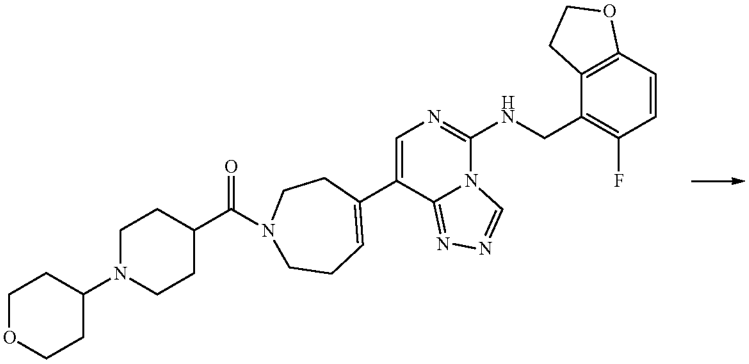

SL-E22

-continued

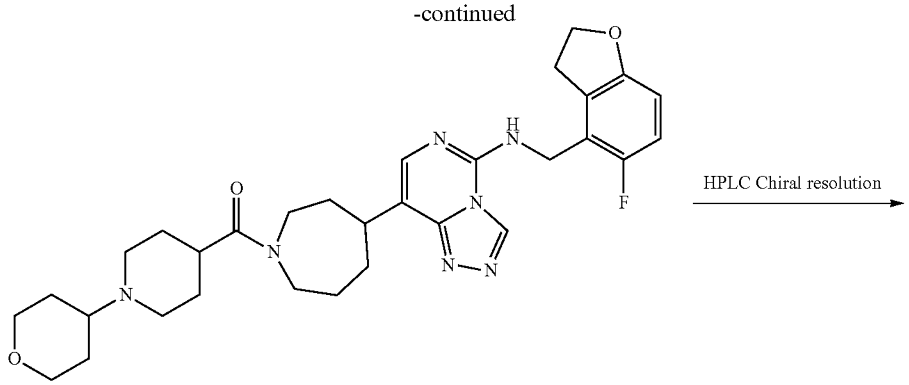

SL-E52

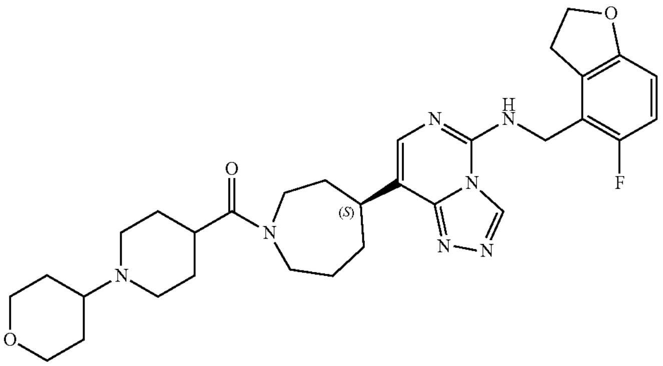

SL-E52-S

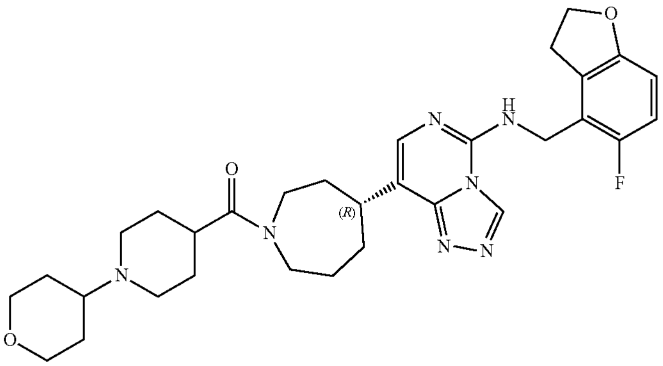

SL-E52-R

SL-E22 (10 mg) was dissolved in 2 mL of methanol, and 10% Pd/C (4 mg) was added and the reaction was performed at room temperature for 6 hours. The resultant was filtered and separated by column chromatography to obtain the target compound SL-E52 (4 mg). LC-MS: $[M+H]^+$=578.2.

Referring to example 56, SL-E52 was separated by chiral chromatography to obtain optically pure compounds SL-E52-S and SL-E52-R.

Example 119: Synthesis of Compound SL-E53

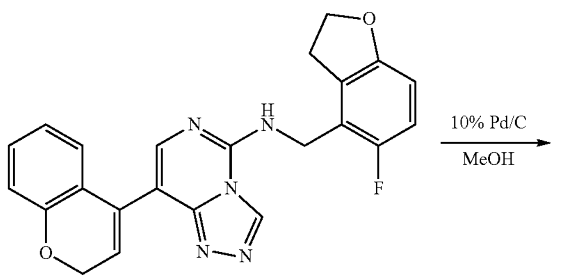

SL-ZYE-28

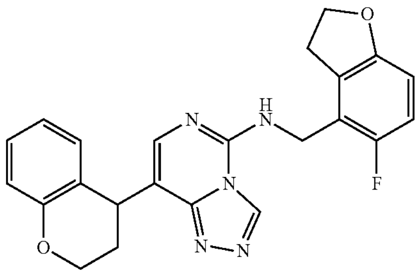

SL-E-53

SL-ZYE-28 (10 mg) was dissolved in 2 mL of methanol, and 10% Pd/C (4 mg) was added and the reaction was performed at room temperature for 6 hours. The resultant was filtered and separated by column chromatograph to obtain the target compound SL-E53 (4 mg). LC-MS: $[M+H]^+$=418.2.

Example 120: Synthesis of Compound SL-ZYE-119

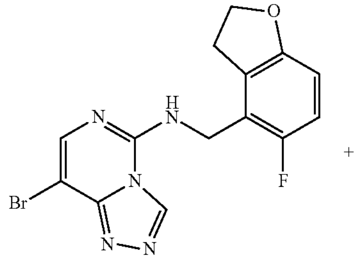

4-1

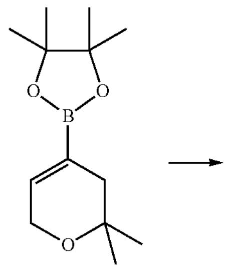

SL-B3

-continued

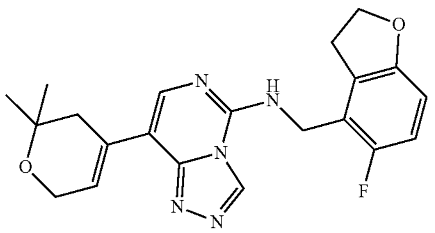

SL-ZYE-119

Bromide 4-1 (36 mg, 0.1 mmol) was dissolved in 6 mL of 1,4-dioxane and 2 mL of a 2 M $Na_2CO_3$ solution, and borate SL-B3 (48 mg, 0.2 mmol) was added thereto. The reaction solution was stirred at room temperature for 10 min under Ar atmosphere protection. 10% of allyl palladium (II) chloride dimer (3.5 mg, 0.01 mmol) and 20% of sodium 2'-dicyclohexylphosphino-2,6-dimethoxy-1,1'-biphenyl-3-sulfonate hydrate (11 mg, 0.02 mmol) were added and the reaction was performed at 90° C. for 40 min under Ar atmosphere protection. After being cooled and concentrated under reduced pressure, the resultant was separated by column chromatography to obtain the target compound SL-ZYE-119. (4.1 mg). 1H NMR (400 MHz, DMSO-$d_6$) δ 9.44 (s, 1H), 8.61 (m, 1H), 7.66 (s, 1H), 7.30 (m, 1H), 6.94 (m, 1H), 6.70 (m, 1H), 4.69 (m, 2H), 4.54 (m, 2H), 4.30 (m, 2H), 3.29 (m, 2H), 2.40 (m, 2H), 1.23 (s, 6H). LC-MS: $[M+H]^+$=396.2.

Example 121: Synthesis of Compound SL-ZYE-120

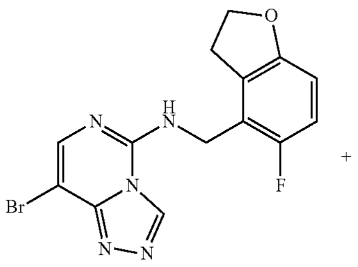

4-1

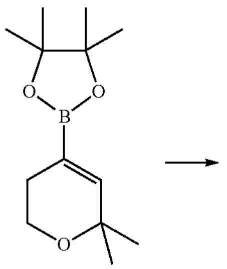

SL-B4

-continued

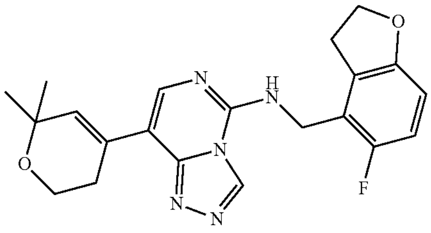

SL-ZYE-120

Bromide 4-1 (36 mg, 0.1 mmol) was dissolved in 6 mL of 1,4-dioxane and 2 mL of a 2 M $Na_2CO_3$ solution, and borate SL-B4 (48 mg, 0.2 mmol) was added thereto. The reaction solution was stirred at room temperature for 10 min under Ar atmosphere protection. 10% of allyl palladium (II) chloride dimer (3.5 mg, 0.01 mmol) and 20% of sodium 2'-dicyclohexylphosphino-2,6-dimethoxy-1,1'-biphenyl-3-sulfonate hydrate (11 mg, 0.02 mmol) were added and the reaction was performed at 90° C. for 40 min under Ar atmosphere protection. After being cooled and concentrated under reduced pressure, the resultant was separated by column chromatography to obtain the target compound SL-ZYE-120. (4.1 mg). $^1H$ NMR (400 MHz, DMSO-$d_6$) δ 9.44 (s, 1H), 8.62 (m, 1H), 7.67 (m, 1H), 7.27 (m, 1H), 6.93 (m, 1H), 6.70 (m, 1H), 4.69 (m, 2H), 4.52 (m, 2H), 3.84 (m, 2H), 3.26 (m 2H), 2.42 (m, 2H), 1.28 (s, 6H). LC-MS: $[M+H]^+$=396.2.

Example 122: Synthesis of Compound SL-ZYE-121

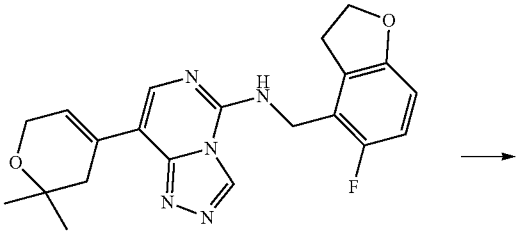

SL-ZYE-119

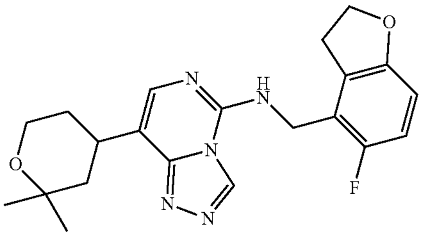

SL-ZYE-121

SL-ZYE-119 (10 mg) was dissolved in 2 mL of methanol, and 10% Pd/C (4 mg) was added and the reaction was performed at room temperature for 6 hours. The resultant was filtered and separated by column chromatography to obtain the target compound SL-ZYE-121 (4 mg). $^1H$ NMR (400 MHz, DMSO-$d_6$) δ 9.32 (s, 1H), 8.32 (s, 1H), 7.38 (m, 1H), 6.85 (m, 1H), 6.62 (m, 1H), 4.56-4.47 (m, 4H), 3.68 (m, 2H), 3.20 (m, 3H), 1.70 (m, 4H), 1.09 (m, 6H). LC-MS: $[M+H]^+$=398.2.

Example 123: Synthesis of Compound SL-ZYE-195

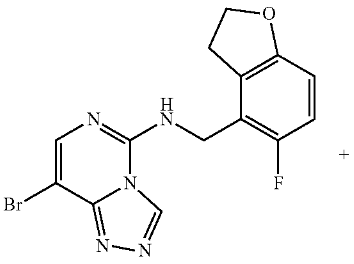

4-1

+

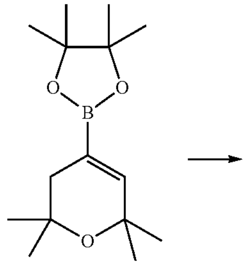

SL-B5

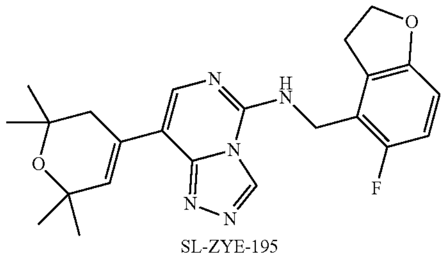

SL-ZYE-195

Bromide 4-1 (36 mg, 0.1 mmol) was dissolved in 6 mL of 1,4-dioxane and 2 mL of a 2 M $Na_2CO_3$ solution, and borate SL-B5 (50 mg, 0.2 mmol) was added thereto. The reaction solution was stirred at room temperature for 10 min under Ar atmosphere protection. 10%6 of allyl palladium (II) chloride dimer (3.5 mg, 0.01 mmol) and 20% of sodium 2'-dicyclohexylphosphino-2,6-dimethoxy-1,1'-biphenyl-3-sulfonate hydrate (11 mg, 0.02 mmol) were added and the reaction was performed at 90° C. for 40 min under Ar atmosphere protection. After being cooled and concentrated under reduced pressure, the resultant was separated by column chromatography to obtain the target compound SL-ZYE-195 (4.1 mg). $^1H$ NMR (400 MHz, DMSO-$d_6$) δ 9.45 (s, 1H), 8.63 (m, 1H), 7.68 (m, 1H), 7.28 (m, 1H), 6.93 (m, 1H), 6.71 (m, 1H), 4.68 (d, J=4.0 Hz, 2H), 4.54 (J=8.0 Hz, 2H), 3.27 (J=8.0 Hz, 2H), 2.38 (m, 2H), 1.29 (s, 6H), 1.24 (s, 6H). LC-MS: $[M+H]^+$=424.2.

Example 124: Synthesis of Compound SL-ZYE-196

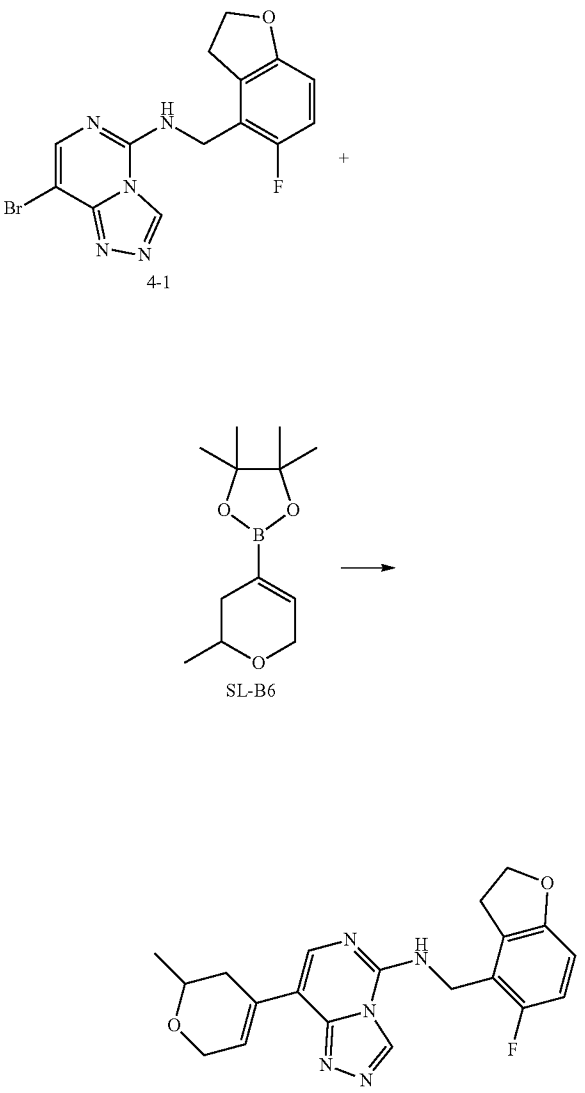

4-1

SL-B6

SL-ZYE-196

Bromide 4-1 (36 mg, 0.1 mmol) was dissolved in 6 mL of 1,4-dioxane and 2 mL of a 2 M $Na_2CO_3$ solution, and borate SL-B6 (49 mg, 0.2 mmol) was added thereto. The reaction solution was stirred at room temperature for 10 min under Ar atmosphere protection. 10% of allyl palladium (II) chloride dimer (3.5 mg, 0.01 mmol) and 20% of sodium 2'-dicyclohexylphosphino-2,6-dimethoxy-1,1'-biphenyl-3-sulfonate hydrate (11 mg, 0.02 mmol) were added and the reaction was performed at 90° C. for 40 min under Ar atmosphere protection. After being cooled and concentrated under reduced pressure, the resultant was separated by column chromatography to obtain the target compound SL-ZYE-196 (4.1 mg). $^1H$ NMR (400 MHz, DMSO-$d_6$) δ 9.44 (s, 1H), 8.61 (m, 1H), 7.66 (m, 1H), 7.32 (m, 1H), 6.94 (m, 1H), 6.70 (m, 1H), 4.68 (d, J=4.0 Hz, 2H), 4.54 (t, J=8.0 Hz, 2H), 4.34 (m, 2H), 3.70 (m, 1H), 3.29 (J=8.0 Hz, 2H), 2.56-2.21 (m, 2H), 1.25 (d, J=4.0 Hz, 3H). LC-MS: $[M+H]^+$=382.2.

Example 125: Synthesis of Compound SL-ZYE-197

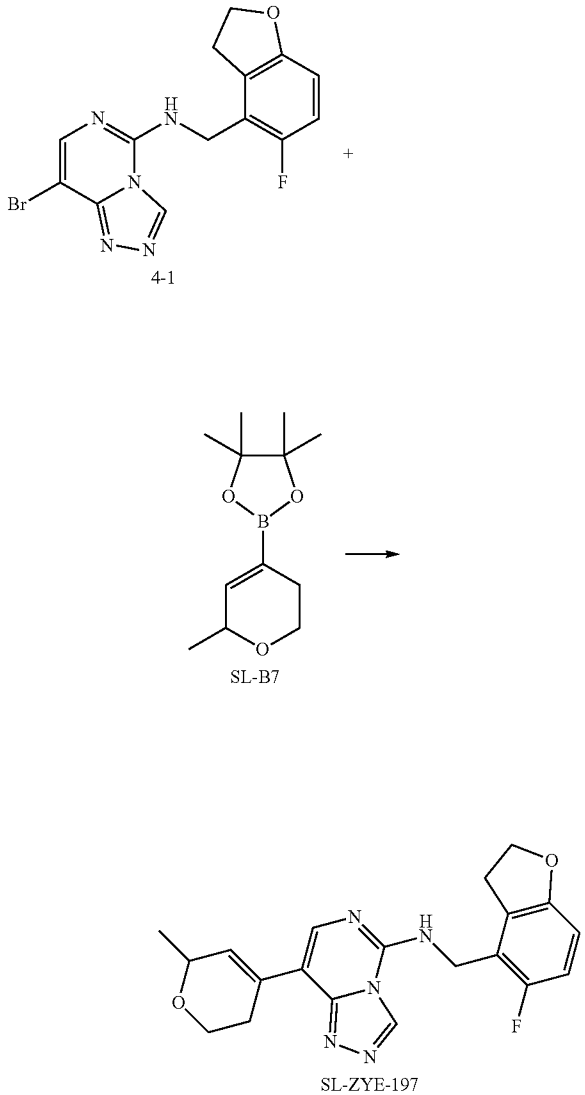

4-1

SL-B7

SL-ZYE-197

Bromide 4-1 (36 mg, 0.1 mmol) was dissolved in 6 mL of 1,4-dioxane and 2 mL of a 2 M $Na_2CO_3$ solution, and borate SL-B7 (49 mg, 0.2 mmol) was added thereto. The reaction solution was stirred at room temperature for 10 min under Ar atmosphere protection. 10%6 of allyl palladium (II) chloride dimer (3.5 mg, 0.01 mmol) and 20% of sodium 2'-dicyclohexylphosphino-2,6-dimethoxy-1,1'-biphenyl-3-sulfonate hydrate (11 mg, 0.02 mmol) were added and the reaction was performed at 90° C. for 40 min under Ar atmosphere protection. After being cooled and concentrated under reduced pressure, the resultant was separated by column chromatography to obtain the target compound SL-ZYE-197 (4.1 mg). $^1H$ NMR (400 MHz, DMSO-$d_6$) δ 9.44 (s, 1H), 8.63 (m, 1H), 7.67 (m, 1H), 7.28 (m, 1H), 6.94 (m, 1H), 6.71 (m, 1H), 4.69 (d, J=4.0 Hz, 2H), 4.53 (t, J=8.0 Hz, 2H), 4.37 (m, 1H), 4.06 (m, 1H), 3.68 (m, 1H), 3.28 (J=8.0 Hz, 2H), 2.60-2.32 (m, 2H), 1.26 (d, J=4.0 Hz, 3H). LC-MS: $[M+H]^+$=382.2.

Example 126: Synthesis of Compound SL-ZYE-144

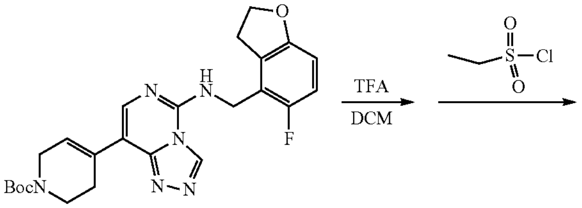

E-Y3

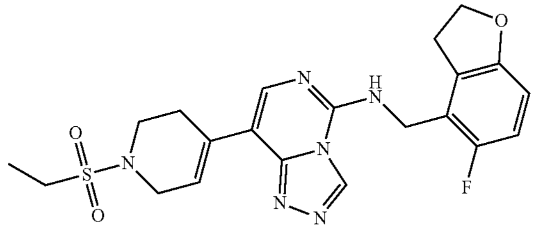

SL-ZYE-144

Compound E-Y3 (46 mg) was dissolved in 5 mL of dichloromethane (DCM) and 1 mL of trifluoroacetic acid (TFA), and the mixture was stirred at room temperature. After the solvent was concentrated, 3 mL of dichloromethane and 0.1 mL of triethylamine (TEA) were added and dissolved by stirring. Ethylsulfonyl chloride (20 mg) was added at room temperature, and the reaction was continued. When the reaction was completed as indicated by TLC, the resultant was directly separated by column chromatography to obtain the target compound SL-ZYE-144 (7 mg).

$^1$H NMR (400 MHz, $CDCl_3$) δ 9.00 (s, 1H), 7.64 (s, 1H), 7.24 (m, 1H), 6.78 (m, 1H), 6.61 (m, 2H), 4.80 (s, 2H), 4.61 (t, J=8.7 Hz, 2H), 4.06 (m, 2H), 3.61 (t, J=5.6 Hz, 2H), 3.38 (t, J=8.7 Hz, 2H), 3.04 (q, J=7.4 Hz, 2H), 2.72 (m, 2H), 1.40 (t, J=7.4 Hz, 3H). LC-MS: $[M+H]^+$=459.1.

Example 127: Synthesis of Compound SL-ZYE-146

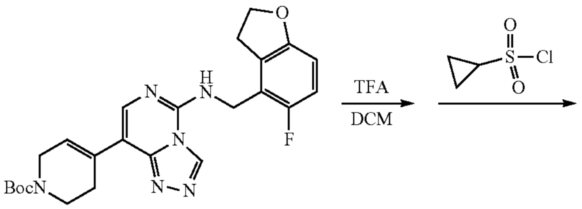

E-Y3

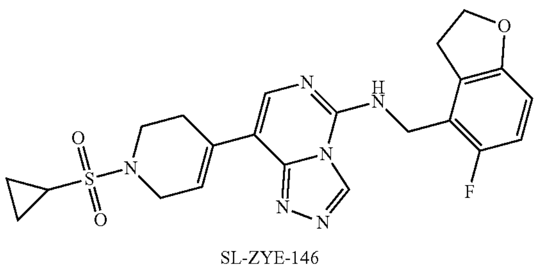

SL-ZYE-146

Compound E-Y3 (46 mg) was dissolved in 5 mL of dichloromethane (DCM) and 1 mL of trifluoroacetic acid (TFA), and the mixture was stirred at room temperature. After the solvent was concentrated, 3 mL of dichloromethane and 0.1 mL of triethylamine (TEA) were added and dissolved by stirring. Cyclopropylsulfonyl chloride (20 mg) was added at room temperature, and the reaction was continued. When the reaction was completed as indicated by TLC, the resultant was directly separated by column chromatography to obtain the target compound SL-ZYE-146 (6 mg).

$^1$H NMR (400 MHz, $CDCl_3$) δ 9.03 (s, 1H), 7.64 (s, 1H), 7.23 (m, 1H), 6.77 (m, 2H), 6.58 (dd, J=8.7, 3.9 Hz, 1H), 4.78 (d, J=5.3 Hz, 2H), 4.60 (t, J=8.7 Hz, 2H), 4.08 (m, 2H), 3.60 (t, J=5.7 Hz, 2H), 3.37 (t, J=8.7 Hz, 2H), 2.74 (m, 2H), 2.42-2.27 (m, 1H), 1.32-1.14 (m, 2H), 1.11-0.88 (m, 2H). LC-MS: $[M-H]^+$=469.2.

Example 128: Synthesis of Compound SL-ZYE-147

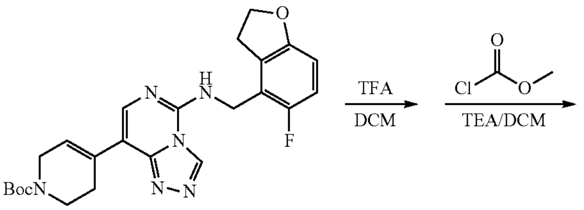

E-Y3

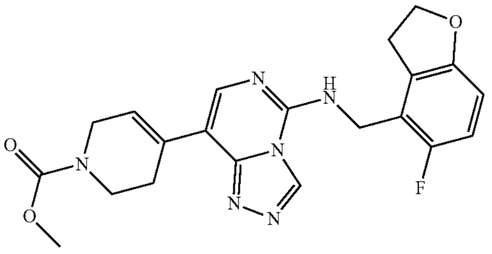

SL-ZYE-147

Compound E-Y3 (46 mg) was dissolved in 5 mL of dichloromethane (DCM) and 1 mL of trifluoroacetic acid (TFA), and the mixture was stirred at room temperature. After the solvent was concentrated, 3 mL of dichloromethane and 0.1 mL of triethylamine (TEA) were added and dissolved by stirring. Methyl chloroformate (15 mg) was added at room temperature, and the reaction was continued. When the reaction was completed as indicated by TLC, the resultant was directly separated by column chromatography to obtain the target compound SL-ZYE-147 (5 mg).

$^1$H NMR (400 MHz, DMSO-$d_6$) δ 9.45 (s, 1H), 8.64 (m, 1H), 7.69 (s, 1H), 7.26 (s, 1H), 6.93 (m, 1H), 6.71 (m, 1H), 4.69 (m, 2H), 4.54 (m, 2H), 4.12 (m, 2H), 3.64 (s, 3H), 3.61 (m, 2H), 3.28 (m, 2H), 2.57 (m, 2H). LC-MS: $[M+H]^+$=425.2.

Example 129: Synthesis of Compound SL-ZYE-148

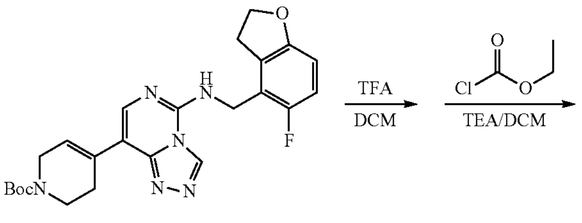

E-Y3

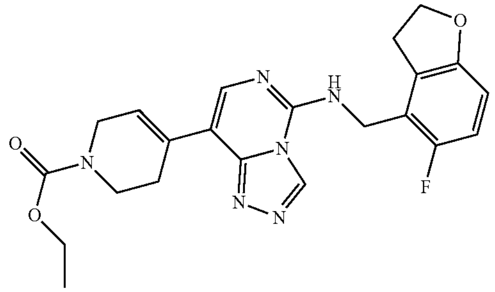

SL-ZYE-148

Compound E-Y3 (46 mg) was dissolved in 5 mL of dichloromethane (DCM) and 1 mL of trifluoroacetic acid (TFA), and the mixture was stirred at room temperature. After the solvent was concentrated, 3 mL of dichloromethane and 0.1 mL of triethylamine (TEA) were added and dissolved by stirring. Ethyl chloroformate (15 mg) was added at room temperature, and the reaction was continued. When the reaction was completed as indicated by TLC, the resultant was directly separated by column chromatography to obtain the target compound SL-ZYE-148 (4 mg).

$^1$H NMR (400 MHz, $CDCl_3$) δ 9.12 (s, 1H), 7.64 (s, 1H), 7.26-7.09 (m, 1H), 7.00 (m, 1H), 6.74 (t, J=9.2 Hz, 1H), 6.57 (dd, J=8.6, 3.9 Hz, 1H), 4.78 (d, J=4.9 Hz, 2H), 4.58 (t, J=8.8 Hz, 2H), 4.23-4.10 (m, 4H), 3.72 (d, J=5.3 Hz, 2H), 3.35 (t, J=9.0 Hz, 2H), 2.63 (m, 2H), 1.29 (t, J=7.0 Hz, 3H). LC-MS: $[M+H]^+$=439.2.

Example 130: Synthesis of Compound SL-ZYE-161

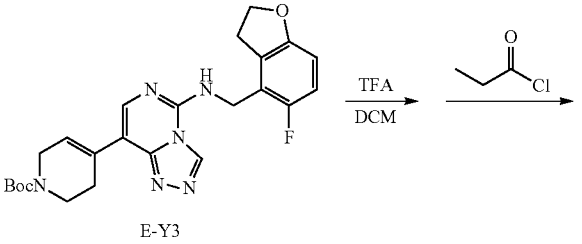

E-Y3

-continued

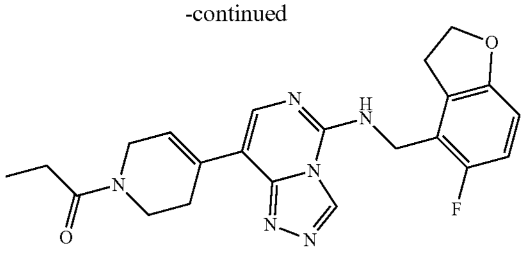

SL-ZYE-161

Compound E-Y3 (46 mg) was dissolved in 5 mL of dichloromethane (DCM) and 1 mL of trifluoroacetic acid (TFA), and the mixture was stirred at room temperature. After the solvent was concentrated, 3 mL of dichloromethane and 0.1 mL of triethylamine (TEA) were added and dissolved by stirring. Propionyl chloride (10 mg) was added at room temperature, and the reaction was continued. When the reaction was completed as indicated by TLC, the resultant was directly separated by column chromatography to obtain the target compound SL-ZYE-161 (4 mg), 1H NMR (400 MHz, $CDCl_3$) δ 9.76 (m, 1H), 8.19 (m, 1H), 7.62 (m, 1H), 7.34-7.13 (m, 1H), 6.82-6.67 (m, 1H), 6.58 (m, 1H), 4.79 (m, 2H), 4.57 (m, 2H), 4.26 (m, 2H), 3.82 (m, 2H), 3.39 (m, 2H), 2.65 (m, 2H), 2.50-2.29 (m, 2H), 1.17 (m, 3H). LC-MS: $[M+H]^+$=423.2.

Example 131: Synthesis of Compound SL-ZYE-162

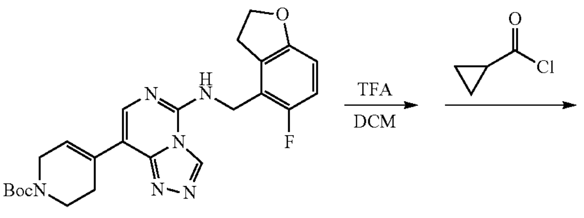

E-Y3

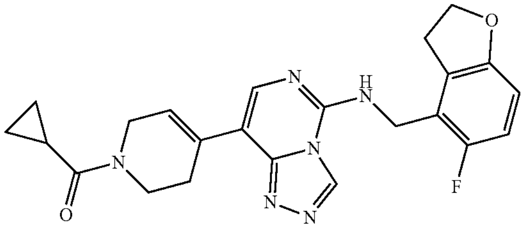

SL-ZYE-162

Compound E-Y3 (46 mg) was dissolved in 5 mL of dichloromethane (DCM) and 1 mL of trifluoroacetic acid (TFA), and the mixture was stirred at room temperature. After the solvent was concentrated, 3 mL of dichloromethane and 0.1 mL of triethylamine (TEA) were added and dissolved by stirring. Cyclopropionyl chloride (10 mg) was added at room temperature, and the reaction was continued. When the reaction was completed as indicated by TLC, the resultant was directly separated by column chromatography to obtain the target compound SL-ZYE-162 (4 mg). $^1$H NMR (400 MHz, $CDCl_3$) δ 9.35 (m, 1H), 7.81 (m, 1H), 7.64 (m, 1H), 7.33-7.10 (m, 1H), 6.74 (m, 1H), 6.57 (m, 1H), 4.77

(m, 2H), 4.57 (m, 2H), 4.29 (m, 2H), 3.85 (m, 2H), 3.34 (m, 2H), 2.77-2.60 (m, 2H), 1.84 (m, 1H), 0.85 (m, 4H). LC-MS: $[M+H]^+$=435.2.

Example 132: Synthesis of Compound SL-ZYE-145

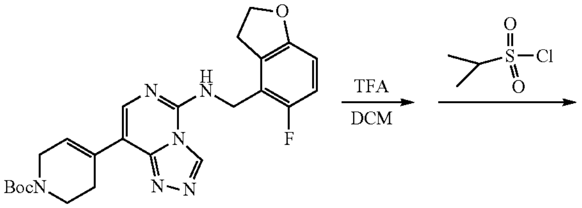

E-Y3

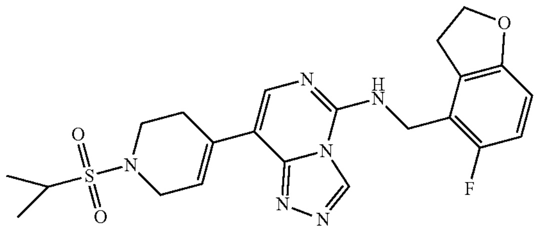

SL-ZYE-145

Compound E-Y3 (46 mg) was dissolved in 5 mL of dichloromethane (DCM) and 1 mL of trifluoroacetic acid (TFA), and the mixture was stirred at room temperature. After the solvent was concentrated, 3 mL of dichloromethane and 0.1 mL of triethylamine (TEA) were added and dissolved by stirring. Isopropylsulfonyl chloride (20 mg) was added at room temperature, and the reaction was continued. When the reaction was completed as indicated by TLC, the resultant was directly separated by column chromatography to obtain the target compound SL-ZYE-145 (7 mg).

$^1$H NMR (400 MHz, DMSO-$d_6$) δ 9.46 (s, 1H), 8.69 (m, 1H), 7.70 (s, 1H), 7.33 (m, 1H), 6.96 (d, J=8.7 Hz, 1H), 6.71 (d, J=3.9 Hz, 1H), 4.69 (m, 2H), 4.55 (d, J=8.7 Hz, 2H), 4.04 (m, 2H), 3.53 (d, J=5.7 Hz, 2H), 3.47-3.37 (m, 1H), 3.32-3.24 (m, 2H), 2.66 (m, 2H), 1.25 (s, 3H), 1.23 (s, 3H). LC-MS: $[M+H]^+$=473.2.

Example 133: Synthesis of Compound SL-ZYE-183

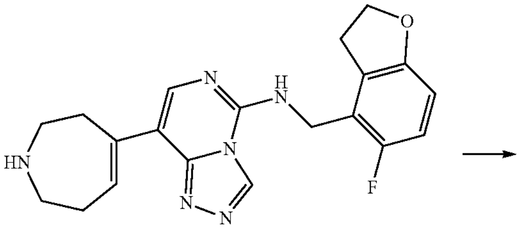

SL-E12

-continued

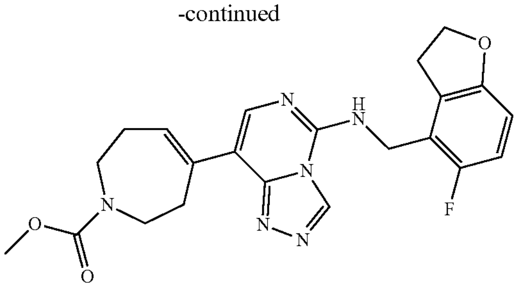

SL-ZYE-183

SL-E12 (30 mg) was dissolved in 3 mL of dichloromethane and 0.1 mL of triethylamine (TEA) by stirring. Methyl chloroformate (15 mg) was added at room temperature, and the reaction was continued. When the reaction was completed as indicated by TLC, the resultant was directly separated by column chromatography to obtain the target compound SL-ZYE-183 (5 mg). $^1$H NMR (400 MHz, DMSO-$d_6$) δ 9.43 (s, 1H), 8.60 (m, 1H), 7.62 (s, 1H), 6.98-6.90 (m, 1H), 6.82 (m, 1H), 6.69 (m, 1H), 4.67 (d, J=5.0 Hz, 2H), 4.53 (t, J=8.7 Hz, 2H), 4.07 (m, 2H), 3.59 (m, 5H), 3.28 (t, J=8.7 Hz, 2H), 2.72 (m, 2H), 1.86 (m, 2H). LC-MS: $[M+H]^+$=439.2.

Example 134: Experiment for Measuring the Multi-Comb Inhibitor Complex 2 (PRC2) Enzyme Activity The TR-FRET method was used to measure the PRC2 enzyme activity. First, the enzyme was mixed with compounds at different concentrations and incubated for 30 min at room temperature. The biotin-labeled histone H3 peptide substrate and the cofactor S-adenosylmethionine (SAM) were added to initiate the enzymatic reaction. After reaction was performed at room temperature for 4 hour, Acceptor and Donor were added and incubated for half an hour. The multifunctional microplate reader EnVision (Perkin Elmer Inc.) was used to detect the fluorescence signal. Data were analyzed using GraphPad Prism 5.0 software, and $IC_{50}$ values were obtained.

The compounds in Table 1 can be prepared by the methods described in the above examples. EED226 is the positive compound (Nat. Chem. Biol. 2017, 13, 381-388), and N/A represents unanalyzed.

| Compound No. | Structure of compound | Enzyme Activity IC$_{50}$ (μM) |
|---|---|---|
| E-Y1 | 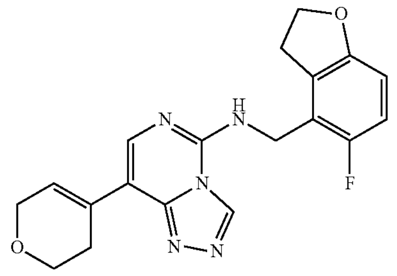 Exact Mass: 367.1445 | 0.018 |
| E-Y2 | 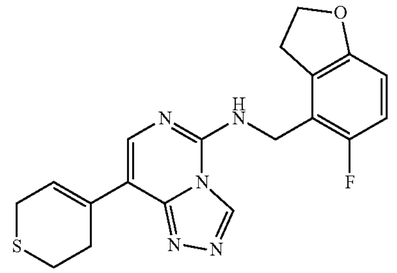 Exact Mass: 383.12 | 0.008 |
| E-Y3 | 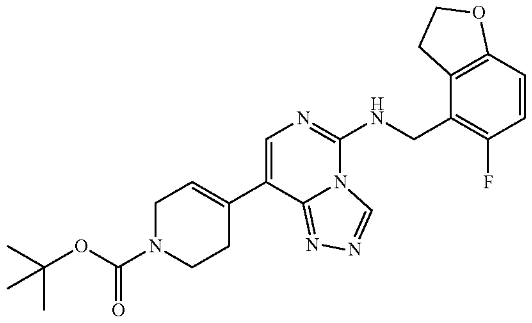 Exact Mass: 466.21 | 0.037 |
| E-Y4 | 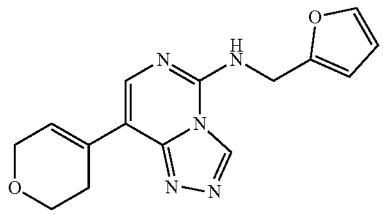 Exact Mass: 297.12 | 0.511 |
| E-Y5 | 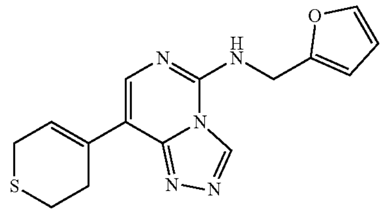 Exact Mass: 313.10 | 0.611 |

-continued
| Compound No. | Structure of compound | Enzyme Activity $IC_{50}$ (μM) |
|---|---|---|
| E-Y6 | 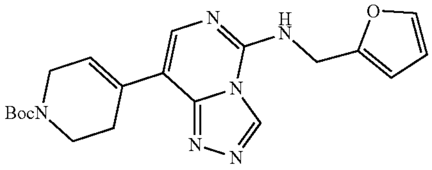 Exact Mass: 396.1910 | 0.307 |
| E-Y10 | 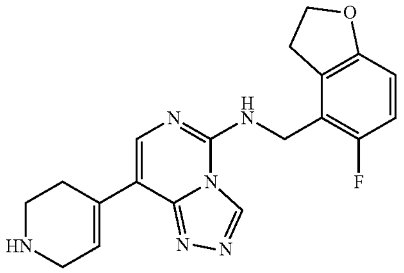 Exact Mass: 366.16 | 0.218 |
| E-Y13 | 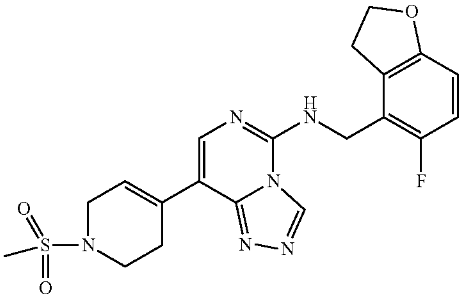 Exact Mass: 444.14 | 0.019 |
| E-Y14 | 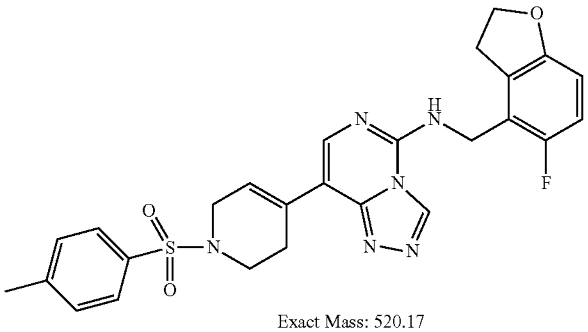 [SMILES: Cc1ccc(S(=O)(=O)N2CC=C(c3cnc(NCc4c(F)ccc5c4CCO5)n4cnnc34)CC2)cc1] Exact Mass: 520.17 | 0.1006 |
| E-Y15 | 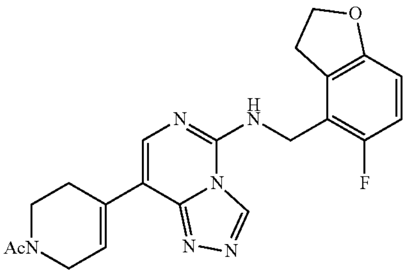 Exact Mass: 408.17 | 0.0056 |

-continued
| Compound No. | Structure of compound | Enzyme Activity IC$_{50}$ (μM) |
| --- | --- | --- |
| E-Y16 | 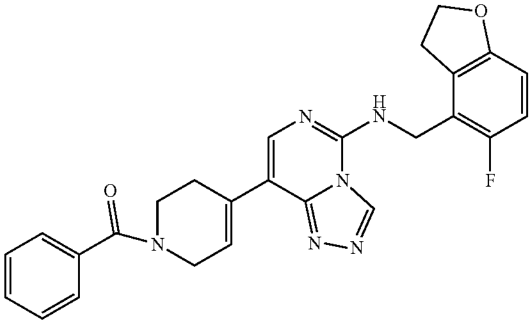 Exact Mass: 470.19 | 0.0177 |
| E-Y17 | 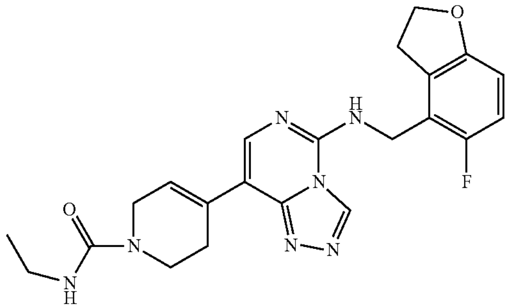 Exact Mass: 437.20 | 0.0061 |
| E-Y18 | 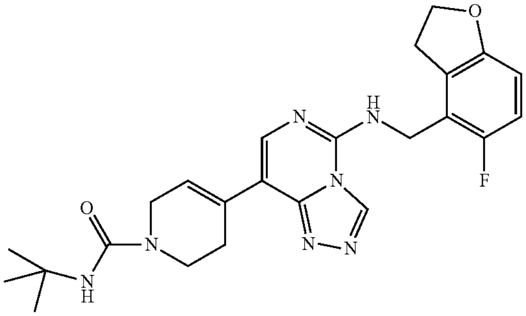 Exact Mass: 437.20 | 0.021 |
| E-Y19 | 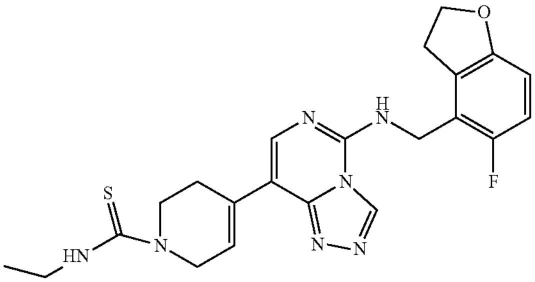 Exact Mass: 453.17 | 0.0093 |

-continued
| Compound No. | Structure of compound | Enzyme Activity IC$_{50}$ (μM) |
|---|---|---|
| E-Y20 | 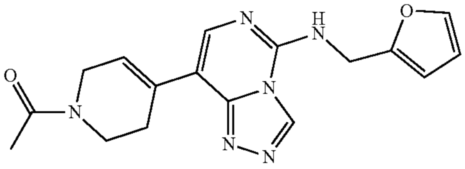 Exact Mass: 338.1491 | 0.166 |
| E-Y21 | 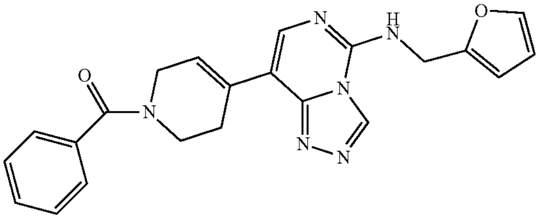 Exact Mass: 400.1648 | 0.351 |
| E-Y22 | 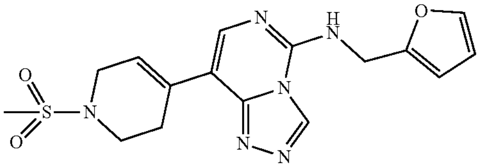 Exact Mass: 374.1161 | 0.334 |
| E-Y23 | 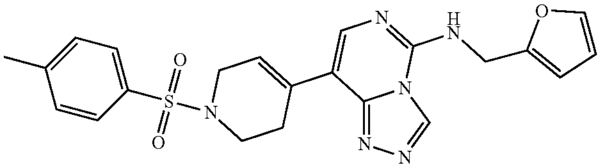 Exact Mass: 450.1474 | 0.350 |
| E-Y24 | 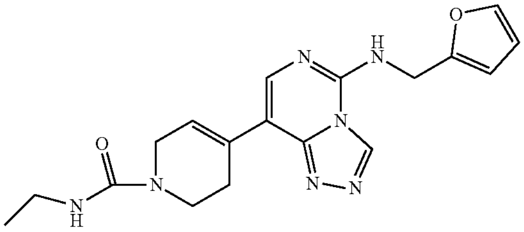 Exact Mass: 367.18 | 0.204 |
| E-Y25 | 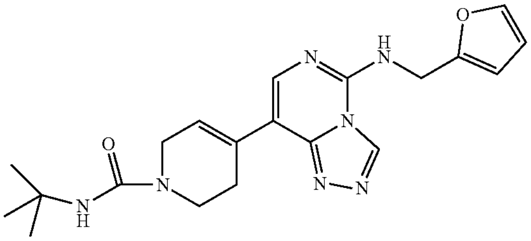 Exact Mass: 395.21 | 0.373 |

-continued
| Compound No. | Structure of compound | Enzyme Activity $IC_{50}$ (μM) |
|---|---|---|
| E-Y26 | 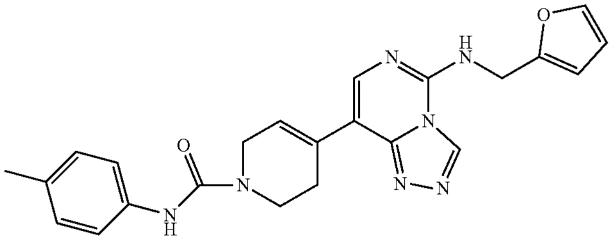 Exact Mass: 429.19 | 0.091 |
| E-Y27 | 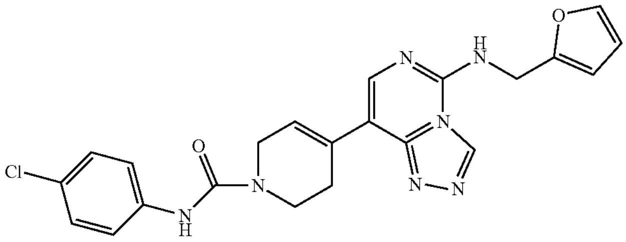 Exact Mass: 449.14 | 0.092 |
| E-Y28 | 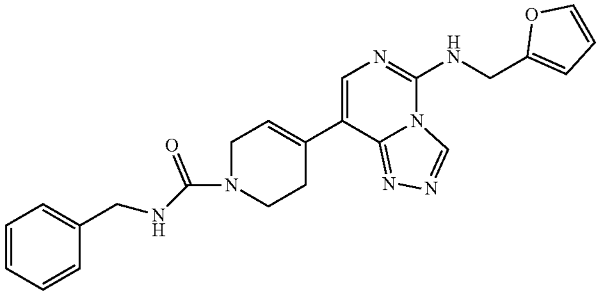 Exact Mass: 429.19 | 0.107 |
| E-Y30 | 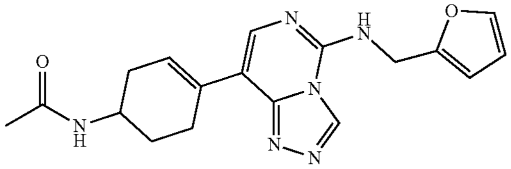 Exact Mass: 352.1648 | 0.793 |
| E-Y31 | 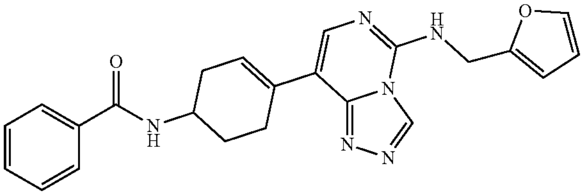 Exact Mass: 414.1804 | 0.758 |
| E-Y32 | 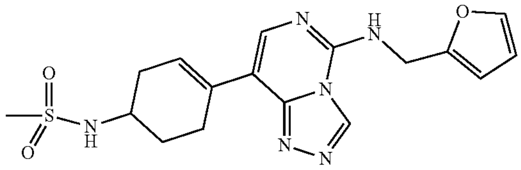 Exact Mass: 388.1318 | 0.342 |

-continued
| Compound No. | Structure of compound | Enzyme Activity IC$_{50}$ (μM) |
|---|---|---|
| E-Y34 | 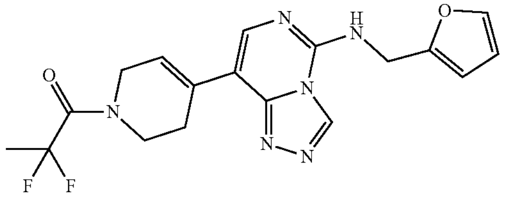 Exact Mass: 388.1459 | 0.907 |
| E-Y35 | 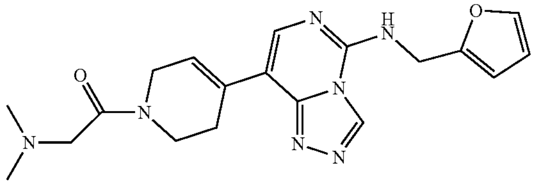 Exact Mass: 381.1913 | 0.318 |
| E-Y36 | 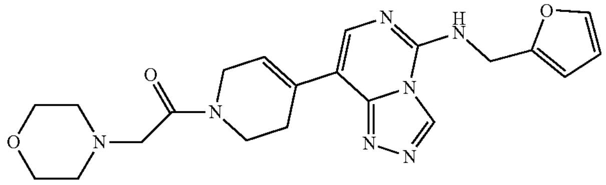 Exact Mass: 423.2019 | 0.543 |
| E-Y37 | 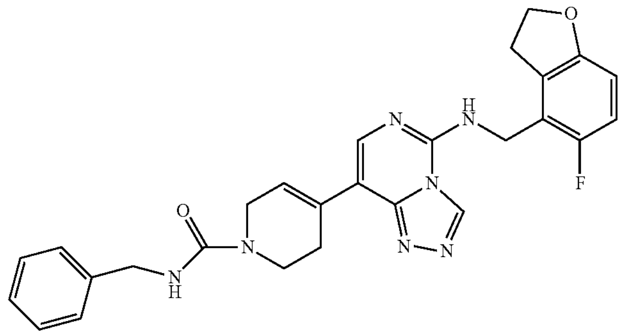 Exact Mass: 499.21 | 0.0328 |
| E-Y38 | 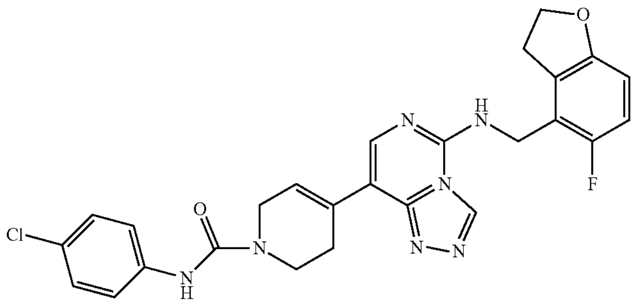 Exact Mass: 519.16 | 0.0585 |

-continued
| Compound No. | Structure of compound | Enzyme Activity IC$_{50}$ (μM) |
|---|---|---|
| E-Y39 | 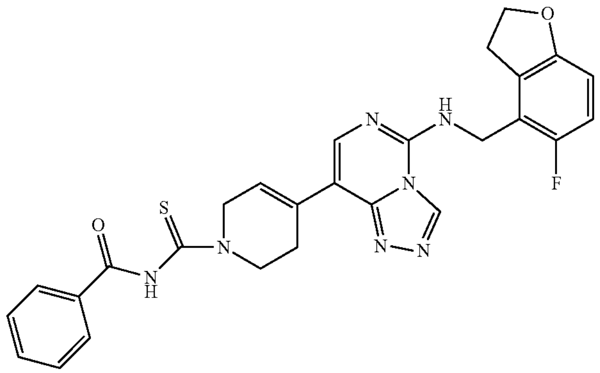 Exact Mass: 529.17 | 0.0545 |
| E-Y40 | 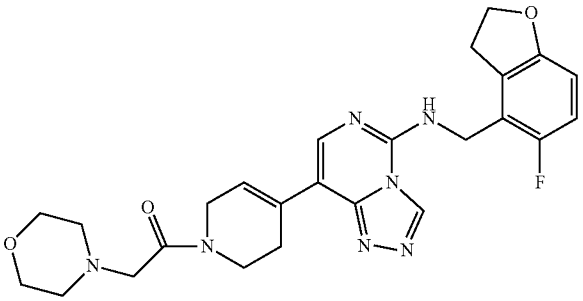 Exact Mass: 493.22 | 0.0161 |
| E-Y41 | 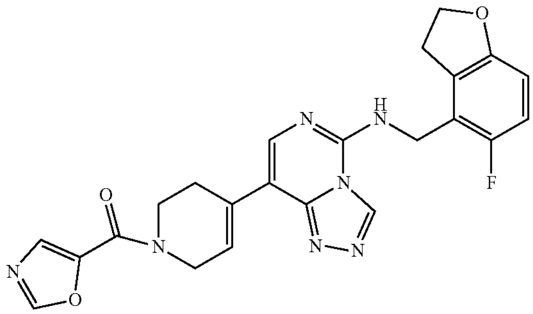 Exact Mass: 461.16 | <0.02 |
| E-Y42 | 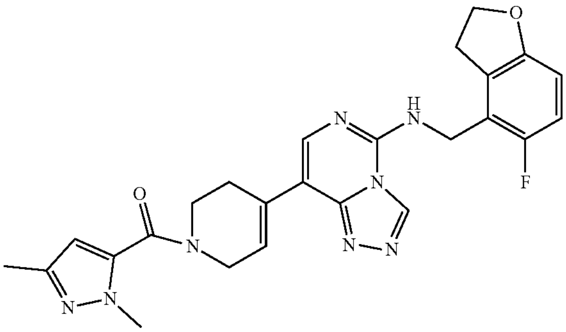 Exact Mass: 488.21 | 0.0048 |

-continued
| Compound No. | Structure of compound | Enzyme Activity IC$_{50}$ (μM) |
|---|---|---|
| E-Y43 | 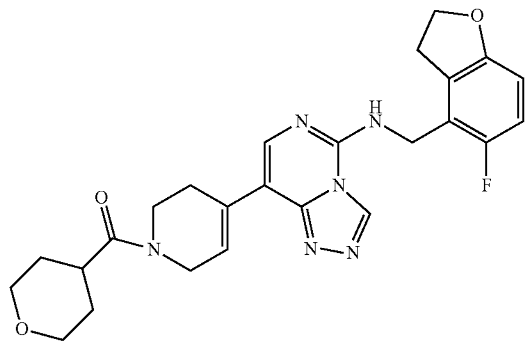 Exact Mass: 478.21 | 0.0085 |
| E-Y44 | 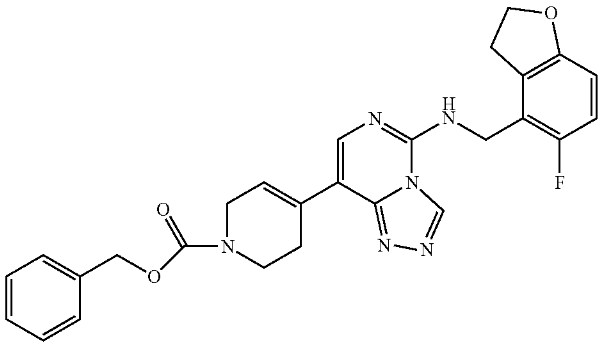 Exact Mass: 500.20 | 0.0858 |
| E-Y45 | 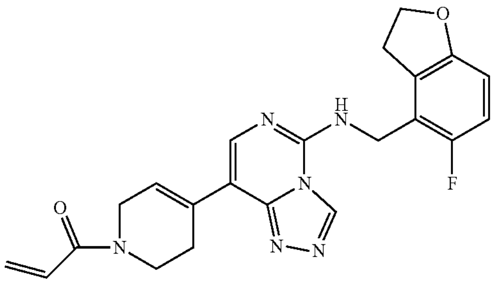 Exact Mass: 420.17 | 0.0034 |
| E-Y46 | 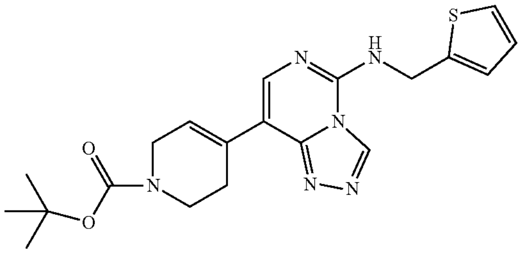 Exact Mass: 412.17 | 0.2957 |

-continued
| Compound No. | Structure of compound | Enzyme Activity $IC_{50}$ (μM) |
|---|---|---|
| E-Y47 | 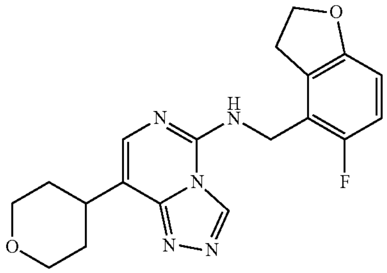 Exact Mass: 369.16 | 0.013 |
| E-Y48 | 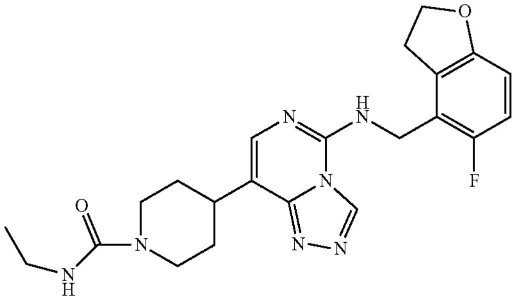 Exact Mass: 439.21 | 0.0054 |
| E-Y49 | 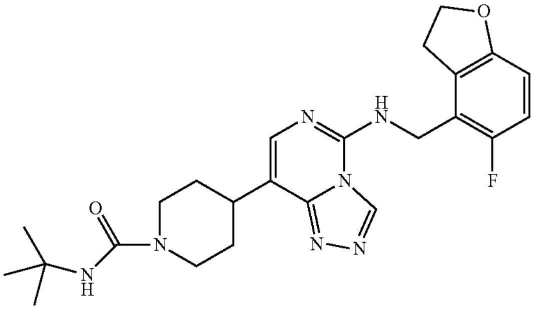 Exact Mass: 467.24 | 0.0066 |
| E-Y50 | 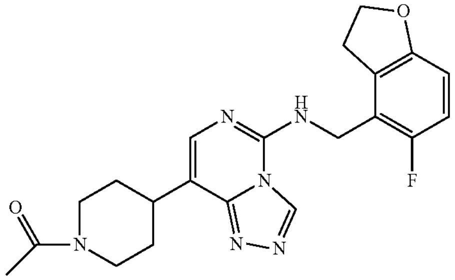 Exact Mass: 410.19 | 0.0053 |
| E-Y51 | 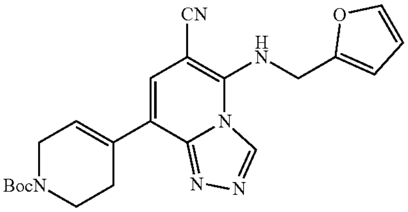 Exact Mass: 420.19 | 0.2 |

-continued
| Compound No. | Structure of compound | Enzyme Activity $IC_{50}$ (μM) |
|---|---|---|
| E-Y54 | 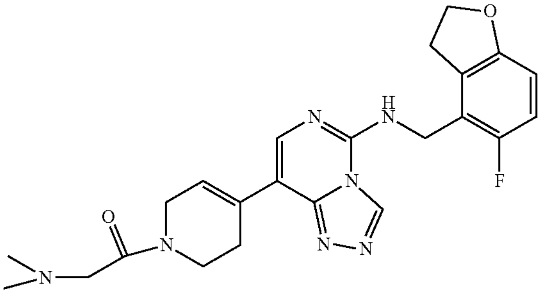 Exact Mass: 451.21 | 0.0041 |
| SL-ZYE-07 | 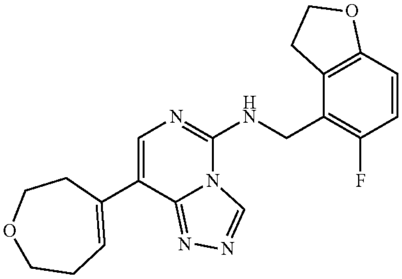 Exact Mass: 381.16 | 0.0073 |
| SL-ZYE-08 | 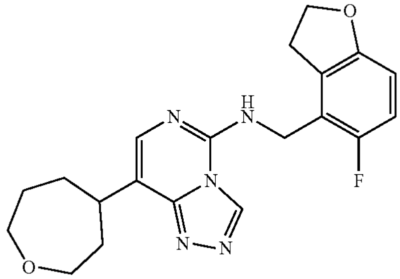 Exact Mass: 383.18 | 0.01193 |
| SL-ZYE-09 | 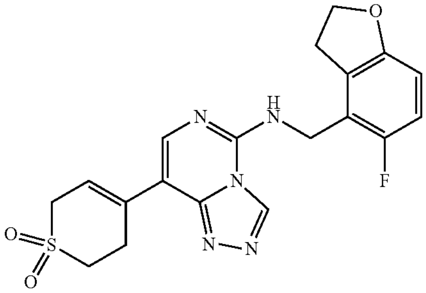 Exact Mass: 415.11 | 0.0045 |
| SL-ZYE-11 | 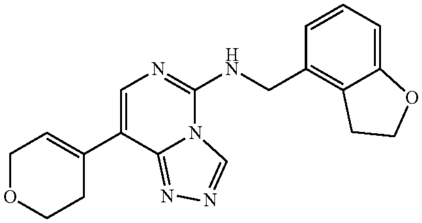 Exact Mass: 349.15 | 0.0179 |

-continued
| Compound No. | Structure of compound | Enzyme Activity $IC_{50}$ (μM) |
|---|---|---|
| SL-ZYE-14 | 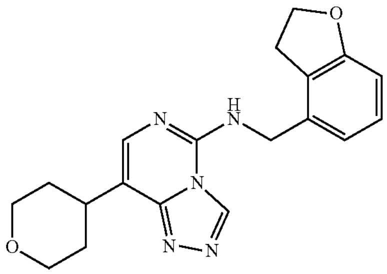 Exact Mass: 351.17 | 0.0840 |
| SL-ZYE-17 | 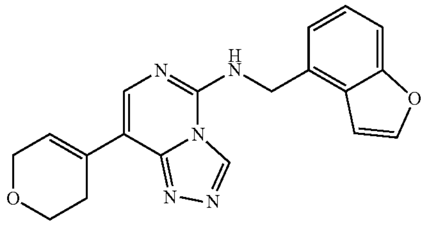 Exact Mass: 347.14 | 0.0560 |
| SL-ZYE-18 | 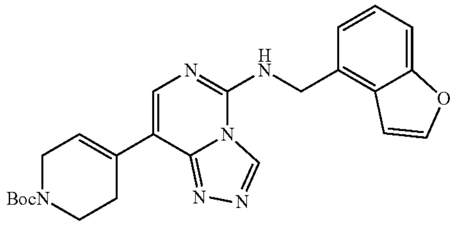 Exact Mass: 446.21 | 0.1153 |
| E-Y20-H | 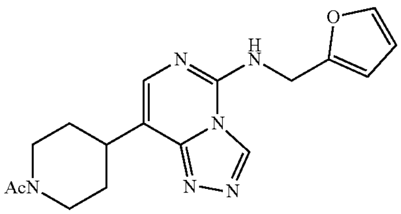 Exact Mass: 340.16 | 0.0939 |
| E-Y13-H | 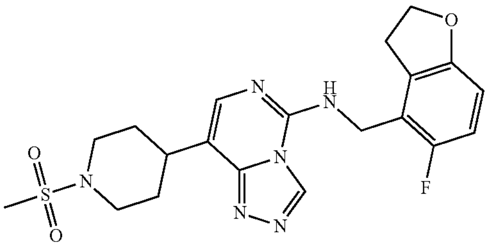 Exact Mass: 446.15 | 0.0107 |

-continued
| Compound No. | Structure of compound | Enzyme Activity $IC_{50}$ (μM) |
|---|---|---|
| SL-ZYE-23 | 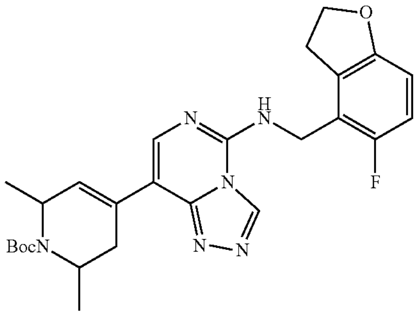 Exact Mass: 494.24 | 0.0476 |
| SL-ZYE-24 | 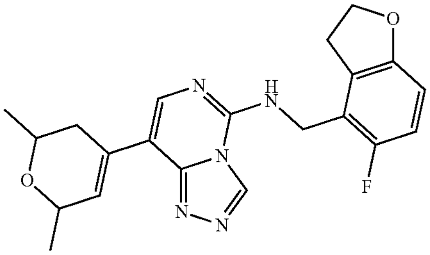 Exact Mass: 395.18 | 0.0083 |
| SL-ZYE-28 | 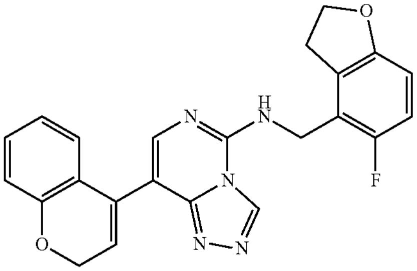 Exact Mass: 415.14 | 0.0225 |
| SL-ZYE-34 | 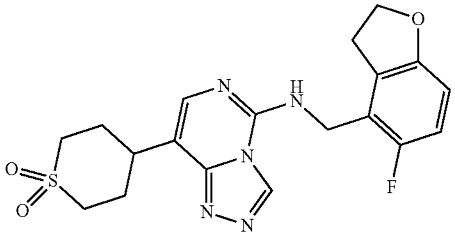 Exact Mass: 417.13 | 0.0032 |
| E-Y54-H | 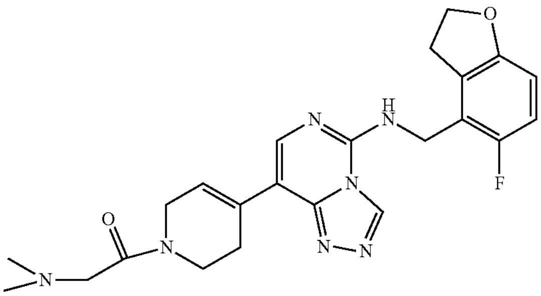 Exact Mass: 453.23 | 0.005 |

-continued
| Compound No. | Structure of compound | Enzyme Activity IC$_{50}$ (μM) |
|---|---|---|
| SL-E23 | 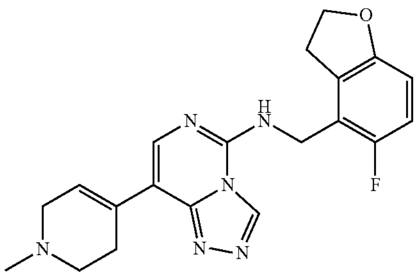 Exact Mass: 380.1761 | 0.0047 |
| SL-E25 | 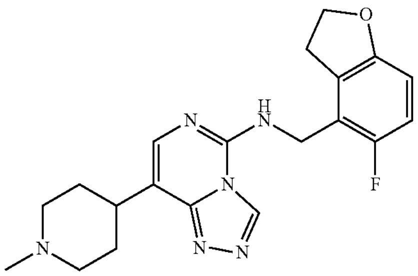 Exact Mass: 382.1917 | 0.015 |
| SL-ZYE-119 | 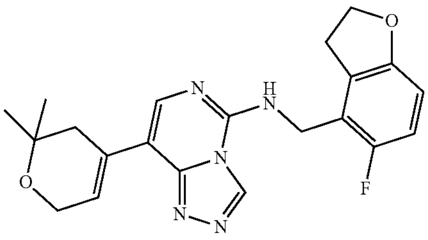 Exact Mass: 395.18 | 0.0233 |
| SL-ZYE-144 | 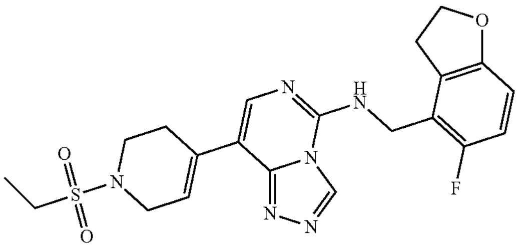 Exact Mass: 458.15 | 0.0035 |
| SL-ZYE-146 | 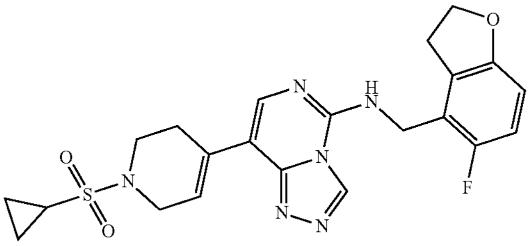 Exact Mass: 470.15 | 0.0029 |

-continued
| Compound No. | Structure of compound | Enzyme Activity $IC_{50}$ (μM) |
|---|---|---|
| SL-ZYE-147 | 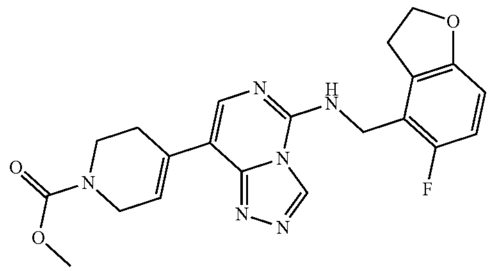 Exact Mass: 424.17 | 0.0025 |
| SL-ZYE-148 | 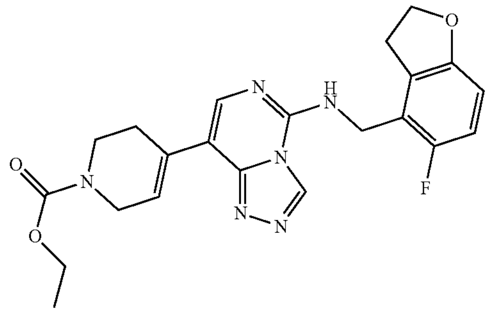 Exact Mass: 438.18 | 0.0047 |
| SL-ZYE-161 | 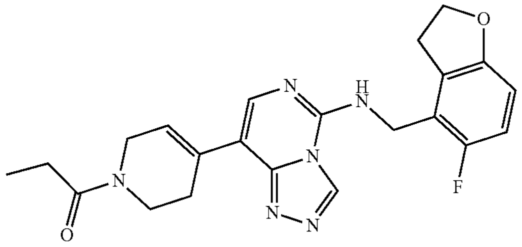 Exact Mass: 422.19 | 0.0408 |
| SL-ZYE-162 | 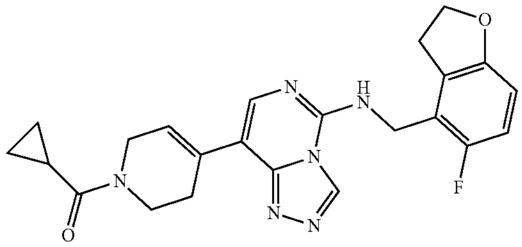 Exact Mass: 434.19 | 0.0052 |
| SL-ZYE-145 | 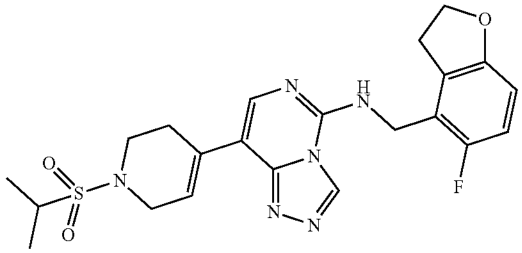 Exact Mass: 472.17 | 0.0089 |

-continued
| Compound No. | Structure of compound | Enzyme Activity $IC_{50}$ (μM) |
|---|---|---|
| SL-E24 | 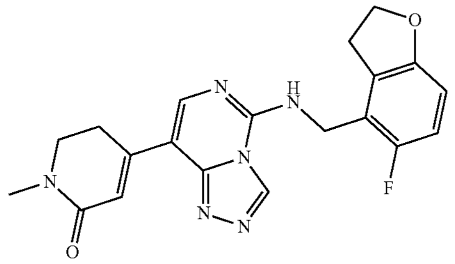 Exact Mass: 394.16 | 0.0039 |
| SL-E26 | 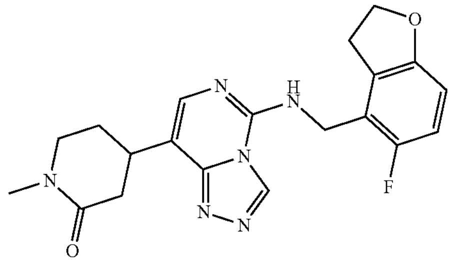 Exact Mass: 396.17 | 0.0084 |
| SL-E13 | 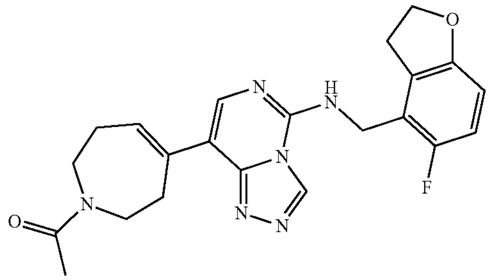 Exact Mass: 422.19 | 0.0033 |
| SL-ZYE-183 | 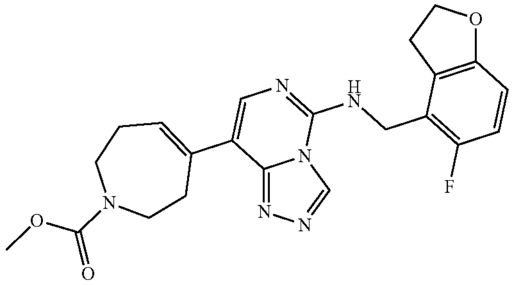 Exact Mass: 438.18 | 0.0022 |
| SL-E14 | 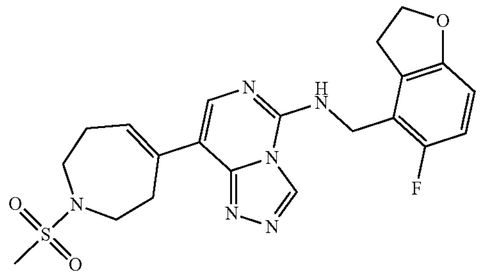 Exact Mass: 458.15 | 0.0017 |

-continued
| Compound No. | Structure of compound | Enzyme Activity IC$_{50}$ (μM) |
|---|---|---|
| SL-ZYE-195 | 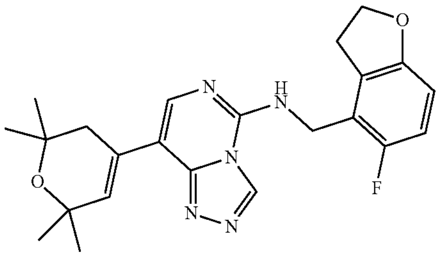 Exact Mass: 423.21 | 0.0223 |
| SL-ZYE-196 | 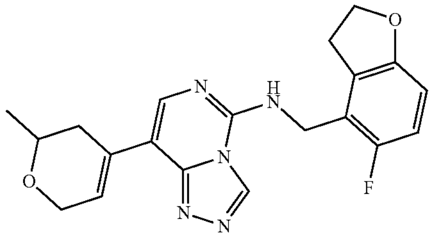 Exact Mass: 381.16 | 0.0141 |
| SL-ZYE-197 | 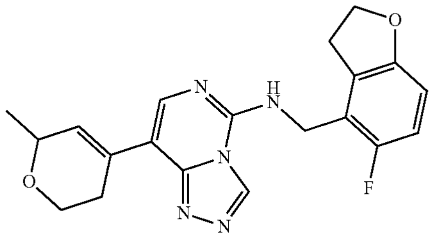 Exact Mass: 381.16 | 0.0078 |
| SL-ZYE-120 | 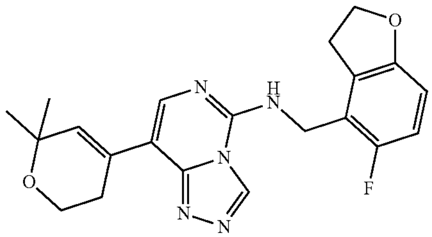 Exact Mass: 395.18 | 0.0036 |
| SL-ZYE-121 | 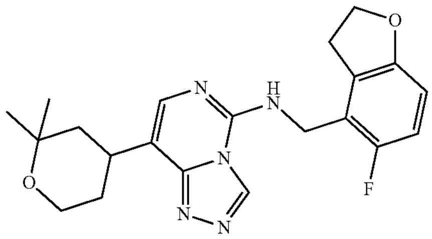 [SMILES: CC1(C)CC(c2cnc(NCc3c(F)ccc4c3CCO4)n3cnnc23)CCO1] | 0.0042 |

-continued

| Compound No. | Structure of compound | Enzyme Activity $IC_{50}$ (μM) |
|---|---|---|
| EED226 | 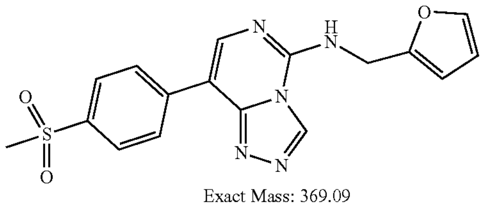 [SMILES: CS(=O)(=O)c1ccc(-c2cnc(NCc3ccco3)n3cnnc23)cc1] Exact Mass: 369.09 | 0.104 |

Example 135: Experiment on Cell Growth Inhibition in a Long Term (11 Days)

Pfeiffer cells in exponential growth phase were seeded in a 24-well plate with a cell density of 1*10E5 cells/mL. Cells were treated on the same day with the compounds at different concentrations. At day 4 and day 7 of compound treatment, fresh media and compounds were changed. After treated with the compounds for 11 days, cell viability was measured using CellTiter-Glo reagent (Promega Corporation). The data was analyzed using GraphPad Prism 5.0 software and $GI_{50}$ values were obtained.

The compounds in Table 2 can be prepared by the methods described in the above examples, and EED226 is the positive compound (Nat. Chem. Biol. 2017, 13, 381-388).

| Compound No. | Structure of compound | Experiment on Pfeiffer cell growth inhibition in a long term (11 days $IC_{50}$ (μM) |
|---|---|---|
| E-Y1 | 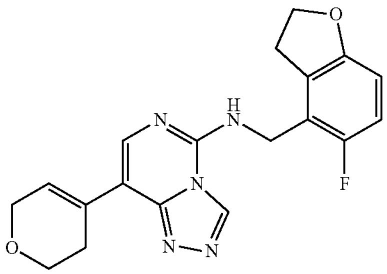 Exact Mass: 367.1445 | 0.008 |
| E-Y6 | 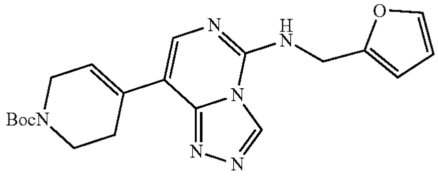 Exact Mass: 396.1910 | 0.083 |
| E-Y9 | 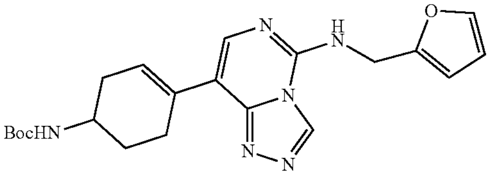 Exact Mass: 410.2066 | 0.32 |

-continued
| Compound No. | Structure of compound | Experiment on Pfeiffer cell growth inhibition in a long term (11 days $IC_{50}$ (μM) |
|---|---|---|
| E-Y13 | 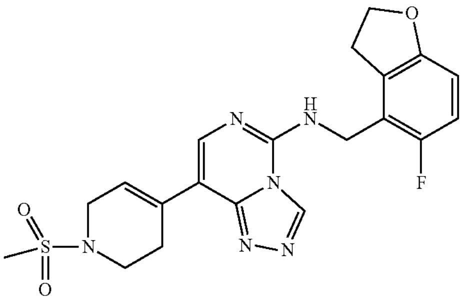 Exact Mass: 444.14 | 0.0032 |
| E-Y15 | 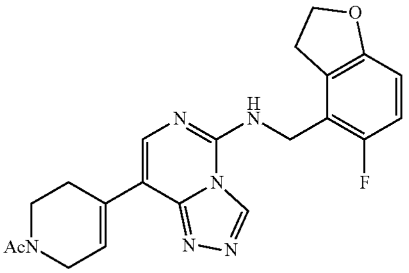 Exact Mass: 408.17 | 0.0019 |
| E-Y16 | 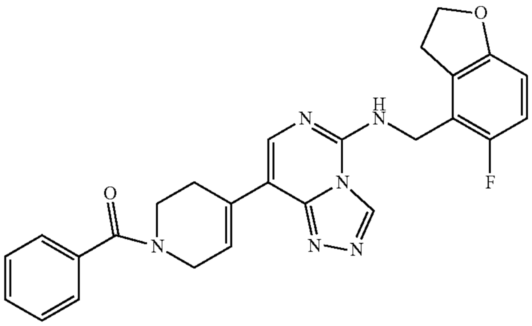 Exact Mass: 470.19 | 0.0048 |
| E-Y17 | 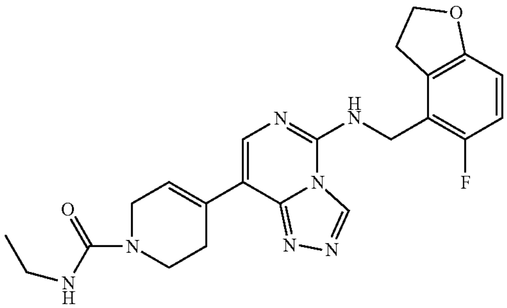 Exact Mass: 437.20 | 0.0027 |

-continued
| Compound No. | Structure of compound | Experiment on Pfeiffer cell growth inhibition in a long term (11 days $IC_{50}$ (μM) |
|---|---|---|
| E-Y18 | 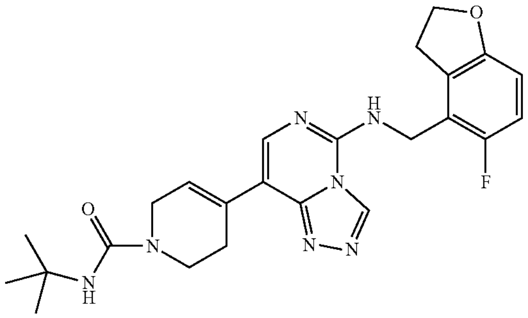 Exact Mass: 465.23 | 0.0027 |
| E-Y19 | 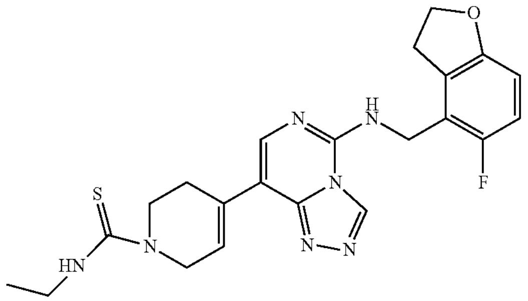 Exact Mass: 453.17 | 0.003 |
| E-Y20 | 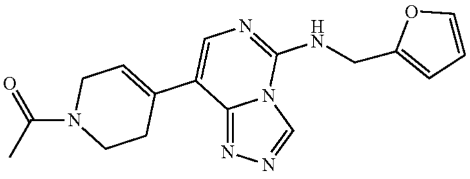 Exact Mass: 338.1491 | 0.158 |
| E-Y21 | 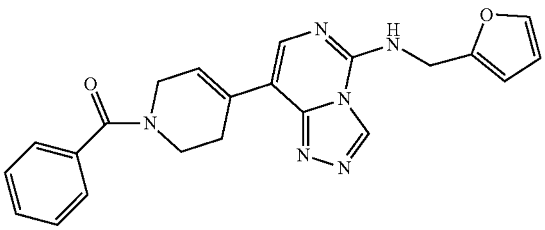 Exact Mass: 400.1648 | 0.185 |
| E-Y23 | 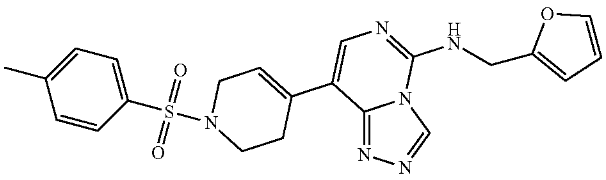 Exact Mass: 450.1474 | 0.107 |

-continued
| Compound No. | Structure of compound | Experiment on Pfeiffer cell growth inhibition in a long term (11 days $IC_{50}$ (μM) |
|---|---|---|
| E-Y24 | 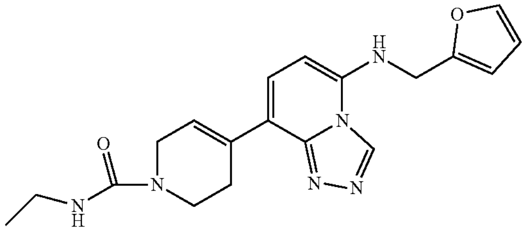 Exact Mass: 367.18 | 0.204 |
| E-Y36 | 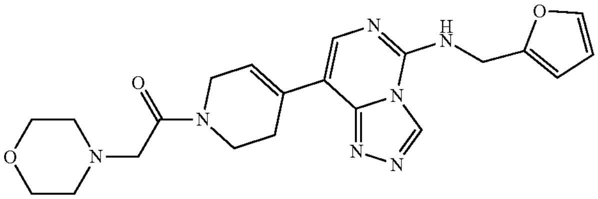 Exact Mass: 493.2019 | 0.289 |
| E-Y40 | 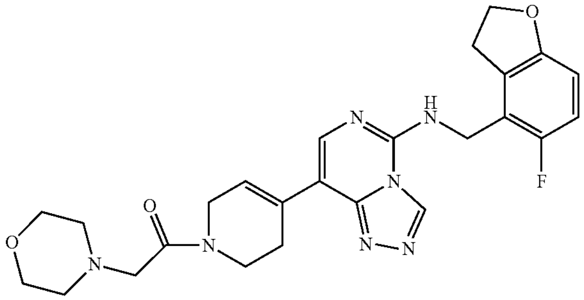 Exact Mass: 493.22 | 0.0054 |
| E-Y43 | 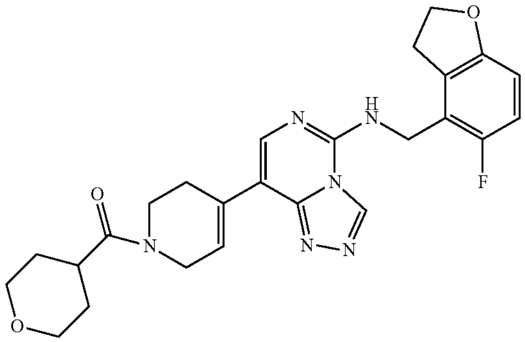 Exact Mass: 478.21 | 0.0033 |

-continued
| Compound No. | Structure of compound | Experiment on Pfeiffer cell growth inhibition in a long term (11 days $IC_{50}$ (μM) |
|---|---|---|
| E-Y44 | 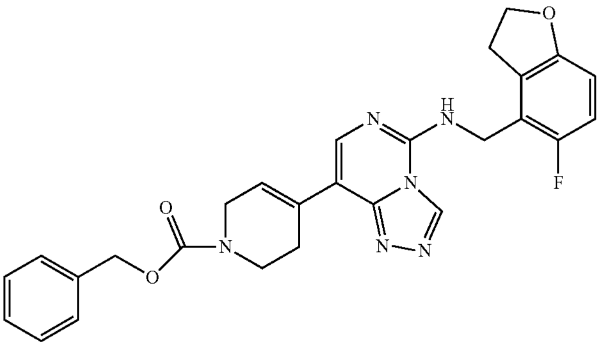 Exact Mass: 500.20 | 0.0023 |
| E-Y41 | 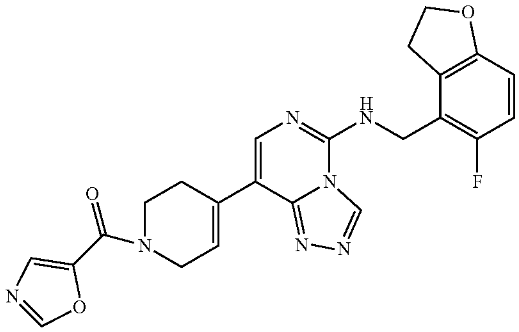 Exact Mass: 461.16 | 0.0045 |
| E-Y42 | 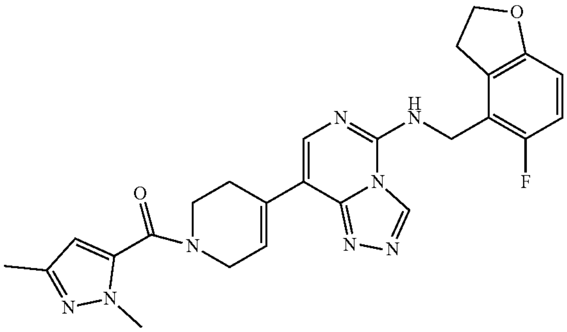 Exact Mass: 488.21 | 0.0036 |
| E-Y45 | 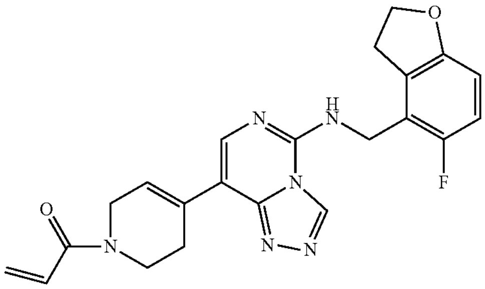 Exact Mass: 420.17 | 0.0018 |

-continued
| Compound No. | Structure of compound | Experiment on Pfeiffer cell growth inhibition in a long term (11 days $IC_{50}$ (μM) |
|---|---|---|
| E-Y48 | 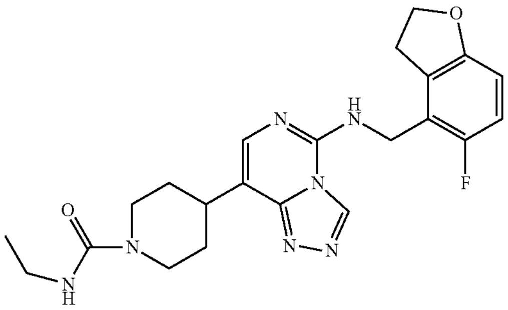 Exact Mass: 439.21 | 0.0159 |
| E-Y49 | 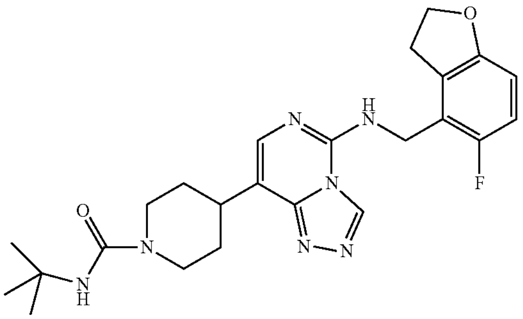 Exact Mass: 467.24 | 0.01 |
| E-Y50 | 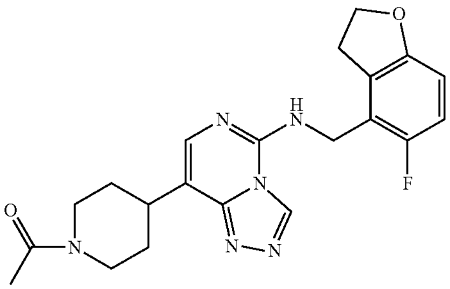 Exact Mass: 410.19 | 0.0038 |
| SL-E23 | 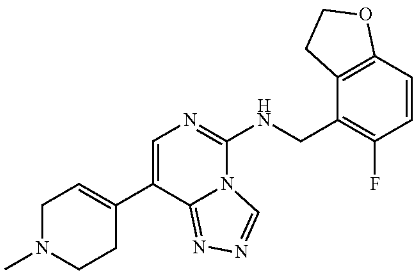 [SMILES: CN1CC=C(c2cnc(NCc3c(F)ccc4c3CCO4)n3cnnc23)CC1] | 0.0077 |
| SL-ZYE-119 | 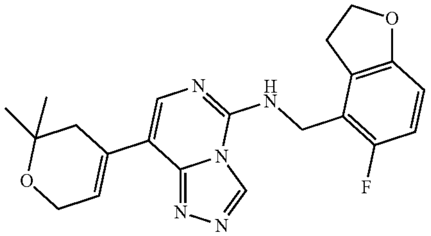 [SMILES: CC1(C)CC(c2cnc(NCc3c(F)ccc4c3CCO4)n3cnnc23)=CCO1] | 0.0081 |

-continued
| Compound No. | Structure of compound | Experiment on Pfeiffer cell growth inhibition in a long term (11 days $IC_{50}$ (μM) |
|---|---|---|
| SL-ZYE-144 | 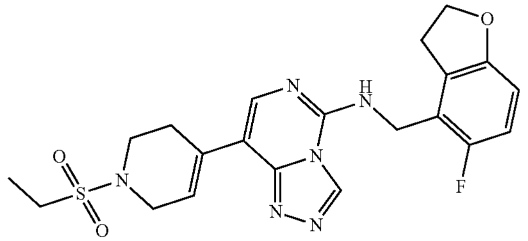 [SMILES: CCS(=O)(=O)N1CC=C(c2cnc(NCc3c(F)ccc4c3CCO4)n3cnnc23)CC1] | 0.0018 |
| SL-ZYE-146 | 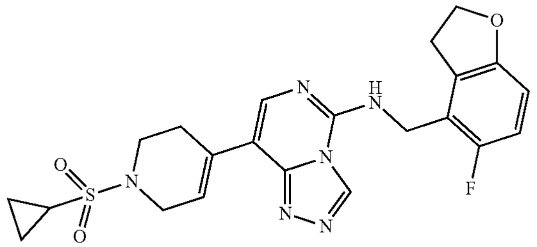 [SMILES: O=S(=O)(C1CC1)N1CC=C(c2cnc(NCc3c(F)ccc4c3CCO4)n3cnnc23)CC1] | 0.0045 |
| SL-ZYE-147 | 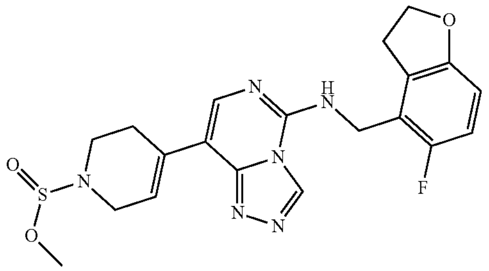 [SMILES: COS(=O)N1CC=C(c2cnc(NCc3c(F)ccc4c3CCO4)n3cnnc23)CC1] | 0.001-0.003 |
| SL-ZYE-148 | 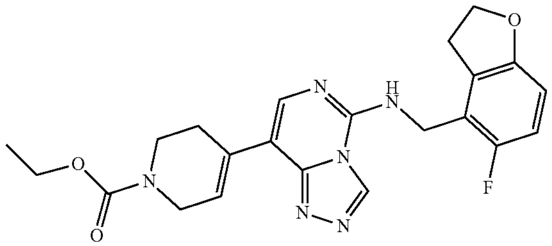 [SMILES: CCOC(=O)N1CC=C(c2cnc(NCc3c(F)ccc4c3CCO4)n3cnnc23)CC1] | 0.001-0.003 |
| SL-ZYE-161 | 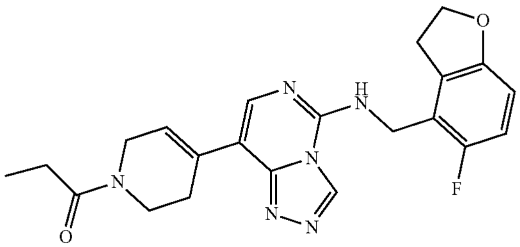 [SMILES: CCC(=O)N1CC=C(c2cnc(NCc3c(F)ccc4c3CCO4)n3cnnc23)CC1] | 0.009-0.027 |
| SL-ZYE-162 | 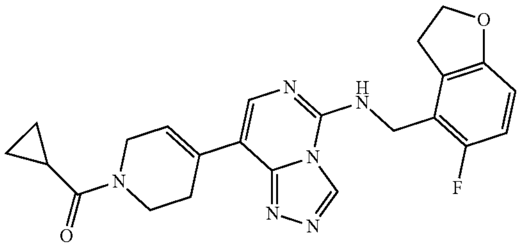 [SMILES: O=C(C1CC1)N1CC=C(c2cnc(NCc3c(F)ccc4c3CCO4)n3cnnc23)CC1] | 0.0027 |

-continued
| Compound No. | Structure of compound | Experiment on Pfeiffer cell growth inhibition in a long term (11 days $IC_{50}$ (μM) |
|---|---|---|
| SL-ZYE-145 | 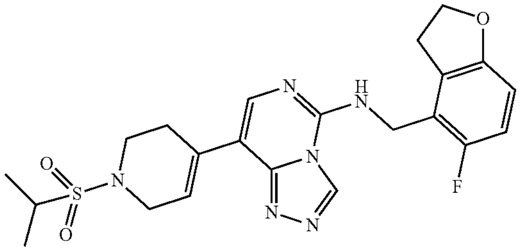 [SMILES: CC(C)S(=O)(=O)N1CC=C(c2cnc(NCc3c(F)ccc4c3CCO4)n3cnnc23)CC1] | 0.0017 |
| SL-E24 | 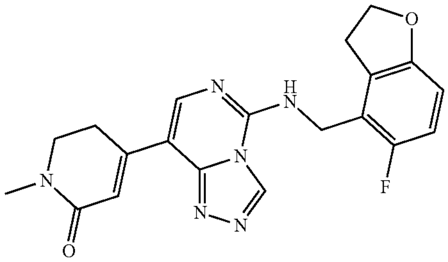 [SMILES: CN1CCC(c2cnc(NCc3c(F)ccc4c3CCO4)n3cnnc23)=CC1=O] | 0.0051 |
| SL-E13 | 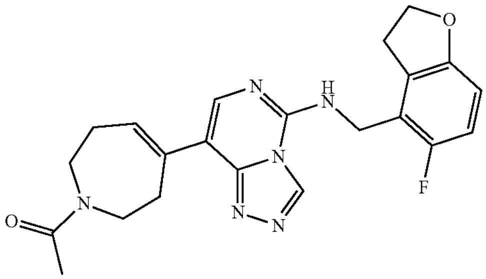 [SMILES: CC(=O)N1CCC=C(c2cnc(NCc3c(F)ccc4c3CCO4)n3cnnc23)CC1] | 0.006 |
| SL-ZYE-196 | 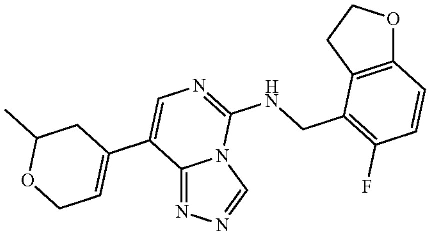 [SMILES: CC1CC(c2cnc(NCc3c(F)ccc4c3CCO4)n3cnnc23)=CCO1] | 0.007 |
| SL-ZYE-197 | 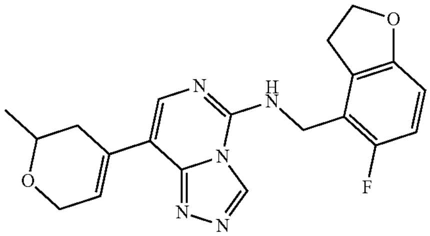 [SMILES: CC1CC(c2cnc(NCc3c(F)ccc4c3CCO4)n3cnnc23)=CCO1] | 0.010 |
| EED226 | 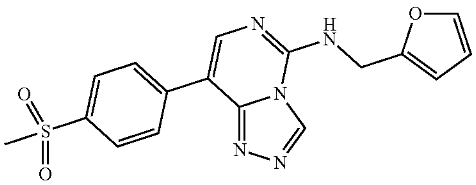 Exact Mass: 369.09 | 0.052 |

Example 136: Experiment on Growth Inhibition of Pfeiffer Cells in a Long Term (14 Days)

In a $CO_2$ cell incubator (37° C., 5% $CO_2$), Human diffuse large B-cell lymphoma (DLBCL) cell line, pfeiffer (obtained from ATCC, CRL-2632) were incubated with RPMI 1640 medium (Gibco, purchased from Life Technologies, 22400-089) containing 10% fetal bovine serum (Gibco, purchased from Life Technologies, 10099-141) and 1% antibiotics (penicillin and streptomycin, purchased from Life Technologies, 10378016). In the Experiment on growth inhibition of cells in a long term, pfeiffer cells in exponential growth phase were seeded in 24-well plates (purchased from Corning Corporation, 3524) with a volume of 1 mL/well and a cell density of 2*10E5 cells/mL. After seeding the cells, they were placed in a $CO_2$ incubator and allowed to stand for 1 hour. In a 24-well plate containing cells, 2 μL of three-fold gradient of the compounds at 9 different concentrations or DMSO were added to each well, such that the final concentration of the compounds was 0.003-20 μM or 0.3-2000 nM, and the final concentration of DMSO was 0.2%. At day 4, day 7, and day 11 of compound treatment, the fresh medium and compounds were changed, and the cell density of the DMSO control well was diluted to 2*10E5 cells/mL. The cell dilution ratio for other compound wells was the same as that of the DMSO control well. Cell viability was determined by using CellTiter-Glo reagent (purchased from Promega Inc., G7572): cells treated with the compounds for 14 days were transferred to a white 384-well plate (OptiPlate-384, purchased from PerkinElmer, 6007299) at 40 μL/well, an equal volume of CellTiter-Glo reagent was further added. After incubating at room temperature for 10 min, the cold luminescence signal was detected with a multifunctional microplate reader EnVision (PerkinElmer) at a wavelength of 400 to 700 nm. Data were analyzed using GraphPad Prism 5.0 software, and $IC_{50}$ values were obtained.

The compounds in Table 3 can be prepared by the methods described in the above examples, and EED226 is the positive compound (Nat. Chem. Biol. 2017, 13, 381-388).

| Compound No. | Structure of compound | Pfeiffer (14 days) $IC_{50}$ (μM) |
|---|---|---|
| E-Y1 | 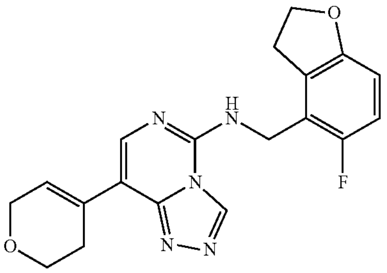 [SMILES: Fc1ccc2c(c1CNc1ncc(C3=CCOCC3)c3nncn13)CCO2] | 0.004 |
| E-Y13 | 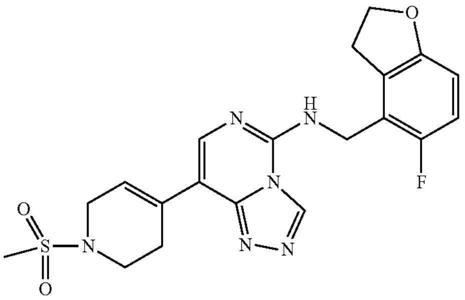 [SMILES: CS(=O)(=O)N1CC=C(c2cnc(NCc3c(F)ccc4c3CCO4)n3cnnc23)CC1] | 0.001 |
| E-Y15 | 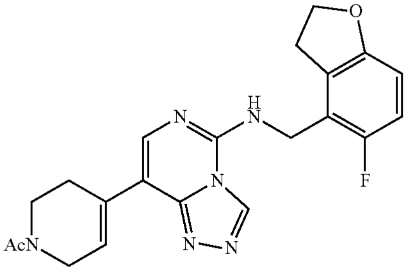 | 0.0007 |

-continued
| Compound No. | Structure of compound | Pfeiffer (14 days) $IC_{50}$ (μM) |
|---|---|---|
| E-Y42 | 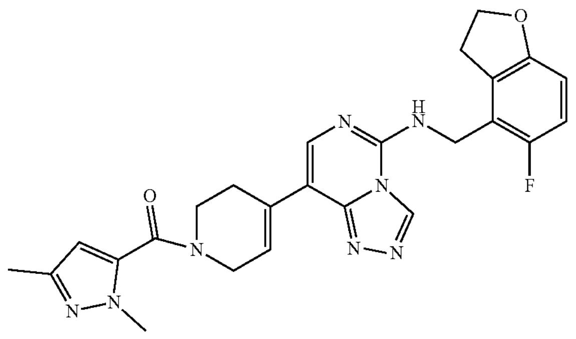 [SMILES: Cc1cc(C(=O)N2CC=C(c3cnc(NCc4c(F)ccc5c4CCO5)n4cnnc34)CC2)n(C)n1] | 0.0015 |
| E-Y47 | 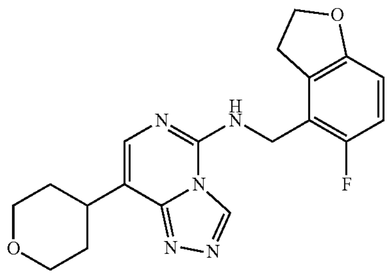 [SMILES: Fc1ccc2c(c1CNc1ncc(C3CCOCC3)c3nncn13)CCO2] | 0.006 |
| SL-ZYE-07 | 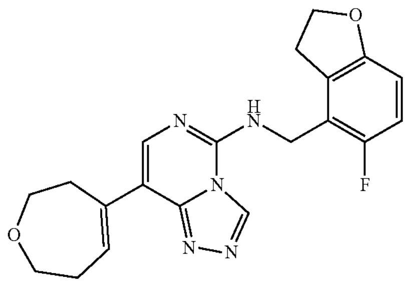 [SMILES: Fc1ccc2c(c1CNc1ncc(C3=CCCOCC3)c3nncn13)CCO2] | 0.001 |
| SL-ZYE-09 | 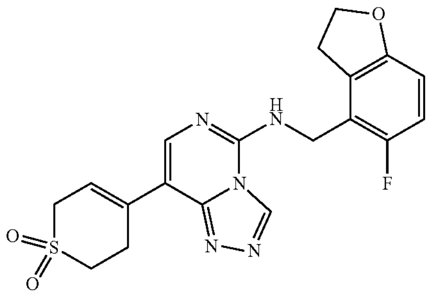 [SMILES: O=S1(=O)CC=C(c2cnc(NCc3c(F)ccc4c3CCO4)n3cnnc23)CC1] | 0.0032 |
| SL-ZYE-24 | 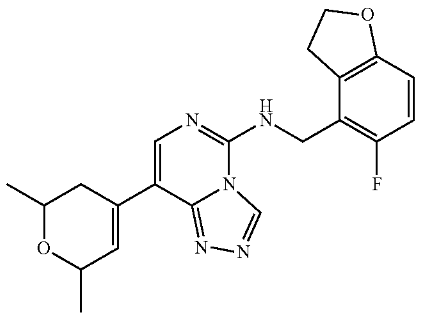 [SMILES: CC1C=C(c2cnc(NCc3c(F)ccc4c3CCO4)n3cnnc23)CC(C)O1] | 0.006 |

-continued
| Compound No. | Structure of compound | Pfeiffer (14 days) $IC_{50}$ (μM) |
|---|---|---|
| SL-ZYE-28 | 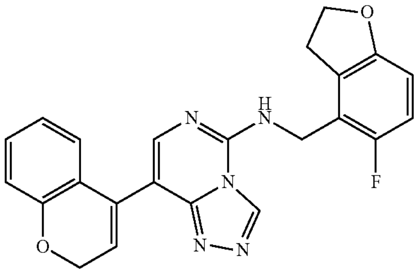 [SMILES: Fc1ccc2c(c1CNc1ncc(C3=CCOc4ccccc43)c3nncn13)CCO2] | 0.010 |
| SL-E23 | 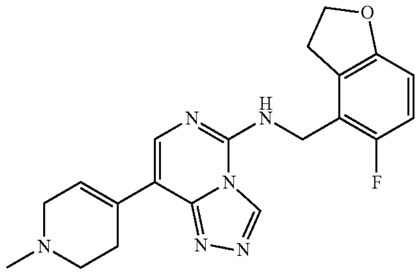 [SMILES: CN1CC=C(c2cnc(NCc3c(F)ccc4c3CCO4)n3cnnc23)CC1] | 0.002 |
| SL-ZYE-119 | 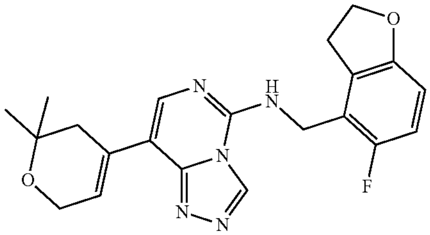 [SMILES: CC1(C)CC(c2cnc(NCc3c(F)ccc4c3CCO4)n3cnnc23)=CCO1] | 0.004 |
| SL-ZYE-144 | 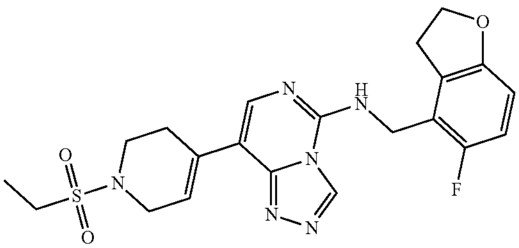 [SMILES: CCS(=O)(=O)N1CC=C(c2cnc(NCc3c(F)ccc4c3CCO4)n3cnnc23)CC1] | 0.0008 |
| SL-ZYE-146 | 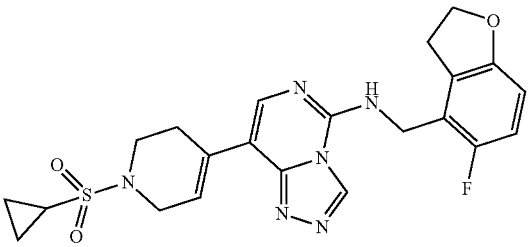 [SMILES: O=S(=O)(C1CC1)N1CC=C(c2cnc(NCc3c(F)ccc4c3CCO4)n3cnnc23)CC1] | 0.003 |
| SL-ZYE-162 | 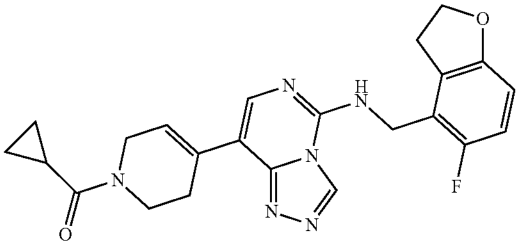 [SMILES: O=C(C1CC1)N1CC=C(c2cnc(NCc3c(F)ccc4c3CCO4)n3cnnc23)CC1] | 0.0012 |

-continued

| Compound No. | Structure of compound | Pfeiffer (14 days) $IC_{50}$ (μM) |
|---|---|---|
| SL-ZYE-145 | 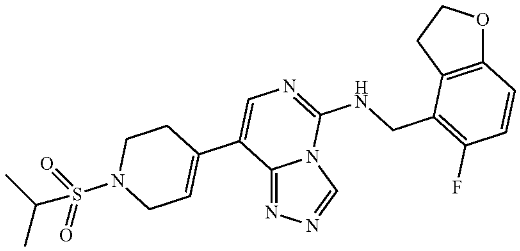 [SMILES: CC(C)S(=O)(=O)N1CC=C(c2cnc(NCc3c(F)ccc4c3CCO4)n3cnnc23)CC1] | 0.0010 |
| SL-E24 | 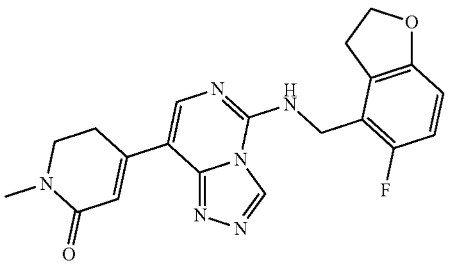 [SMILES: CN1CCC(c2cnc(NCc3c(F)ccc4c3CCO4)n3cnnc23)=CC1=O] | 0.003 |
| SL-ZYE-196 | 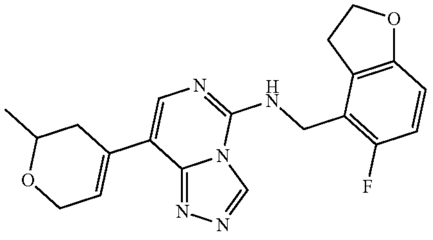 [SMILES: CC1CC(c2cnc(NCc3c(F)ccc4c3CCO4)n3cnnc23)=CCO1] | 0.004 |
| SL-ZYE-197 | 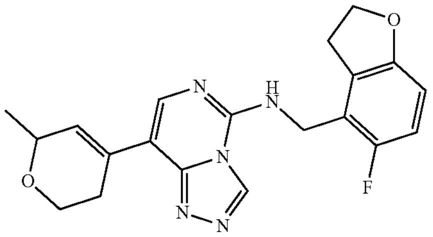 [SMILES: CC1C=C(c2cnc(NCc3c(F)ccc4c3CCO4)n3cnnc23)CCO1] | 0.005 |
| EED226 | 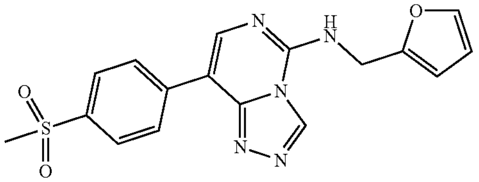 Exact Mass: 369.09 | 0.044 |

Example 137: Experiment on Growth Inhibition of Cell Karpas-422, SU-DHL-4 in a Long Term (11 Days)

In a $CO_2$ cell incubator (37° C., 5% $CO_2$), Human diffuse large B-cell lymphoma (DLBCL) cell line, Karpas-422, SU-DHL-4 (obtained from ATCC, CRL-2957) were incubated with RPMI 1640 medium (Gibco, purchased from Life Technologies, 22400-089) containing 10% fetal bovine serum (Gibco, purchased from Life Technologies, 10099-141) and 1% antibiotics (penicillin and streptomycin, purchased from Life Technologies, 10378016). In the Experiment on growth inhibition of cells in a long term, Karpas-422, SU-DHL-4 cells in exponential growth phase were seeded in 24-well plates (purchased from Corning Corporation, 3524) with a cell density of 1*10E5/mL and a cell medium volume of 1 mL. After incubating in a 24-well plate for 1 hour, 2 μL of the compounds or DMSO were added to each well. For each compound, there were 9 different concentrations, such that the final concentration in the cell medium was 0.003-20 μM or 0.3-2000 nM, and the final concentration of DMSO was 0.2%. At day 4, day 7 of compound treatment, the fresh cell medium and compounds were changed, and the cell density of the DMSO control well was diluted to 1*10E5/mL. The cell dilution ratio for compound wells was the same as that of the DMSO control well. Cell viability was determined by using CellTiter-Glo reagent (purchased from Promega Inc., G7572): cells treated with the compounds for 11 days were transferred to a white 384-well plate (OptiPlate-384, purchased from PerkinElmer, 6007299) at 40 μL/well, an equal volume of CellTiter-Glo reagent was further added. After incubating at room temperature for 10 min, the cold luminescence signal was detected with a multifunctional microplate reader EnVision (purchased from PerkinElmer) at a wavelength of 400 to 700 nm. Data were analyzed using GraphPad Prism 5.0 software, and $IC_{50}$ values were obtained.

The compounds in Table 4 can be prepared by the methods described in the above examples, and EED226 is the positive compound (Nat. Chem. Biol. 2017, 13, 381-388).

| Compound No. | Structure of compound | Karpas-422 (11 days) $IC_{50}$ (μM) | SU-DHL-4 (11 days) $IC_{50}$ (μM) |
|---|---|---|---|
| E-Y1 | 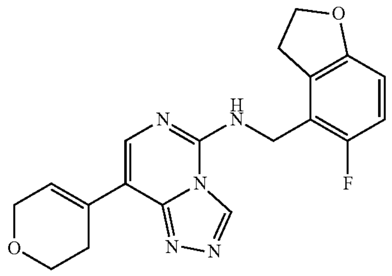 [SMILES: Fc1ccc2c(c1CNc1ncc(C3=CCOCC3)c3nncn13)CCO2] | 0.019 | 0.004 |
| E-Y13 | 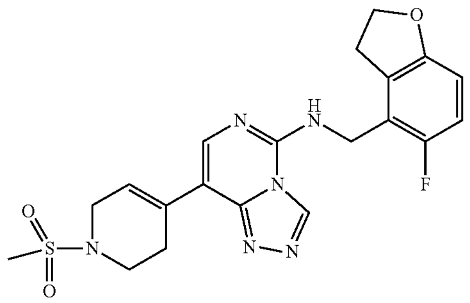 [SMILES: CS(=O)(=O)N1CC=C(c2cnc(NCc3c(F)ccc4c3CCO4)n3cnnc23)CC1] | 0.013 | / |
| E-Y15 | 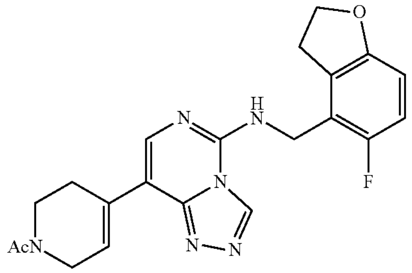 | 0.007 | 0.003 |
| E-Y42 | 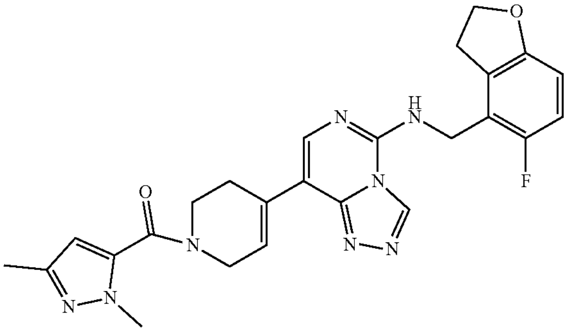 [SMILES: Cc1cc(C(=O)N2CC=C(c3cnc(NCc4c(F)ccc5c4CCO5)n4cnnc34)CC2)n(C)n1] | 0.010 | / |

-continued
| Compound No. | Structure of compound | Karpas-422 (11 days) $IC_{50}$ (μM) | SU-DHL-4 (11 days) $IC_{50}$ (μM) |
|---|---|---|---|
| E-Y47 | 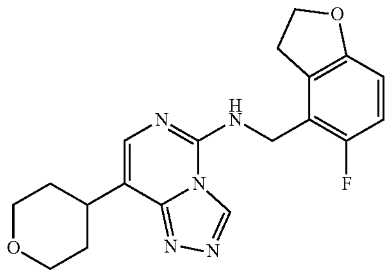 [SMILES: Fc1ccc2c(c1CNc1ncc(C3CCOCC3)c3nncn13)CCO2] | 0.018 | / |
| SL-ZYE-07 | 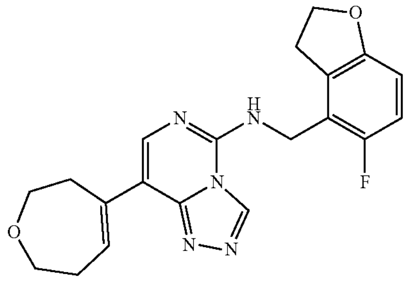 [SMILES: Fc1ccc2c(c1CNc1ncc(C3=CCCOCC3)c3nncn13)CCO2] | 0.025 | 0.005 |
| SL-E23 | 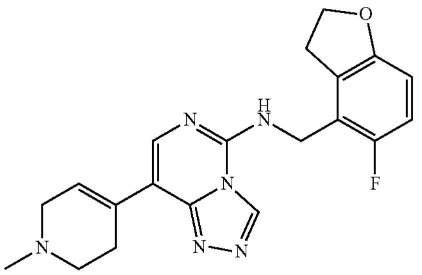 [SMILES: CN1CC=C(c2cnc(NCc3c(F)ccc4c3CCO4)n3cnnc23)CC1] | 0.0028 | / |
| SL-ZYE-144 | 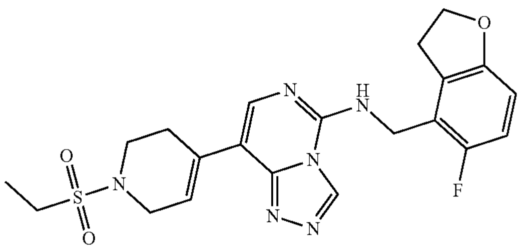 [SMILES: CCS(=O)(=O)N1CC=C(c2cnc(NCc3c(F)ccc4c3CCO4)n3cnnc23)CC1] | 0.004 | 0.003 |
| SL-ZYE-146 | 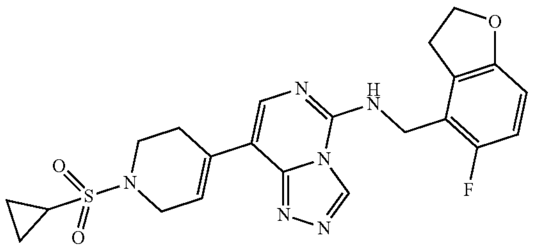 [SMILES: O=S(=O)(C1CC1)N1CC=C(c2cnc(NCc3c(F)ccc4c3CCO4)n3cnnc23)CC1] | 0.004 | 0.004 |

-continued
| Compound No. | Structure of compound | Karpas-422 (11 days) $IC_{50}$ (μM) | SU-DHL-4 (11 days) $IC_{50}$ (μM) |
|---|---|---|---|
| SL-ZYE-162 | 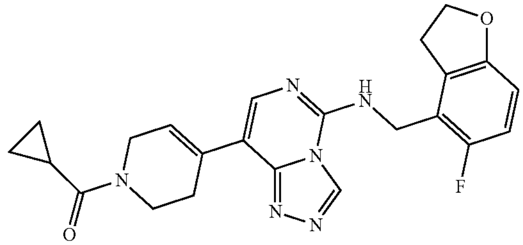 [SMILES: O=C(C1CC1)N1CC=C(c2cnc(NCc3c(F)ccc4c3CCO4)n3cnnc23)CC1] | 0.0028 | 0.0031 |
| SL-ZYE-145 | 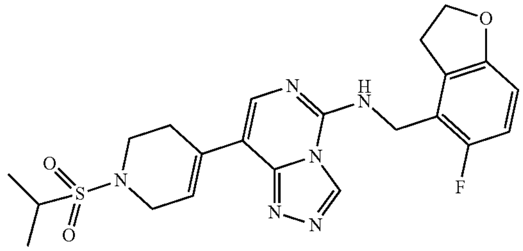 [SMILES: CC(C)S(=O)(=O)N1CC=C(c2cnc(NCc3c(F)ccc4c3CCO4)n3cnnc23)CC1] | 0.0032 | 0.001 |
| SL-E24 | 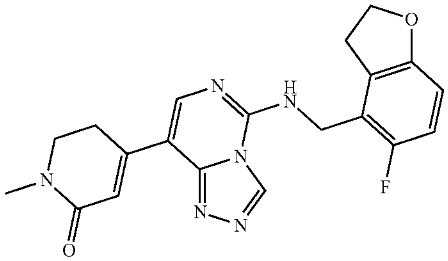 [SMILES: CN1CCC(c2cnc(NCc3c(F)ccc4c3CCO4)n3cnnc23)=CC1=O] | 0.0031 | 0.003 |
| SL-ZYE-196 | 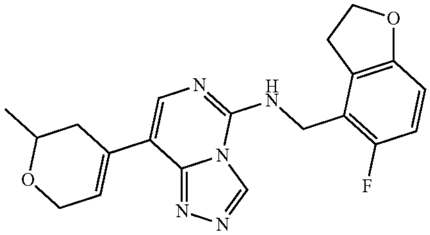 [SMILES: CC1CC(c2cnc(NCc3c(F)ccc4c3CCO4)n3cnnc23)=CCO1] | 0.0199 | 0.009-0.05 |
| SL-ZYE-197 | 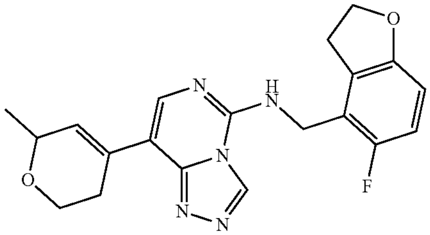 [SMILES: CC1C=C(c2cnc(NCc3c(F)ccc4c3CCO4)n3cnnc23)CCO1] | 0.0160 | 0.0560 |
| EED226 | 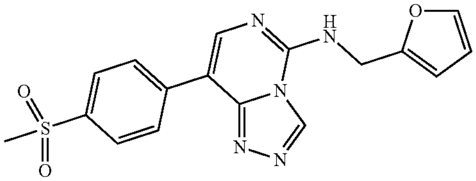 Exact Mass: 369.09 | 0.167 | 0.095 |

From the data in the above Tables 1 to 4, it can be seen that the $IC_{50}$ value of some compounds of the present invention on PRC2 enzyme can be up to a nM level, which is significantly higher than that of the positive control compound EED226; similarly, in the experiments on growth inhibition of Pfeiffer, Karpas-422, and SU-DHL-4 cells in a long term, the $IC_{50}$ values of several compounds of the present invention also is up to a nM level in single digit, which are significantly higher than the positive control EED226 compound.

Example 138: Study on Oral Pharmacokinetics in Rats

1. Healthy male SD rats were used as test animals, EED226, E-Y1, E-Y13, E-Y47, SL-ZYE-07 (3 mg/kg) were administered intragastrically, and the drug concentrations in rat plasma were determined by LC/MS/MS method at different time points after drug administration. The pharmacokinetic behavior of the compounds of the present invention in rats was studied, and the pharmacokinetic properties were evaluated.

2. The test animals were healthy adult male SD rats, with 3 rats in each group, purchased from Shanghai Xipuer-Bikai Laboratory Animal Limited Company.

3. Drug preparation: Compounds EED226, E-Y1, E-Y13, E-Y47 were dissolved in DMSO/0.5% HPMC (5/95, v/v) for preparation. The compound SL-ZYE-07 was dissolved in 0.5% HPMC (containing 0.5% Tween 80), vortexed, and sonicated to disperse the solid matter uniformly to obtain a pale white suspension.

4, Operation: EED226, E-Y1, E-Y13, E-Y47, SL-ZYE-07 were administered to rats by intragastric administration (3 mg/kg), 45 μL of blood was taken through the femoral vein at 0.25, 0.5, 1, 2, 4, 8, 24 hour after administration, and centrifuged in a heparinized centrifuge tube for 5 min, and the plasma samples were separated for analysis. The contents of test compounds in rat plasma after intragastric administration of different compounds were determined by Liquid chromatography-mass spectrometry (LC-MS/MS).

The pharmacokinetic parameters of the compounds of the present invention are as follows:

| | Pharmacokinetic experiment (3 mg/kg) | | | | |
|---|---|---|---|---|---|
| No. | Half life $T_{1/2}$ (h) | Peak concentration $C_{max}$ (ng/mL) | $AUC_{last}$ (h*ng/mL) | $AUC_{INF\_obs}$ (h*ng/mL) | Average residence time $MRT_{INF\_obs}$ (h) |
| EED226 | 1.63 ± 0.411 | 464 ± 429 | 886 ± 336 | 915 ± 316 | 2.55 ± 1.08 |
| E-Y1 | 2.32 ± 0.268 | 302 ± 6.4 | 2198 ± 237 | 2201 ± 239 | 5.46 ± 0.342 |
| E-Y13 | 1.37 ± 0.212 | 376 ± 273 | 529 ± 150 | 539 ± 150 | 2.06 ± 0.484 |
| E-Y47 | 2.56 ± 0.302 | 1305 ± 628 | 7886 ± 2432 | 7905 ± 2444 | 4.92 ± 0.369 |
| SL-ZYE-07 | 3.77 ± 1.69 | 155 ± 34.8 | 891 ± 164 | 910 ± 174 | 4.71 ± 0.896 |

$AUC_{last}$: AUC from the time of beginning the administration to the last time point $AUC_{INF\_obs}$: AUC from the time of beginning the administration to the time point that is theoretical extrapolated to infinity Conclusion: The compounds of the present invention show good pharmacokinetic absorption and have prominent advantages in pharmacokinetic.

Example 139: Experiment on Liver Microsomal Stability (Mouse, Rat, Human): Reagents and Materials

| Name | Supplier | Code/Lot Number |
|---|---|---|
| Liver microsomes of human | BD | H34 |
| Liver microsomes of mouse | Rild | M11 |
| Liver microsomes of rat | BD | R40/R42 |
| NADPH | Roche | N8100-1000 |
| VIVID BOMCC | Life | P2980 |
| 384-well black plate | Greiner | 781209 |
| 96-well incubating plate | Corning | 3957 |
| 96-well compound plate | Apricotdesigns | DWP-16-96-SQ-C |
| $MgCl_2$ | Sigma | M9272-100G |
| TRIZMA BASE | Sigma | T1503-1KG |
| BSA | Roche pack | A8020-100 |
| DMSO | Merck | K42958652 225 |
| methanol | Merck | I622207203 |

Compound Information

Stock Solutions of Compounds E-Y1, E-Y13, E-Y15, E-Y40, E-Y43, E-Y47, E-Y50, E-Y54, E-Y54-H, SL-E23 (10 mM in DMSO)

Experimental Steps

1. JANUS and temperature control device was turned on. After being initialized, the pipes were flushed until there was no air bubble in the pipes.

2. Preparation of buffers used for the experiment

Preparation of Tris pH 7.4 buffer (0.1 M): 12.12 g of Tris was dissolved in 1000 mL of $H_2O$, the resulting solution was adjusted to pH 7.4 with 2N HCl, aliquoted at 50 mL per tube, and stored at −20° C.

Preparation of $H_2O$/0.1% BSA buffer: 200 μL of 25% BSA was added to 50 mL of $H_2O$.

Preparation of VIVID stock solution: 1 mg of VIVID was dissolved in 1 mL of acetonitrile, aliquoted at 50 μL per tube, and stored at −20° C.

Preparation of $MgCl_2$ solution (100 mM): 1.016 g of $MgCl_2$ was dissolved in 50 mL Tris pH 7.4 buffer, and aliquoted at 1 mL per tube, and stored at −20° C.

Preparation of NADPH solution (10 mM): 355 mg of NADPH was dissolved in 42.6 mL of Tris pH 7.4 buffer, aliquoted at 1.8 mL per tube, and stored at −20° C.

Preparation of Blank control: 7.937 mL of Tris, 163 μL of RLM, 450 μL of $MgCl_2$ solution, 450 μL of NADPH solution and 9 mL of methanol were mixed uniformly, aliquoted at 1 mL per tube, and stored at −20° C.

3. Preparation of Compound Working Solution

Dilution step 1:10 μL of compound stock solution was added to 90 μL of DMSO=1 mM stock solution.

Dilution step 2: 2 μL of 1 mM stock solution was added to 1 mL of $H_2O$/0.1%6 BSA buffer=0.2 μM working solution.

Dilution step 3: 245 μL of the working solution was added to a 96-well compound plate and added with 5 μL of VIVID stock solution.

The 96-well compound plate was shaken on a shaker for 5 min.

4. The STM in the JANUS in the computer was open to run the EXCEL file, and the JANUS program was operated and run by following the instructions in the EXCEL file.

5. After the JANUS program was finished, acetonitrile/water 50:50 (V/V) was added to column 20 of the 384-well black plate, and blank control was added to column 21 of the 384-well black plate.

6. the plate (420 nm-465 nm) was read on a microplate reader to determine the VIVID fluorescence intensity.

7. After the plate was sealed, shaken and centrifuged, the sample plate was subjected to the LC/MS instrument for sample analysis.

Data Analysis:

A profile of the logarithmic value of the remaining rate of the drug in the incubation system versus the incubation time was plotted, and the slope k was obtained by linear regression. The intrinsic clearance rate in vivo (Clint, mL/min/g) value, the clearance rate in vivo (Cl, mL)/min), liver clearance (Clhep, mL/min) and metabolic bioavailability (% MF) were predicted according to the following equations:

$$Cl_{int} = \frac{1000 \times \text{slope}}{P}$$

$$Cl = \frac{Cl_{int} \times \text{Houston} \times LW}{1000}$$

$$Cl_{hep} = \frac{HBF \times fu \times Cl}{HBF + (fu \times Cl)}$$

$$\%\ MF = 100 - \frac{Cl_{hep} \times 100}{HBF}$$

Results of Liver Microsomal Stability of the Compounds:

| Compound | Species | Half life T-half (min) | Intrinsic clearance rate in vivo Clint In Vitro (mL/min/gprot) | Clearance rate in vivo Clint In Vivo Extpl (ml/min) | Liver clearance rate Clint Hep In Vivo Extpl (ml/min) | Metabolic bioavailability MF % |
|---|---|---|---|---|---|---|
| E-Y1 | human | 99.6 | 21.1 | 1613 | 777 | 48.2 |
| | rat | 59.6 | 35.2 | 15.9 | 8.85 | 55.8 |
| | mouse | 71.5 | 29.4 | 1.98 | 1.19 | 60.2 |
| E-Y13 | human | 92.8 | 22.6 | 1732 | 804 | 46.4 |
| | rat | 55.2 | 35.2 | 15.9 | 8.85 | 53.9 |
| | mouse | 94.6 | 22.2 | 1.50 | 1.00 | 66.7 |
| E-Y15 | human | 126 | 16.7 | 1280 | 691 | 54.0 |
| | rat | 14.6 | 144 | 64.7 | 15.3 | 23.6 |
| | mouse | 25.7 | 81.6 | 5.51 | 1.94 | 35.3 |
| E-Y40 | human | 63.7 | 33.0 | 2522 | 941 | 37.3 |
| | rat | 15.9 | 133 | 59.6 | 15.0 | 25.1 |
| | mouse | 6.11 | 344 | 23.2 | 2.66 | 11.4 |
| E-Y43 | human | 110 | 19.1 | 1464 | 741 | 50.6 |
| | rat | 21.1 | 99.6 | 44.8 | 13.8 | 30.9 |
| | mouse | 13.0 | 161 | 10.9 | 2.35 | 21.6 |

-continued

| Compound | Species | Half life T-half (min) | Intrinsic clearance rate in vivo Clint In Vitro (mL/min/gprot) | Clearance rate in vivo Clint In Vivo Extpl (ml/min) | Liver clearance rate Clint Hep In Vivo Extpl (ml/min) | Metabolic bioavailability MF % |
|---|---|---|---|---|---|---|
| E-Y47 | human | 309 | 6.79 | 519 | 386 | 74.3 |
| | rat | 139 | 15.1 | 6.79 | 5.07 | 74.7 |
| | mouse | 121 | 17.3 | 1.17 | 0.841 | 72.0 |
| E-Y50 | human | 922 | 2.28 | 174 | 156 | 89.6 |
| | rat | 86.9 | 24.2 | 10.9 | 7.05 | 64.8 |
| | mouse | 154 | 13.6 | 0.921 | 0.705 | 76.5 |
| E-Y54 | human | 853 | 2.46 | 188 | 167 | 88.8 |
| | rat | 94.4 | 22.3 | 10.0 | 6.67 | 66.6 |
| | mouse | 36.8 | 57.1 | 3.86 | 1.69 | 43.7 |
| E-Y54-H | human | 479 | 4.39 | 336 | 274 | 81.7 |
| | rat | 222 | 9.47 | 4.26 | 3.51 | 82.4 |
| | mouse | 117 | 17.9 | 1.21 | 0.862 | 71.3 |
| SL-E23 | human | 199 | 10.5 | 807 | 525 | 65.0 |
| | rat | 60.0 | 35.0 | 15.8 | 8.81 | 55.9 |
| | mouse | 38.6 | 54.4 | 3.67 | 1.65 | 45.0 |

Conclusion: The compounds of the present invention have good liver microsomal stability in human, rat, and mouse, and thus having prominent advantages.

The invention claimed is:

1. A compound represented by the formula I, pharmaceutically acceptable salts, enantiomers, diastereomers or racemates thereof:

Formula I

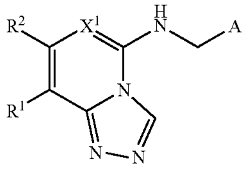

$X^1$ is independently selected from N and C—CN;

$R^2$ is independently selected from H, halogen, $C_1$-$C_4$ haloalkyl and $C_1$-$C_4$ alkyl;

A is independently selected from the following structures:

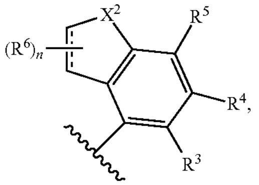

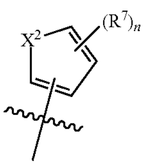

------ is a single bond or double bond;

$R^3$, $R^4$ and $R^5$ are independently selected from H, halogen, $C_1$-$C_4$ alkyl, $C_1$-$C_4$ haloalkyl, —O—($C_1$-$C_4$ alkyl), $C_1$-$C_4$ haloalkoxy, $C_3$-$C_6$ cycloalkyl;

$R^6$ is independently selected from H, OH, =O and $C_1$-$C_4$ alkyl;

$R^7$ is independently selected from H, OH, halogen, CN and $C_1$-$C_4$ alkyl;

n is each independently selected from 0, 1 and 2;

$X^2$ is independently selected from 0, $NR^a$ and $S(O)_p$ heteroatoms;

each $R^a$ is independently selected from H, O, $C_1$-$C_{10}$ alkyl substituted by 0-2 $R^b$, $C_1$-$C_6$ haloalkyl, —O—($C_1$-$C_6$ alkyl), $C_1$-$C_6$ haloalkoxy, $C_3$-$C_6$ cycloalkyl, —C(=O)($C_1$-$C_4$ alkyl), —$CO_2$($C_1$-$C_4$ alkyl), heteroalkyl and heterocycloalkyl comprising carbon atoms and 1-4 heteroatoms selected from O, N, $S(O)_p$, —C(=O)H, aryl, 5- to 6-membered heteroaryl comprising carbon atoms and 1 to 2 heteroatoms selected from N, O and S;

$R^b$ is independently selected from halogen, OH, $NH_2$, NHC(=O)($C_1$-$C_4$ alkyl), NHS(=O)$_2$($C_1$-$C_4$ alkyl), =O, CN, $C_1$-$C_4$ alkyl and $C_1$-$C_4$ alkoxy;

p is each independently selected from 0, 1 and 2;

$R^1$ is independently selected from the following structures:

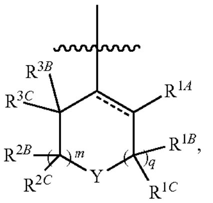

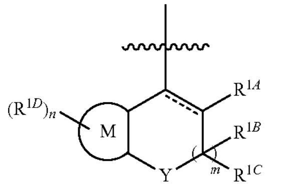

------ is a single bond or double bond;

$R^{1A}$ is independently selected from H, hydroxy, halogen, CN, —$(O)_z$—($C_1$-$C_{10}$ alkyl comprising 0-2 of substituent $R^c$), $C_1$-$C_6$ alkyl group, $C_1$-$C_6$ alkoxy, $C_1$-$C_6$ haloalkyl, $C_1$-$C_6$ haloalkoxy, $SCF_3$, $C_3$-$C_8$ cycloalkyl, —C(=O)($C_1$-$C_4$ alkyl), —C(=O)NH($C_1$-$C_4$ alkyl), amino, $C_1$-$C_6$ linear, branched and cyclic alkylamino, heteroalkyl and heterocycloalkyl comprising carbon atoms and 1-4 heteroatoms selected from O, N, $S(O)_p$, —C(=O)H, aryl, 5- to 6-membered heteroaryl comprising carbon atoms and 1 to 2 heteroatoms selected from N, O and S; wherein the aryl and heteroaryl may be substituted by 0-2 of $R^{1X}$;

p is each independently selected from 0, 1 and 2;

$R^c$ is independently selected from OH, halogen, CN, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, —$(OCH_2CH_2)_m OR^d$, NHC(=O)$NR^dR^e$, NHC(=S)$NR^dR^e$, —NHC(=NH)$NR^dR^e$, $(OCH_2CH_2)_m NR^dR^e$, —C(=O)$R^d$, —S(=O)$R^d$, —C(=O)$NR^dR^e$, —S(=O)$_2R^d$, —NHC(=O)$R^d$, —NHC(=S)$R^d$, —NHS(=O)$_2R^d$, —S(=O)$_2NHR^d$, heteroalkyl and heterocycloalkyl comprising carbon atoms and 1 to 2 heteroatoms selected from N, $NR^a$, O and $S(O)_p$, aryl, and heteroaryl comprising carbon atoms and 1 to 2 heteroatoms selected from N, $NR^a$, O and $S(O)_p$, wherein the aryl and heteroaryl may be substituted by 0-2 of $R^{1X}$;

$R^d$ and $R^e$ are independently selected from H, $C_1$-$C_6$ alkyl comprising 0-2 of $R^b$, $C_1$-$C_6$ haloalkyl, $C_3$-$C_6$ cycloalkyl, —C(═O)($C_1$-$C_4$ alkyl), —$CO_2$($C_1$-$C_4$ alkyl), —C(═O)NH($C_1$-$C_4$ alkyl), $C_1$-$C_6$ branched or cyclic heteroalkyl comprising 0-2 of heteroatoms selected from O, N, and $S(O)_p$, —C(═O)H, aryl, and heteroaryl comprising carbon atoms and 1 to 2 heteroatoms selected from N, $NR^a$, O and $S(O)_p$, wherein the aryl and heteroaryl may be substituted by 0-2 of $R^{1X}$;

each $R^a$ is independently selected from H; O; $C_1$-$C_{10}$ alkyl substituted by 0-2 of $R^b$; $C_1$-$C_6$ haloalkyl; —O—($C_1$-$C_6$ alkyl); $C_1$-$C_6$ haloalkoxy; $C_3$-$C_6$ cycloalkyl; —C(═O)($C_1$-$C_4$ alkyl); —$CO_2$($C_1$-$C_4$ alkyl); heteroalkyl and heterocycloalkyl comprising carbon atoms and 1-4 heteroatoms selected from O, N, $S(O)_p$; —C(═O)H; aryl; 5- to 6-membered heteroaryl comprising carbon atoms and 1 to 2 heteroatoms selected from N, O and S;

$R^b$ is independently selected from halogen, OH, $NH_2$, NHC(═O)($C_1$-$C_4$ alkyl), NHS(═O)$_2$($C_1$-$C_4$ alkyl), ═O, CN, $C_1$-$C_4$ alkyl and $C_1$-$C_4$ alkoxy;

p is each independently selected from 0, 1 and 2;

$R^d$ and $R^e$ can be connected in the form of $R^d$—$R^e$ or 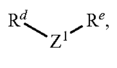

wherein the $Z^1$ may be selected from $C_1$-$C_6$ alkyl comprising 0-2 of substituent $R^b$, $C_1$-$C_6$ heteroalkyl comprising 0-2 of substituent heteroatoms of O, N, $S(O)_p$, O, —N($C_1$-$C_6$ alkyl), —NH, —N(C═O) $C_1$-$C_6$ alkyl, —NS(═O)$_2$($C_1$-$C_6$ alkyl), $S(O)_p$; $R^b$ is independently selected from halogen, OH, $NH_2$, —NHC(═O)($C_1$-$C_4$ alkyl), —NHS(═O)$_2$($C_1$-$C_4$ alkyl), ═O, CN, $C_1$-$C_4$ alkyl and $C_1$-$C_4$alkoxy; p is each independently selected from 0, 1 and 2;

$R^{1X}$ is independently selected from halogen, OH, CN, $C_1$-$C_4$ alkyl, $C_1$-$C_4$ haloalkyl, $C_1$-$C_4$ alkoxy, $C_1$-$C_4$ haloalkoxy, $C_3$-$C_8$ cycloalkyl and cyclic heteroalkyl;

$R^{1B}$ and $R^{1C}$ are independently selected from H, OH, halogen, CN, —$(O)_z$—($C_1$-$C_{10}$ alkyl comprising 0-2 of substituent $R^c$), $C_1$-$C_6$ alkyl group, $C_1$-$C_6$ alkoxy, $C_1$-$C_6$ haloalkyl, $C_1$-$C_6$ haloalkoxy, $SCF_3$, $C_3$-$C_8$ cycloalkyl, —C(═O)($C_1$-$C_4$ alkyl), —C(═O)NH($C_1$-$C_4$ alkyl), heteroalkyl and heterocycloalkyl comprising carbon atoms and 1-4 heteroatoms selected from O, N, $S(O)_p$, —C(═O)H, aryl, 5- to 6-membered heteroaryl comprising carbon atoms and 1 to 2 heteroatoms selected from N, O and S; wherein the aryl and heteroaryl may be substituted by 0-2 of $R^{1X}$; p is each independently 0, 1 and 2;

$R^{2B}$ and $R^{2C}$ are independently selected from H, OH, halogen, CN, —$(O)_z$—($C_1$-$C_{10}$ alkyl comprising 0-2 of substituent $R^c$), $C_1$-$C_6$ alkyl group, $C_1$-$C_6$ alkoxy, $C_1$-$C_6$ haloalkyl, $C_1$-$C_6$ haloalkoxy, $SCF_3$, $C_3$-$C_8$ cycloalkyl, —C(═O)($C_1$-$C_4$ alkyl), —C(═O)NH($C_1$-$C_4$ alkyl), heteroalkyl and heterocycloalkyl comprising carbon atoms and 1-4 heteroatoms selected from O, N, $S(O)_p$, —C(═O)H, aryl, 5- to 6-membered heteroaryl comprising carbon atoms and 1 to 2 heteroatoms selected from N, O and S; wherein the aryl and heteroaryl may be substituted by 0-2 of $R^{1X}$; p is each independently 0, 1 and 2;

$R^{3B}$ and $R^{3C}$ are independently selected from H, OH, halogen, CN, —$(O)_z$—($C_1$-$C_{10}$ alkyl comprising 0-2 of substituent $R^c$), $C_1$-$C_6$ alkyl group, $C_1$-$C_6$ alkoxy, $C_1$-$C_6$ haloalkyl, $C_1$-$C_6$ haloalkoxy, $SCF_3$, $C_3$-$C_8$ cycloalkyl, —C(═O)($C_1$-$C_4$ alkyl), —C(═O)NH($C_1$-$C_4$ alkyl), heteroalkyl and heterocycloalkyl comprising carbon atoms and 1-4 heteroatoms selected from O, N, $S(O)_p$, —C(═O)H, aryl, 5- to 6-membered heteroaryl comprising carbon atoms and 1 to 2 heteroatoms selected from N, O and S; wherein the aryl and heteroaryl may be substituted by 0-2 of $R^{1X}$; p is each independently 0, 1 and 2;

alternatively, $R^{1B}$ and $R^{1C}$, $R^{2B}$ and $R^{2C}$, $R^{3B}$ and $R^{3C}$ may form a carbonyl group (═O) with a carbon atom to which they are attached or a thiocarbonyl group (═S);

$R^{1D}$ is independently selected from H, —OH, halogen, CN, —C(═O)H, —$(O)_z$—($C_1$-$C_6$ alkyl comprising 0-2 of substituent $R^c$), $C_1$-$C_6$ haloalkyl, $C_1$-$C_6$ haloalkoxy, $SCF_3$, $R^f$, —$OR^f$, —C(═O)$R^c$, $NR^dR^e$, —C(═O)$NR^dR^e$, —NHC(═O)$R^c$, —S(═O)$_2R^c$, —S(═O)$_2NR^dR^e$, —NHS(═O)$_2R^d$, —($OCH_2CH_2$)m$OR^d$, —$(OCH_2CH_2)_m NR^dR^e$;

$R^f$ is independently selected from $C_3$-$C_8$ cycloalkyl, heteroalkyl and heterocycloalkyl comprising carbon atoms and 1-4 heteroatoms selected from O, N, $S(O)_p$, aryl, heteroaryl comprising carbon atoms and 1 to 2 heteroatoms selected from N, $NR^a$, O and $S(O)_p$; wherein the aryl and heteroaryl are substituted by 0-2 of $R^{1X}$;

M is independently selected from a 3 to 7 membered saturated or unsaturated cycloalkyl, a heterocycloalkyl comprising carbon atoms and 1-4 heteroatoms selected from O, N, $S(O)_p$, an aryl, 5- to 6-membered heteroaryl comprising carbon atoms and 1 to 2 heteroatoms selected from N, O and S;

in the definitions of $R^{1B}$ and $R^{1C}$, $R^{2B}$ and $R^{2C}$, $R^{3B}$ and $R^{3C}$, $R^{1D}$ and $R^f$, the definitions of $R^a$, $R^c$, $R^d$, $R^e$, p, z, m and $R^{1X}$ are the same as those of $R^{1A}$;

n is each independently selected from 0, 1 and 2;

m is each independently selected from 0-4;

p is each independently selected from 0-2;

q is each independently selected from 0-3; and z is each independently selected from 0 and 1;

Y is independently selected from heteroatoms of O, $NR^g$, $S(O)_p$, etc., and $CH_2$, C═O, —$CR^i(CH_2)_m NR^gR^h$ and —$CR^i(CH_2)_m OR^g$;

$R^g$ and $R^h$ are independently selected from H, O, $C_1$-$C_{10}$ alkyl comprising 0-3 of substituent $R^s$, $C_1$-$C_6$ haloalkyl, $C_3$-$C_6$ cycloalkyl,

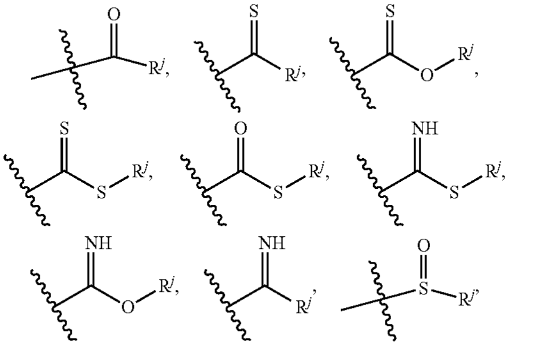

-continued

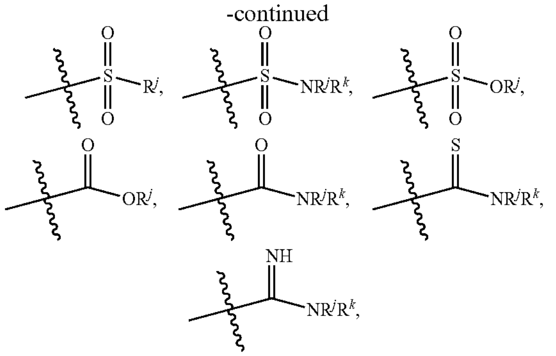

—C(═S)NHC(═O)—$R^j$, heteroalkyl and heterocycloalkyl comprising carbon atoms and 1-4 heteroatoms selected from O, N, $S(O)_p$, aryl, 5- to 6-membered heteroaryl comprising carbon atoms and 1 to 2 heteroatoms selected from N, O and S; wherein the aryl and heteroaryl may be substituted by 0-2 of $R^{1X}$;

$R^s$ is independently selected from OH, CN, halogen, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, —$(OCH_2CH_2)$m$OR^d$, NHC(═O)$NR^dR^e$, NHC(═S)$NR^dR^e$, —NHC(═NH) $NR^dR^e$, $(OCH_2CH_2)$m$NR^dR^e$, —C(═O)$R^d$, —C(═S) $R^d$, —S(═O) $R^d$, —C(═O)$NR^dR^e$, —$S(═O)_2R^d$, —NHC(═O)$R^d$, —NHC(═S)$R^d$, —$NHS(═O)_2R^d$, —$S(═O)_2NR^dR^e$, —$NHS(═O)_2NR^dR^e$, —C(═S) $NR^dR^e$, NHC(═O)$OR^d$, NHC(═S)$OR^d$, —NHS $(═O)_2OR^d$, NHC(═O)$SR^d$, NHC(═S)$SR^d$, —NHC (═NH)$OR^d$, —C(═O)$OR^d$, —C(═O)$SR^d$, —$S(═O)_2OR^d$, heteroalkyl and heterocycloalkyl comprising carbon atoms and 1 to 2 heteroatoms selected from N, $NR^a$, O and $S(O)_p$, aryl, heteroaryl comprising carbon atoms and 1 to 2 heteroatoms selected from N, $NR^a$, O and $S(O)_p$; wherein the aryl and heteroaryl may be substituted by 0-2 of $R^{1Y}$;

$R^d$ and $R^e$ are independently selected from H, $C_1$-$C_6$ alkyl comprising 0-2 of $R^b$, $C_1$-$C_6$ haloalkyl, $C_3$-$C_6$ cycloalkyl, —C(═O)($C_1$-$C_4$ alkyl), —$CO_2$($C_1$-$C_4$ alkyl), —C(═O)NH($C_1$-$C_4$ alkyl), $C_1$-$C_6$ branched or cyclic heteroalkyl comprising 0-2 of heteroatoms selected from O, N, and $S(O)_p$, —C(═O)H, aryl, and heteroaryl comprising carbon atoms and 1 to 2 heteroatoms selected from N, $NR^a$, O and $S(O)_p$, wherein the aryl and heteroaryl may be substituted by 0-2 of $R^{1X}$;

$R^d$ and $R^e$ may be connected by the following manner $R^d$—$R^e$ or 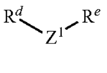

to form a ring, wherein $Z^1$ can be selected from $C_1$-$C_6$ alkyl comprising from 0-2 of substituent $R^b$; $C_1$-$C_6$ alkyl comprising 0-2 heteroatoms of O, N, $S(O)_p$; O; —N($C_1$-$C_6$ alkyl); —NH; —N(C═O) $C_1$-$C_6$ alkyl; —$NS(═O)_2$($C_1$-$C_6$ alkyl); $S(O)_p$;

each $R^a$ is independently selected from H; O; $C_1$-$C_{10}$ alkyl substituted by 0-2 of $R^b$; $C_1$-$C_6$ haloalkyl; —O—($C_1$-$C_6$ alkyl); $C_1$-$C_6$ haloalkoxy; $C_3$-$C_6$ cycloalkyl; —C(═O)($C_1$-$C_4$ alkyl); —$CO_2$($C_1$-$C_4$ alkyl); heteroalkyl and heterocycloalkyl comprising carbon atoms and 1-4 heteroatoms selected from O, N, $S(O)_p$; —C(═O) H; aryl; 5- to 6-membered heteroaryl comprising carbon atoms and 1 to 2 heteroatoms selected from N, O and S; $R^b$ is independently selected from halogen, OH, $NH_2$, NHC(═O)($C_1$-$C_4$ alkyl), $NHS(═O)_2$($C_1$-$C_4$ alkyl), ═O, CN, $C_1$-$C_4$ alkyl and $C_1$-$C_4$ alkoxy; p is independently selected from 0, 1 and 2;

$R^{1X}$ is independently selected from halogen, OH, CN, $C_1$-$C_4$ alkyl, $C_1$-$C_4$ haloalkyl, $C_1$-$C_4$ alkoxy, $C_1$-$C_4$ haloalkoxy, $C_3$-$C_8$ cycloalkyl and cyclic heteroalkyl;

$R^{1Y}$ is independently selected from $C_1$-$C_{10}$ alkyl; halogen; CN; —$(O)_z$—($C_1$-$C_{10}$ alkyl comprising 0-2 of the substituent $R^c$); $C_1$-$C_6$ haloalkyl; $C_1$-$C_6$ haloalkoxy; $SCF_3$; $C_3$-$C_8$ cycloalkyl; —C(═O)($C_1$-$C_4$ alkyl); —$CO_2$($C_1$-$C_4$ alkyl); $NR^dR^e$; —C(═O)$NR^dR^e$; —$S(═O)_2R^d$; —NHC(═O)$R^d$; —NHC(═S)$R^d$; —$NHS(═O)_2R^d$; —NHC(═O)$NR^dR^e$; —NHC(═S)$NR^dR^e$; —NHS $(═O)_2NR^dR^e$; —C(═S)$NR^dR^e$; —$S(═O)_2NHR^d$; heteroalkyl and heterocycloalkyl comprising carbon atoms and 1-4 heteroatoms selected from O, N, $S(O)_p$; —C(═O)H; p is each independently 0, 1 and 2;

wherein, $R^d$ and $R^e$ may be connected by the manner of $R^d$—$R^e$ or 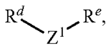

wherein $Z^1$ can be selected from $C_1$-$C_6$ alkyl comprising from 0-2 of substituent $R^b$; $C_1$-$C_6$ heteroalkyl comprising 0-2 heteroatoms of O, N, $S(O)_p$; O; —N($C_1$-$C_6$ alkyl); —NH; —N(C═O) $C_1$-$C_6$ alkyl; —$NS(═O)_2$($C_1$-$C_6$ alkyl); $S(O)_p$;

$R^b$ is independently selected from halogen, OH, $NH_2$, NHC(═O)($C_1$-$C_4$ alkyl), $NHS(═O)_2$($C_1$-$C_4$ alkyl), ═O, CN, $C_1$-$C_4$ alkyl and $C_1$-$C_4$ alkoxy; p is independently selected from 0, 1 and 2;

$R^j$ and $R^k$ are independently selected from H, CN, $C_1$-$C_{10}$ alkyl comprising 0-3 of substituent $R^s$, $C_1$-$C_6$ haloalkyl, C3-C10 cycloalkyl, heteroalkyl and heterocycloalkyl comprising carbon atoms and 1-4 heteroatoms selected from O, N, $S(O)_p$, alkenyl or alkynyl group substituted by $R^y$ ( 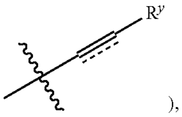 ), 6 to 10 membered aryl, 5 to 10 membered heteroaryl comprising carbon atoms and 1 to 2 heteroatoms selected from N, O, and S; wherein the aryl and heteroaryl groups may be substituted by 0-2 of $R^{1Y}$;

$R^y$ is independently selected from H; $C_1$-$C_{10}$ alkyl comprising 0-3 of substituent $R^c$; $C_1$-$C_6$ haloalkyl; C3-C10 cycloalkyl; heteroalkyl and heterocycloalkyl comprising carbon atoms and 1-4 heteroatoms selected from O, N, $S(O)_p$; $NR^dR^e$; $OR^d$; aryl; 5- to 6-membered heteroaryl comprising carbon atoms and 1 to 2 heteroatoms selected from N, O and S; wherein the aryl and heteroaryl may be substituted by 0-2 of $R^{1X}$; $R^{1X}$ is independently selected from halogen, OH, CN, $C_1$-$C_4$ alkyl, $C_1$-$C_4$ haloalkyl, $C_1$-$C_4$ alkoxy, $C_1$-$C_4$ haloalkoxy, $C_3$-$C_8$ cycloalkyl and cyclic heteroalkyl;

$R^g$ and $R^h$, as well as $R^j$ and $R^k$ may be connected by the following manner $R^g$—$R^h$, 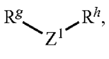 $R^j$—$R^k$, and 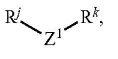

wherein $Z^1$ may be selected from $C_1$-$C_6$ alkyl comprising 0-2 of substituent $R^c$; $C_1$-$C_6$ alkyl comprising 0-2 heteroatoms of O, N, $S(O)_p$; O; —N($C_1$-$C_6$ alkyl); —NH; —N(C═O) $C_1$-$C_6$ alkyl; —NS(═O)$_2$($C_1$-$C_6$ alkyl); $S(O)_p$; p is each independently selected from 0, 1 and 2;

$R^i$ is independently selected from H, CN, $C_1$-$C_4$ alkyl;

m is each independently selected from 0-4.

2. The compound, pharmaceutically acceptable salts, enantiomers, diastereomers or racemates thereof according to claim 1, wherein, the compound of formula I has formula Ia-1 or Ia-2:

Ia-1

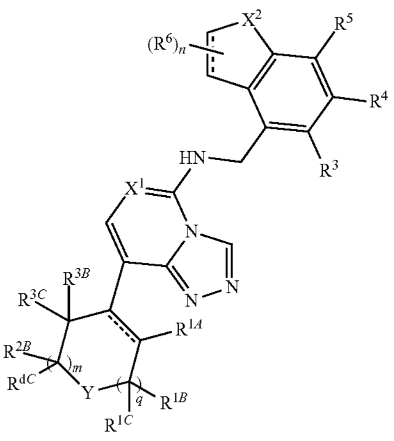

Ia-2

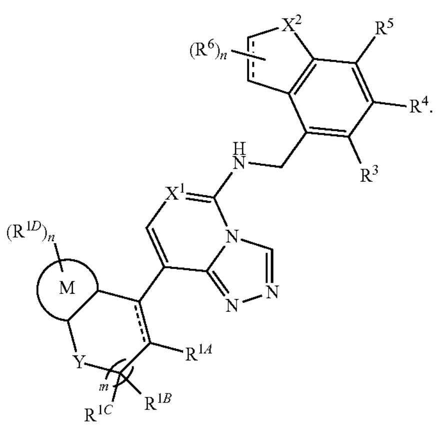

3. The compound, pharmaceutically acceptable salts, enantiomers, diastereomers or racemates thereof according to claim 1, wherein, the compound of formula I has formula Ia-3 or Ia-4:

Ia-3

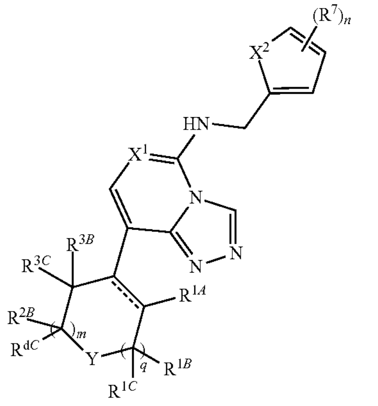

Ia-4

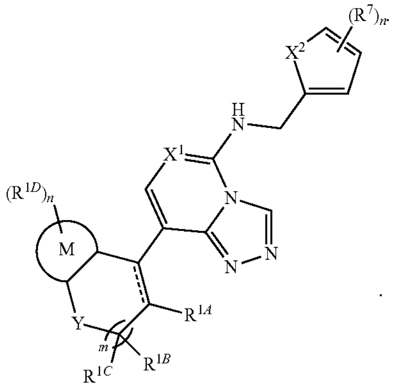

4. The compound, pharmaceutically acceptable salts, enantiomers, diastereomers or racemates thereof according to claim 1, wherein, the compound of formula I has formula Ia-5 or Ia-6:

Ia-5

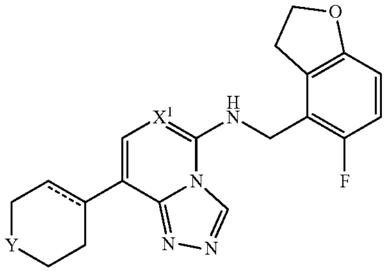

Ia-6

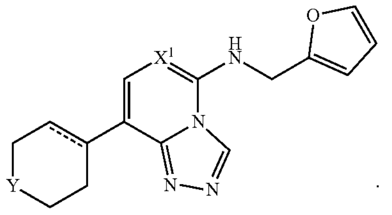

5. The compound, pharmaceutically acceptable salts, enantiomers, diastereomers or racemates thereof according to claim 1, wherein, the compound of formula I has formula Ia-7 or Ia-8:

Ia-7

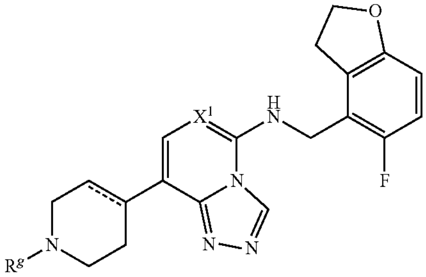

Ia-8

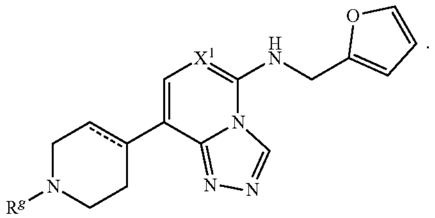

6. The compound, pharmaceutically acceptable salts, enantiomers, diastereomers or racemates thereof according to claim 1, wherein, the compound of formula I has formula Ia-9:

Ia-9

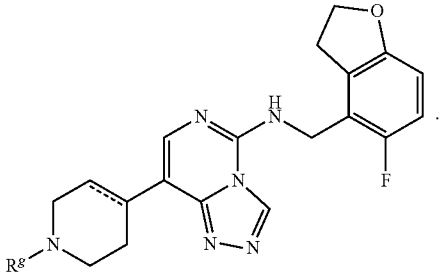

7. The compound, pharmaceutically acceptable salts, enantiomers, diastereomers or racemates thereof according to claim 1, wherein, the compound of formula I has one of the following formulae:

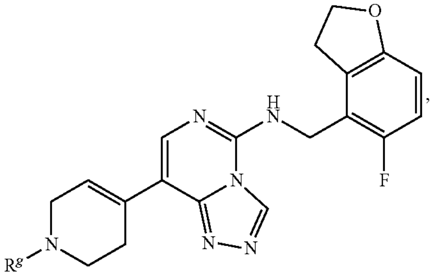

-continued

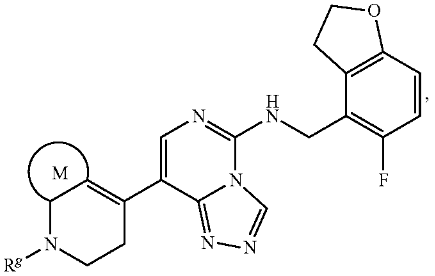

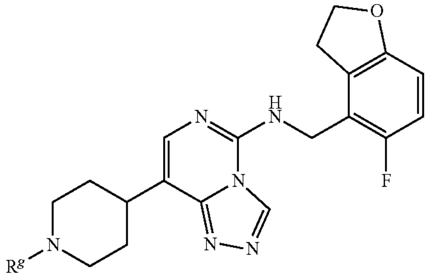

or

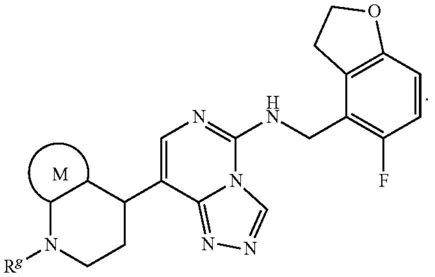

8. The compound, pharmaceutically acceptable salts, enantiomers, diastereomers or racemates thereof according to claim 1, wherein, the compound of formula I is selected from the following compounds:

E-Y1

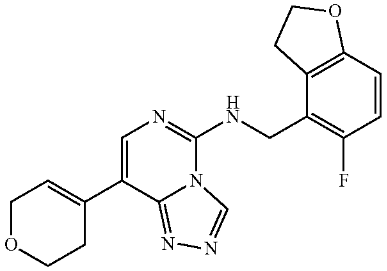

E-Y2

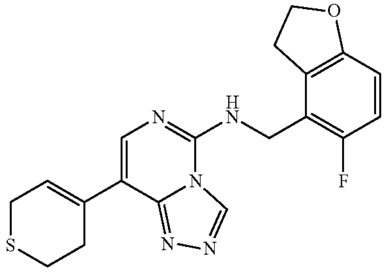

-continued
E-Y3
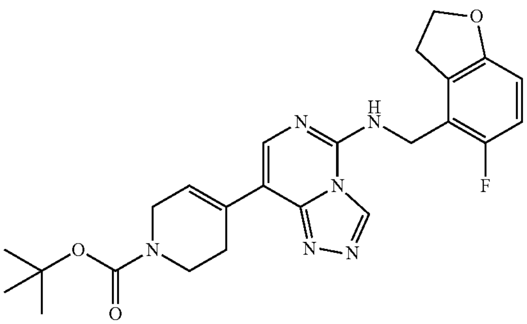
E-Y4
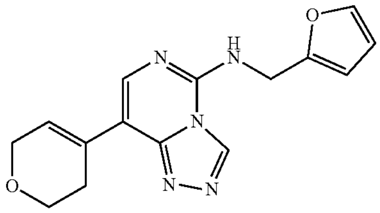
E-Y5
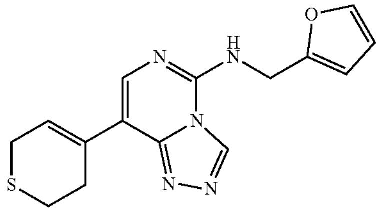
E-Y6
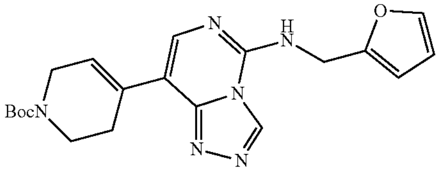
E-Y7
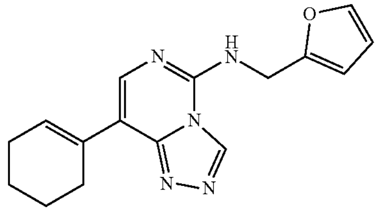
E-Y8
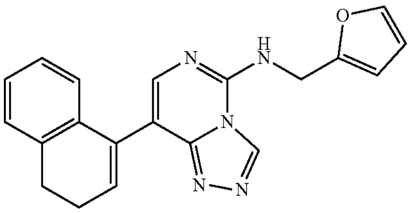
E-Y9
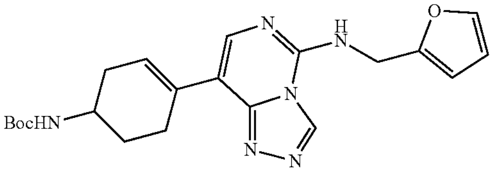
-continued
E-Y10
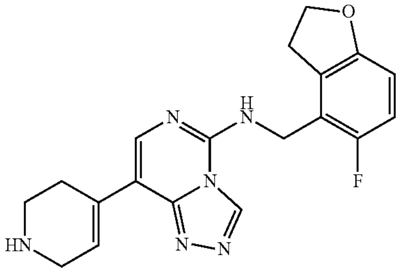
E-Y11
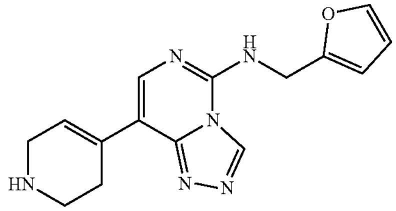
E-Y12
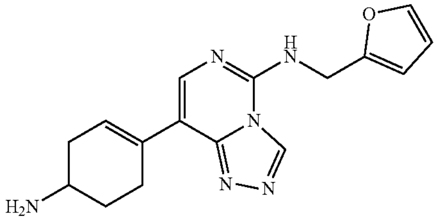
E-Y13
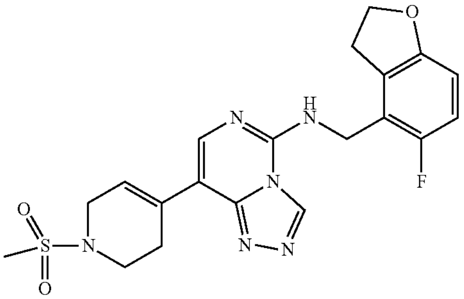
E-Y14
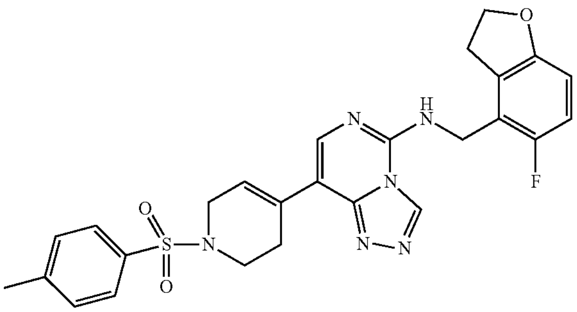
E-Y15
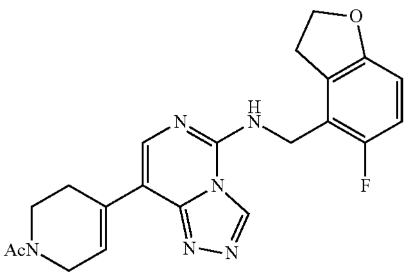

-continued
E-Y16
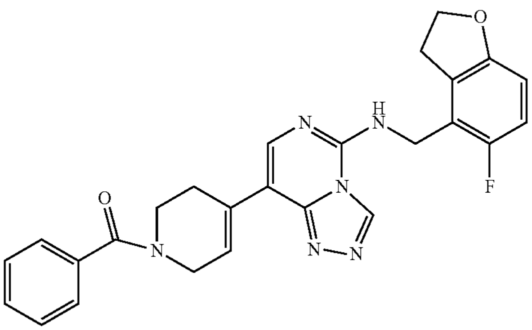
E-Y17
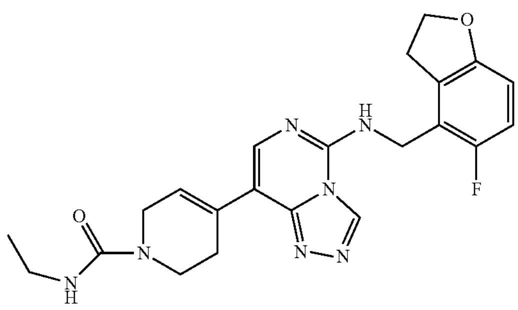
E-Y18
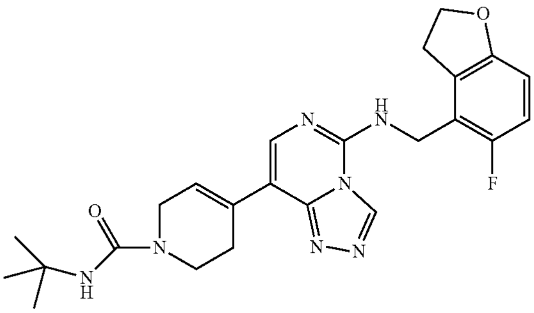
E-Y19
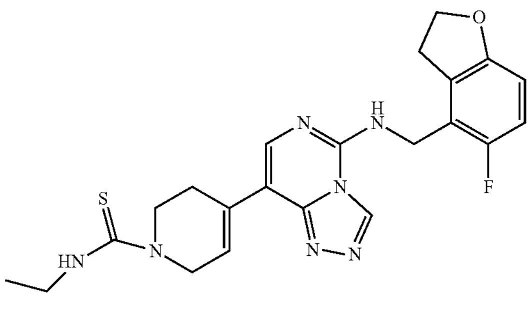
E-Y20
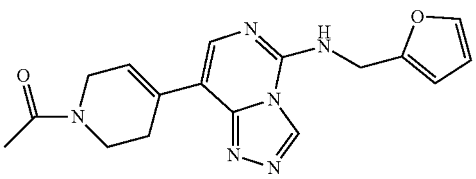
-continued
E-Y21
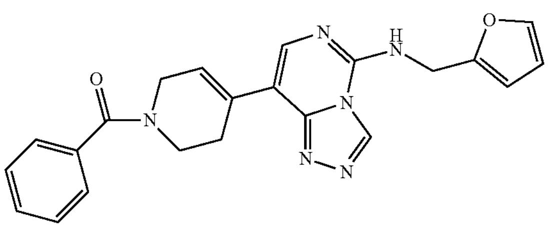
E-Y22
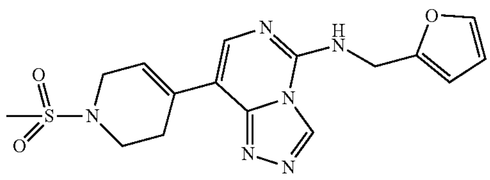
E-Y23
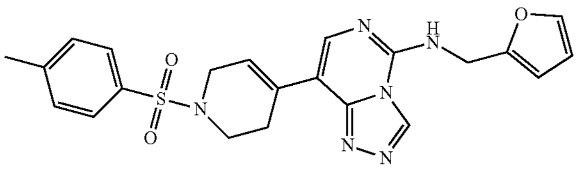
E-Y24
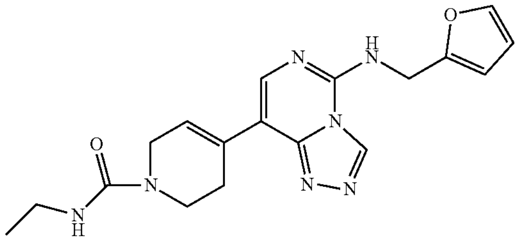
E-Y25
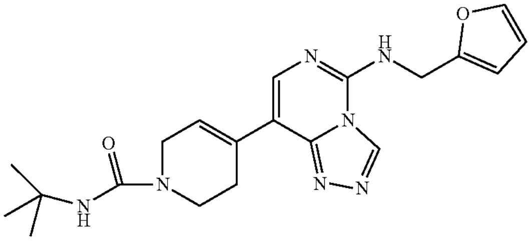
E-Y26
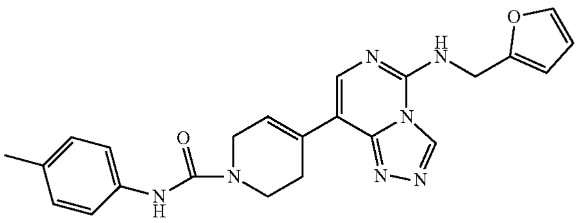

-continued
E-Y27
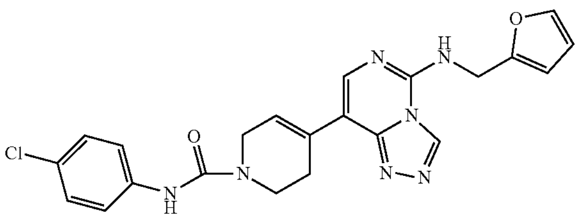
E-Y28
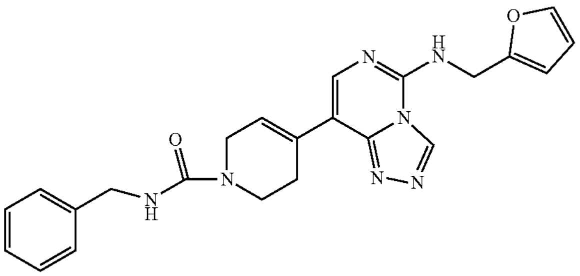
E-Y29
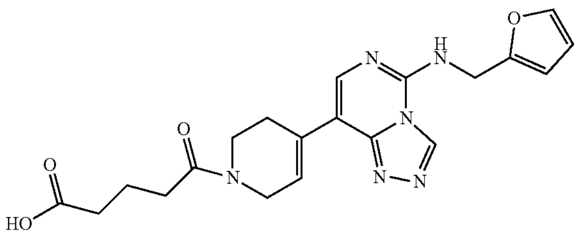
E-Y30
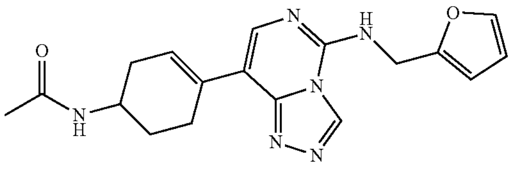
E-Y31
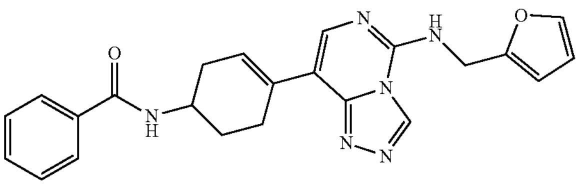
E-Y32
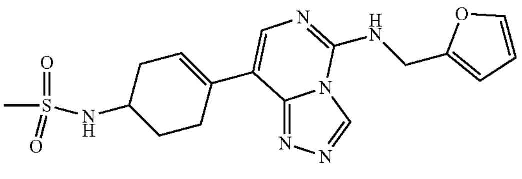
-continued
E-Y33
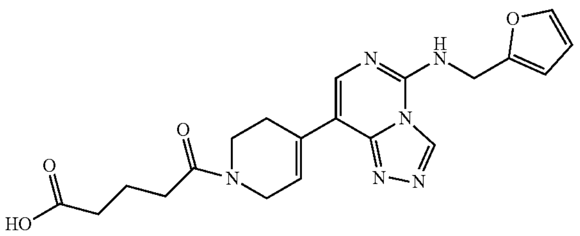
E-Y34
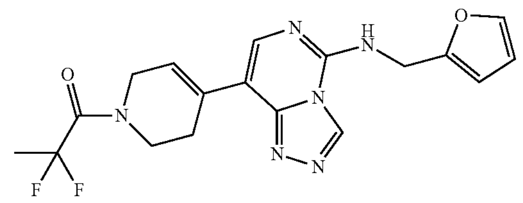
E-Y35
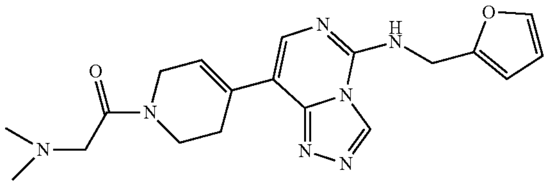
E-Y36
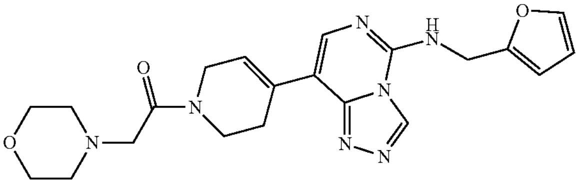
E-Y37
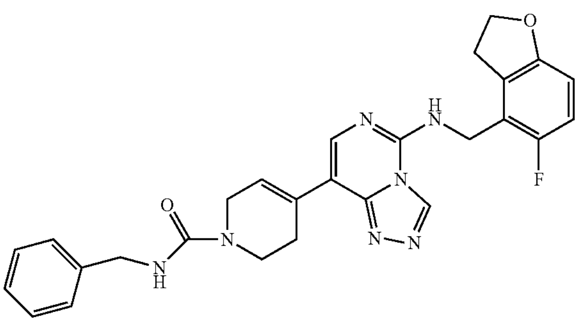
E-Y38
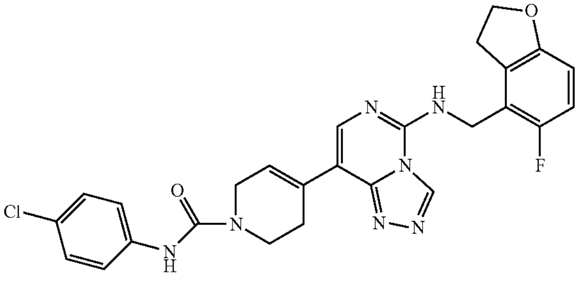

E-Y39
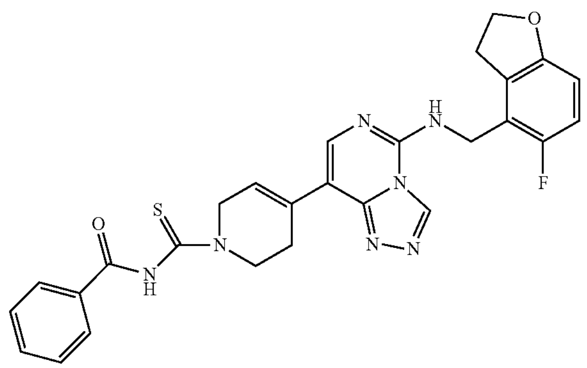
E-Y40
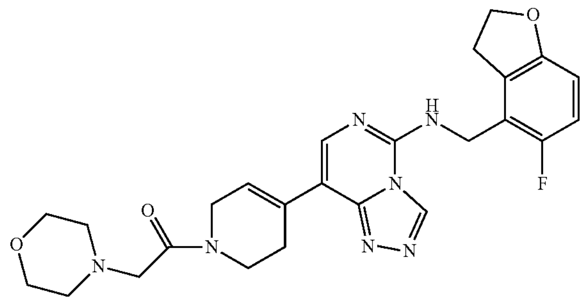
E-Y41
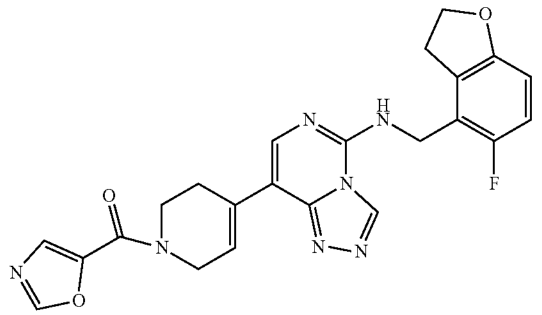
E-Y42
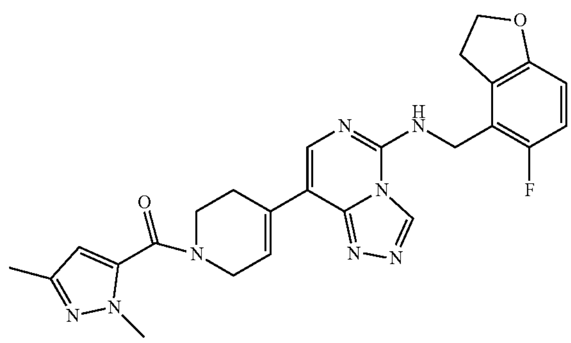
E-Y43
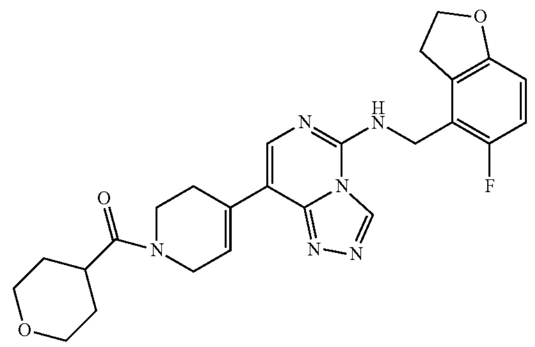
E-Y44
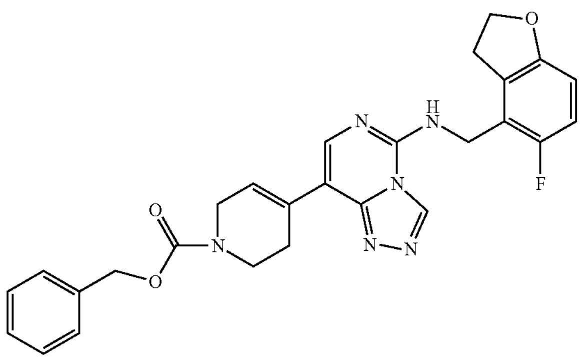
E-Y45
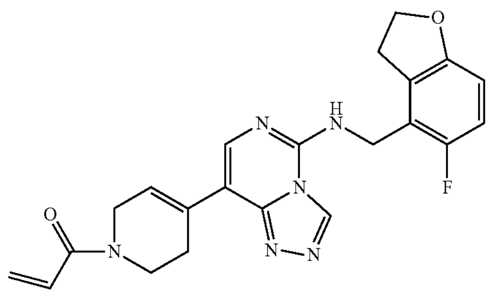
E-Y46
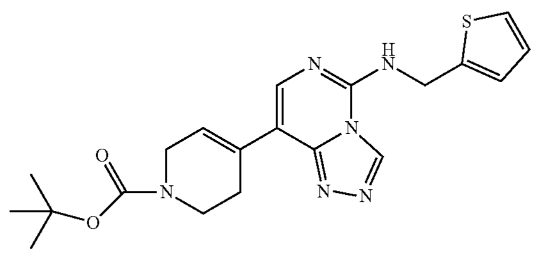
E-Y47
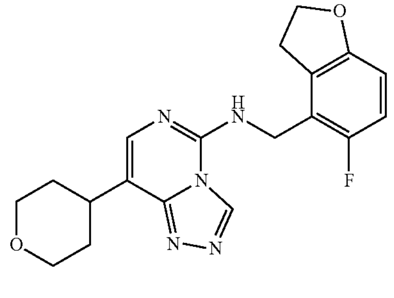

-continued
E-Y48
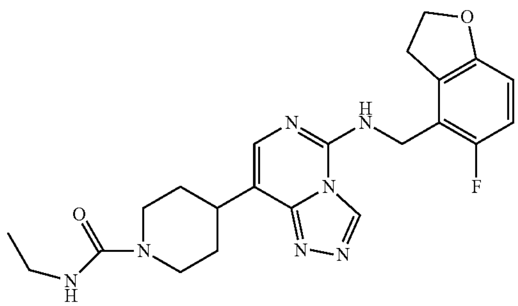
E-Y49
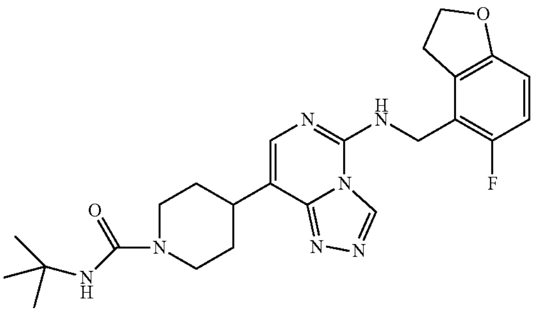
E-Y50
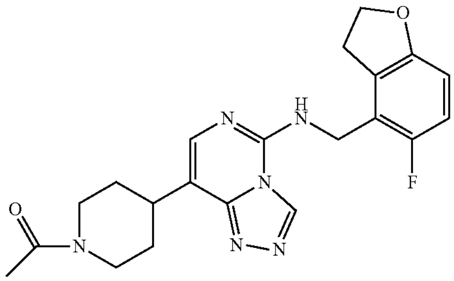
E-Y51
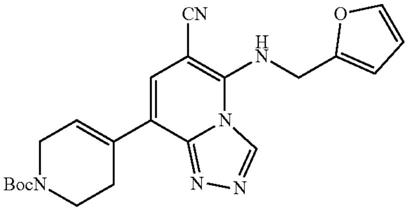
E-Y52
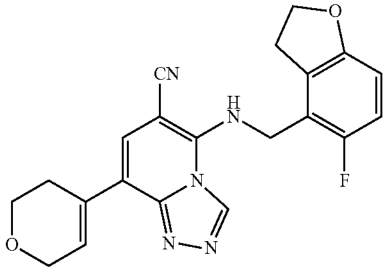
-continued
E-Y53
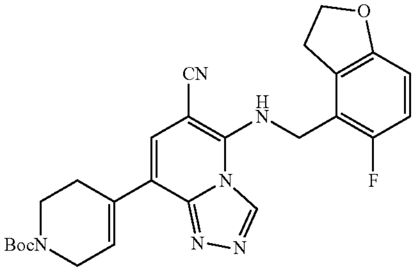
E-Y54
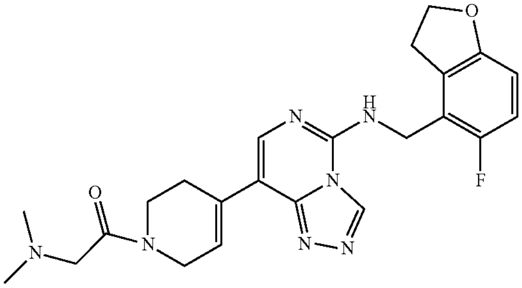
SL-ZYE-07
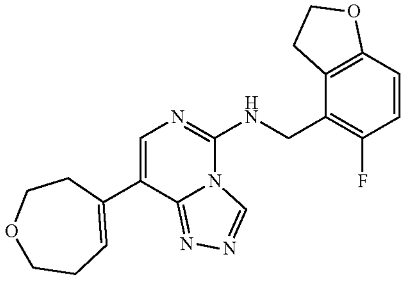
SL-ZYE-08
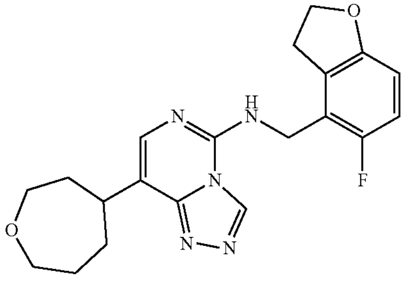
SL-ZYE-09
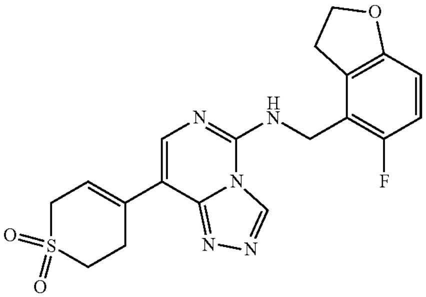

-continued
SL-ZYE-11
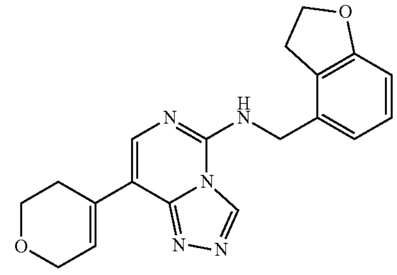
SL-ZYE-14
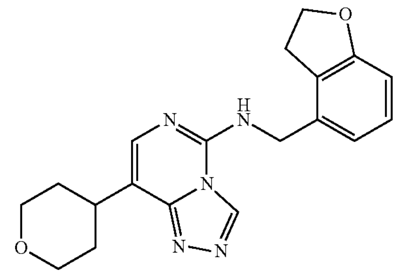
SL-ZYE-17
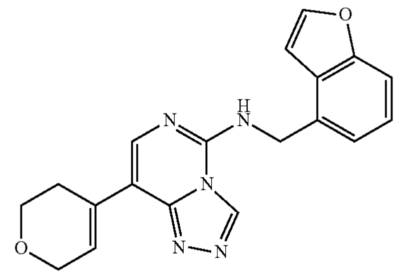
SL-ZYE-18
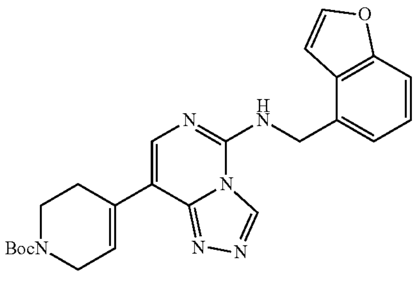
E-Y20-H
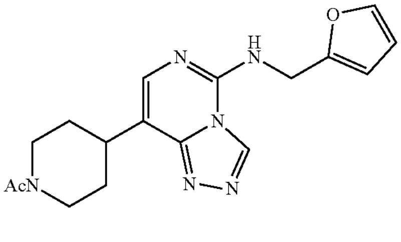
-continued
E-Y13-H
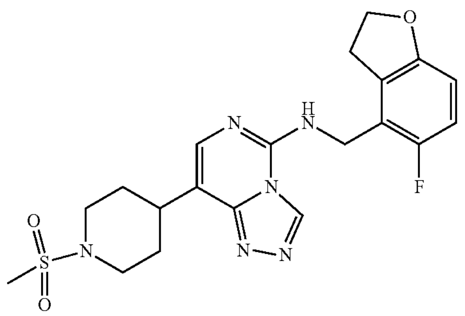
SL-ZYE-34
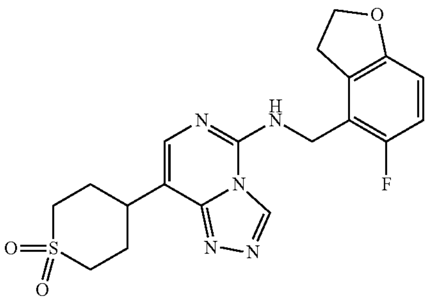
SL-ZYE-23
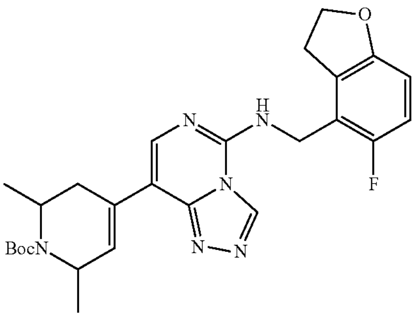
SL-ZYE-24
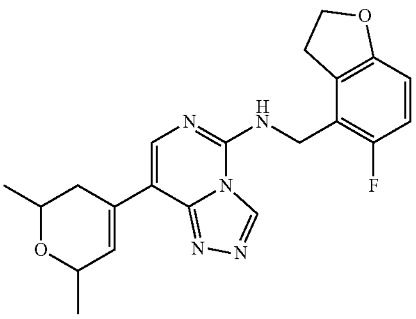
SL-ZYE-28
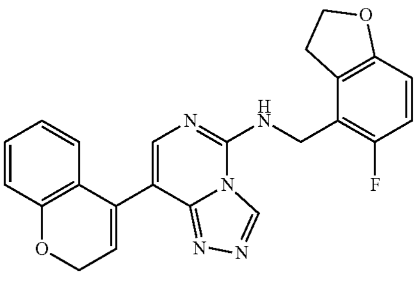

-continued
E-Y54-H
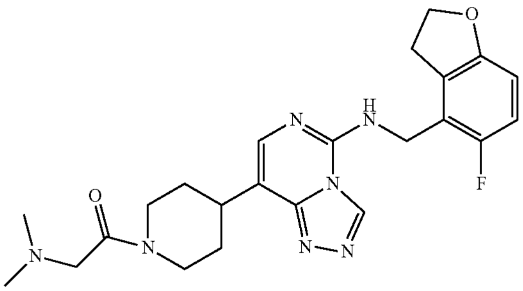
SL-E1
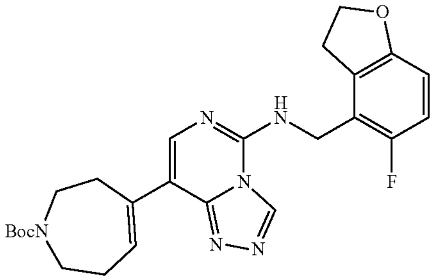
SL-E2
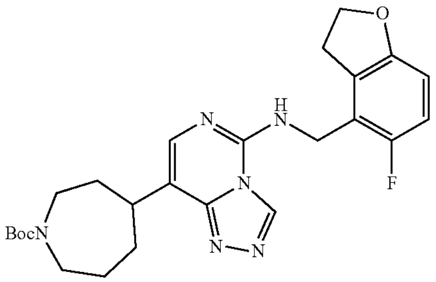
SL-E3
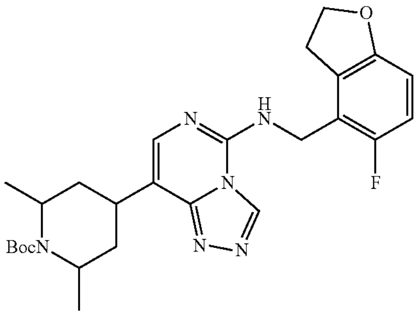
SL-E4
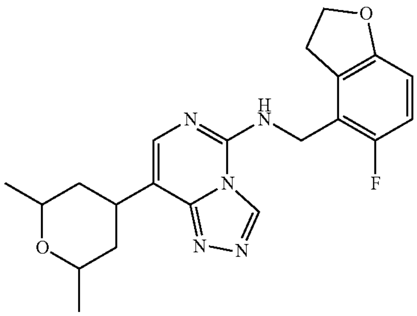
-continued
SL-E5
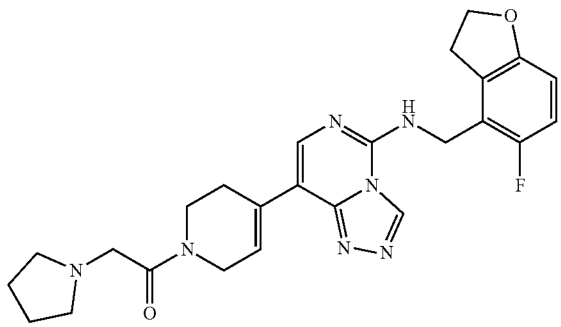
SL-E6
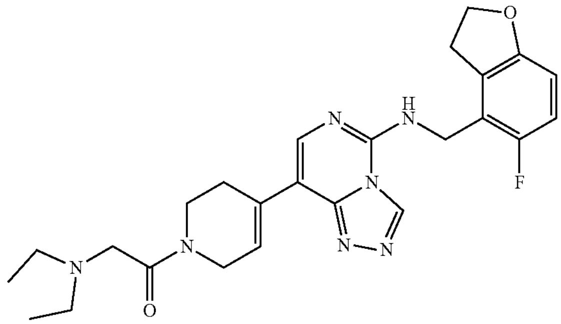
SL-E7
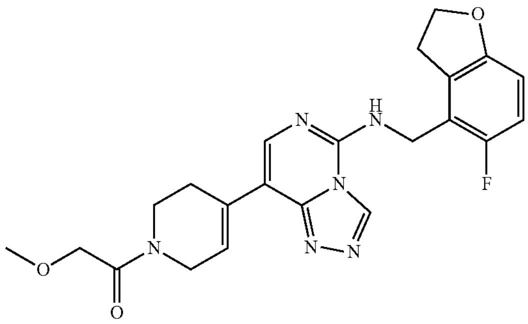
SL-E8
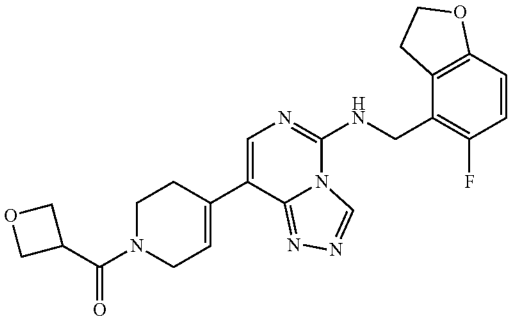

SL-E9
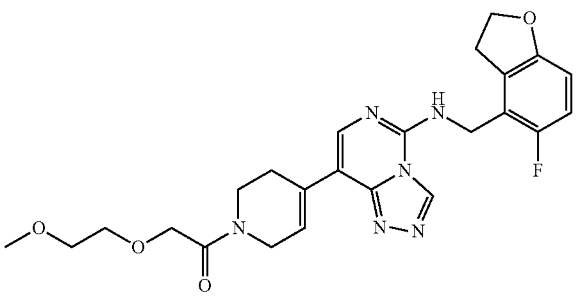
SL-E10
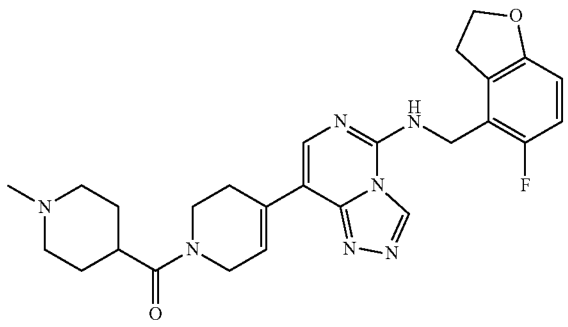
SL-E11
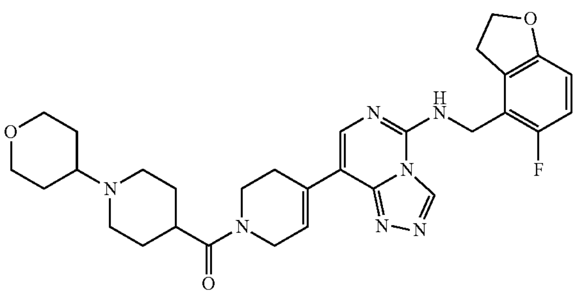
SL-E12
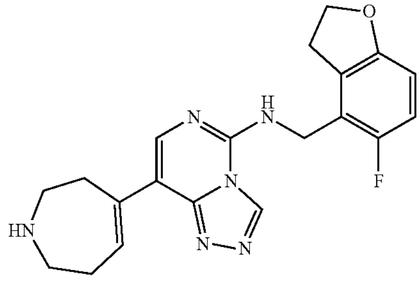
SL-E13
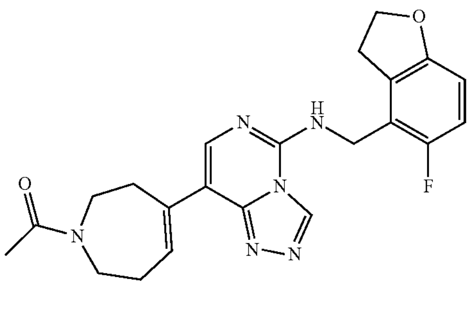
SL-E14
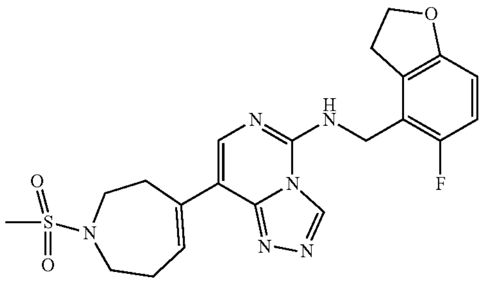
SL-E15
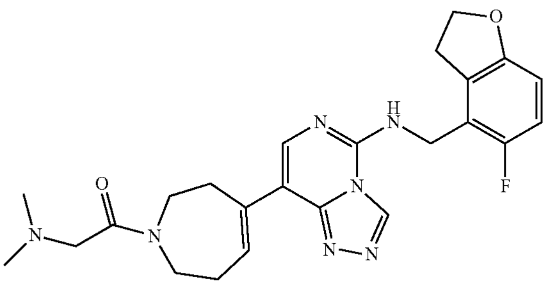
SL-E16
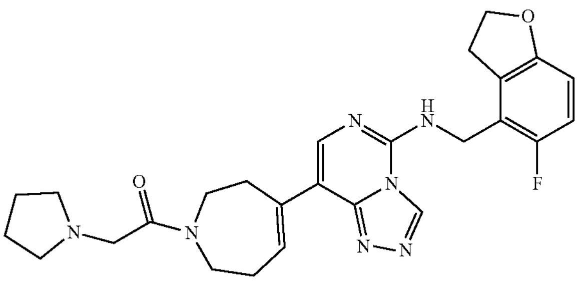
SL-E17
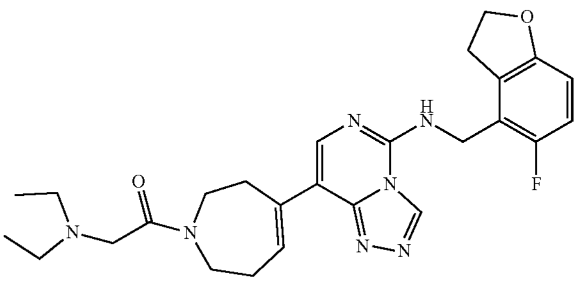
SL-E18
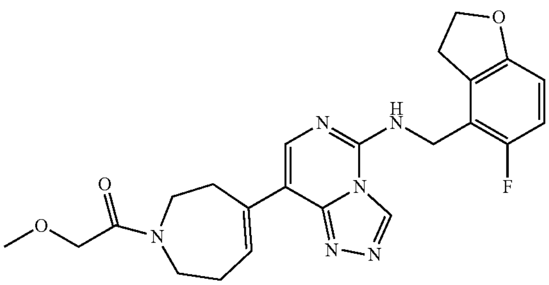

-continued
SL-E19
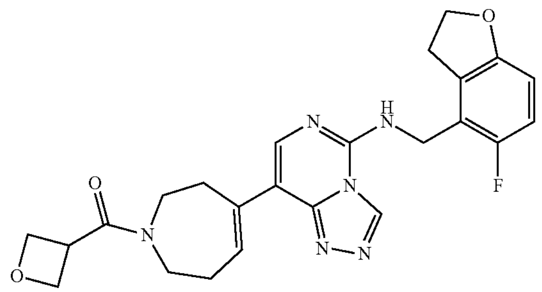
SL-E20
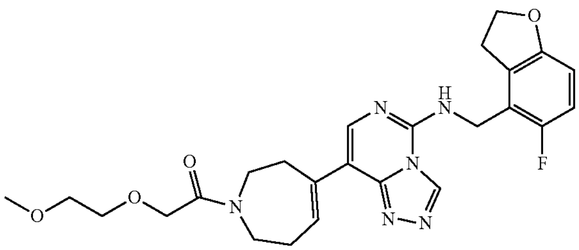
SL-E21
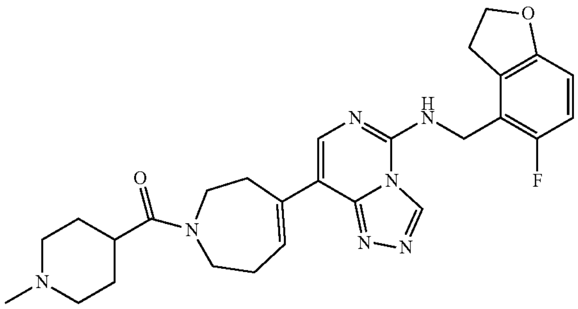
SL-E22
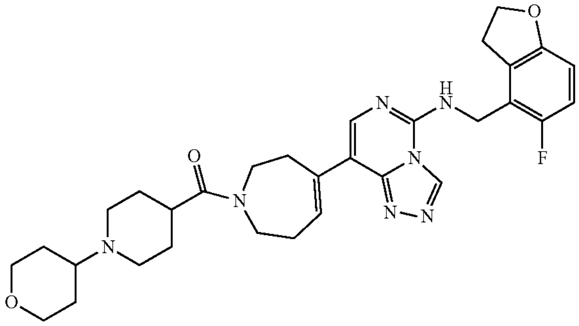
SL-E23
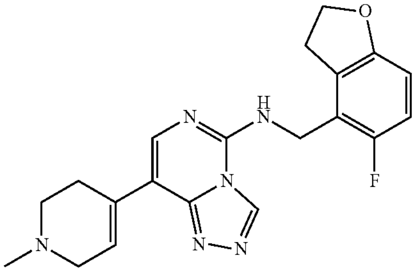
-continued
SL-E24
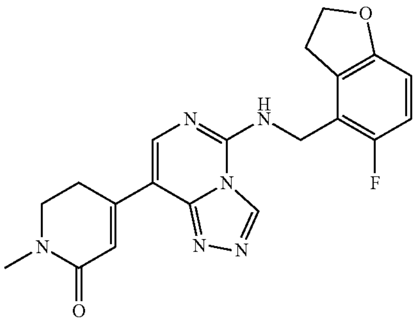
SL-E25
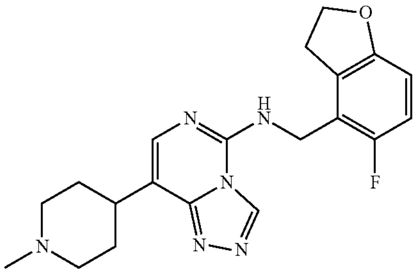
SL-E26
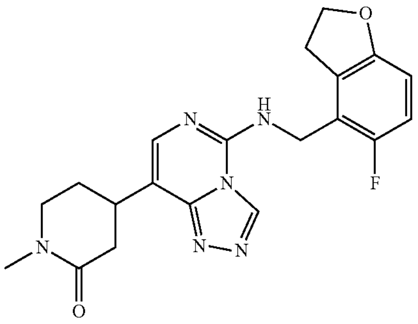
SL-E29
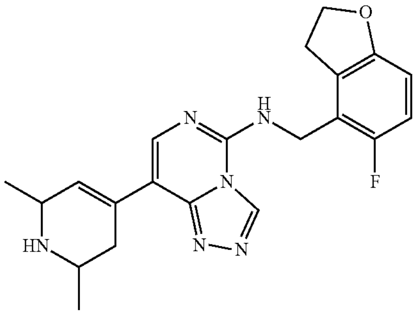
SL-E30
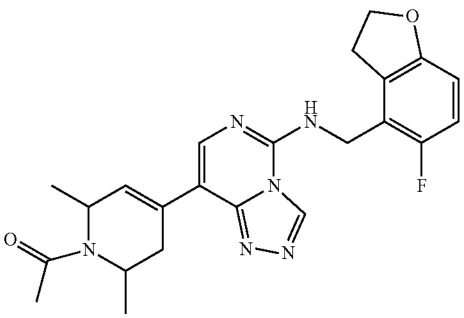

SL-E31
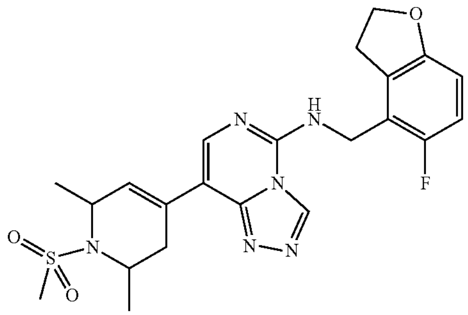
SL-E32
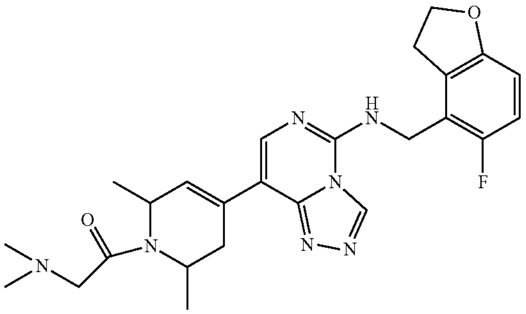
SL-E33
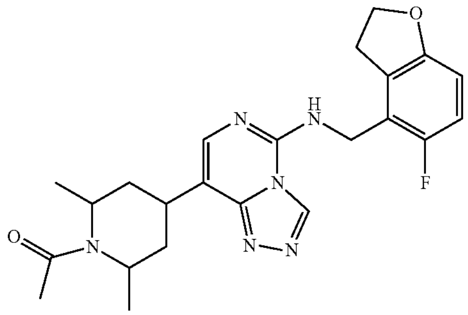
SL-E34
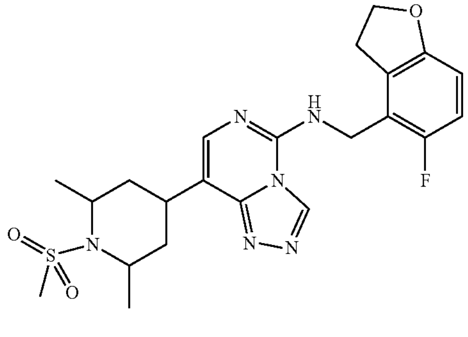
SL-E35
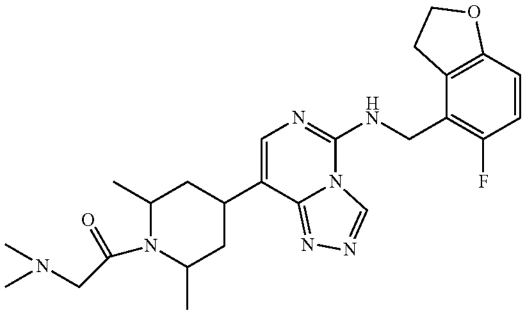
SL-E36
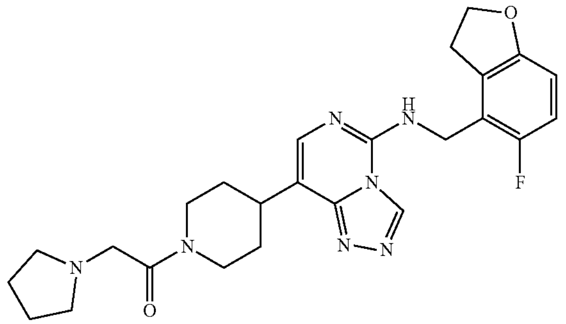
SL-E37
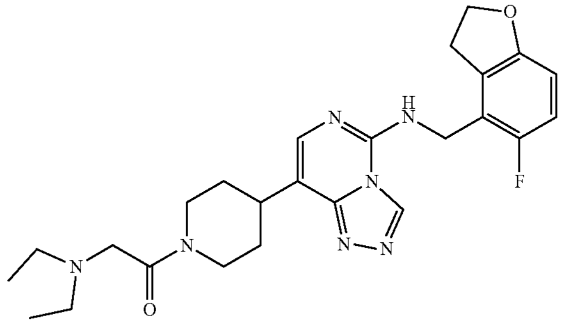
SL-E38
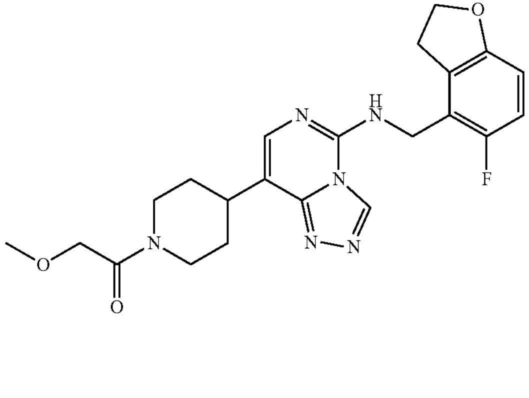

-continued
SL-E39
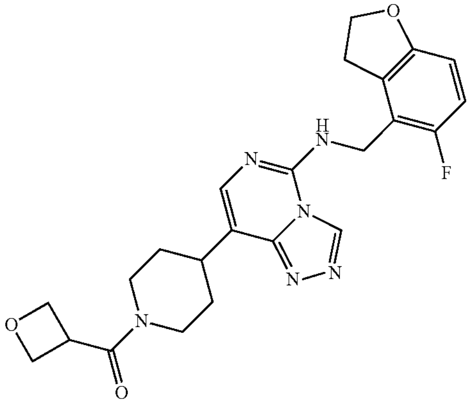
SL-E40
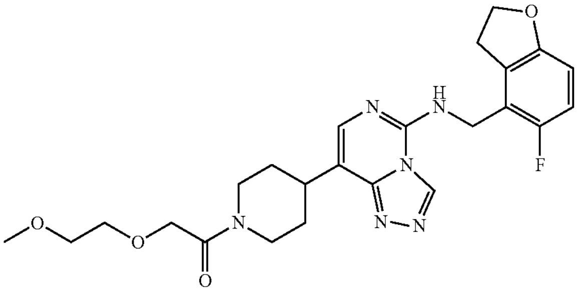
SL-E41
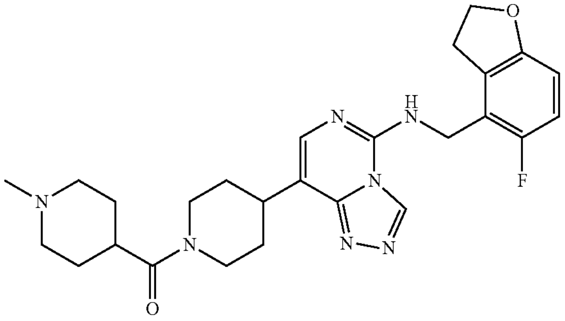
SL-E42
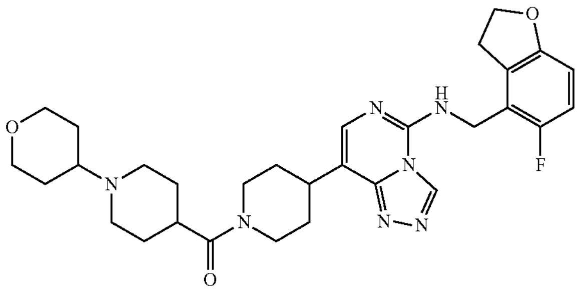
-continued
SL-E43
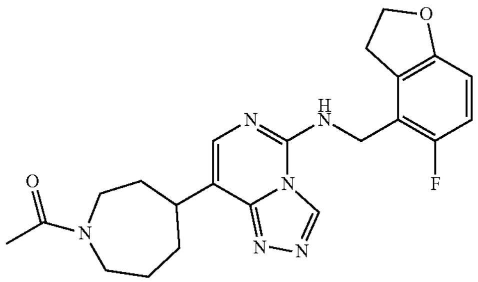
SL-E44
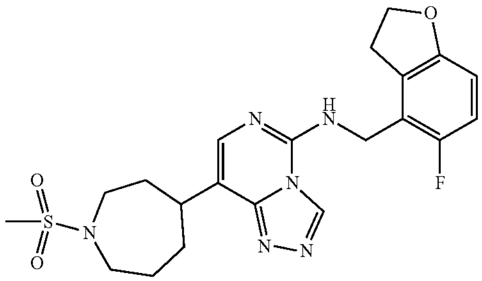
SL-E45
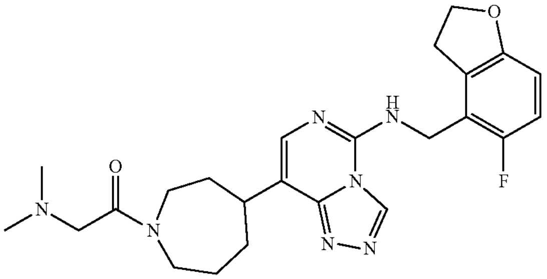
SL-E46
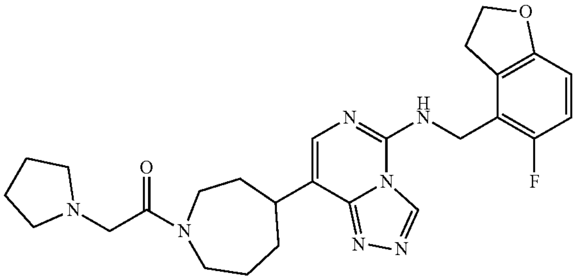
SL-E47
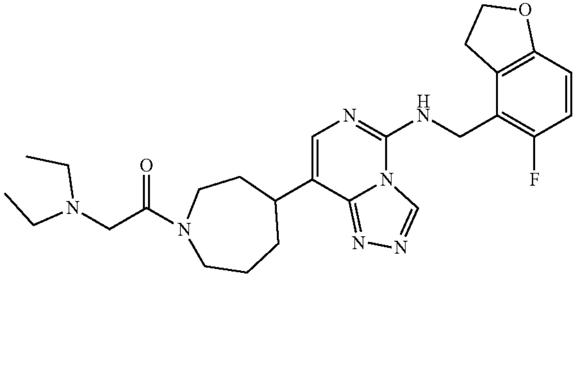

-continued
SL-E48
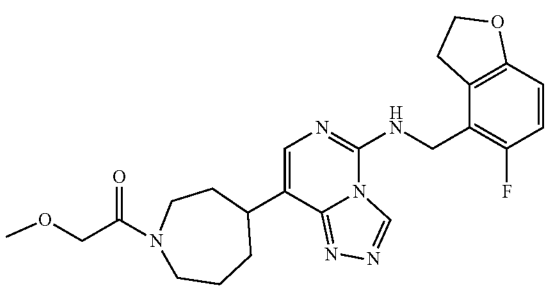
SL-E49
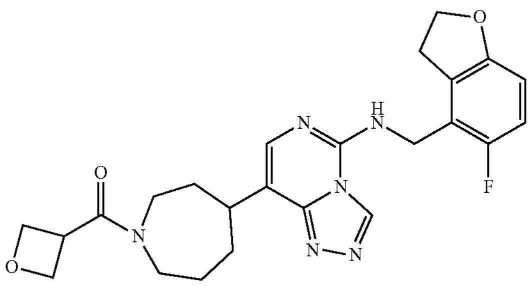
SL-E50
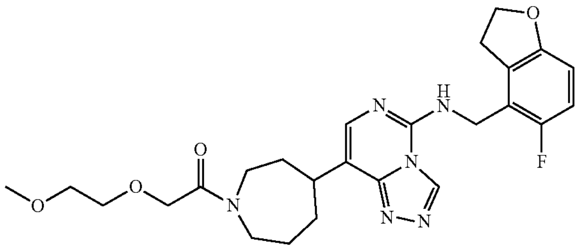
SL-E51
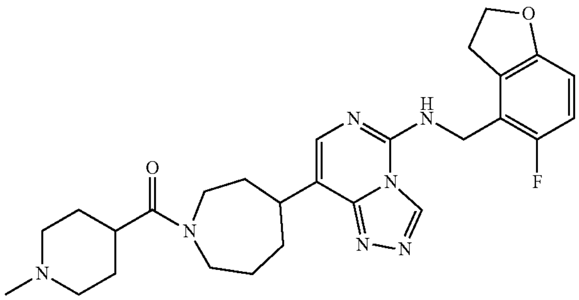
SL-E52
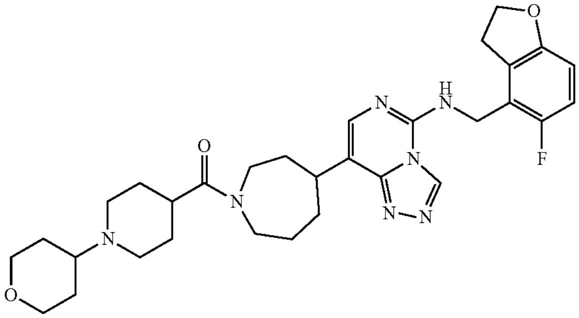
-continued
SL-E53
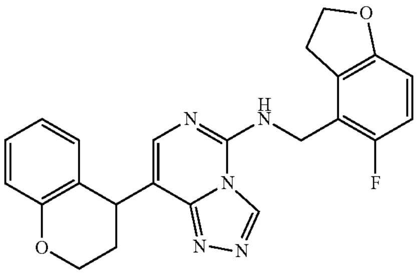
E-Y2-H
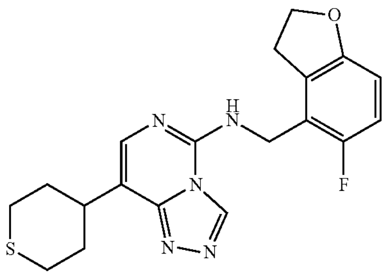
SL-ZYE-08-S
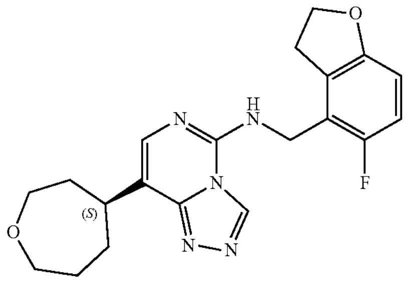
SL-ZYE-08-R
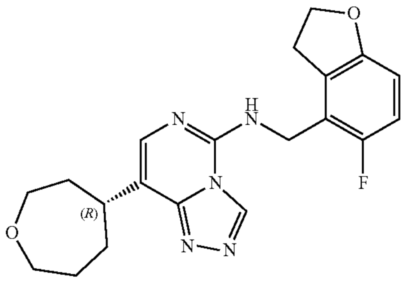
SL-E43-S
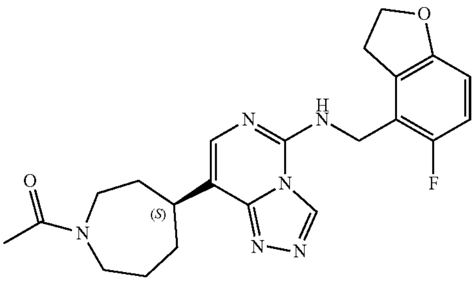

-continued
SL-E43-R
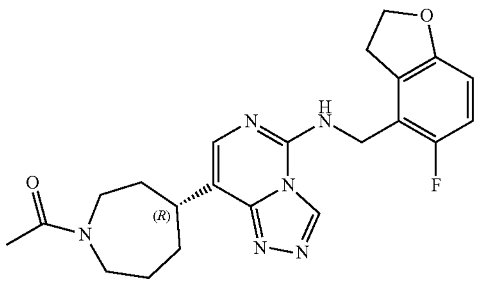
SL-E44-S
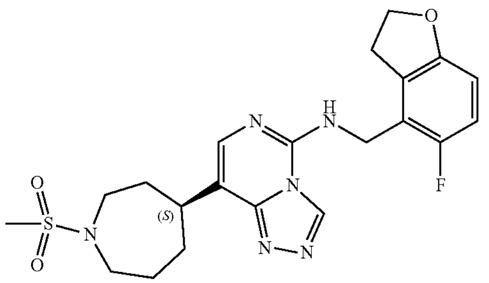
SL-E44-R
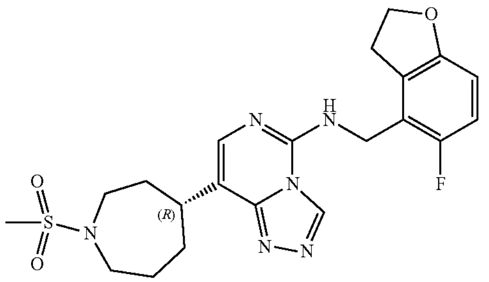
SL-E45-S
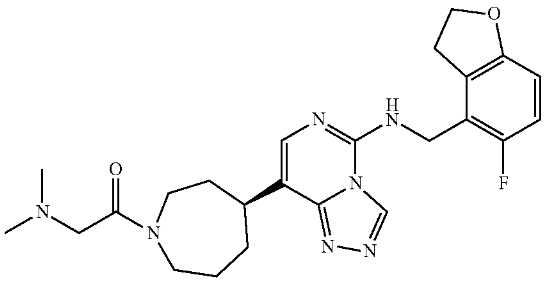
SL-E45-R
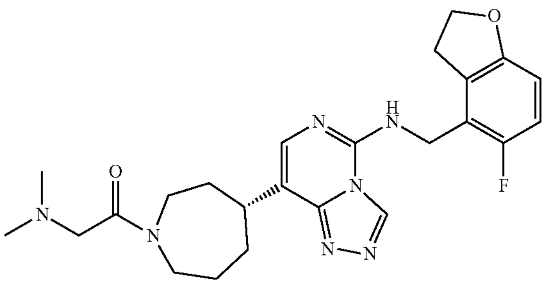
-continued
SL-E46-S
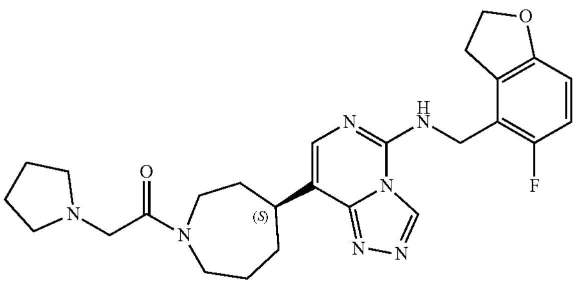
SL-E46-R
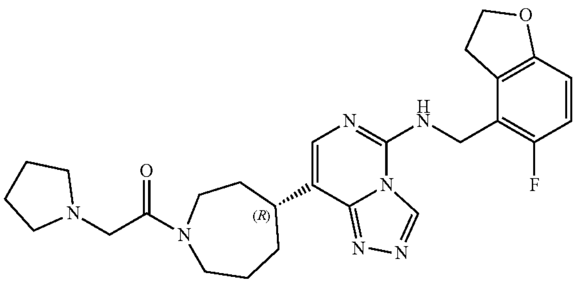
SL-E47-S
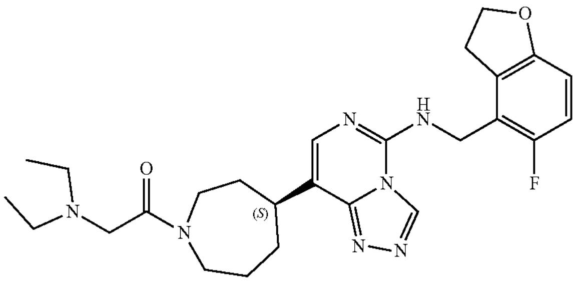
SL-E47-R
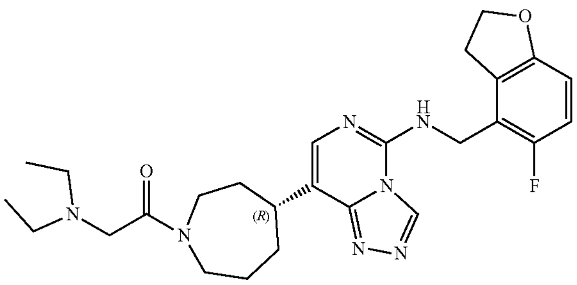
SL-E48-S
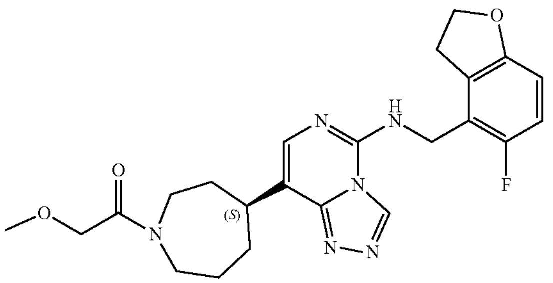

-continued
SL-E48-R
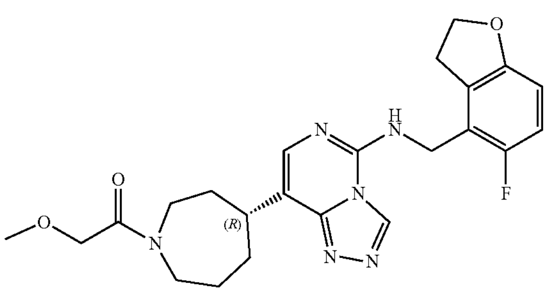
SL-E49-S
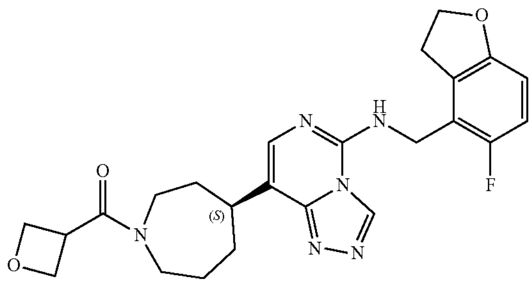
SL-E49-R
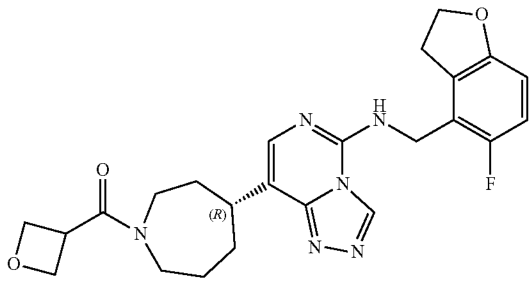
SL-E50-S
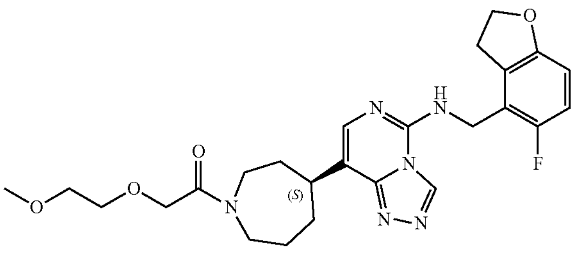
SL-E50-R
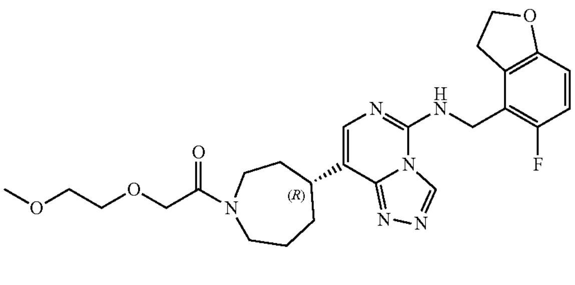
-continued
SL-E51-S
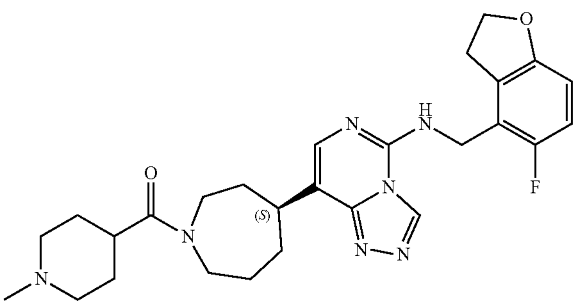
SL-E51-R
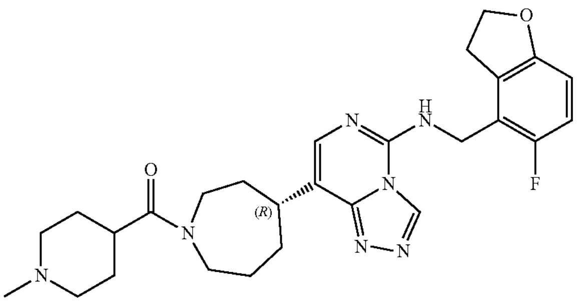
SL-E52-S
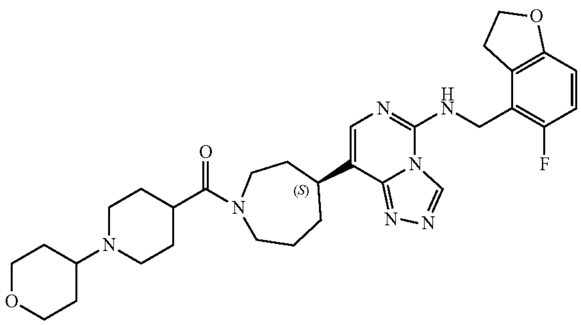
SL-E52-R
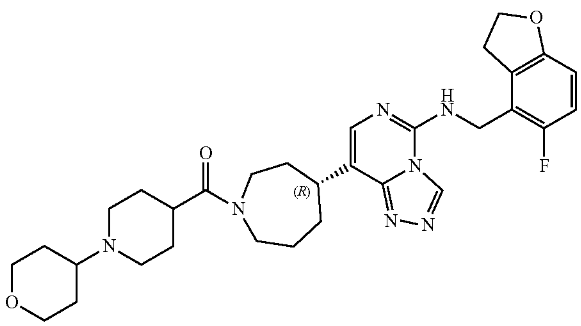
SL-E2-S
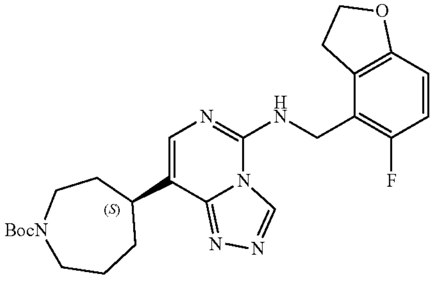

-continued
SL-E2-R
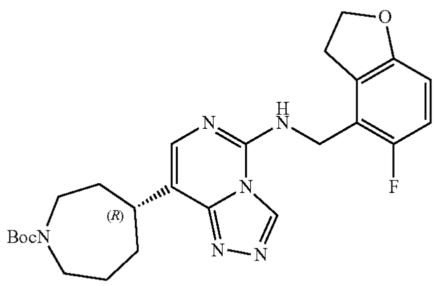
SL-ZYE-120
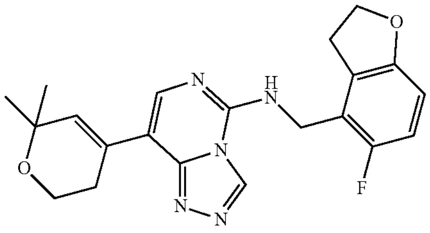
SL-ZYE-119
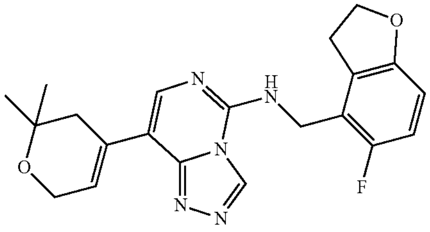
SL-ZYE-144
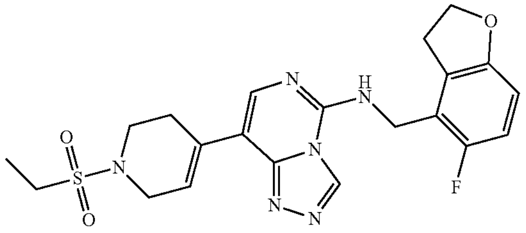
SL-ZYE-146
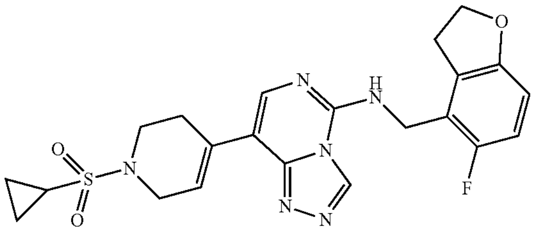
SL-ZYE-147
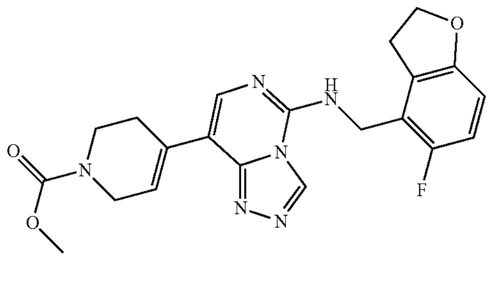
-continued
SL-ZYE-148
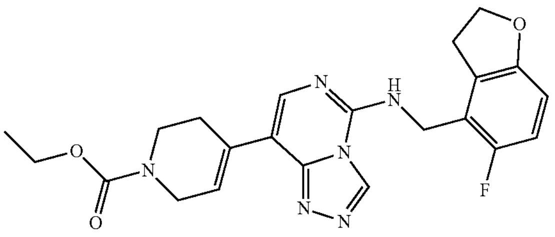
SL-ZYE-161
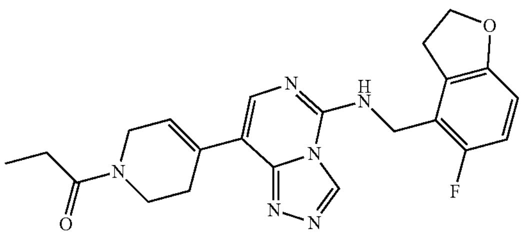
SL-ZYE-162
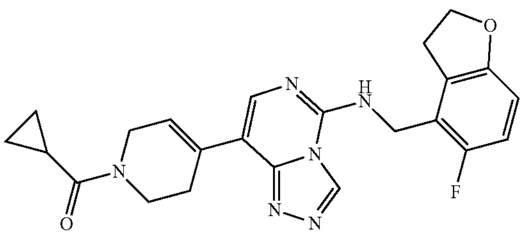
SL-ZYE-145
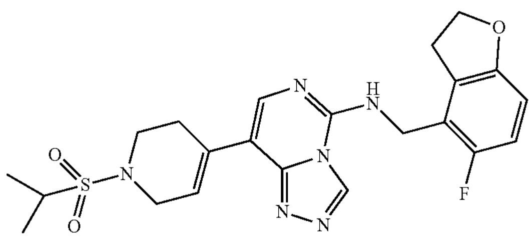
SL-ZYE-121
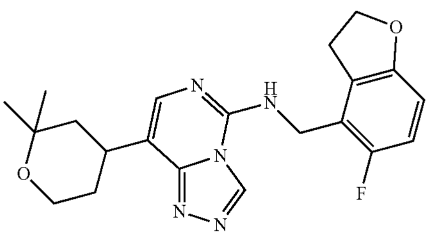
SL-ZYE-183
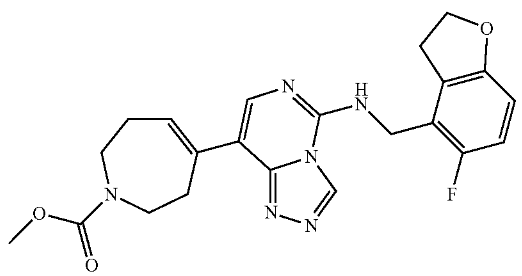

-continued

SL-ZYE-195

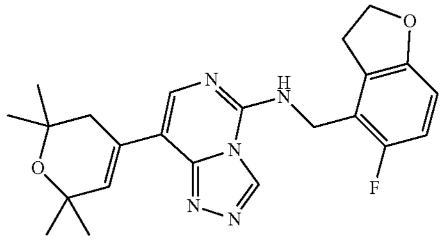

SL-ZYE-196

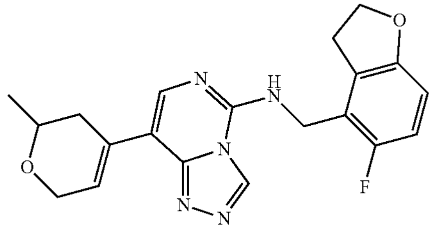

SL-ZYE-197

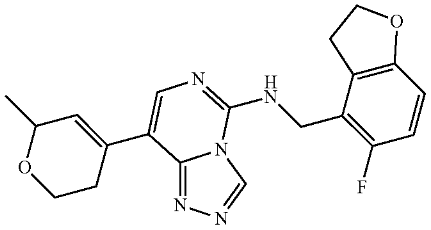

.

9. A method for preparing a compound represented by formula I according to claim 1, the method comprising the following steps:

Scheme 1

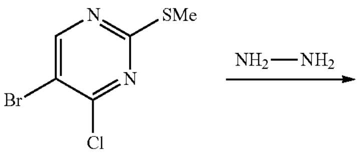

1

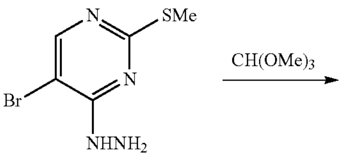

2

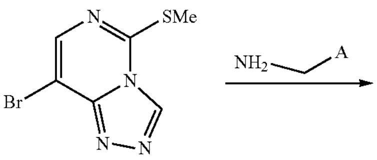

3

-continued

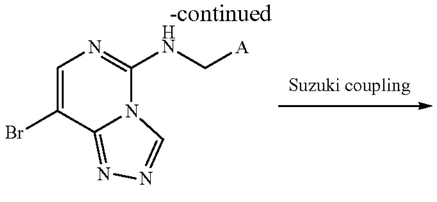

4

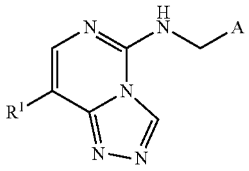

5

(1a) treating 5-bromo-4-chloro-2-(methylthio) pyrimidine 1 with hydrated hydrazine to produce 5-bromo-4-hydrazinyl-2-(methylthio) pyrimidine 2, (1b) converting 5-bromo-4-hydrazinyl-2-(methylthio) pyrimidine 2 with trimethyl orthoformate to triazole product 3, (1c) conducting a substitution reaction of triazole product 3 with an amine $NH_2CH_2A$ to produce compound 4, (1d) conducting a suzuki coupling reaction of compound 4 with various of boric acid having $R^1$ group or its equivalent under the action of palladium catalyst to obtain product 5, wherein, the definitions of A, $R^1$ are the same as defined in claim 1;

Scheme 2

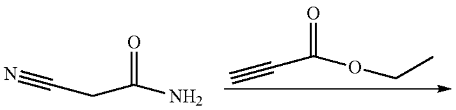

6

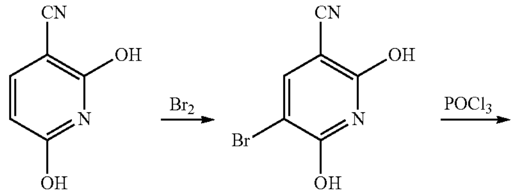

7 8

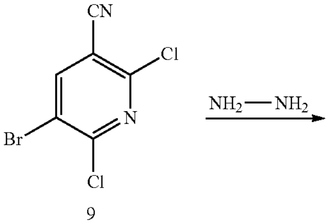

9

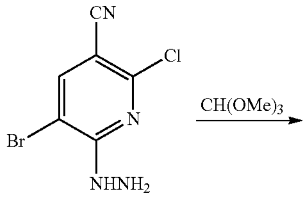

10

-continued

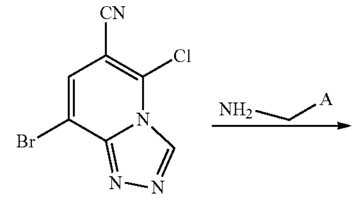

11

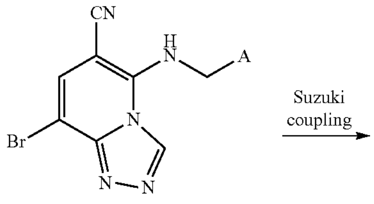

12

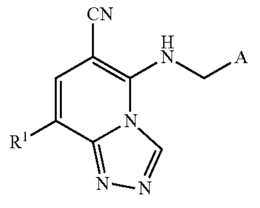

13

(2a) reacting the cyanoethyl amide 6 with ethyl propiolate to produce intermediate 7, (2b) treating intermediate 7 with bromine to conduct a bromation reaction to obtain bromide 8, (2c) reacting bromide 8 with phosphorus oxychloride to obtain intermediate 9, (2d) treating intermediate 9 with hydrated hydrazine to produce intermediate 10, (2e) converting intermediate 10 with trimethyl orthoformate to triazole product 11, (2f) conducting a substitution reaction of triazole product 11 with various amines to produce compound 12, (2g) conducting a suzuki coupling reaction of compound 12 with various of boric acid having $R^1$ group or its equivalent under the action of palladium catalyst to obtain product 13, wherein, the definitions of A, $R^1$ are the same as defined in claim 1;

Scheme 3

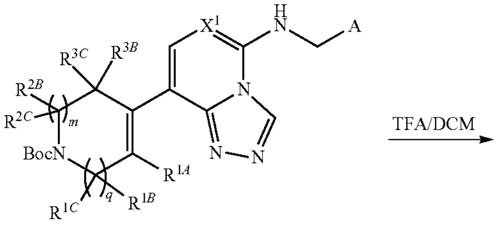

14

-continued

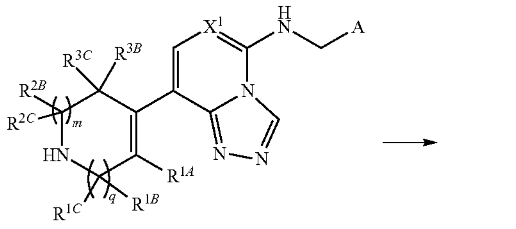

15

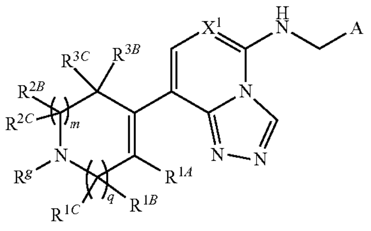

16

(3a) removing the Boc protecting group in 14 using dichloromethane as a solvent and under the action of trifluoroacetic acid to obtain an amine compound 15, (3b) further reacting the amine compound 15 with a reagent or compound having $R^g$ under basic conditions to give a compound 16, the agent or compound is, for example, but not limited to acid anhydrides, sulfonic anhydride, isocyanate, thioisocyanate, acyl chloride, sulfonyl chloride, carbonate, chloroformate, urethane, wherein, the definitions of A, $X^1$, $R^g$, $R^{1A}$, $R^{1B}$, $R^{1C}$, $R^{2B}$, $R^{2C}$, $R^{3B}$, $R^{3C}$, q, m are the same as defined in claim 1;

Scheme 4

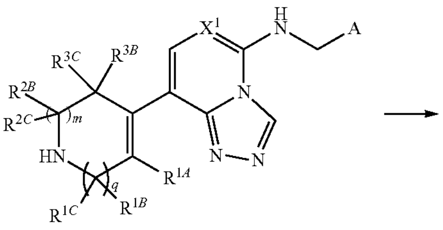

15

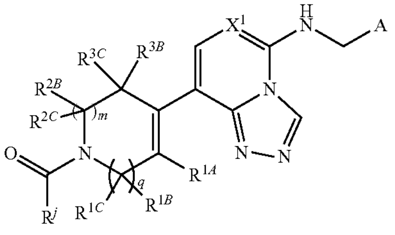

17

(4a) conducting a condensation reaction of product 15 obtained by removing the protective group in step (3a) of Scheme 3 with a carboxylic acid having an $R^j$ group under the action of a condensing agent to obtain an amide compound 17, wherein, the definitions of A, $X^1$, $R^j$, $R^{1A}$, $R^{1B}$, $R^{1C}$, $R^{2B}$, $R^{2C}$, $R^{3B}$, $R^{3C}$, q, m are the same as defined in claim 1;

Scheme 5

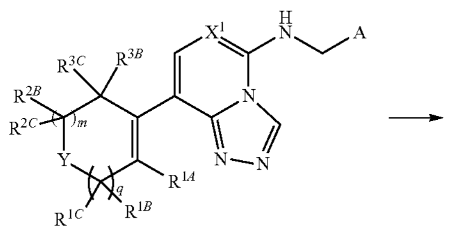

18

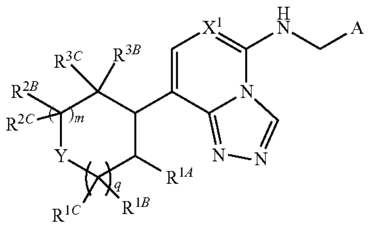

19

(5a) dissolving 18 in a solvent, the solvent is, for example, but not limited to, methanol, ethanol, ethyl acetate, and tetrahydrofuran, adding a metal catalyst, the metal catalyst is, for example, but not limited to 10% palladium carbon, $Pd(OH)_2$, Raney nickel, $RhCl(PPh_3)_3$, introducing hydrogen gas, and reacting at room temperature to obtain compound 19 with double bond reduction, wherein, the definitions of A, $X^1$, Y, $R^{1A}$, $R^{1B}$, $R^{1C}$, $R^{2B}$, $R^{2C}$, $R^{3B}$, $R^{3C}$, q, m are the same as defined in claim 1;

Scheme 6

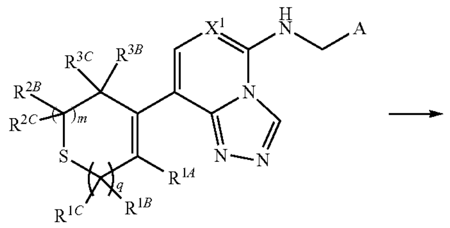

20

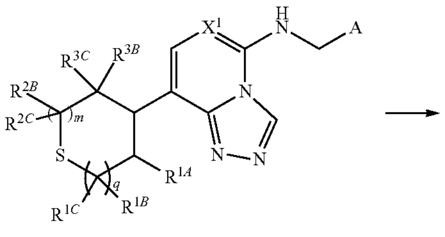

21

-continued

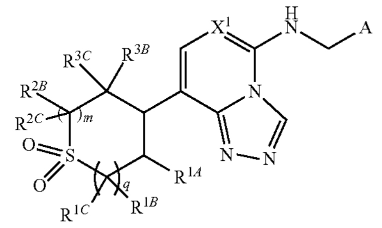

22

(6a) obtaining the compound 21 by reduction reaction of 20, and then conducting an oxidation reaction with mCPBA (m-chloroperoxybenzoic acid) or hydrogen peroxide to obtain compound 22, wherein, the definitions of A, $X^1$, $R^{1A}$, $R^{1B}$, $R^{1C}$, $R^{2B}$, $R^{2C}$, $R^{3B}$, $R^{3C}$, q, m are the same as defined in claim 1;

Scheme 7

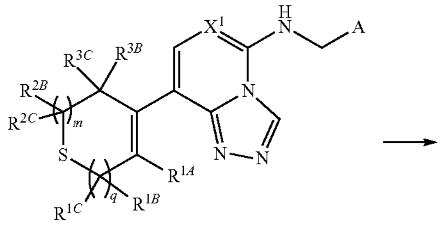

20

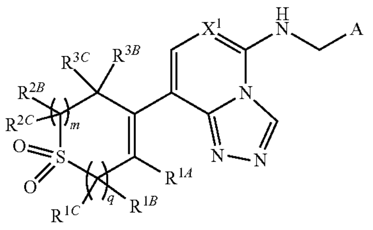

23

(7a) conducting an oxidation reaction of 20 with mCPBA or hydrogen peroxide to obtain compound 23, wherein, the definitions of A, $X^1$, $R^{1A}$, $R^{1B}$, $R^{1C}$, $R^{2B}$, $R^{2C}$, $R^{3B}$, $R^{3C}$, q, m are the same as defined in claim 1;

Scheme 8

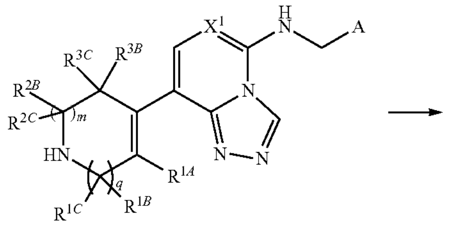

15

-continued

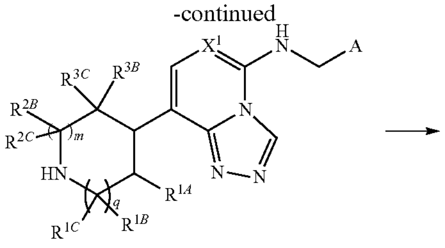

24

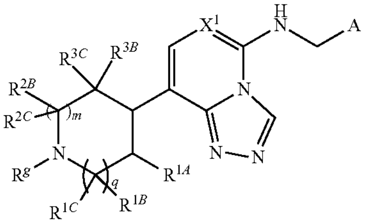

25 reducing the double bond of 15 to obtain 24, and then reacting with a reagent or compound having an $R^g$ group in the presence of a base to obtain 25, said reagent or compound is, for example, but not limited to acid anhydrides, sulfonic anhydride, isocyanate, thioisocyanate, acyl chloride, sulfonyl chloride, carbonate, chloroformate, urethane; or conducting a condensation reaction of 24 with various carboxylic acids in the presence of a condensing agent to obtain an amide compound 25, wherein, the definitions of A, $X^1$, $R^{1A}$, $R^{1B}$, $R^{1C}$, $R^{2B}$, $R^{2C}$, $R^{3B}$, $R^{3C}$, q, m are the same as defined in claim 1.

10. A pharmaceutical composition, comprising one or more of the compound, pharmaceutically acceptable salts, enantiomers, diastereomers or racemates thereof according to claim 1, and at least one pharmaceutically acceptable carrier, diluent, or excipient.

11. The pharmaceutical composition according to claim 10, wherein the pharmaceutical composition further comprises at least one other therapeutic agent.

12. A method of treating a disease or condition mediated by EED and/or PRC2 comprising administering to a patient in need thereof, a compound, pharmaceutically acceptable salts, enantiomers, diastereomers or racemates thereof according to claim 1.

13. The method of claim 12, wherein the disease or condition mediated by EED and/or PRC2 includes diffuse large B-cell lymphoma, follicular lymphoma, other lymphoma, leukemia, multiple myeloma, mesothelioma, gastric cancer, malignant rhabdoid tumor, hepatocellular carcinoma, prostate Cancer, breast cancer, bile duct and gallbladder cancer, bladder cancer; brain tumors, including neuroblastoma, schwannoma, glioma, glioblastoma and astrocytoma; cervical cancer, colon cancer, melanin tumor, endometrial cancer, esophageal cancer, head and neck cancer, lung cancer, nasopharyngeal cancer, ovarian cancer, pancreatic cancer, renal cell cancer, rectal cancer, thyroid cancer, parathyroid tumor, uterine tumor and soft tissue sarcoma.

14. The compound, pharmaceutically acceptable salts, enantiomers, diastereomers or racemates thereof according to claim 1, wherein $R^1$ is independently selected from the following structures:

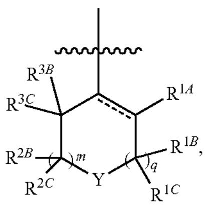

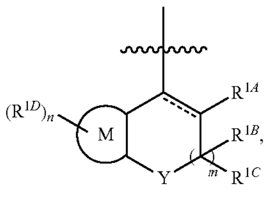

wherein $\overset{-----}{=====}$ is a single bond or double bond;

$R^{1A}$ is independently selected from H, hydroxy, halogen, CN, —$(O)_z(C_1$-$C_{10}$ alkyl comprising 0-2 of substituent $R^c$), $C_1$-$C_6$ alkyl, $C_1$-$C_6$ alkoxy, $C_1$-$C_6$ haloalkyl, $C_1$-$C_6$ haloalkoxy, $SCF_3$, $C_3$-$C_8$ cycloalkyl, —C(═O)($C_1$-$C_4$ alkyl), —C(═O)NH($C_1$-$C_4$ alkyl), —C(═O)H;

$R^c$ is independently selected from OH, halogen, CN, $C_1$-$C_6$ alkyl, carboxyl, $C_1$-$C_6$ haloalkyl, $C_1$-$C_6$ alkoxy, $C_1$-$C_6$ haloalkoxy, $C_3$-$C_8$ cycloalkyl;

$R^{1B}$ and $R^{1C}$, $R^{2B}$ and $R^{2C}$, and $R^{3B}$ and $R^{3C}$ are independently selected from H, OH, halogen, CN, —$(O)_z$—($C_1$-$C_{10}$ alkyl comprising 0-2 of substituent $R^c$), $C_1$-$C_6$ alkyl group, $C_1$-$C_6$ alkoxy, $C_1$-$C_6$ haloalkyl, $C_1$-$C_6$ haloalkoxy, $SCF_3$, $C_3$-$C_8$ cycloalkyl, —C(═O)($C_1$-$C_4$ alkyl), —C(═O)NH($C_1$-$C_4$ alkyl);

alternatively, $R^{1B}$ and $R^{1C}$, $R^{2B}$ and $R^{2C}$, $R^{3B}$ and $R^{3C}$ may form a carbonyl group (═O) or a thiocarbonyl group (═S) with a carbon atom to which they are attached;

$R^{1D}$ is independently selected from H, —OH, halogen, CN, —C(═O)H, —$(O)_z$—($C_1$-$C_6$ alkyl comprising 0-2 of substituent $R^c$), $C_1$-$C_6$ haloalkyl, $C_1$-$C_6$ haloalkoxy, $SCF_3$, $C_3$-$C_8$ cycloalkyl;

$R^c$ is independently selected from OH, halogen, CN, $C_1$-$C_6$ alkyl, carboxyl, $C_1$-$C_6$ haloalkyl, $C_1$-$C_6$ alkoxy, $C_1$-$C_6$ haloalkoxy, $C_3$-$C_8$ cycloalkyl;

M is independently selected from a 3 to 7 membered saturated or unsaturated cycloalkyl, a heterocycloalkyl comprising carbon atoms and 1-4 heteroatoms selected from O, N, $S(O)_p$, an aryl, 5- to 6-membered heteroaryl comprising carbon atoms and 1 to 2 heteroatoms selected from N, O and S;

n is each independently selected from 0, 1 and 2;

m is each independently selected from 0-4;

p is each independently selected from 0-2;

q is each independently selected from 0-3; and z is each independently selected from 0 and 1.

15. The compound, pharmaceutically acceptable salts, enantiomers, diastereomers or racemates thereof according to claim 1, wherein $R^{1A}$ is independently selected from H, hydroxyl, halogen, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl;

$R^{1B}$ and $R^{1C}$, $R^{2B}$ and $R^{2C}$, and $R^{3B}$ and $R^{3C}$ are independently selected from H, OH, halogen, $C_1$-$C_6$ alkyl group, $C_1$-$C_6$ alkoxy, $C_1$-$C_6$ haloalkyl, $C_1$-$C_6$ haloalkoxy, $C_3$-$C_8$ cycloalkyl;

Alternatively, $R^{1B}$ and $R^{1C}$, $R^{2B}$ and $R^{2C}$, $R^{3B}$ and $R^{3C}$ may form a carbonyl group (═O) or a thiocarbonyl group (═S) with a carbon atom to which they are attached;

$R^{1D}$ is independently selected from H, —OH, halogen, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl;

M is independently selected from a 5 to 6 membered saturated or unsaturated cycloalkyl, a heterocycloalkyl comprising carbon atoms and 1-4 heteroatoms selected from O, N, $S(O)_p$, an aryl, 5- to 6-membered heteroaryl comprising carbon atoms and 1 to 2 heteroatoms selected from N, O and S;

n is each independently selected from 0, 1 and 2;

m is each independently selected from 0-4;

p is each independently selected from 0-2;

q is each independently selected from 0-3; and z is each independently selected from 0 and 1.

16. The compound, pharmaceutically acceptable salts, enantiomers, diastereomers or racemates thereof according to claim 1, wherein Y is independently selected from O, $NR^g$, $S(O)_p$, $—CR^i(CH_2)_mNR^gR^h$ and $—CR^i(CH_2)_mOR^g$;

$R^g$ and $R^h$ are independently selected from H; $C_1$-$C_6$ haloalkyl;

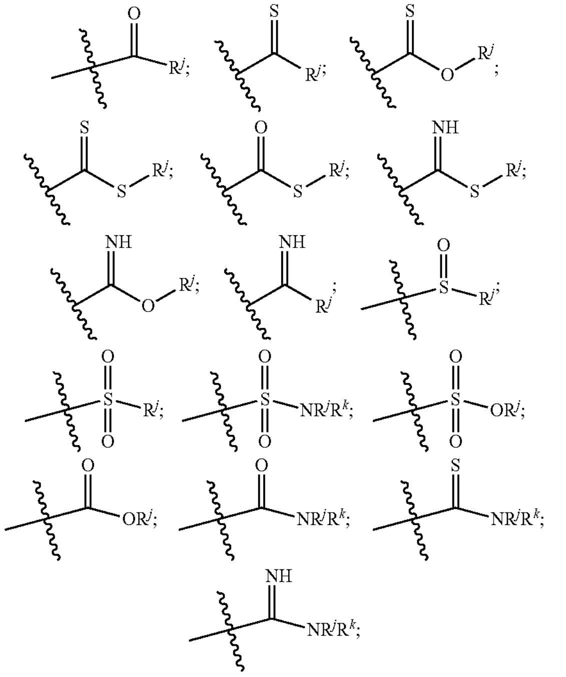

$—C(═S)NHC(═O)—R^j$; heteroalkyl and heterocycloalkyl comprising carbon atoms and 1-4 heteroatoms selected from O, N, $S(O)_p$; aryl; 5- to 6-membered heteroaryl comprising carbon atoms and 1 to 2 heteroatoms selected from N, O and S; wherein the aryl and heteroaryl may be substituted by 0-2 of $R^{1X}$;

$R^j$ and $R^k$ are independently selected from H; CN; $C_1$-$C_{10}$ alkyl comprising 0-3 of substituent $R^s$; $C_1$-$C_6$ haloalkyl; $C_3$-$C_{10}$ cycloalkyl; heteroalkyl and heterocycloalkyl comprising carbon atoms and 1-4 heteroatoms selected from O, N, $S(O)_p$; $C_2$-$C_{10}$ alkenyl or alkynyl; 6 to 10 membered aryl; 5 to 10 membered heteroaryl comprising carbon atoms and 1 to 2 heteroatoms selected from N, O, and S; wherein the aryl and heteroaryl may be substituted by 0-2 of $R^{1Y}$;

p is each independently selected from 0, 1 and 2;

$R^{1X}$ is independently selected from halogen, OH, CN, $C_1$-$C_4$ alkyl, $C_1$-$C_4$ haloalkyl, $C_1$-$C_4$ alkoxy, $C_1$-$C_4$ haloalkoxy, $C_3$-$C_8$ cycloalkyl and cyclic heteroalkyl;

$R^{1Y}$ is independently selected from $C_1$-$C_{10}$ alkyl, halogen, CN, $C_1$-$C_6$ haloalkyl, $C_1$-$C_6$ haloalkoxy, $C_3$-$C_8$ cycloalkyl;

p is each independently 0, 1 and 2;

In particular, $R^g$ and $R^h$, as well as $R^j$ and $R^k$ may be connected by the following manner

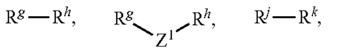 and 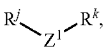

wherein $Z^1$ may be selected from $C_1$-$C_6$ alkyl comprising 0-2 of substituent $R^c$; $C_1$-$C_6$ alkyl comprising 0-2 heteroatoms of O, N, $S(O)_p$; O; $—N(C_1$-$C_6$ alkyl); —NH; $—N(C═O)$ $C_1$-$C_6$ alkyl; $—NS(═O)_2(C_1$-$C_6$ alkyl); $S(O)_p$;

p is each independently selected from 0, 1 and 2;

$R^i$ is independently selected from H, CN and $C_1$-$C_4$ alkyl;

m is each independently selected from 0-4.

17. The compound, pharmaceutically acceptable salts, enantiomers, diastereomers or racemates thereof according to claim 1, wherein Y is independently selected from O, $NR^g$, S, $—CR^iNR^gR^h$ and $—CR^iOR^g$;

$R^g$ and $R^h$ are independently selected from H; $C_1$-$C_6$ haloalkyl;

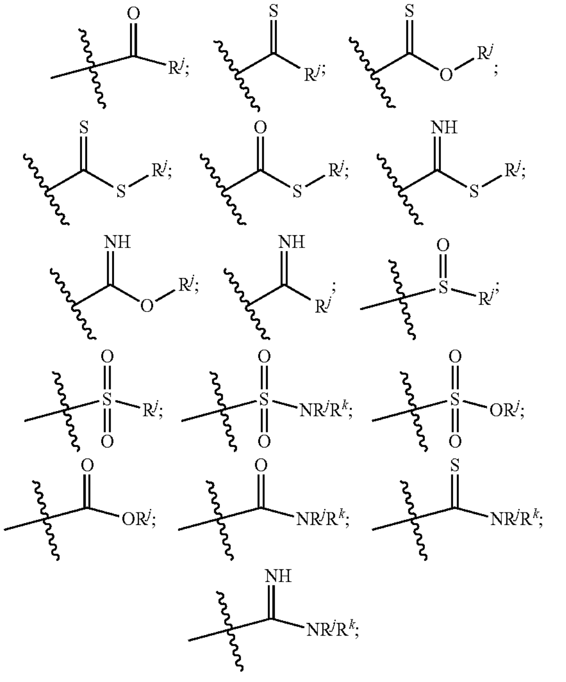

$—C(═S)NHC(═O)—R^j$; heteroalkyl and heterocycloalkyl comprising carbon atoms and 1-4 heteroatoms selected from O, N, S; aryl; 5- to 6-membered heteroaryl comprising carbon atoms and 1 to 2 heteroatoms selected from N, O and S; wherein the aryl and heteroaryl may be substituted by 0-2 of $R^{1X}$;

$R^j$ and $R^k$ are independently selected from H; CN; $C_1$-$C_{10}$ alkyl comprising 0-3 of substituent $R^s$; $C_1$-$C_6$ haloalkyl; C3-C10 cycloalkyl; heteroalkyl and heterocycloalkyl comprising carbon atoms and 1-4 heteroatoms selected from O, N, S; $C_2$-$C_{10}$ alkenyl or alkynyl; 6 to 10 membered aryl; 5 to 10 membered heteroaryl comprising carbon atoms and 1 to 2 heteroatoms selected from N, O, and S; wherein the aryl and heteroaryl may be substituted by 0-2 of $R^{1Y}$;

$R^s$ is independently selected from OH; CN; halogen; $C_1$-$C_6$ alkyl; $C_1$-$C_6$ haloalkyl; $C_1$-$C_6$ alkoxy; $C_1$-$C_6$ haloalkoxy; $C_3$-$C_8$ cycloalkyl, —$(OCH_2CH_2)mOR^d$, $(OCH_2CH_2)mNR^dR^e$, heteroalkyl and heterocycloalkyl comprising carbon atoms and 1 to 2 heteroatoms selected from N, O, S; aryl; and heteroaryl comprising carbon atoms and 1 to 2 heteroatoms selected from N, O, and S; wherein the aryl and heteroaryl may be substituted by 0-2 of $R^{1Y}$;

$R^{1Y}$ is independently selected from $C_1$-$C_{10}$ alkyl, halogen, CN, $C_1$-$C_6$ haloalkyl, $C_1$-$C_6$ haloalkoxy, $C_3$-$C_8$ cycloalkyl;

$R^g$ and $R^h$, as well as $R^j$ and $R^k$ may be connected by the following manner

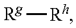, 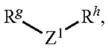, 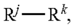, and 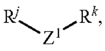, wherein $Z^1$ may be selected from $C_1$-$C_6$ alkyl comprising 0-2 of substituent $R^c$; $C_1$-$C_6$ alkyl comprising 0-2 heteroatoms of O, N, $S(O)_p$; O; —N($C_1$-$C_6$ alkyl); —NH; —N(C═O) $C_1$-$C_6$ alkyl; —NS(═O)$_2$($C_1$-$C_6$ alkyl); $S(O)_p$;

p is each independently selected from 0, 1 and 2;

$R^i$ is independently selected from H, CN and $C_1$-$C_4$ alkyl;

m is each independently selected from 0-4.

18. The pharmaceutical composition according to claim 10, wherein the pharmaceutical composition further comprises at least one other therapeutic agent, the at least one other therapeutic agent is selected from other anticancer agents, immunomodulators, antiallergic agents, antiemetics, pain relief agents, cytoprotective agents, and combinations thereof.

* * * * *